(12) United States Patent
Petrukhin et al.

(10) Patent No.: US 10,072,016 B2
(45) Date of Patent: *Sep. 11, 2018

(54) SUBSTITUTED 4-PHENYLPIPERIDINES, THEIR PREPARATION AND USE

(71) Applicant: The Trustees of Columbia University in the City of New York, New York, NY (US)

(72) Inventors: Konstantin Petrukhin, New Windsor, NY (US); Christopher Cioffi, Albany, NY (US); Graham Johnson, Sanbornton, NH (US); Rando Allikmets, Cornwall on Hudson, NY (US); Emily Freeman, Albany, NY (US); Ping Chen, Albany, NY (US); Michael Conlon, Albany, NY (US); Lei Zhu, Albany, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,760

(22) Filed: Oct. 2, 2017

(65) Prior Publication Data
US 2018/0030060 A1    Feb. 1, 2018

Related U.S. Application Data

(63) Continuation of application No. 15/254,966, filed on Sep. 1, 2016, now Pat. No. 9,777,010, which is a
(Continued)

(51) Int. Cl.
*A61K 31/437* (2006.01)
*C07D 211/06* (2006.01)
(Continued)

(52) U.S. Cl.
CPC ......... *C07D 487/04* (2013.01); *C07D 471/04* (2013.01)

(58) Field of Classification Search
CPC .. C07D 401/14; C07D 211/06; C07D 295/00; A61K 31/437
(Continued)

(56) References Cited

U.S. PATENT DOCUMENTS 5,231,083 A   7/1993 Linz et al.
5,312,814 A   5/1994 Biller et al.
(Continued)

FOREIGN PATENT DOCUMENTS

DE   4130514        3/1993
EP   1190710 A1     3/2002
(Continued)

OTHER PUBLICATIONS

Office Action dated May 31, 2017 in connection with U.S. Appl. No. 15/093,179.
Final Office Action dated Dec. 11, 2017 in connection with U.S. Appl. No. 15/093,179.
Office Action dated Aug. 7, 2017 in connection with U.S. Appl. No. 14/775,532.
(Continued)

*Primary Examiner* — Niloofar Rahmani
(74) *Attorney, Agent, or Firm* — John P. White; Cooper & Dunham LLP

(57) ABSTRACT

The present invention provides a compound having the structure:

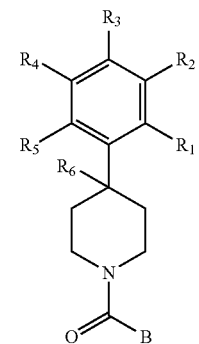

wherein
$R_1$, $R_2$, $R_3$, $R_4$, and $R_5$ are each independently H, halogen, $CF_3$ or $C_1$-$C_4$ alkyl,
  wherein two or more of $R_1$, $R_2$, $R_3$, $R_4$, or $R_5$ are other than H;
$R_6$ is H, OH, or halogen; and
B is a substituted or unsubstituted heterobicycle,
wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

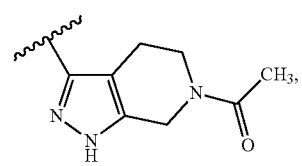

or a pharmaceutically acceptable salt thereof.

19 Claims, 9 Drawing Sheets

Related U.S. Application Data continuation of application No. 14/699,672, filed on Apr. 29, 2015, now Pat. No. 9,434,727.

(60) Provisional application No. 61/986,578, filed on Apr. 30, 2014.

(51) Int. Cl.
   *C07D 401/14* (2006.01)
   *C07D 487/04* (2006.01)
   *C07D 471/04* (2006.01)

(58) Field of Classification Search
   USPC .............................. 514/303; 546/119, 184
   See application file for complete search history.

(56) References Cited

U.S. PATENT DOCUMENTS

| | | | |
|---|---|---|---|
| 5,523,430 | A | 6/1996 | Patel et al. |
| 5,532,243 | A | 7/1996 | Gilligan et al. |
| 5,703,091 | A | 12/1997 | Steiner et al. |
| 6,372,793 | B1 | 4/2002 | Lamango et al. |
| 6,638,980 | B1 | 10/2003 | Su et al. |
| 7,157,451 | B2* | 1/2007 | Atwal .................. A61K 31/519 514/183 |
| 7,501,405 | B2 | 3/2009 | Kampen et al. |
| 7,718,669 | B2 | 5/2010 | Petry et al. |
| 7,781,436 | B2 | 8/2010 | Bissantz et al. |
| 7,947,692 | B2 | 5/2011 | Brinkman et al. |
| 8,168,783 | B2 | 5/2012 | Kokubo et al. |
| 8,586,571 | B2 | 11/2013 | Kasai et al. |
| 8,980,924 | B2 | 3/2015 | Petrukhin et al. |
| 9,333,202 | B2 | 5/2016 | Petrukhin et al. |
| 9,434,727 | B2 | 9/2016 | Petrukhin et al. |
| 9,637,450 | B2 | 5/2017 | Petrukhin et al. |
| 2003/0195195 | A1 | 10/2003 | Haviv et al. |
| 2004/0097575 | A1 | 5/2004 | Doherty et al. |
| 2004/0180877 | A1 | 9/2004 | Peters et al. |
| 2004/0220171 | A1 | 11/2004 | Pauls et al. |
| 2005/0043354 | A1 | 2/2005 | Wager et al. |
| 2006/0074121 | A1 | 4/2006 | Chen et al. |
| 2006/0089378 | A1 | 4/2006 | Xia et al. |
| 2006/0111366 | A1 | 5/2006 | Anderson et al. |
| 2006/0135460 | A1 | 6/2006 | Widder et al. |
| 2006/0199837 | A1 | 9/2006 | Thompson et al. |
| 2006/0270688 | A1 | 11/2006 | Chong et al. |
| 2007/0015827 | A1 | 1/2007 | Widder et al. |
| 2007/0027163 | A1 | 2/2007 | Bissantz et al. |
| 2007/0254911 | A1 | 11/2007 | Xia et al. |
| 2008/0039442 | A1 | 2/2008 | Blom et al. |
| 2008/0051409 | A1 | 2/2008 | Gmeiner et al. |
| 2008/0139552 | A1 | 6/2008 | Bissantzet et al. |
| 2008/0254140 | A1 | 10/2008 | Widder et al. |
| 2009/0054532 | A1 | 2/2009 | Mata et al. |
| 2009/0088435 | A1 | 4/2009 | Mata et al. |
| 2009/0143376 | A1 | 6/2009 | Milburn et al. |
| 2010/0022530 | A1 | 1/2010 | Schiemann et al. |
| 2010/0063047 | A1 | 3/2010 | Borchardt et al. |
| 2010/0222357 | A1 | 9/2010 | Bizzantz et al. |
| 2010/0292206 | A1 | 11/2010 | Kasai et al. |
| 2011/0003820 | A1 | 1/2011 | Henrich et al. |
| 2011/0201657 | A1 | 8/2011 | Boueres et al. |
| 2011/0251182 | A1 | 10/2011 | Sun et al. |
| 2011/0251187 | A1 | 10/2011 | Kasai et al. |
| 2011/0257196 | A1 | 10/2011 | Lu et al. |
| 2011/0294854 | A1 | 12/2011 | Searle et al. |
| 2011/0319393 | A1 | 12/2011 | Chassaing et al. |
| 2011/0319412 | A1 | 12/2011 | Sakagami et al. |
| 2012/0010186 | A1 | 1/2012 | Lachance et al. |
| 2012/0065189 | A1 | 3/2012 | Takahashi et al. |
| 2012/0071489 | A1 | 3/2012 | Kasai et al. |
| 2012/0071503 | A1 | 3/2012 | Cosford et al. |
| 2012/0077844 | A1 | 3/2012 | Cavezza et al. |
| 2012/0077854 | A1 | 3/2012 | Petrassi et al. |
| 2014/0031392 | A1 | 1/2014 | Petrukhin et al. |
| 2015/0057320 | A1 | 2/2015 | Petrukhin et al. |
| 2015/0315197 | A1 | 11/2015 | Petrukhin et al. |
| 2016/0024007 | A1 | 1/2016 | Petrukhin et al. |
| 2016/0030422 | A1 | 2/2016 | Petrukhin et al. |
| 2016/0046632 | A1 | 2/2016 | Petrukhin et al. |
| 2016/0046648 | A1 | 2/2016 | Petrukhin et al. |
| 2016/0046649 | A1 | 2/2016 | Petrukhin et al. |
| 2016/0287607 | A1 | 10/2016 | Petrukhin et al. |
| 2016/0368925 | A1 | 12/2016 | Petrukhin et al. |

FOREIGN PATENT DOCUMENTS

| | | |
|---|---|---|
| JP | 2006-0770063 | 3/2006 |
| JP | 2006-176503 | 7/2006 |
| WO | WO 97/17954 | 5/1997 |
| WO | WO 97/38665 | 10/1997 |
| WO | WO 98/39000 | 9/1998 |
| WO | WO 99/37304 | 7/1999 |
| WO | WO 99/65867 | 12/1999 |
| WO | WO 00/021557 | 4/2000 |
| WO | WO 00/42852 | 7/2000 |
| WO | WO 00/061606 | 10/2000 |
| WO | WO 01/07436 | 2/2001 |
| WO | WO 2011/059881 A1 | 5/2001 |
| WO | WO 01/66114 A1 | 9/2001 |
| WO | WO 01/87921 A2 | 11/2001 |
| WO | WO 02/05819 A1 | 1/2002 |
| WO | WO 02/088097 A1 | 11/2002 |
| WO | WO 03/024450 A1 | 3/2003 |
| WO | WO 03/024456 A1 | 3/2003 |
| WO | WO 03/032914 A2 | 4/2003 |
| WO | WO 2003/066581 A1 | 8/2003 |
| WO | WO 03/076400 A1 | 9/2003 |
| WO | WO 2004/002531 A1 | 1/2004 |
| WO | WO 2004/010942 A2 | 2/2004 |
| WO | WO 2004/014374 A1 | 2/2004 |
| WO | WO 2004/017950 A1 | 3/2004 |
| WO | WO 2004/034963 A2 | 4/2004 |
| WO | WO 2004/089416 A1 | 10/2004 |
| WO | WO 2005/074535 A3 | 8/2005 |
| WO | WO 2005/087226 A1 | 9/2005 |
| WO | WO 2005/116009 | 12/2005 |
| WO | WO 2006/003030 A1 | 1/2006 |
| WO | WO 2006/004201 | 1/2006 |
| WO | WO 2006/034441 A1 | 3/2006 |
| WO | WO 2006/034446 A1 | 3/2006 |
| WO | WO 2006/049880 A1 | 5/2006 |
| WO | WO 2006/065479 A2 | 6/2006 |
| WO | WO 2006/085108 A1 | 8/2006 |
| WO | WO 03/092606 A2 | 11/2006 |
| WO | WO 2006/138657 A1 | 12/2006 |
| WO | WO 2007/020888 A1 | 2/2007 |
| WO | WO 2007/027532 A2 | 3/2007 |
| WO | WO 2007/037187 A1 | 4/2007 |
| WO | WO 2007/073432 A2 | 6/2007 |
| WO | WO 2007/086584 A1 | 8/2007 |
| WO | WO 2008/045393 A2 | 4/2008 |
| WO | WO 2008080455 A1 | 7/2008 |
| WO | WO 2008/157791 A2 | 12/2008 |
| WO | WO 2009/023179 A2 | 2/2009 |
| WO | WO 2009/042444 A2 | 4/2009 |
| WO | WO 2009/051244 | 4/2009 |
| WO | WO 2010/077915 A1 | 7/2010 |
| WO | WO 2010/088050 A2 | 8/2010 |
| WO | WO 2010/091409 A1 | 8/2010 |
| WO | WO 2010/108268 A1 | 9/2010 |
| WO | WO 2010/119992 A1 | 10/2010 |
| WO | WO 2010/120741 A1 | 10/2010 |
| WO | WO 2010/138487 A1 | 12/2010 |
| WO | WO 2011/033255 | 3/2011 |
| WO | WO 2011/116123 A1 | 9/2011 |
| WO | WO 2011/156632 A2 | 12/2011 |
| WO | WO 2012/025164 A1 | 3/2012 |
| WO | WO 2012/071369 A2 | 5/2012 |
| WO | WO 2012/125904 A1 | 9/2012 |
| WO | WO 2012/158844 A1 | 11/2012 |
| WO | WO 2007/044804 A2 | 11/2013 |
| WO | WO 2013/166037 A1 | 11/2013 |
| WO | WO 2013/166040 A1 | 11/2013 |

(56) References Cited

FOREIGN PATENT DOCUMENTS

| WO | WO 2013/166041 A1 | 11/2013 |
|---|---|---|
| WO | WO 2014/133182 A1 | 9/2014 |
| WO | WO 2014/151936 A1 | 9/2014 |
| WO | WO 2014/151959 A1 | 9/2014 |
| WO | WO/2014/152013 A1 | 9/2014 |
| WO | WO 2014/152018 A1 | 9/2014 |
| WO | WO 2014/160409 A1 | 10/2014 |
| WO | WO 2004/108135 A1 | 12/2014 |
| WO | WO 2015/168286 A1 | 11/2015 |

OTHER PUBLICATIONS

Communication Pursuant to Article 94(3) dated Oct. 17, 2017 in connection with European Patent Application No. 14769462.4.
Office Action dated Jun. 21, 2017 in connection with U.S. Appl. No. 15/457,821.
Office Action dated Jun. 6, 2017 in connection with European Patent Application No. 14769383.2.
Office Action dated Feb. 22, 2017 in connection with U.S. Appl. No. 14/775,546.
Office Action dated Jun. 2, 2017 in connection with U.S. Appl. No. 14/775,546.
Office Action dated Aug. 30, 2017 in connection with U.S. Appl. No. 14/775,546.
Final Office Action dated Sep. 14, 2017 in connection with U.S. Appl. No. 14/775,565.
Office Action dated Feb. 13, 2017 in connection with U.S. Appl. No. 15/254,966.
International Search Report in connection with PCT/US2011/061763 dated May 29, 2012.
International Preliminary Report on Patentability in connection with PCT/US2011/061763 dated May 29, 2012.
Written Opinion dated May 29, 2012 in connection with PCT/US2011/061763.
Notification of Transmittal of the International Search Report and the Written Opinion of the International Searching Authority, or the Declaration dated May 29, 2012 in counecLion with PCT/US2011/061763.
Office Action dated Apr. 10, 2014 in connection with U.S. Appl. No. 13/988,754.
Notice of Allowance dated Feb. 10, 2015 in connection with U.S. Appl. No. 13/988,754.
Extended European Search Report dated Aug. 19, 2014 in connection with European Patent Application No. 11842785.5.
Office Action (including English Language summary thereof prepared by Japanese agent) dated Sep. 29, 2015 in connection with Japanese Patent application No. 2013-541006.
International Search Report in connection with PCT/US2013/038908 dated Sep. 20, 2013.
International Preliminary Report on Patentability in connection with PCT/US2013/038908 dated Nov. 4, 2014.
Written Opinion dated Sep. 20, 2013 in connection with PCT/US2013/038908.
Notification of Transmittal of the International Search Report and the Written Opinion of the International Searching Authority, or the Declaration dated Sep. 20, 2013 in connection with PCT/US2013/038908.
International Search Report in connection with PCT/US2013/038905 dated Sep. 27, 2013.
International Preliminary Report on Patentability in connection with PCT/US2013/038905 dated Nov. 4, 2014.
Written Opinion dated Sep. 24, 2013 in connection with PCT/US2013/038905.
International Search Report in connection with PCT/US2013/038910 dated Sep. 24, 2013.
International Preliminary Report on Patentability in connection with PCT/US2013/038910 dated Nov. 4, 2014.
Written Opinion dated Sep. 24, 2013 in connection with PCT/US2013/038910.
Notification of Transmittal of the International Search Report and the Written Opinion of the International Searching Authority, or the Declaration dated Sep. 24, 2013 in connection with PCT/US2013/038910.
International Search Report in connection with PCT/US2014/026813 dated Jul. 18, 2014.
International Preliminary Report on Patentability in connection with PCT/US2014/026813 dated Sep. 15, 2015.
Written Opinion of the International Searching Authority dated Jul. 18, 2014 in connection with PCT/US2014/026813.
Notification of Transmittal of the International Search Report and the Written Opinion of the International Searching Authority, or the Declaration dated Jul. 18, 2014 in connection with PCT/US2014/026813.
International Search Report in connection with PCT/US2014/026523 dated Aug. 22, 2014.
International Preliminary Report on Patentability in connection with PCT/US2014/026523 dated Sep. 15, 2015.
Written Opinion dated Aug. 22, 2014 in connection with PCT/US2014/026523.
Notification of Transmittal of the International Search Report and the Written Opinion of the International Searching Authority, or the Declaration dated Aug. 22, 2014 in connection with PCT/US2014/026523.
International Search Report in connection with PCT/US2014/026818 dated Jul. 18, 2014.
International Preliminary Report on Patentability in connection with PCT/US2014/026818 dated Sep. 15, 2015.
Written Opinion dated Jul. 18, 2014 in connection with PCT/US2014/026818.
Notification of Transmittal of the International Search Report and the Written Opinion of the International Searching Authority, or the Declaration dated Jul. 18, 2014 in connection with PCT/US2014/026818.
International Search Report in connection with PCT/US2014/026730 dated Jul. 21, 2014.
International Preliminary Report on Patentability in connection with PCT/US2014/026730 dated Sep. 15, 2015.
Written Opinion dated Jul. 21, 2014 in connection with PCT/US2014/026730.
Notification of Transmittal of the International Search Report and the Written Opinion of the International Searching Authority, or the Declaration dated Jul. 21, 2014 in connection with PCT/US2014/026730.
International Search Report in connection with PCT/US2014/026699 dated Jul. 18, 2014.
International Preliminary Report on Patentability in connection with PCT/US2014/026699 dated Sep. 15, 2015.
Written Opinion of the International Searching Authority in connection with PCT/US2014/026699 dated Jul. 18, 2014.
Notification of Transmittal of the International Search Report and the Written Opinion of the International Searching Authority, or the Declaration dated Jul. 18, 2014 in connection with PCT/US2014/026699.
International Search Report in connection with PCT/US2015/028293 dated Jul. 10, 2015.
Written Opinion dated Jul. 10, 2015 in connection with PCT/US2015/028293.
Notification of Transmittal of the International Search Report and the Written Opinion of the International Searching Authority, or the Declaration dated May 11, 2015 in connection with PCT/US2015/028293.
Petrukhin (2007) New therapeutic targets in atrophic age-related macular degeneration. Expert Opin Ther Targets. 11(5):625-639; p. 629.
Sparrow, et al. (2010) Phospholipid meets all-trans-retinal: the making of RPE bisretinoids. Lipid Res 51(2): 247-261.
Elenewski, et al (2010) Free energy landscape of the retinol/serum retinol binding protein complex: a biological host-guest system. J Phys Chem B 02, 114(34):11315-11322.

(56) References Cited

OTHER PUBLICATIONS

Sharif et al (2009) Time-resolved fluorescence resonance energy transfer and surface plasmon resonance-based assays for retinoid and transthyretin binding to retinol-binding protein 4. Anal Biochem, 392(2):162-168.
Bourgault, S. et al. (2011) Mechanisms of transthyretin cardiomyocyte toxicity inhibition by resveratrol analogs.Biochem Biophys Res Commun.410(4):707-13.
Wu et al (2009) Novel Lipofuscin bisretinoids prominent in human retina and in a model of recessive Stragardt disease. J. Biol. Chem. 284(30) 20155-20166.
Sparrow, et al. (2010) Interpretations of Fundus Autofluorescence from Studies of the Bisretinoids of the Retina. Invest. Ophthalmol. Vis. Sci. vol. 51 No. 9 4351-4357.
Dobri et al (2013) A1120, a Nonretinoid RBP4 Antagonist, Inhibits Formation of Cytotoxic Bisretinoids in the Animal Model of Enhanced Retinal Lipofuscinogenesis. Investigative Ophthalmology & Visual Science, 54, 1, 85.
Nov. 8, 2010 CAS Search Report.
Feb. 24, 2013 CAS Search Report.
Mar. 5, 2013 CAS Search Report.
Dec. 9, 2014 CAS Search Report.
Office Action dated Dec. 10, 2015 in connection with U.S. Appl. No. 14/530,516.
Notification of Transmittal of the International Search Report and the Written Opinion of the International Searching Authority, or the Declaration dated Sep. 27, 2013 in connection with PCT/US2013/038905.
Motani, et al. (2009) Identification and Characterization of a Non-retinoid Ligand for Retinol-binding Protein 4 Which Lowers Serum Retinol-binding Protein 4 Levels in Vivo. Journal of Biological Chemistry, 284(12):7673-7680.
Petrukhin, K. et al. (1998) Identification of the gene responsible for Best macular dystrophy. Nature Genetics, 19, 241-247.
Cioffi, C. et al. (2014) Design, Synthesis, and Evaluation of Nonretinoid Retinol Binding Protein 4 Antagonists for the Potential Treatment of Atrophic Age-Related Macular Degeneration and Stargardt Disease. J. Med. Chem. 57, 18, 7731-7757.
Cioffi, C. et al. (2015) Bicyclic [3.3.0]-Octahydrocyclopenta[c]pyrrolo Antagonists of Retinol Binding Protein 4: Potential Treatment of Atrophic Age-Related Macular Degeneration and Stargardt Disease. J. Med. Chem. 58, 15, 5863-5888.
Office Action dated Jul. 5, 2016 in connection with U.S. Appl. No. 14/530,516.
Office Action dated Jun. 27, 2016 in connection with U.S. Appl. No. 14/775,532.
Office Action dated Sep. 23, 2016 in connection with U.S. Appl. No. 14/775,532.
Office Action dated Mar. 23, 2016 in connection with U.S. Appl. No. 14/775,552.
Office Action dated Sep. 8, 2016 in connection with U.S. Appl. No. 14/775,540.
Office Action dated Mar. 18, 2016 in connection with U.S. Appl. No. 14/775,546.
Office Action dated Aug. 9, 2016 in connection with U.S. Appl. No. 14/775,546.
Office Action dated Nov. 25, 2015 in connection with U.S. Appl. No. 14/699,672.
Amendment filed Mar. 25, 2016 in connection with U.S. Appl. No. 14/699,672.
Notice of Allowance dated May 12, 2016 in connection with U.S. Appl. No. 14/699,672.
Office Action dated Sep. 28, 2016 in connection with U.S. Appl. No. 14/775,552.
Office Action dated Oct. 31, 2016 in connection with U.S. Appl. No. 15/093,179.
Office Action dated Dec. 2, 2016 in connection with U.S. Appl. No. 14/530,516.
Office Action dated Dec. 2, 2016 in connection with U.S. Appl. No. 14/775,565.
European Search Report dated Sep. 23, 2016 in connection with European Patent Application No. 14769383.2.
International Preliminary Report on Patentability in connection with PCT/US2015/028293 dated Nov. 1, 2016.
JP 59-036670 A, published Feb. 28, 1984 (GOTO).
Bonilha, V. (2008) Age and Disease-Related Structural Changes in the Retinal Pigment Epithelium. Clinical Ophthalmology: 2(2) 413-424.
STN-Chemical database registry # 1179485-09 for Methanone, [4-(4-chlorophenyl)-4-hydroxy-1-piperidinyl] (5,6,7,8-tetrahydro-4H- cyclohept[d]isoxazol-3-yl). Sep. 2, 2009.
Wakefield, B.1 "Fluorinated Pharmaceuticals" Innovations in Pharmaceutical Technology 2003, 74, 76-78.
Princeton Biomolecular Research Inc.: "http://web.archive.org/web/20100930184751/http://www.princetonbio.com/pages4.html", accessed Apr. 30, 2015.
Communication Pursuant to Article 94(3) dated Apr. 11, 2017 in connection with European Patent Application No. 11842785.5.
Final Office Action dated Apr. 13, 2017 in connection with U.S. Appl. No. 14/775,532.
European Search Report dated Jul. 11, 2016 in connection with European Patent Application No. 14769462.4.
Communication Pursuant to Article 94(3) dated Mar. 29, 2017 in connection with European Patent Application No. European Patent Application No. 14769462.4.
Office Action dated Mar. 22, 2017 in connection with U.S. Appl. No. 14/775,565.
Japanese Application Publication No. JP 2012/184205 A, published Sep. 27, 2012 (Dainippon Sumitomo Pharma Co.), including English language abstract.
Wang, Y. et al. (2014) Structure-assisted discovery of the first non-retinoid ligands for Retinol-Binding Protein 4. Bioorganic & Medicinal Chemistry Letters. 24, 2885-2891.
Yingcai Wang et al. (2011) Structure-Assisted Discovery of Non-Retinoid Ligands for Retinol-Binding Protein 4. Poster presented at 2011 conference.
Jones, N. (1997) Organic Chemistry. p. 84-99.
Lachance et al (2012) Bioorganic & Medicinal Chemistry Letters. 22(2), 980-984.
Feb. 13, 2017 Office Action issued in connection with U.S. Appl. No. 15/254,966.
Amendment in Response to Feb. 13, 2017 Office Action submitted May 15, 2017 in connection with U.S. Appl. No. 15/254,966.
May 26, 2017 Notice of Allowance issued in connection with U.S. Appl. No. 15/254,966.

* cited by examiner

SUBSTITUTED 4-PHENYLPIPERIDINES, THEIR PREPARATION AND USE

This application is a continuation of U.S. Ser. No. 15/254,966, filed Sep. 1, 2016, now allowed, which is a continuation of U.S. Ser. No. 14/699,672, filed Apr. 29, 2015, now U.S. Pat. No. 9,434,727, issued Sep. 6, 2016, claiming the benefit of U.S. Provisional Application No. 61/986,578, filed Apr. 30, 2014, the contents of each of which are hereby incorporated by reference in its entirety into this application.

The invention was made with government support under Grant numbers NS067594 and NS074476 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Age-related macular degeneration (AMD) is the leading cause of blindness in developed countries. It is estimated that 62.9 million individuals worldwide have the most prevalent atrophic (dry) form of AMD; 8 million of them are Americans. Due to increasing life expectancy and current demographics this number is expected to triple by 2020. There is currently no FDA-approved treatment for dry AMD. Given the lack of treatment and high prevalence, development of drugs for dry AMD is of upmost importance. Clinically, atrophic AMD represents a slowly progressing neurodegenerative disorder in which specialized neurons (rod and cone photoreceptors) die in the central part of the retina called macula (1). Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD (2-9). In addition to AMD, dramatic accumulation of lipofuscin is the hallmark of Stargardt Disease (STGD), an inherited form of juvenile-onset macular degeneration. The major cytotoxic component of RPE lipofuscin is pyridinium bisretinoid A2E (FIG. 1). Additional cytotoxic bisretinoids are isoA2E, atRAL di-PE, and A2-DHP-PE (40, 41). Formation of A2E and other lipofuscin bisretinoids, such as A2-DHP-PE (A2-dihydro-pyridine-phosphatidylethanolamine) and atRALdi-PE (all-trans-retinal dimer-phosphatidylethanolamine), begins in photoreceptor cells in a non-enzymatic manner and can be considered as a by-product of the properly functioning visual cycle.

A2E is a product of condensation of all-trans retinaldehyde with phosphatidyl-ethanolamine which occurs in the retina in a non-enzymatic manner and, as illustrated in FIG. 4, can be considered a by-product of a properly functioning visual cycle (10). Light-induced isomerization of 11-cis retinaldehyde to its all-trans form is the first step in a signaling cascade that mediates light perception. The visual cycle is a chain of biochemical reactions that regenerate visual pigment (11-cis retinaldehyde conjugated to opsin) following exposure to light.

As cytotoxic bisretinoids are formed during the course of a normally functioning visual cycle, partial pharmacological inhibition of the visual cycle may represent a treatment strategy for dry AMD and other disorders characterized by excessive accumulation of lipofuscin (25-27, 40, 41).

SUMMARY OF THE INVENTION

The present invention provides a compound having the structure:

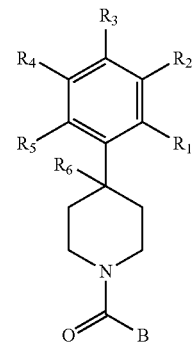

wherein
$R_1$, $R_2$, $R_3$, $R_4$, and $R_5$ are each independently H, halogen, $CF_3$ or $C_1$-$C_4$ alkyl,
  wherein two or more of $R_1$, $R_2$, $R_3$, $R_4$, or $R_5$ are other than H;
$R_6$ is H, OH, or halogen; and
B is a substituted or unsubstituted heterobicycle,
wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

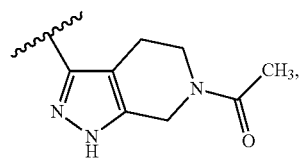 [SMILES: *c1n[nH]c2c1CCN(C(C)=O)C2]

or a pharmaceutically acceptable salt thereof.

DETAILED DESCRIPTION OF THE INVENTION

Figure 1:
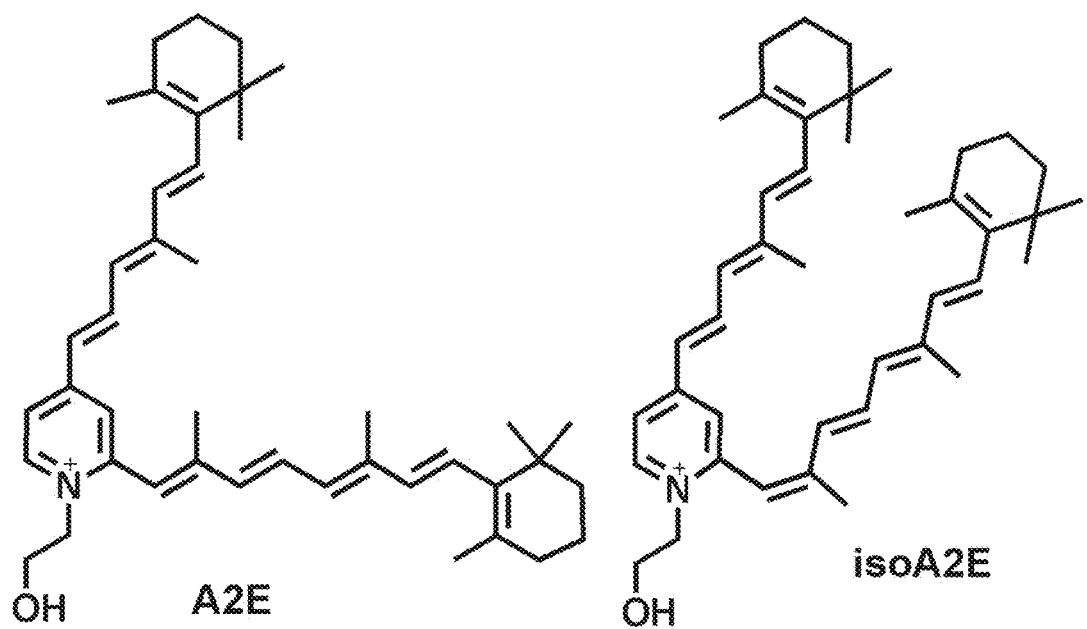
FIG. 1. Structure of bisretinoid A2E, a cytotoxic component of retinal lipofuscin.

The present invention provides a compound having the structure:

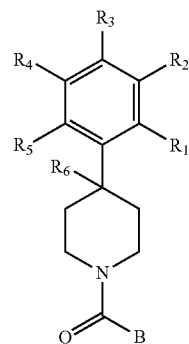

wherein $R_1$, $R_2$, $R_3$, $R_4$, and $R_5$ are each independently H, halogen, $CF_3$ or $C_1$-$C_4$ alkyl,
  wherein two or more of $R_1$, $R_2$, $R_3$, $R_4$, or $R_5$ are other than H;
$R_6$ is H, OH, or halogen; and
B is a substituted or unsubstituted heterobicycle,
  wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

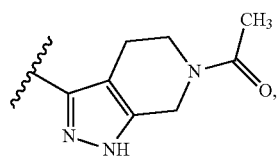 [SMILES: *c1n[nH]c2c1CCN(C(C)=O)C2]

or a pharmaceutically acceptable salt thereof.

The present invention also provides a compound having the structure:

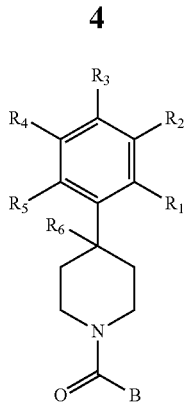

wherein $R_1$, $R_2$, $R_3$, $R_4$, and $R_5$ are each independently H, halogen, $CF_3$ or $C_1$-$C_4$ alkyl,
  wherein two or more of $R_1$, $R_2$, $R_3$, $R_4$, or $R_5$ are other than H;
$R_6$ is H, OH, or halogen; and
B is a substituted or unsubstituted heterobicycle,
  wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

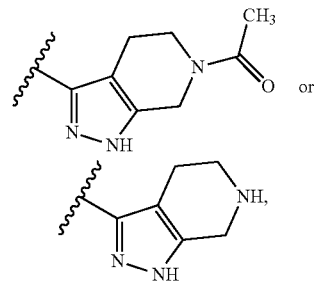

or a pharmaceutically acceptable salt thereof.

In some embodiment, the compound
wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, then B is other than

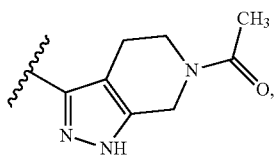 [SMILES: *c1n[nH]c2c1CCN(C(C)=O)C2]

In some embodiment, the compound
wherein when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

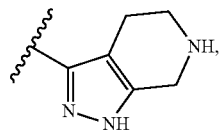 [SMILES: *c1n[nH]c2c1CCNC2]

or a pharmaceutically acceptable salt thereof.

In some embodiment, the compound having the structure:

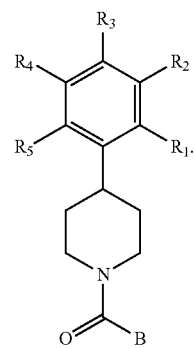

In some embodiment, the compound wherein $R_1$, $R_2$, $R_3$, $R_4$, $R_5$ and $R_6$ are each independently H, Cl, F, or $CF_3$.

In some embodiment, the compound wherein
$R_1$ is $CF_3$, $R_2$ is F, $R_3$ is F, $R_4$ is H, and $R_5$ is H, or
$R_1$ is $CF_3$, $R_2$ is F, $R_3$ is H, $R_4$ is H, and $R_5$ is H, or
$R_1$ is $CF_3$, $R_2$ is F, $R_3$ is H, $R_4$ is F, and $R_5$ is H, or
$R_1$ is $CF_3$, $R_2$ is H, $R_3$ is F, $R_4$ is F, and $R_5$ is H, or
$R_1$ is $CF_3$, $R_2$ is H, $R_3$ is H, $R_4$ is H, and $R_5$ is F, or
$R_1$ is $CF_3$, $R_2$ is H, $R_3$ is F, $R_4$ is H, and $R_5$ is H, or
$R_1$ is $CF_3$, $R_2$ is H, $R_3$ is H, $R_4$ is Cl, and $R_5$ is H, or
$R_1$ is $CF_3$, $R_2$ is Cl, $R_3$ is H, $R_4$ is H, and $R_5$ is H, or
$R_1$ is H, $R_2$ is $CF_3$, $R_3$ is H, $R_4$ is $CF_3$, and $R_5$ is H, or
$R_1$ is Cl, $R_2$ is H, $R_3$ is H, $R_4$ is F, and $R_5$ is H, or
$R_1$ is Cl, $R_2$ is F, $R_3$ is H, $R_4$ is H, and $R_5$ is H.

In some embodiment, the compound wherein B has the structure:

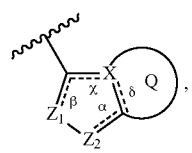

wherein
α, β, χ, and δ are each independently absent or present, and when present each is a bond;
X is C or N;
$Z_1$ is N;
$Z_2$ is N or $NR_7$,
    wherein $R_7$ is H, $C_1$-$C_4$ alkyl, or oxetane;
Q is a substituted or unsubstituted 5, 6, or 7 membered ring structure.

In some embodiment, the compound wherein B has the structure:

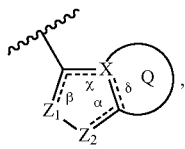

wherein
when α is present, then $Z_1$ and $Z_2$ are N, X is N, β is present, and χ and δ are absent; and
when α is absent, then $Z_1$ is N, $Z_2$ is N—$R_7$, X is C, β and δ are present, and χ is absent.

In some embodiment, the compound wherein B has the structure:

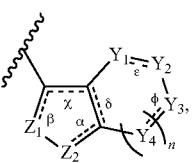

wherein
n is an integer from 0-2;
α, β, χ, δ, ε, and φ are each independently absent or present, and when present each is a bond;
$Z_1$ is N;
$Z_2$ is N or N—$R_7$,
    wherein $R_7$ is H, $C_1$-$C_{10}$ alkyl, or oxetane;
X is C or N; and
$Y_1$, $Y_2$, $Y_3$, and each occurrence of $Y_4$ are each independently $CR_8$, $CH_2$, or N—$R_9$,
wherein
$R_8$ is H, halogen, $OCH_3$, CN, or $CF_3$; and
$R_9$ is H, CN, oxetane, $C_1$-$C_6$ alkyl, $C_3$-$C_6$ cycloalkyl, ($C_1$-$C_4$ alkyl)($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), C(O)$_2$—($C_1$-$C_6$ alkyl), C(O)—$NH_2$C(O)NH—($C_1$-$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2$H, ($C_1$-$C_6$ alkyl)-$CO_2$($C_1$-$C_6$ alkyl) or $SO_2$—($C_1$-$C_6$ alkyl).

In some embodiment, the compound wherein B has the structure:

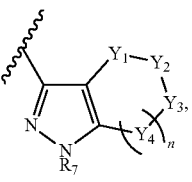

wherein
n is 0;
$R_7$ is H, $C_1$-$C_4$ alkyl, or oxetane;
$Y_1$ and $Y_3$ are each $CH_2$; and
$Y_2$ is N—$R_9$,
    wherein
    $R_9$ is H, CN, oxetane, $C_1$-$C_6$ alkyl, $C_3$-$C_6$ cycloalkyl, ($C_1$-$C_4$ alkyl)($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), C(O)$_2$—($C_1$-$C_6$ alkyl), C(O)—$NH_2$C(O)NH—($C_1$-

$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2H$, ($C_1$-$C_6$ alkyl)-$CO_2$ ($C_1$-$C_6$ alkyl) or $SO_2$—($C_1$-$C_6$ alkyl).

In some embodiment, the compound wherein B has the structure:

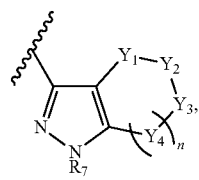

wherein
n is 1;
$R_7$ is H, $C_1$-$C_4$ alkyl, or oxetane;
$Y_1$, $Y_2$ and $Y_4$ are each $CH_2$; and
$Y_3$ is N—$R_9$,
  wherein
    $R_9$ is H, CN, oxetane, $C_1$-$C_6$ alkyl, $C_3$-$C_6$ cycloalkyl, ($C_1$-$C_4$ alkyl) ($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), $C(O)_2$—($C_1$-$C_6$ alkyl), C(O)—$NH_2C(O)NH$—($C_1$-$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2H$, ($C_1$-$C_6$ alkyl)-$CO_2$ ($C_1$-$C_6$ alkyl) or $SO_2$—($C_1$-$C_6$ alkyl).

In some embodiment, the compound wherein B has the structure:

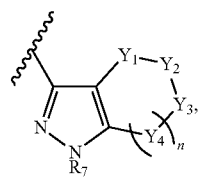

wherein
n is 1;
$R_7$ is H, $C_1$-$C_4$ alkyl, or oxetane;
$Y_1$, $Y_3$ and $Y_4$ are each $CH_2$; and
$Y_2$ is N—$R_9$,
  wherein
    $R_9$ is H, CN, oxetane, $C_1$-$C_6$ alkyl, $C_3$-$C_6$ cycloalkyl, ($C_1$-$C_4$ alkyl) ($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), $C(O)_2$—($C_1$-$C_6$ alkyl), C(O)—$NH_2C(O)NH$—($C_1$-$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2H$, ($C_1$-$C_6$ alkyl)-$CO_2$ ($C_1$-$C_6$ alkyl) or $SO_2$—($C_1$-$C_6$ alkyl).

In some embodiment, the compound wherein B has the structure:

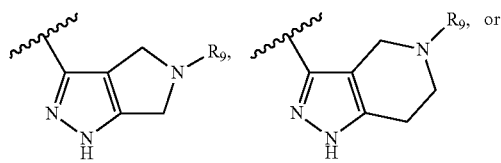

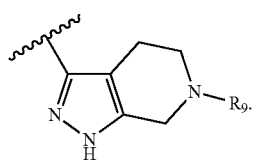

In some embodiment, the compound wherein
$R_9$ is H, CN, $CH_3$, $CH_2CH_3$, $CH_2CH_2CH_3$, $CH(CH_3)_2$, $CH_2CH(CH_3)_2$, t-Bu, $CH_2CH(CH_3)_2$, $CH_2C(CH_3)_3$, $CH_2CF_3$, $CH_2CH_2CF_3$, $CH_2OCH_3$, $CH_2CH_2OCH_3$,

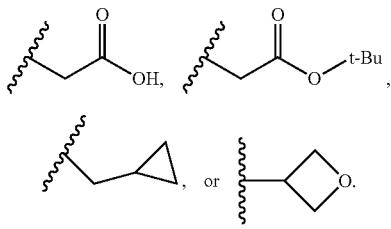

In some embodiment, the compound wherein
$R_9$ is $SO_2$—$CH_3$, C(O)—$CH_3$, C(O)—$CH_2CH_3$, C(O)—$CH_2CH_2CH_3$, C(O)—$CH(CH_3)_2$, C(O)—$CH_2CH(CH_3)_2$, C(O)-t-Bu, C(O)—$OCH_3$, C(O)—$NHCH_3$,

[structures of acyl groups: benzoyl, picolinoyl, nicotinoyl, isonicotinoyl, pyrrolidine-1-carbonyl, piperidine-1-carbonyl, or piperazine-1-carbonyl (NH)]

In some embodiment, the compound wherein
$R_7$ is H, $CH_3$, $CH_2CH_3$, $CH(CH_3)_2$, or

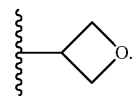

In some embodiment, the compound wherein B has the structure:

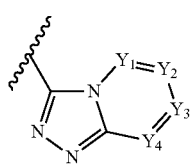
wherein
$Y_1$, $Y_2$, $Y_3$ and $Y_4$ are each independently $CR_8$ or N,
wherein each $R_8$ is independently H, halogen, $OCH_3$, CN, or $CF_3$.
In some embodiment, the compound wherein B has the structure:
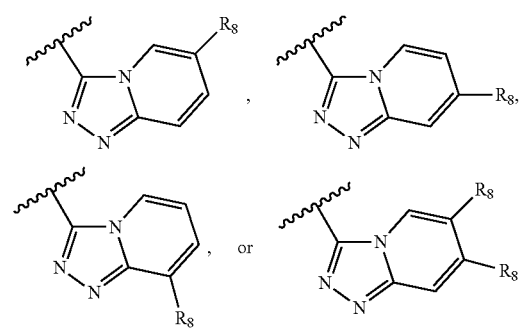
In some embodiment, the compound wherein each $R_8$ is CN or $OCH_3$.
In some embodiment, the compound having the structure:
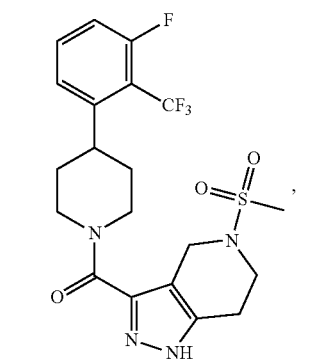
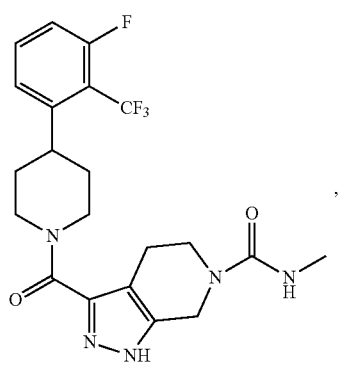
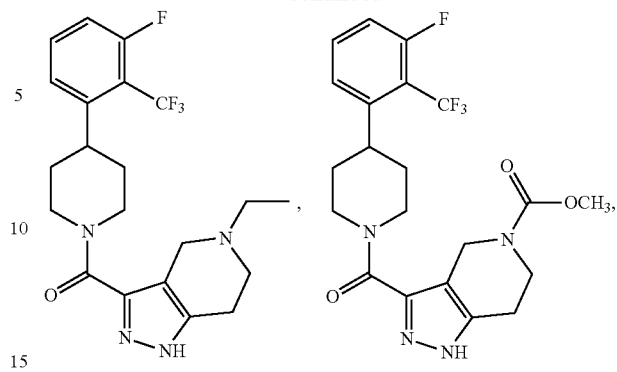
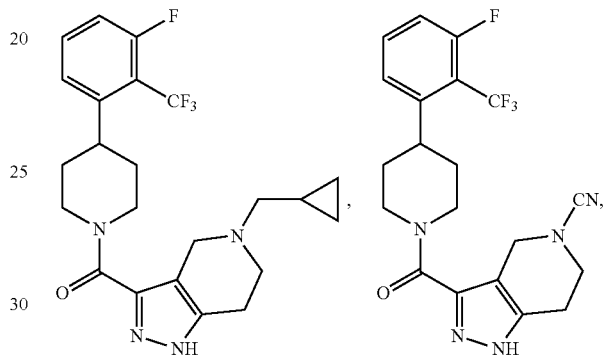
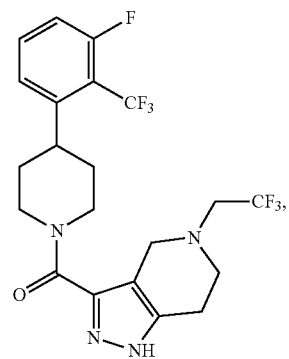
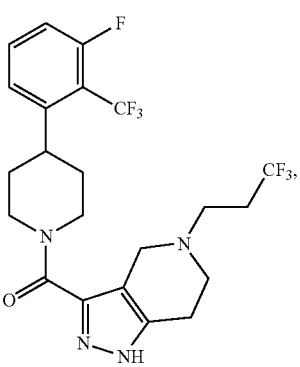

11
-continued
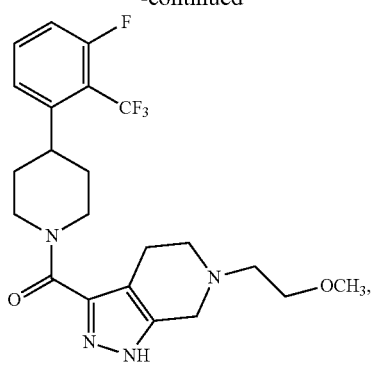
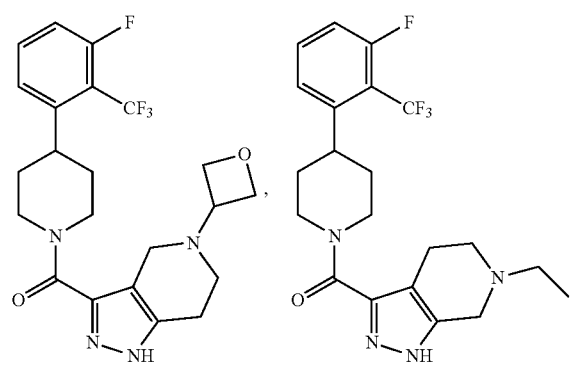
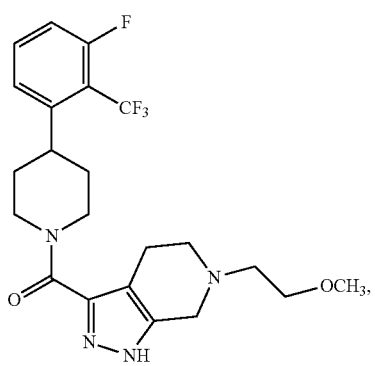
12
-continued
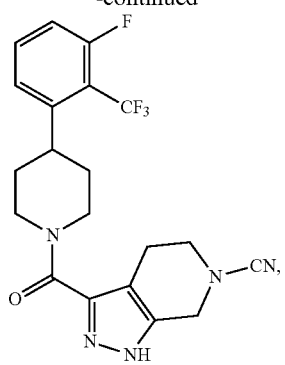
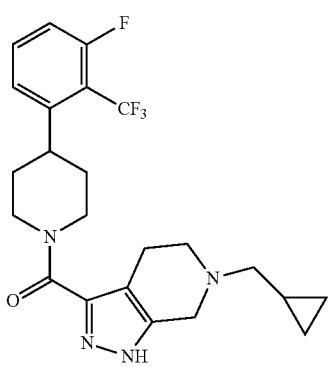
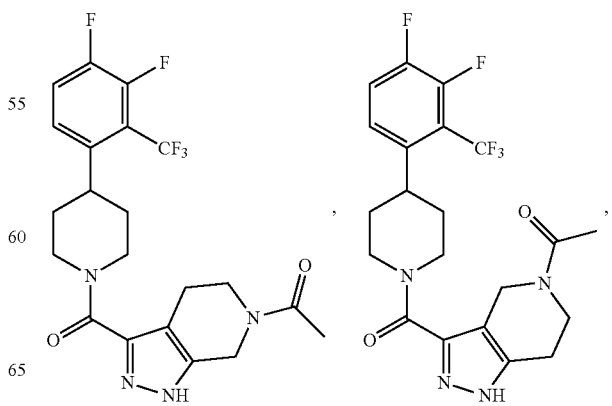

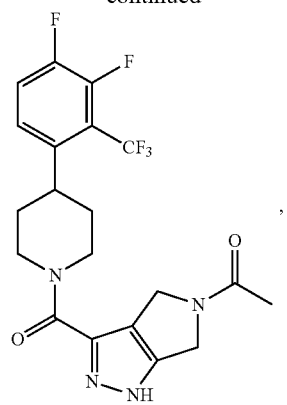
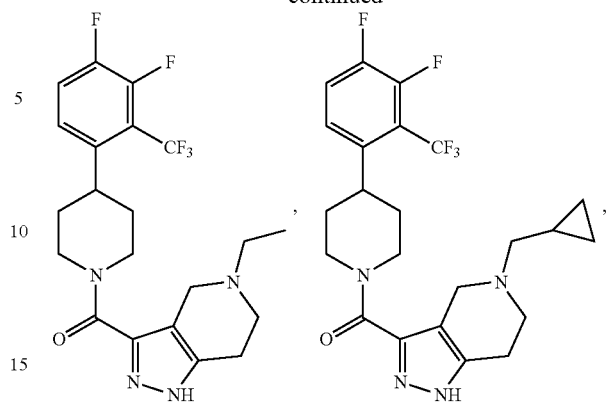
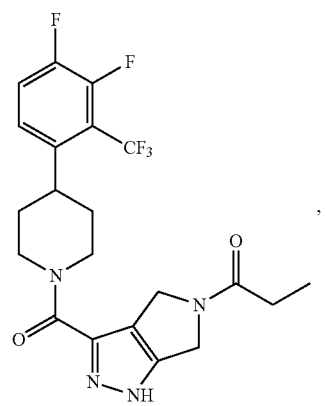
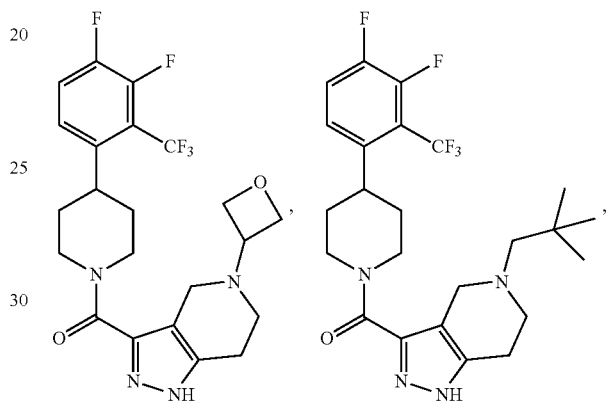
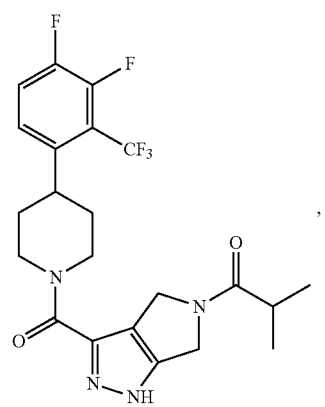
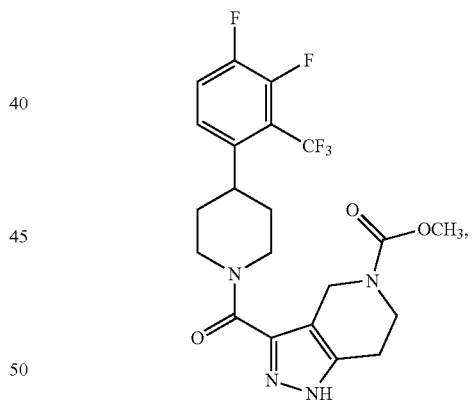
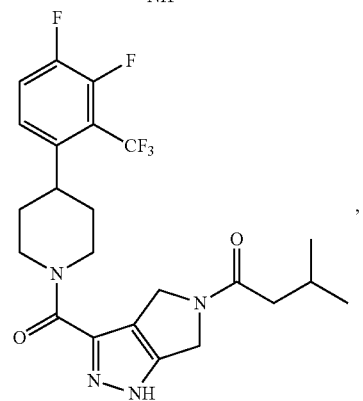
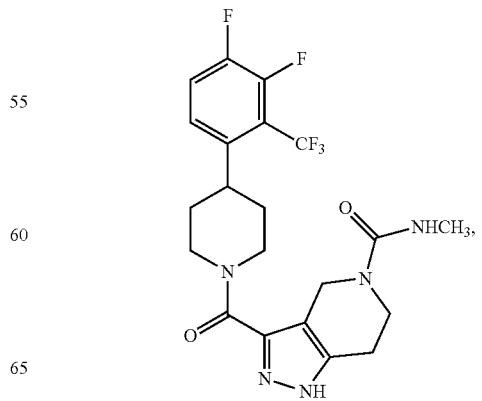

-continued
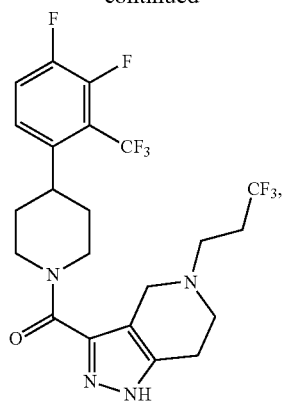
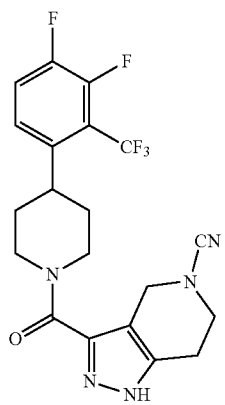
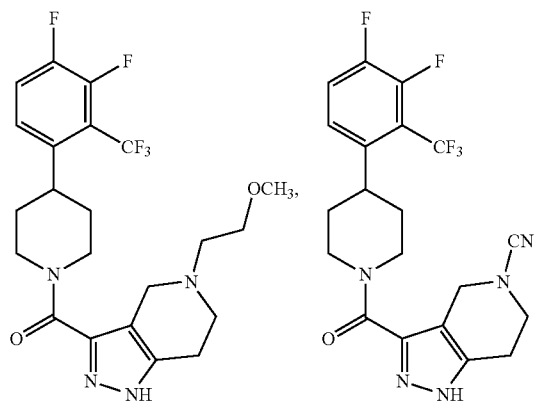
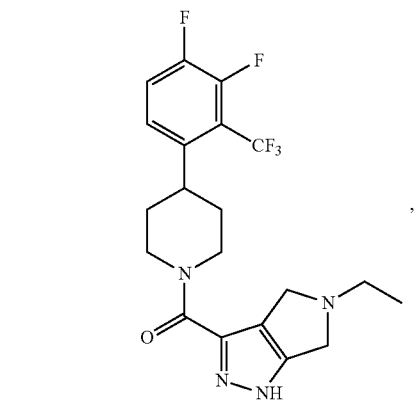
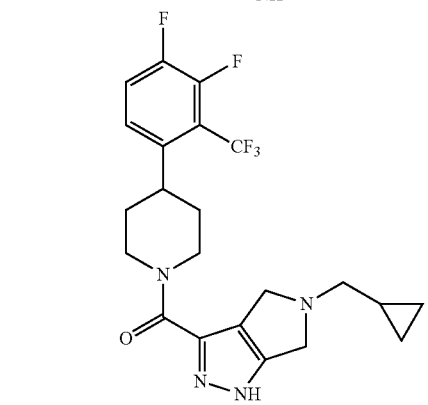
-continued
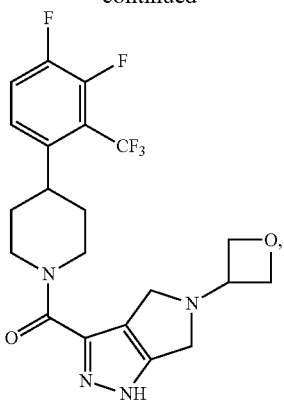
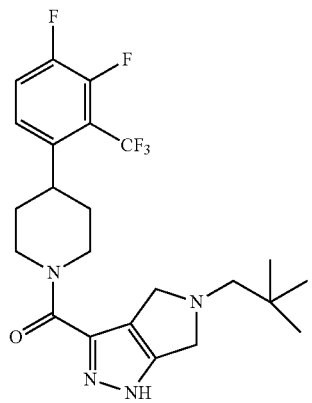
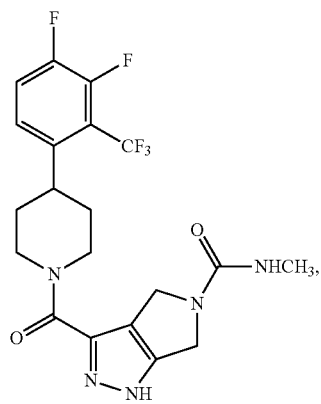
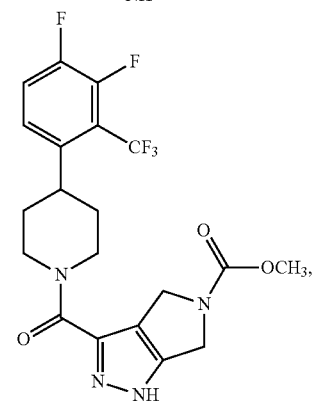

-continued
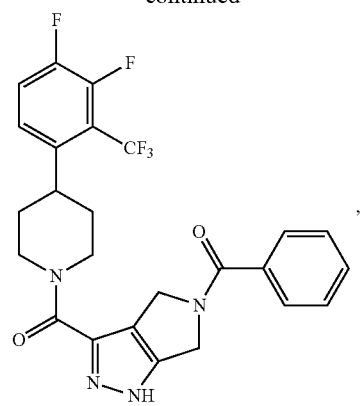
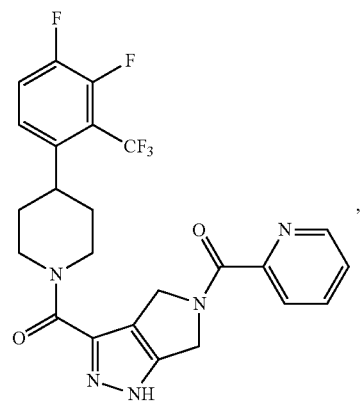
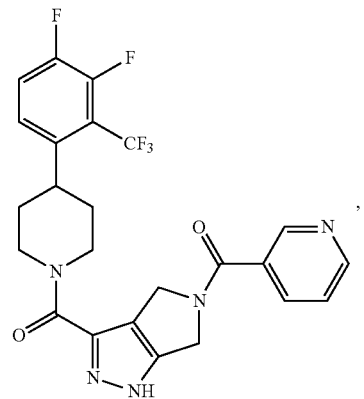
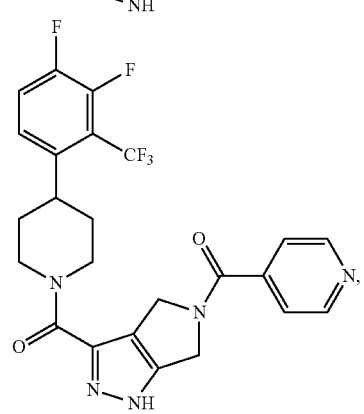
-continued
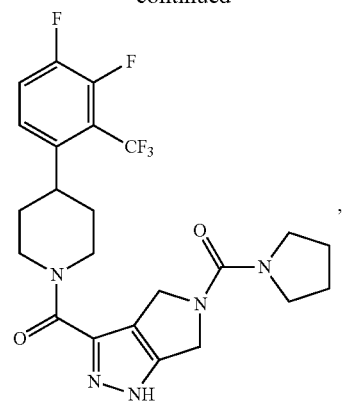
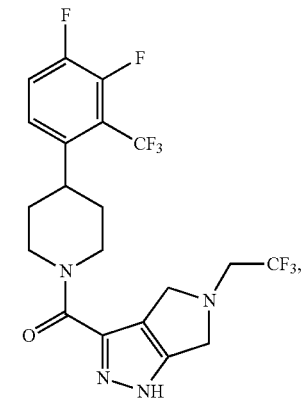
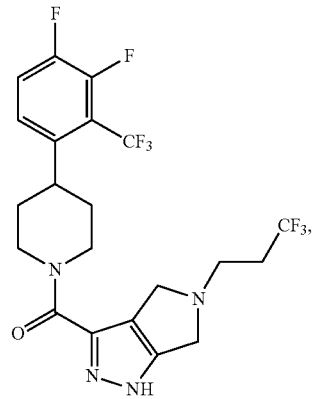
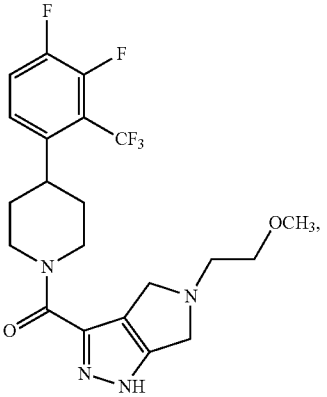

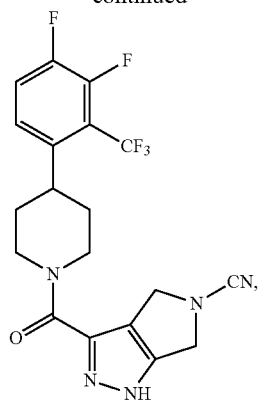
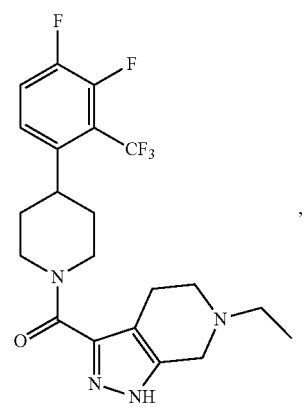
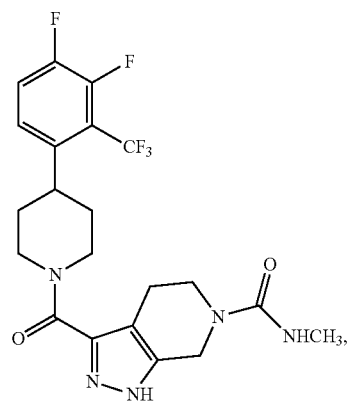
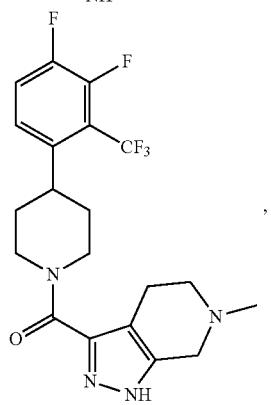
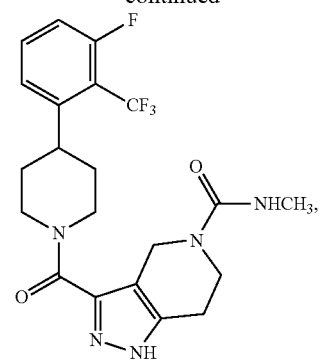
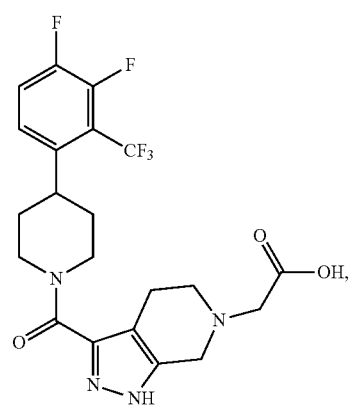
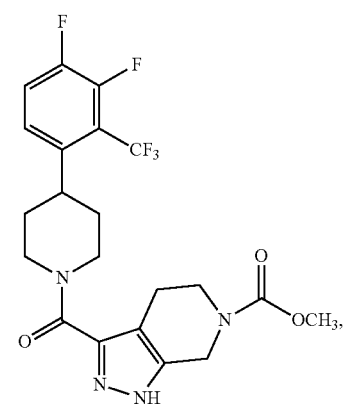
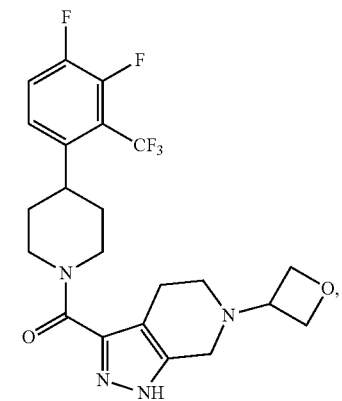

-continued
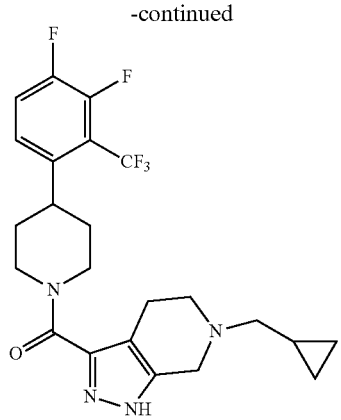
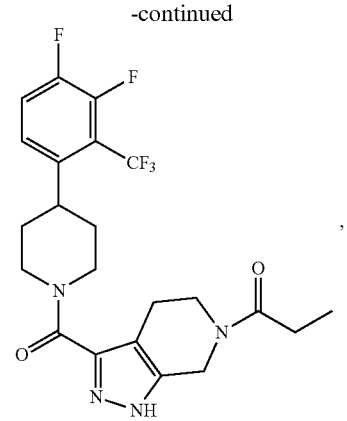
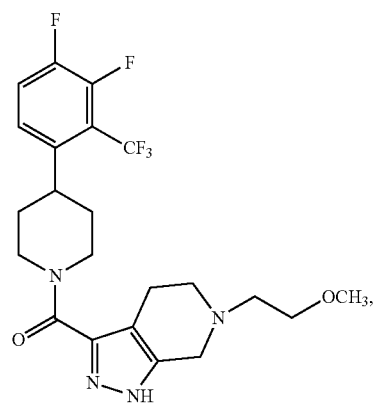
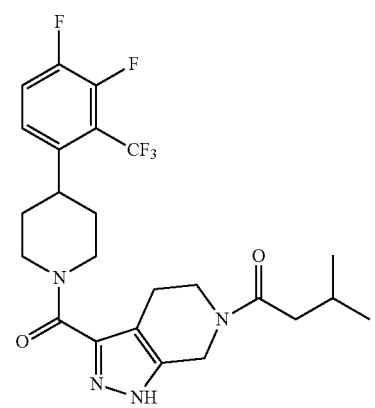
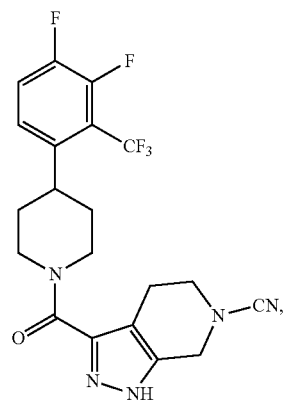
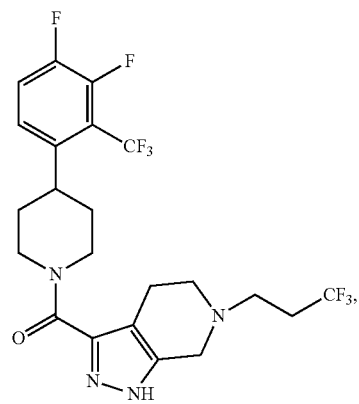
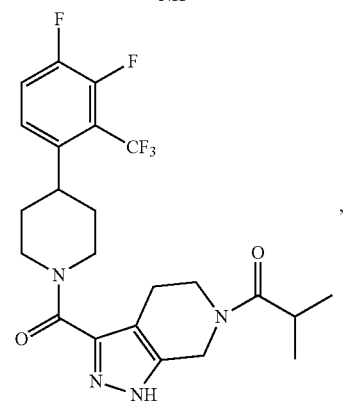
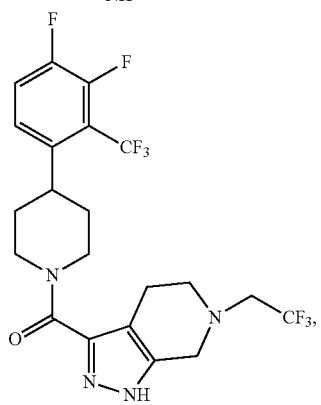

-continued
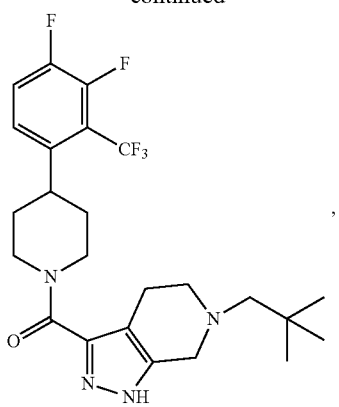
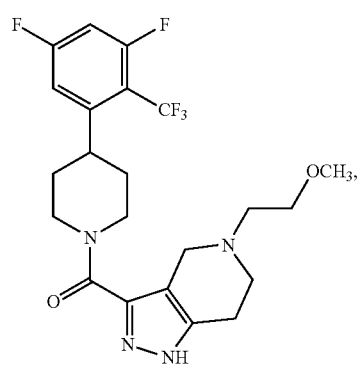
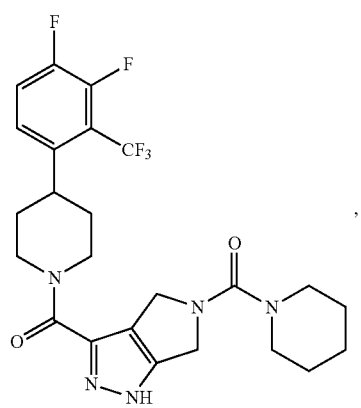
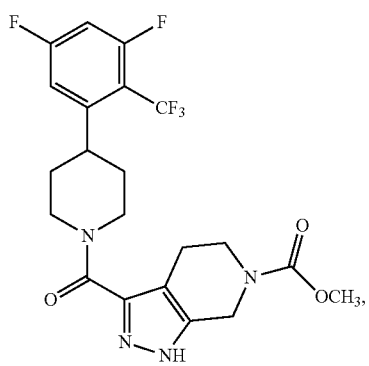
-continued
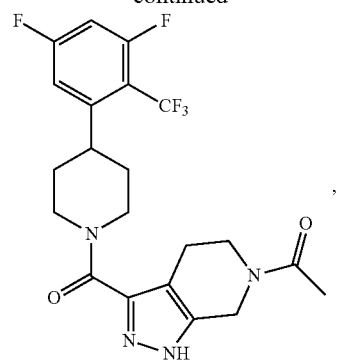
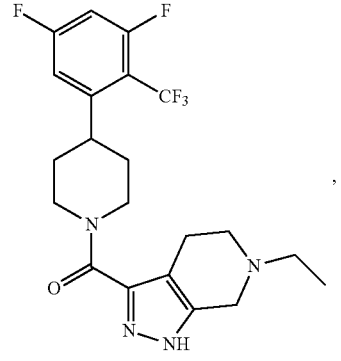
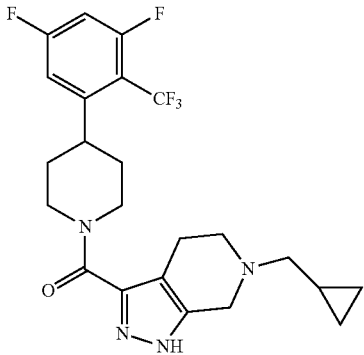
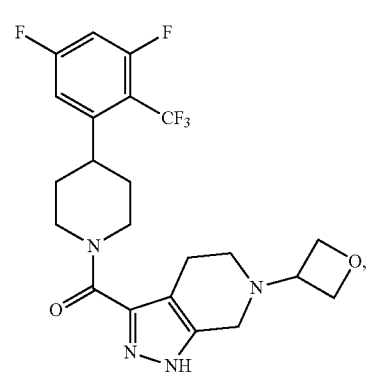

-continued
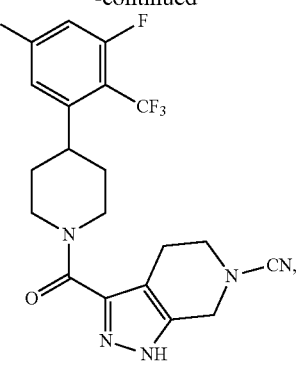
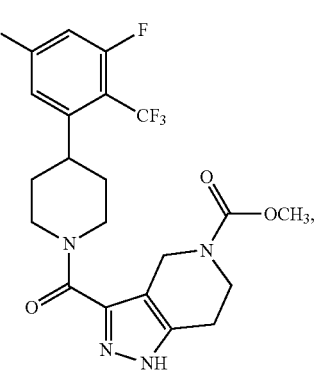
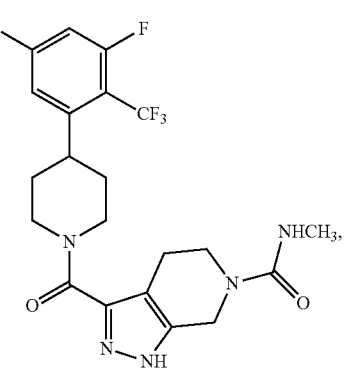
-continued
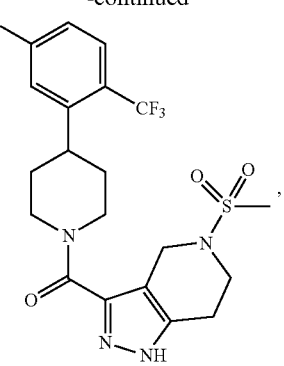
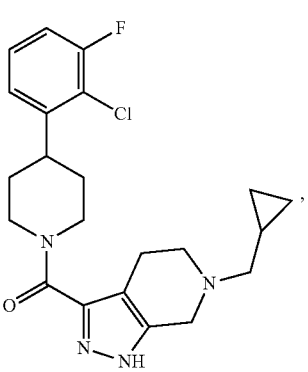
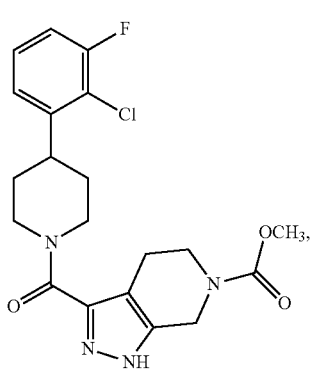

-continued
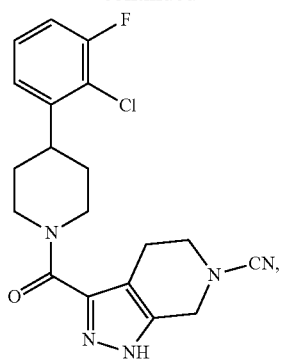
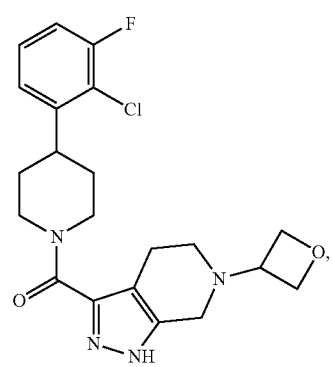
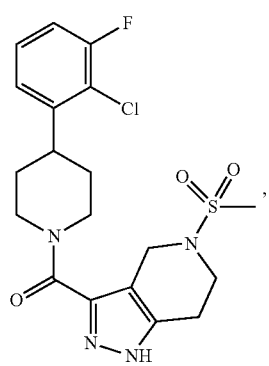
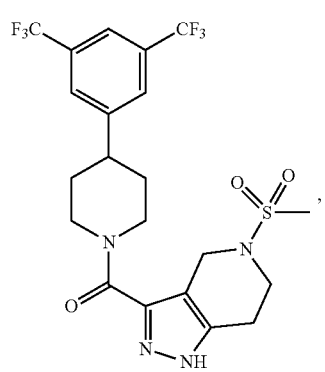
-continued
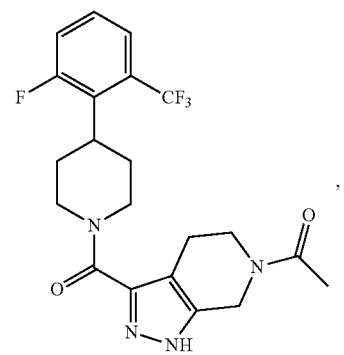
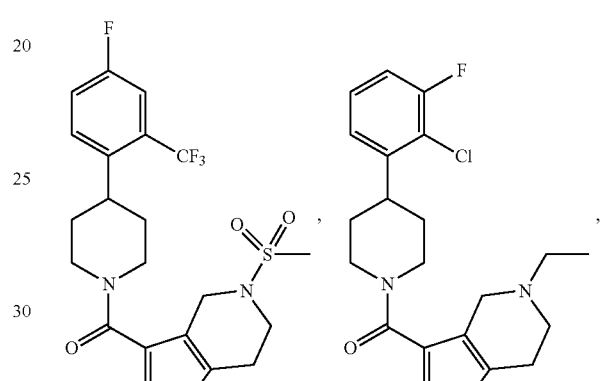
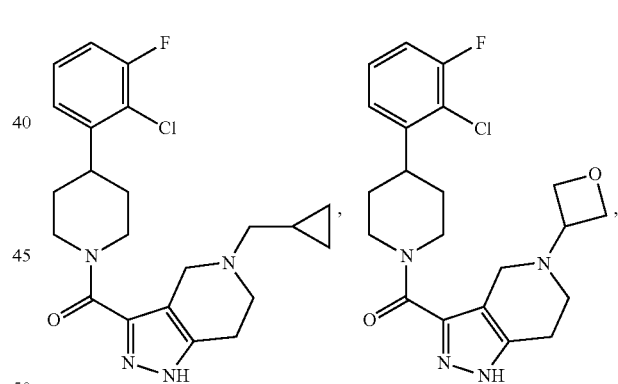
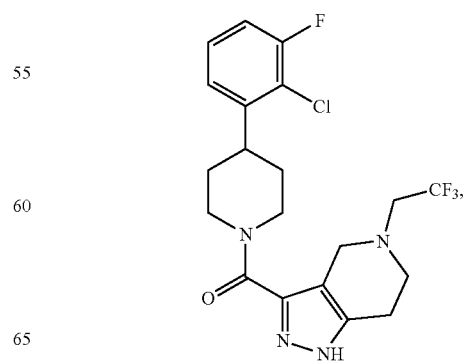

-continued
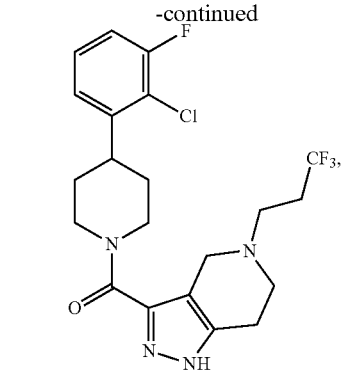
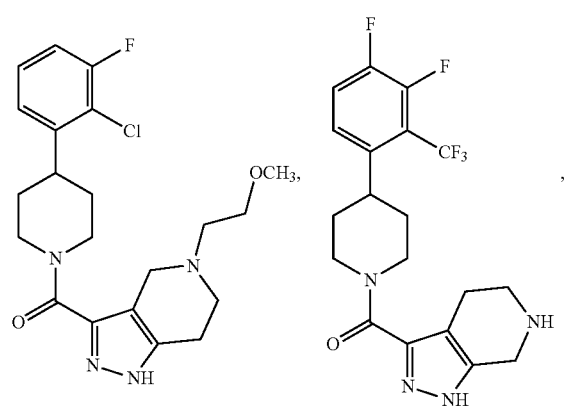
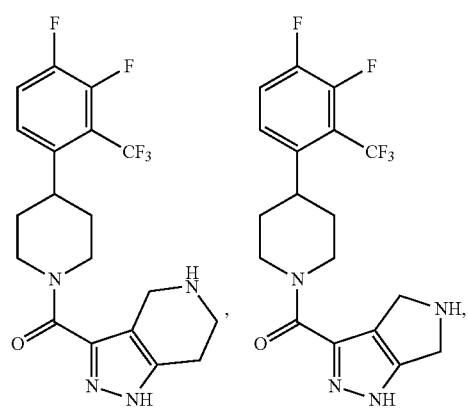
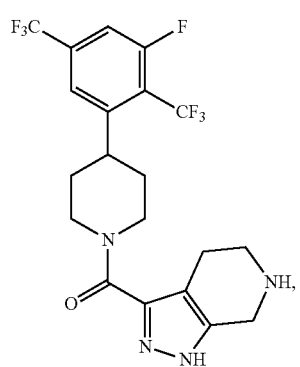
-continued
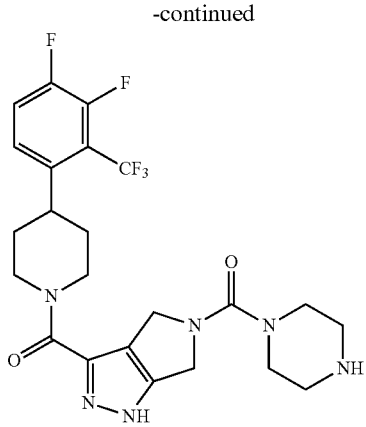
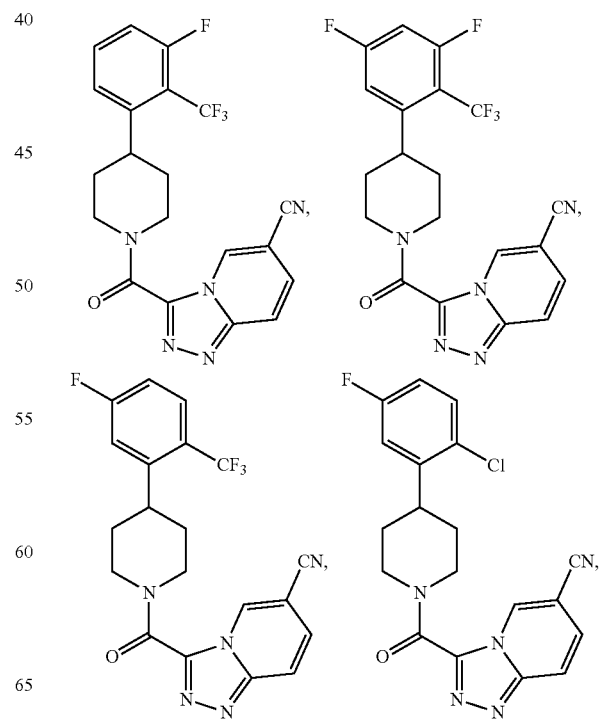
or a pharmaceutically acceptable salt of the compound.
In some embodiment, the compound wherein the structure:

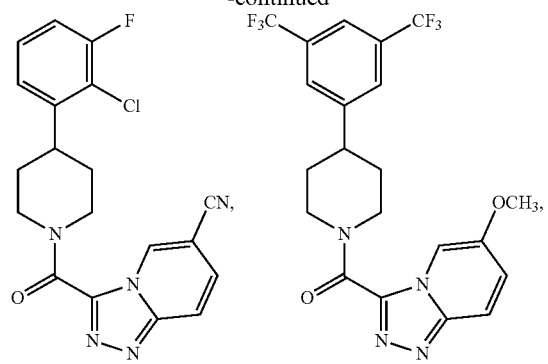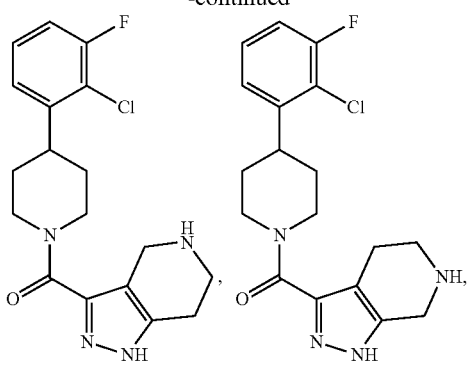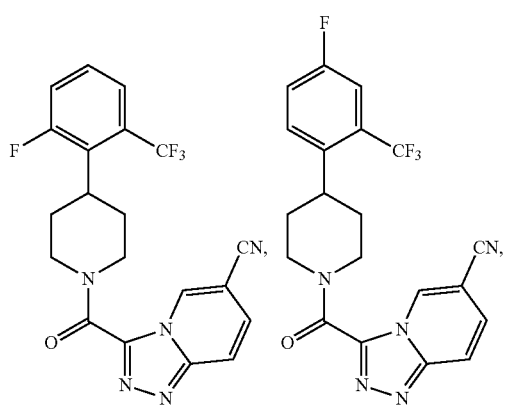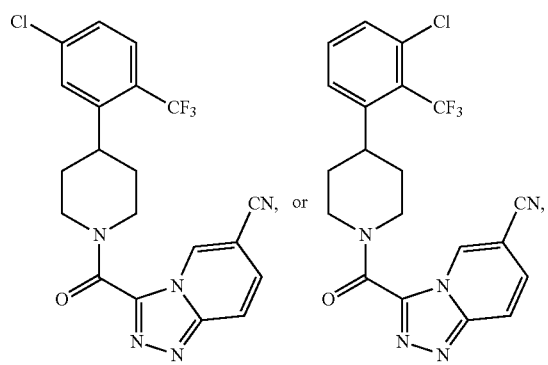 [SMILES: N#Cc1ccc2nnc(C(=O)N3CCC(c4cc(Cl)ccc4C(F)(F)F)CC3)n2c1 ; "or" ; N#Cc1ccc2nnc(C(=O)N3CCC(c4cccc(Cl)c4C(F)(F)F)CC3)n2c1]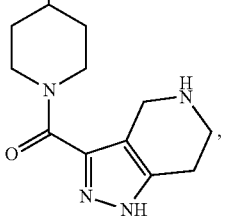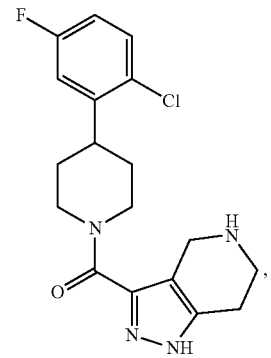
or a pharmaceutically acceptable salt of the compound.
In some embodiment, the compound having the structure:
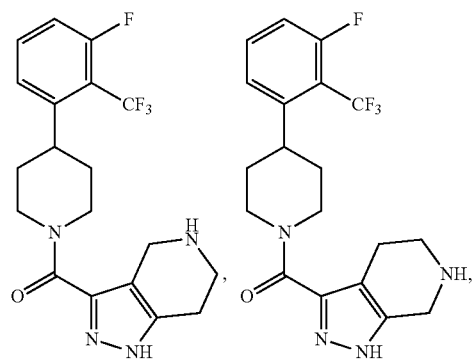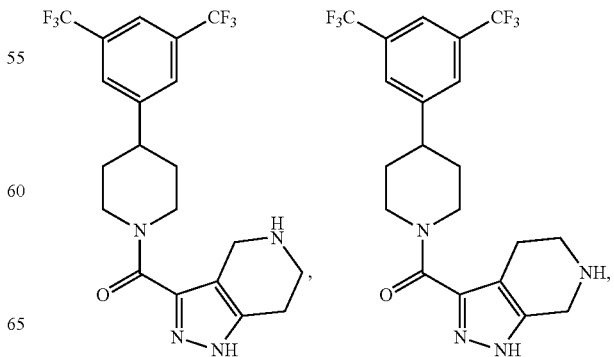

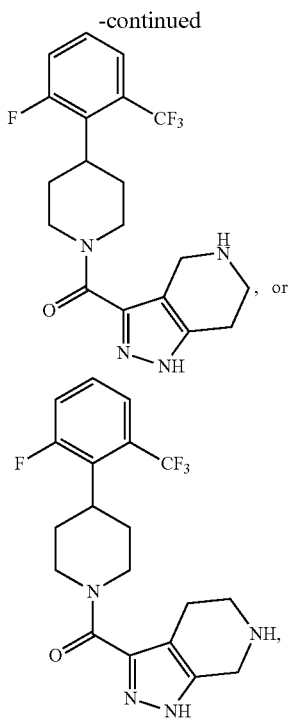

or a pharmaceutically acceptable salt of the compound.

The present invention provides a pharmaceutical composition comprising any one of the above compounds and a pharmaceutically acceptable carrier.

The present invention provides a method for treating a disease characterized by excessive lipofuscin accumulation in the retina in a subject afflicted therewith comprising administering to the subject an effective amount of any one of the above compounds.

The present invention provides a pharmaceutical composition comprising the compound of the present invention and a pharmaceutically acceptable carrier.

The present invention provides a method for treating a disease characterized by excessive lipofuscin accumulation in the retina in a subject afflicted therewith comprising administering to the subject an effective amount of the compound of the present invention or a composition of the present invention.

In some embodiments, the disease is further characterized by bisretinoid-mediated macular degeneration.

In some embodiments, the amount of the compound is effective to lower the serum concentration of RBP4 in the subject.

In some embodiments, the amount of the compound is effective to lower the retinal concentration of a bisretinoid in lipofuscin in the subject.

In some embodiments, the bisretinoid is A2E. In some embodiments, the bisretinoid is isoA2E. In some embodiments, the bisretinoid is A2-DHP-PE. In some embodiments, the bisretinoid is atRAL di-PE.

In some embodiments, the disease characterized by excessive lipofuscin accumulation in the retina is Age-Related Macular Degeneration.

In some embodiments, the disease characterized by excessive lipofuscin accumulation in the retina is dry (atrophic) Age-Related Macular Degeneration.

In some embodiments, the disease characterized by excessive lipofuscin accumulation in the retina is Stargardt Disease.

In some embodiments, the disease characterized by excessive lipofuscin accumulation in the retina is Best disease.

In some embodiments, the disease characterized by excessive lipofuscin accumulation in the retina is adult vitelliform maculopathy.

In some embodiments, the disease characterized by excessive lipofuscin accumulation in the retina is Stargardt-like macular dystrophy In some embodiments, the subject is a mammal. In some embodiments, the mammal is a human.

In some embodiments, $R_9$ is H, $C_1$-$C_4$ alkyl, $C_3$-$C_6$ cycloalkyl, ($C_1$-$C_4$ alkyl)-$CF_3$, ($C_1$-$C_4$ alkyl)-$OCH_3$, ($C_1$-$C_4$ alkyl)-halogen, $SO_2$—($C_1$-$C_4$ alkyl), $SO_2$—($C_1$-$C_4$ alkyl)-$CF_3$, $SO_2$—($C_1$-$C_4$ alkyl)-$OCH_3$, $SO_2$—($C_1$-$C_4$ alkyl)-halogen, $C(O)$—($C_1$-$C_4$ alkyl), $C(O)$—($C_1$-$C_4$ alkyl)-$CF_3$, $C(O)$—($C_1$-$C_4$ alkyl)-$OCH_3$, $C(O)$—($C_1$-$C_4$ alkyl)-halogen, $C(O)$—NH—($C_1$-$C_4$ alkyl), $C(O)$—N($C_1$-$C_4$ alkyl)$_2$, ($C_1$-$C_4$ alkyl)-$C(O)OH$, $C(O)$—$NH_2$ or oxetane.

In some embodiments, $R_9$ is H, $CH_3$, $CH_2CH_3$, $CH_2CH_2CH_3$, $CH(CH_3)_2$, $CH_2CH(CH_3)_2$, t-Bu, $CH_2OCH_3$, $CH_2CF_3$, $CH_2Cl$, $CH_2F$, $CH_2CH_2OCH_3$, $CH_2CH_2CF_3$, $CH_2CH_2Cl$, $CH_2CH_2F$, or

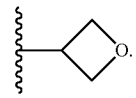

In some embodiments, $R_9$ is $SO_2$—$CH_3$, $SO_2$—$CH_2CH_3$, $SO_2$—$CH_2CH_2CH_3$, $SO_2$—$CH(CH_3)_2$, $SO_2$—$CH_2CH(CH_3)_2$, $SO_2$-t-Bu, $SO_2$—$CH_2OCH_3$, $SO_2$—$CH_2CF_3$, $SO_2$—$CH_2Cl$, $SO_2$—$CH_2F$, $SO_2$—$CH_2CH_2OCH_3$, $SO_2$—$CH_2CH_2CF_3$, $SO_2$—$CH_2CH_2Cl$, $SO_2$—$CH_2CH_2F$, or

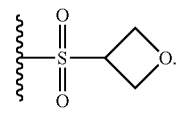

In some embodiments, $R_9$ is $C(O)$—$CH_3$, $C(O)$—$CH_2CH_3$, $C(O)$—$CH_2CH_2CH_3$, $C(O)$—$CH(CH_3)_2$, $C(O)$—$CH_2CH(CH_3)_2$, $C(O)$-t-Bu, $C(O)$—$CH_2OCH_3$, $C(O)$—$CH_2CF_3$, $C(O)$—$CH_2Cl$, $C(O)$—$CH_2F$, $C(O)$—$CH_2CH_2OCH_3$, $C(O)$—$CH_2CH_2CF_3$, $C(O)$—$CH_2CH_2Cl$, $C(O)$—$CH_2CH_2F$,

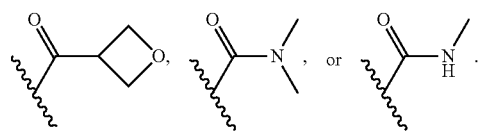

In some embodiments, the compound having the structure:

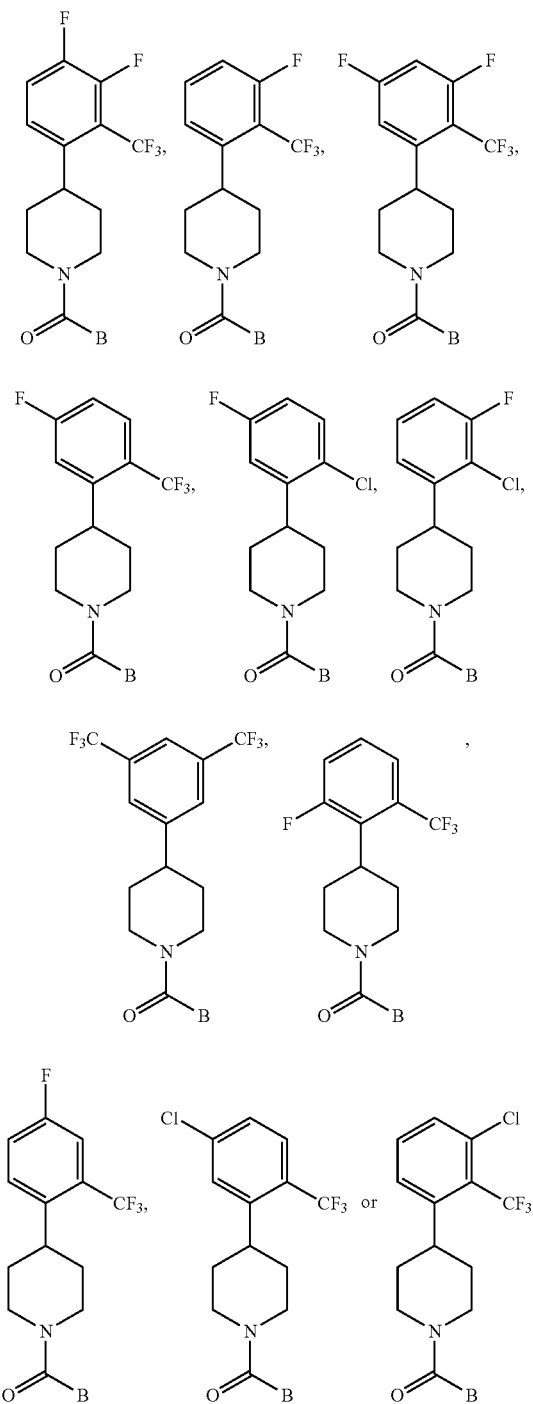
or a pharmaceutically acceptable salt thereof.
In some embodiments of the compound, B has the structure:
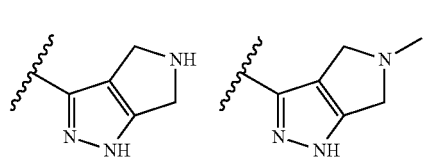
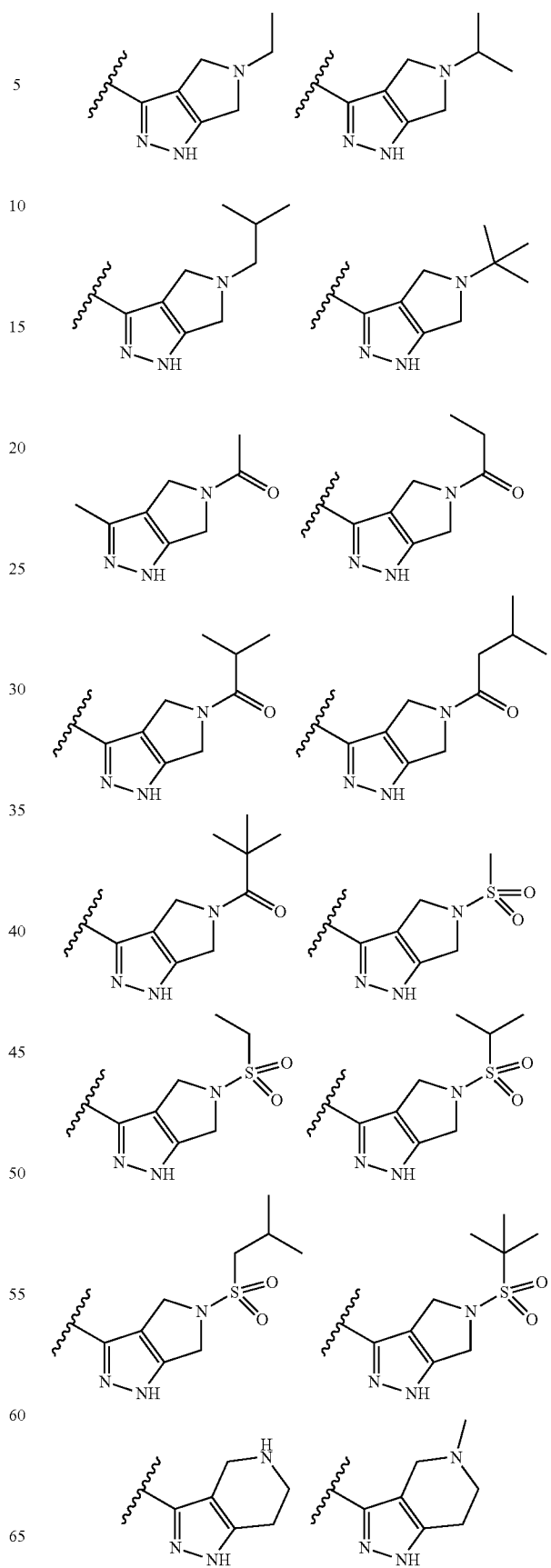

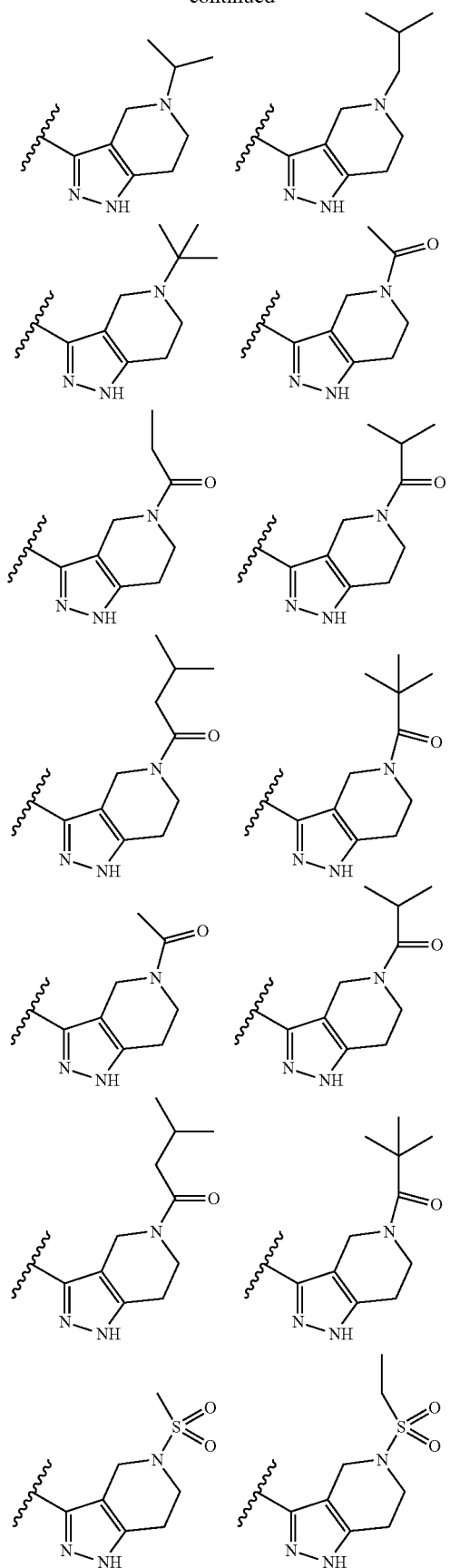
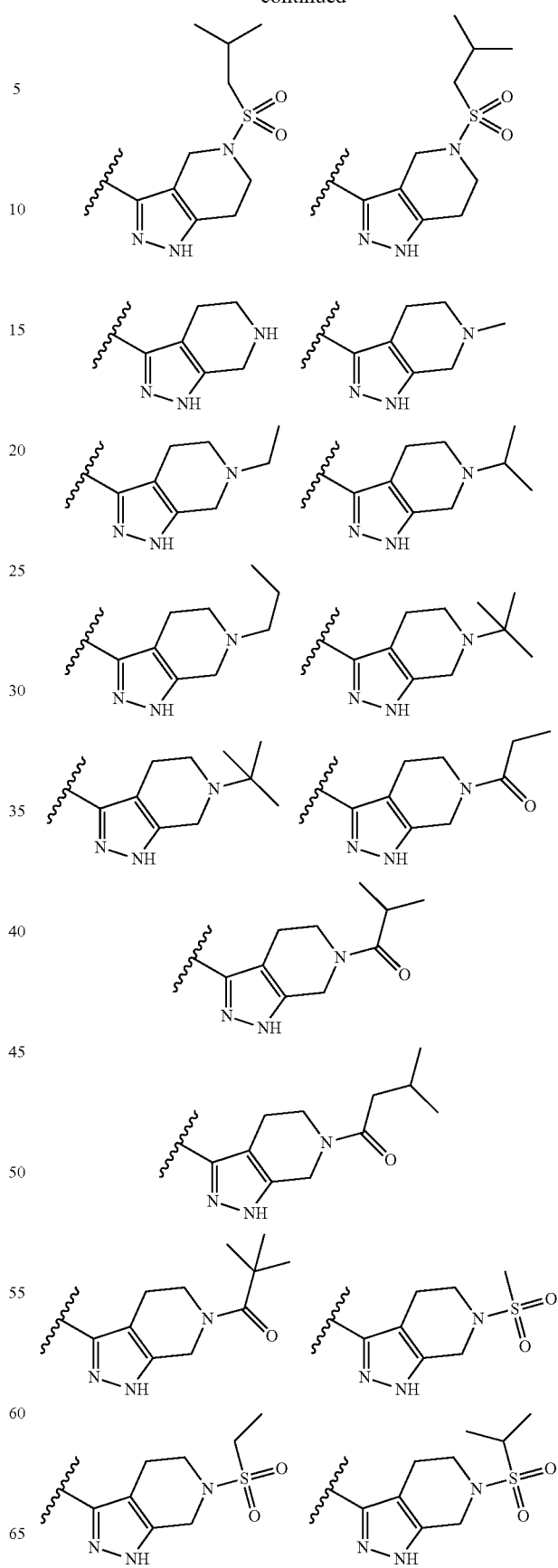

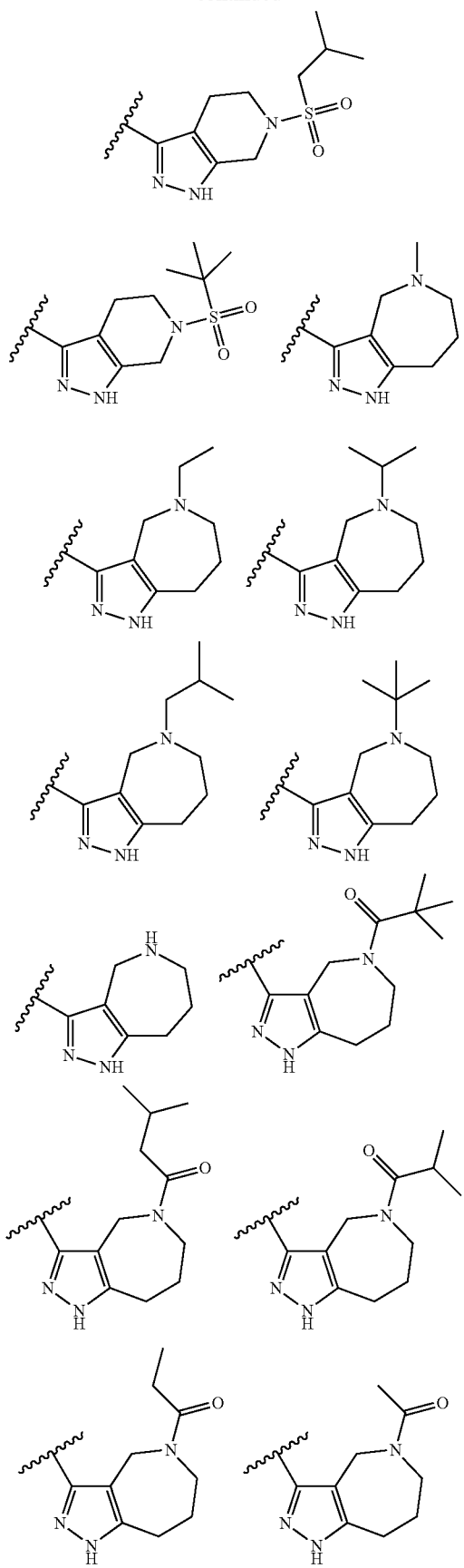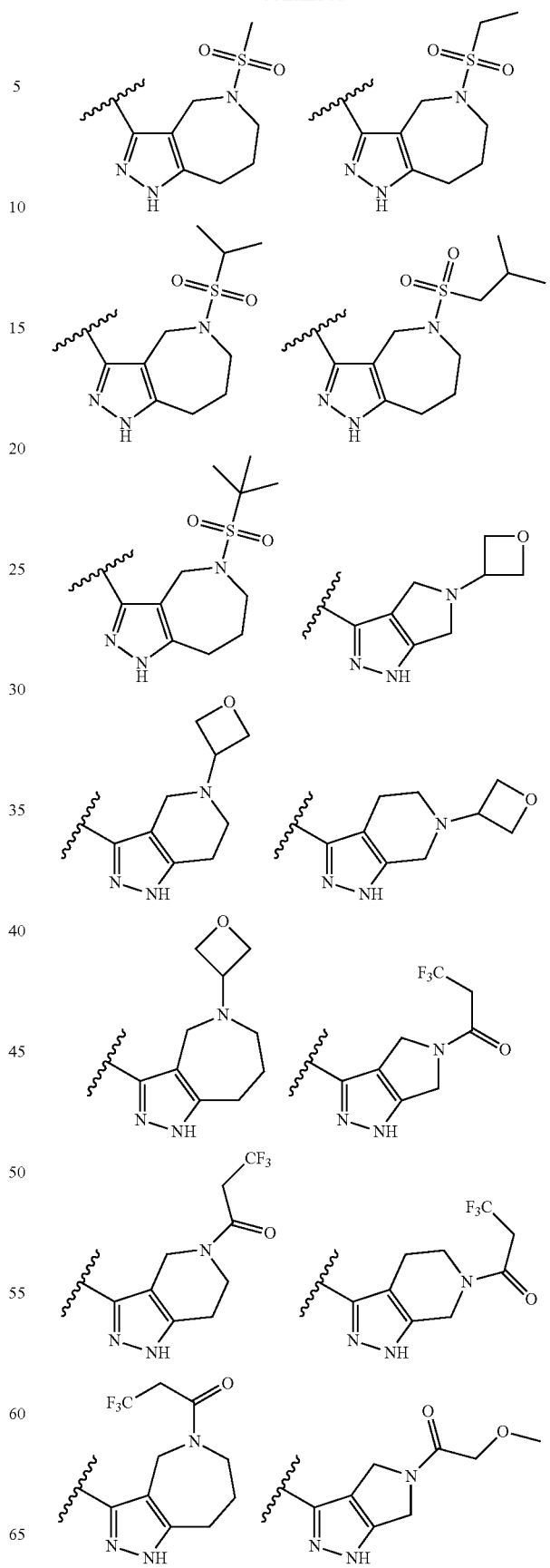

-continued
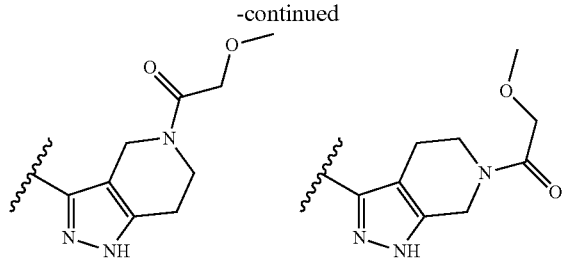
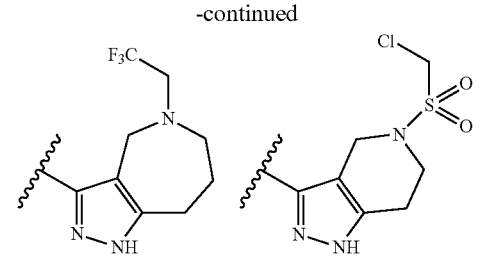

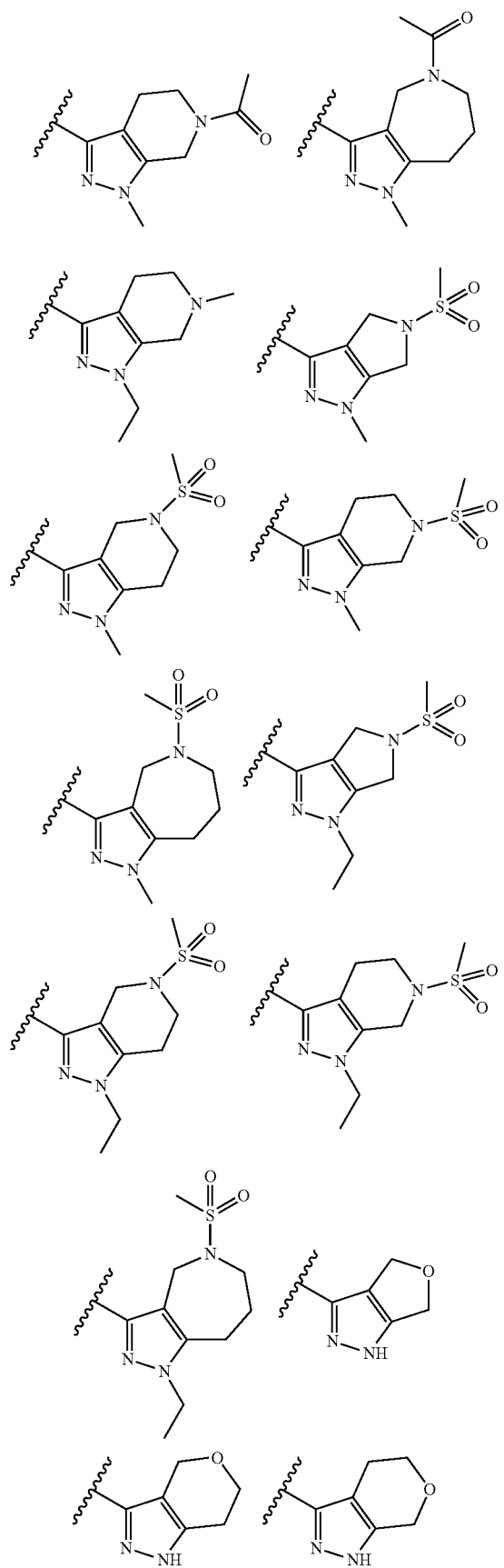
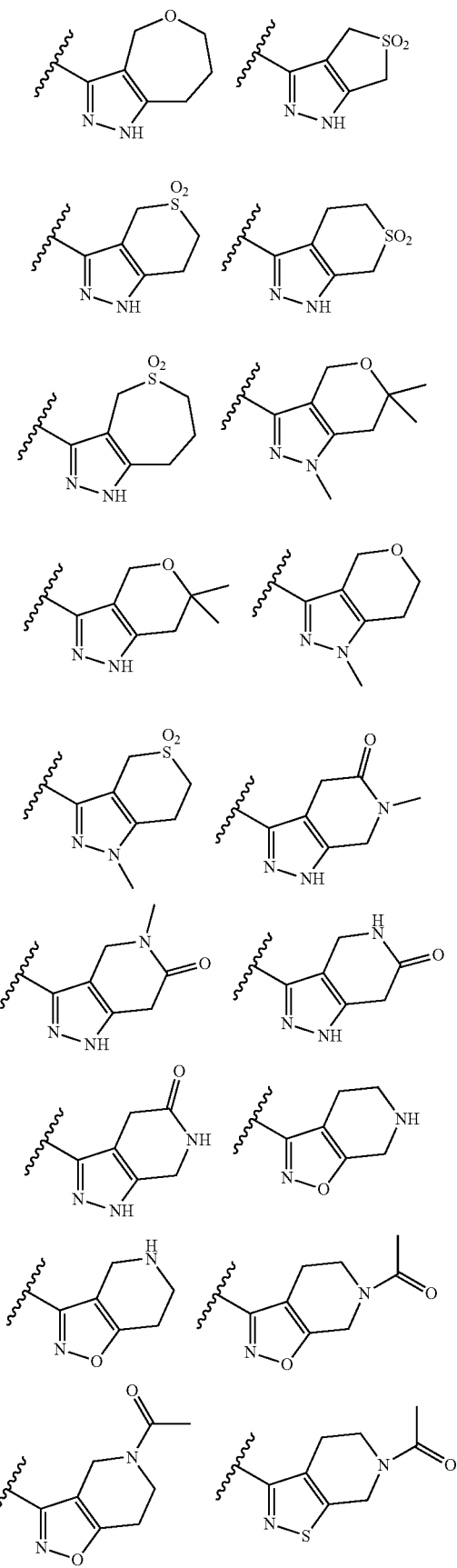

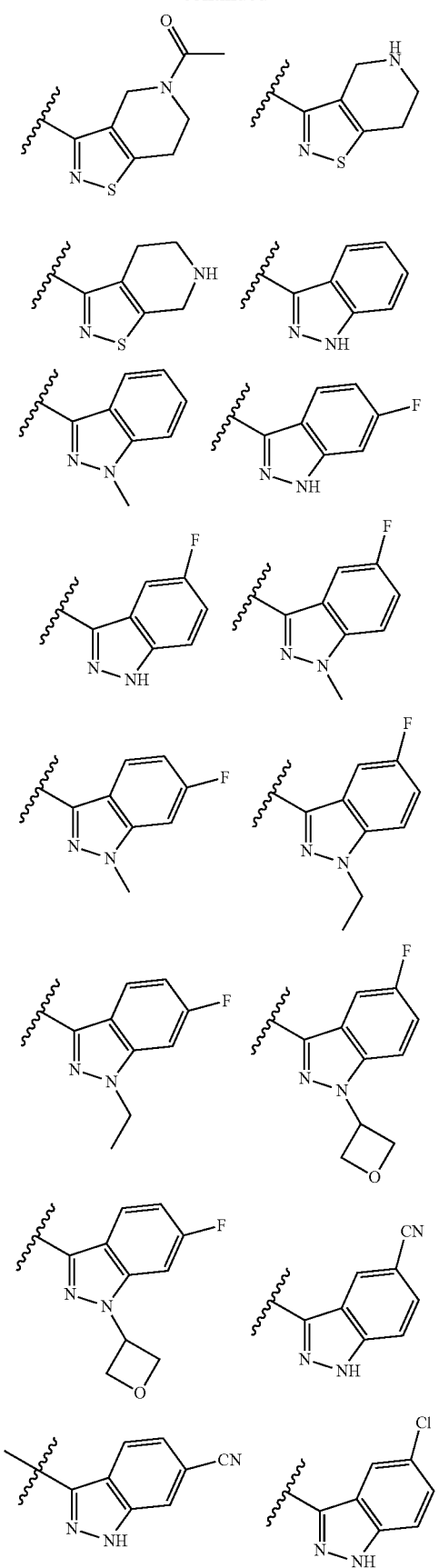
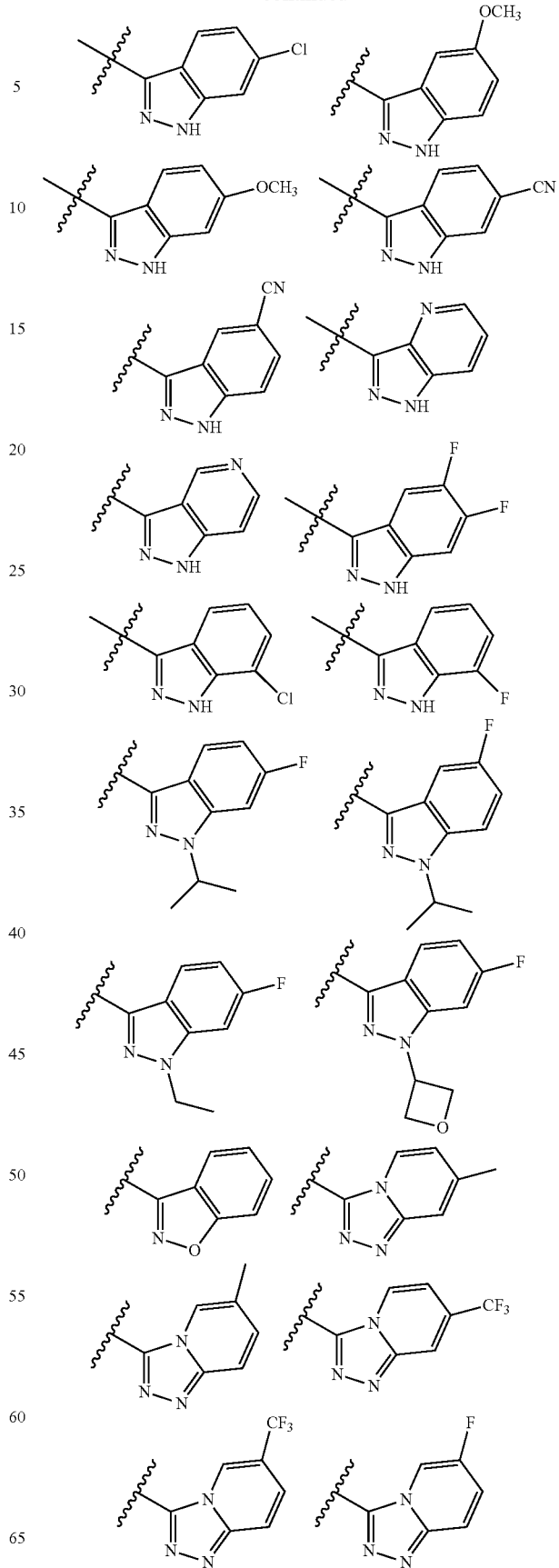

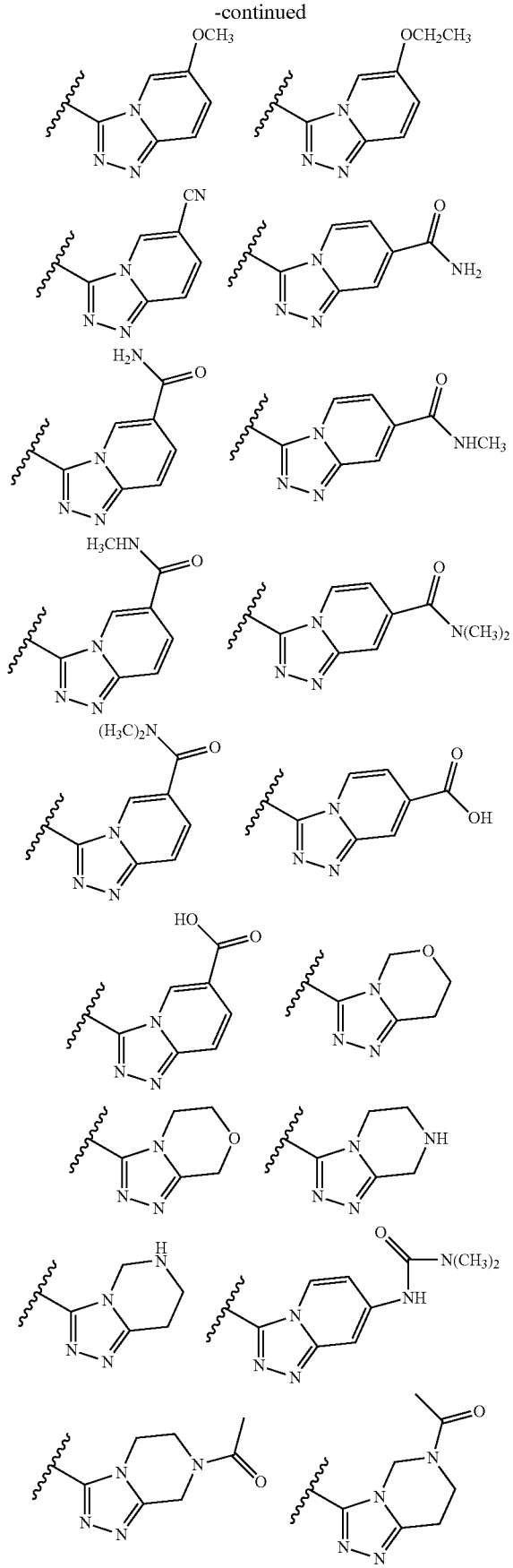
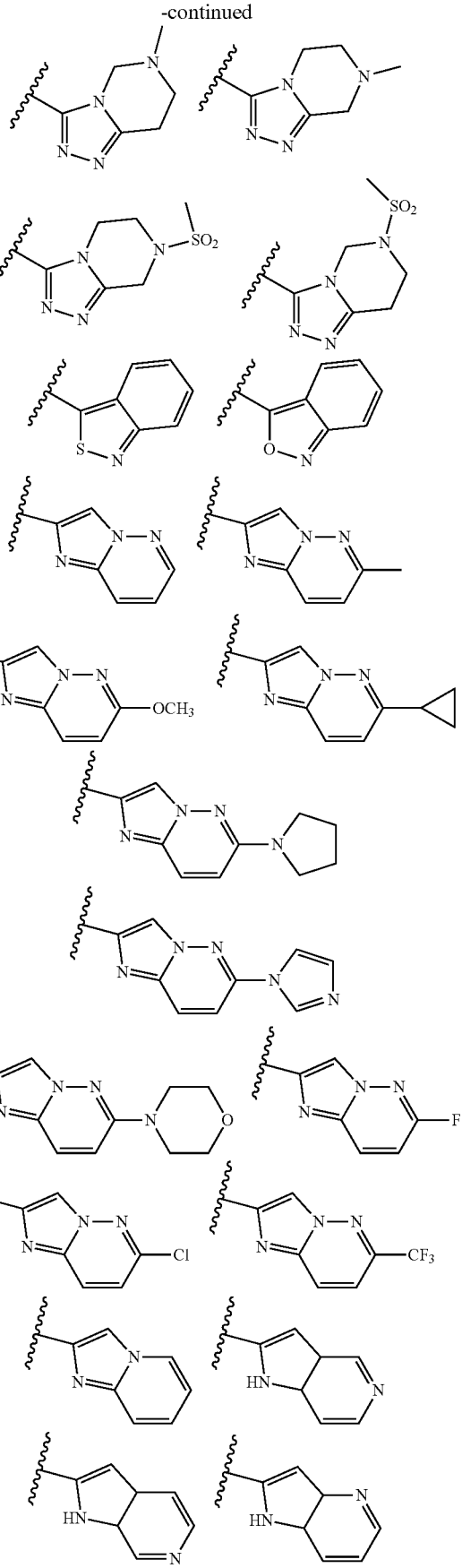

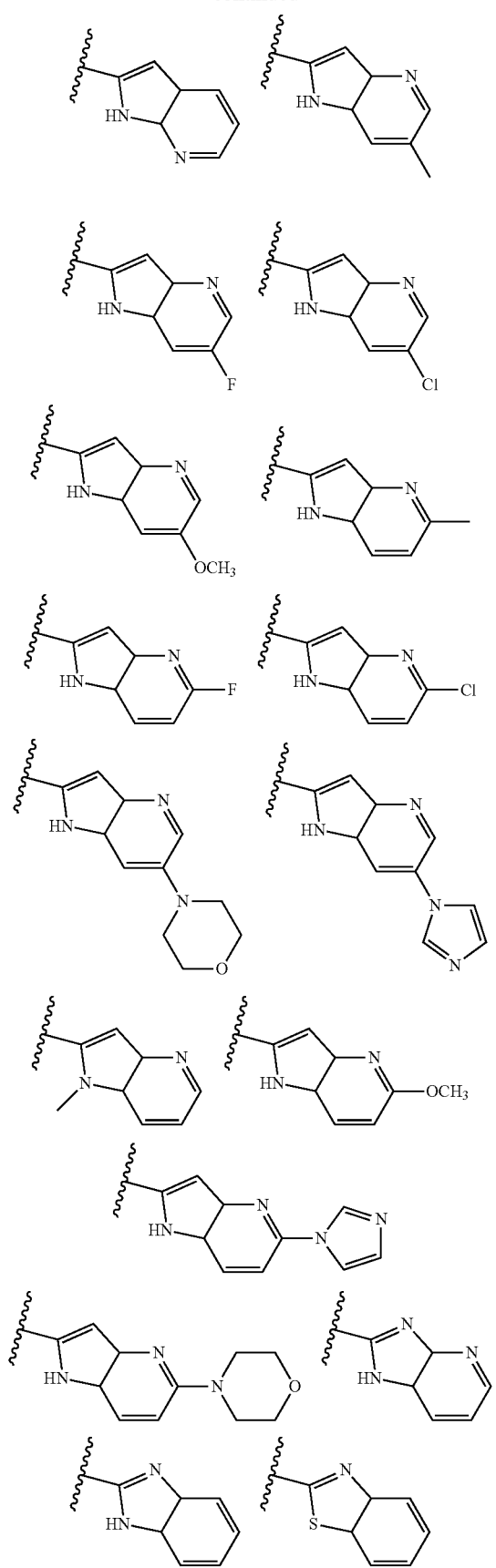
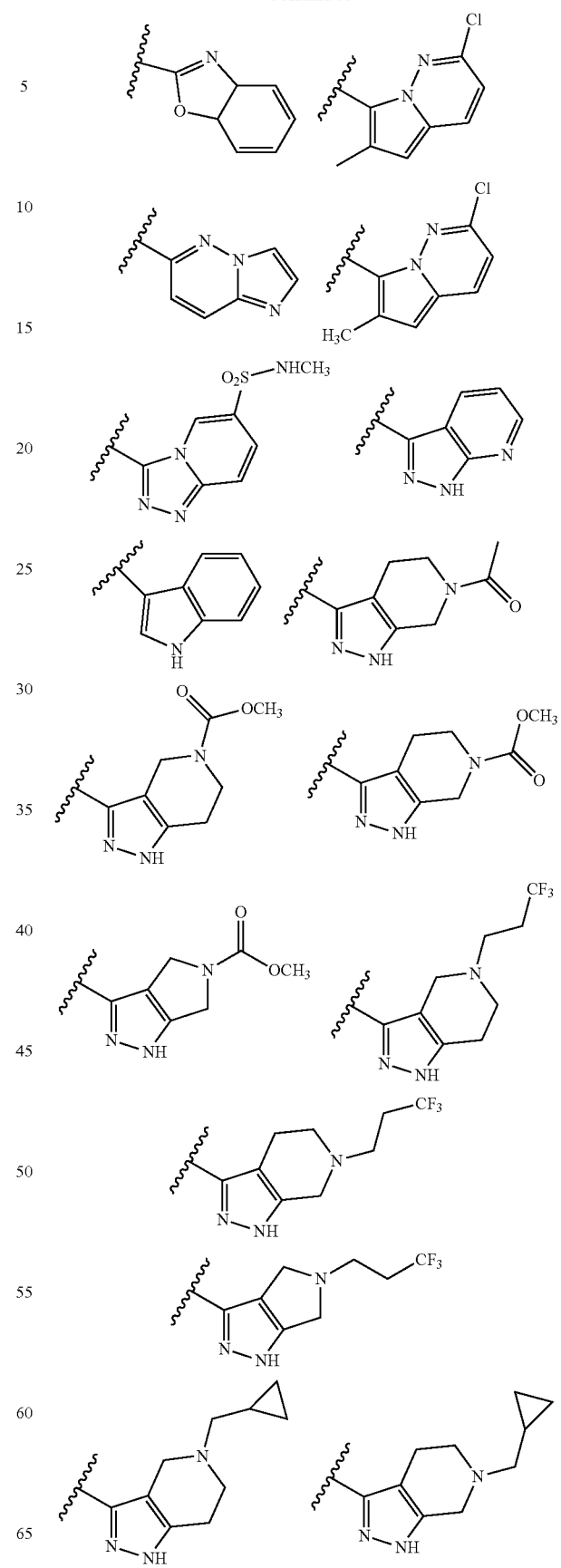

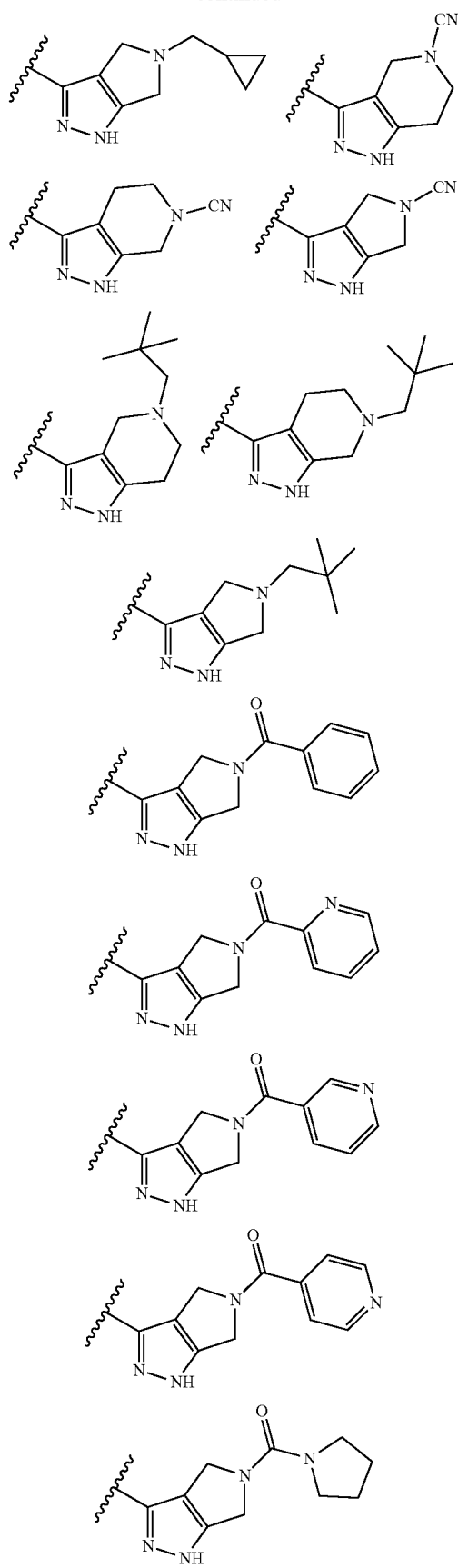

The present invention provides a pharmaceutical composition comprising a compound of the present invention and a pharmaceutically acceptable carrier.

The present invention provides a method for treating a disease characterized by excessive lipofuscin accumulation in the retina in a mammal afflicted therewith comprising administering to the mammal an effective amount of a compound of the present invention or a composition of the present invention In some embodiments of the method, wherein the disease is further characterized by bisretinoid-mediated macular degeneration.

In some embodiments of the method, wherein the amount of the compound is effective to lower the serum concentration of RBP4 in the mammal.

In some embodiments of the method, wherein the amount of the compound is effective to lower the retinal concentration of a bisretinoid in lipofuscin in the mammal.

In some embodiments of the method, wherein the bisretinoid is A2E. In some embodiments of the method, wherein the bisretinoid is isoA2E. In some embodiments of the method, wherein the bisretinoid is A2-DHP-PE. In some embodiments of the method, wherein the bisretinoid is atRAL di-PE.

In some embodiments of the method, wherein the disease characterized by excessive lipofuscin accumulation in the retina is Age-Related Macular Degeneration.

In some embodiments of the method, wherein the disease characterized by excessive lipofuscin accumulation in the retina is dry (atrophic) Age-Related Macular Degeneration.

In some embodiments of the method, wherein the disease characterized by excessive lipofuscin accumulation in the retina is Stargardt Disease.

In some embodiments of the method, wherein the disease characterized by excessive lipofuscin accumulation in the retina is Best disease.

In some embodiments of the method, wherein the disease characterized by excessive lipofuscin accumulation in the retina is adult vitelliform maculopathy.

In some embodiments of the method, wherein the disease characterized by excessive lipofuscin accumulation in the retina is Stargardt-like macular dystrophy.

In some embodiments, bisretinoid-mediated macular degeneration is Age-Related Macular Degeneration or Stargardt Disease.

In some embodiments, the bisretinoid-mediated macular degeneration is Age-Related Macular Degeneration.

In some embodiments, the bisretinoid-mediated macular degeneration is dry (atrophic) Age-Related Macular Degeneration.

In some embodiments, the bisretinoid-mediated macular degeneration is Stargardt Disease.

In some embodiments, the bisretinoid-mediated macular degeneration is Best disease.

In some embodiments, the bisretinoid-mediated macular degeneration is adult vitelliform maculopathy.

In some embodiments, the bisretinoid-mediated macular degeneration is Stargardt-like macular dystrophy.

The bisretinoid-mediated macular degeneration may comprise the accumulation of lipofuscin deposits in the retinal pigment epithelium.

Figure 2:
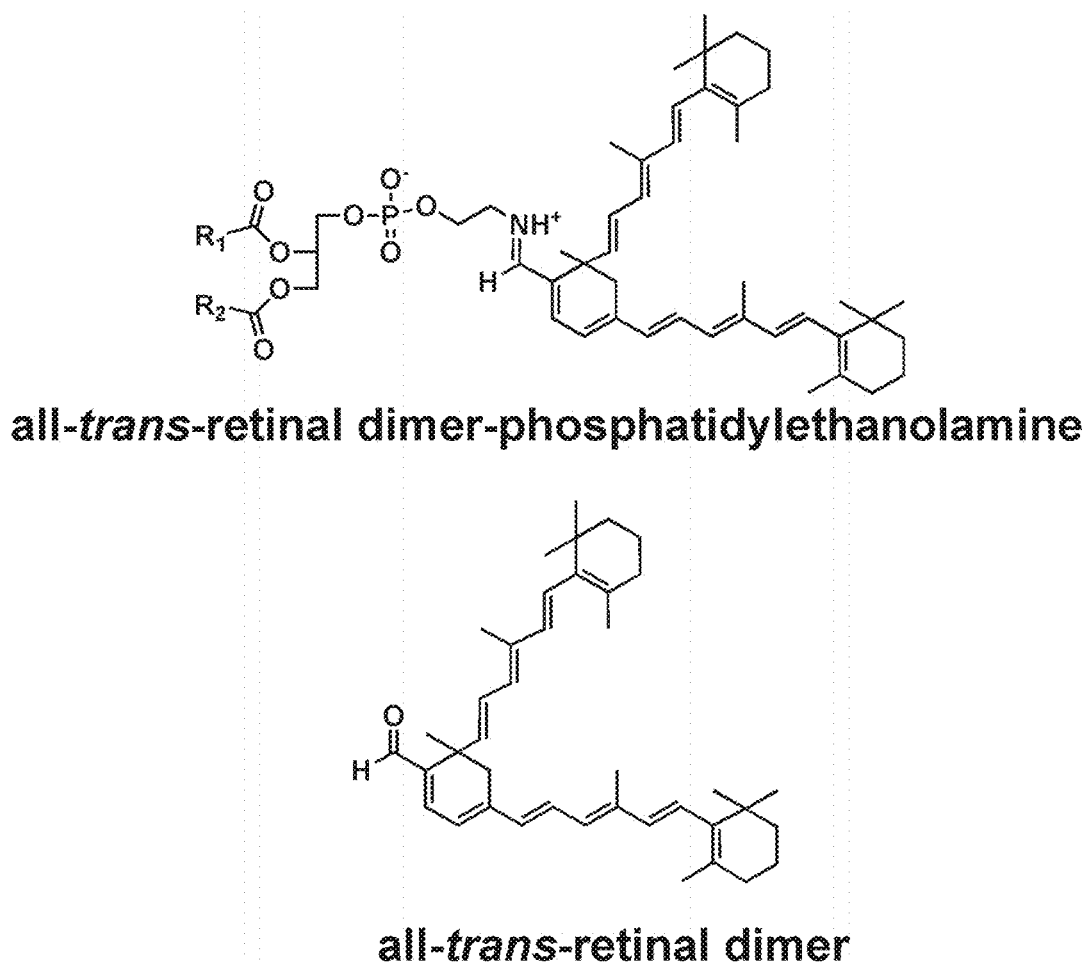
FIG. 2. Structure of bisretinoid atRAL di-PE (all-transretinal dimer-phosphatidyl ethanolamine), a cytotoxic component of retinal lipofuscin. R1 and R2 refer to various fatty acid constituents.
Figure 3:
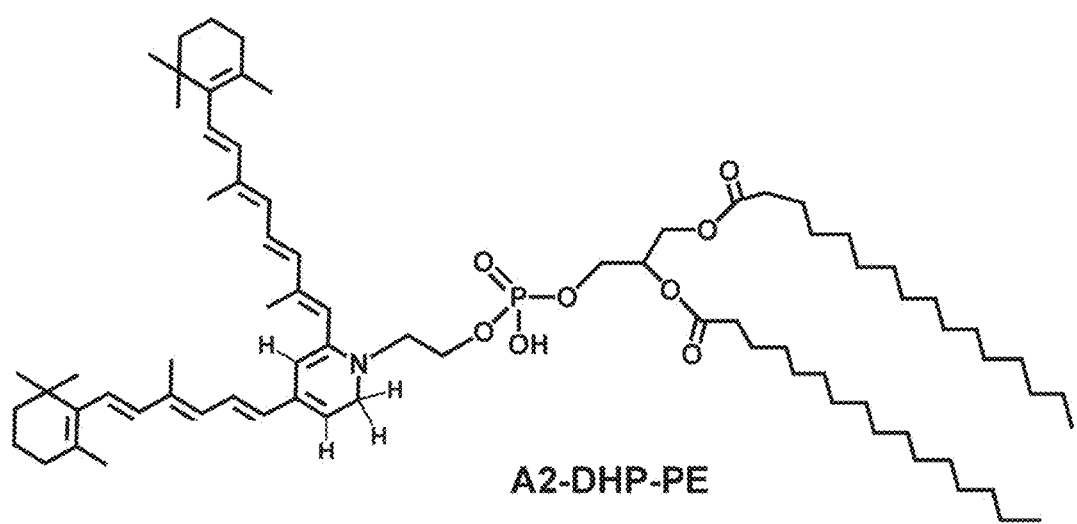
FIG. 3. Structure of bisretinoid A2-DHP-PE, a cytotoxic component of retinal lipofuscin.

As used herein, "bisretinoid lipofuscin" is lipofuscin containing a cytotoxic bisretinoid. Cytotoxic bisretinoids include but are not necessarily limited to A2E, isoA2E, atRAL di-PE, and A2-DHP-PE (FIGS. 1, 2, and 3).

The present invention provides non-retinol piperidine compounds comprising a 3,4-difluoro-2-(trifluoromethyl) phenyl moiety. This feature significantly increases the potency and improves pharmacokinetic characteristics of the molecules.

The present invention provides non-retinol piperidine compounds comprising a 3,5-difluoro-2-(trifluoromethyl) phenyl moiety. This feature significantly increases the potency and improves pharmacokinetic characteristics of the molecules.

The present invention provides non-retinol piperidine compounds comprising di- or trisubstituted phenyl moiety. This feature significantly increases the potency and improves pharmacokinetic characteristics of the molecules.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

Alkyl groups can be unsubstituted or substituted with one or more substituents, including but not limited to halogen, alkoxy, alkylthio, trifluoromethyl, difluoromethyl, methoxy, and hydroxyl.

As used herein, "$C_1$-$C_4$ alkyl" includes both branched and straight-chain $C_1$-$C_4$ alkyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As used herein, "monocycle" includes any stable polycyclic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to:

phenyl. As used herein, "heteromonocycle" includes any monocycle containing at least one heteroatom.

As used herein, "bicycle" includes any stable polycyclic carbon ring of up to 10 atoms that is fused to a polycyclic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene. As used herein, "heterobicycle" includes any bicycle containing at least one heteroatom.

The term "phenyl" is intended to mean an aromatic six membered ring containing six carbons, and any substituted derivative thereof.

The term "benzyl" is intended to mean a methylene attached directly to a benzene ring. A benzyl group is a methyl group wherein a hydrogen is replaced with a phenyl group, and any substituted derivative thereof.

The term "pyridine" is intended to mean a heteroaryl having a six-membered ring containing 5 carbon atoms and 1 nitrogen atom, and any substituted derivative thereof.

The term "pyrazole" is intended to mean a heteroaryl having a five-membered ring containing three carbon atoms and two nitrogen atoms wherein the nitrogen atoms are adjacent to each other, and any substituted derivative thereof.

The term "indole" is intended to mean a heteroaryl having a five-membered ring fused to a phenyl ring with the five-membered ring containing 1 nitrogen atom directly attached to the phenyl ring.

The term "oxatane" is intended to mean a non-aromatic four-membered ring containing three carbon atoms and one oxygen atom, and any substituted derivative thereof.

The compounds used in the method of the present invention may be prepared by techniques well know in organic synthesis and familiar to a practitioner ordinarily skilled in the art. However, these may not be the only means by which to synthesize or obtain the desired compounds.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The compounds of present invention may be prepared by techniques described herein. The synthetic methods used to prepare Examples 1-103 are used to prepare additional piperidine compounds which are described in the embodiments herein.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds of the present invention may be in a salt form. As used herein, a "salt" is a salt of the instant compounds which has been modified by making acid or base salts of the compounds. In the case of compounds used to treat a disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", *J. Pharm. Sci.* 66:1-19).

A salt or pharmaceutically acceptable salt is contemplated for all compounds disclosed herein. In some embodiments, a pharmaceutically acceptable salt or salt of any of the above compounds of the present invention.

As used herein, "treating" means preventing, slowing, halting, or reversing the progression of a disease or infection. Treating may also mean improving one or more symptoms of a disease or infection.

The compounds of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Materials and Methods

TR-FRET Assay for Retinol-induced RBP4-TTR Interaction

Figure 7:
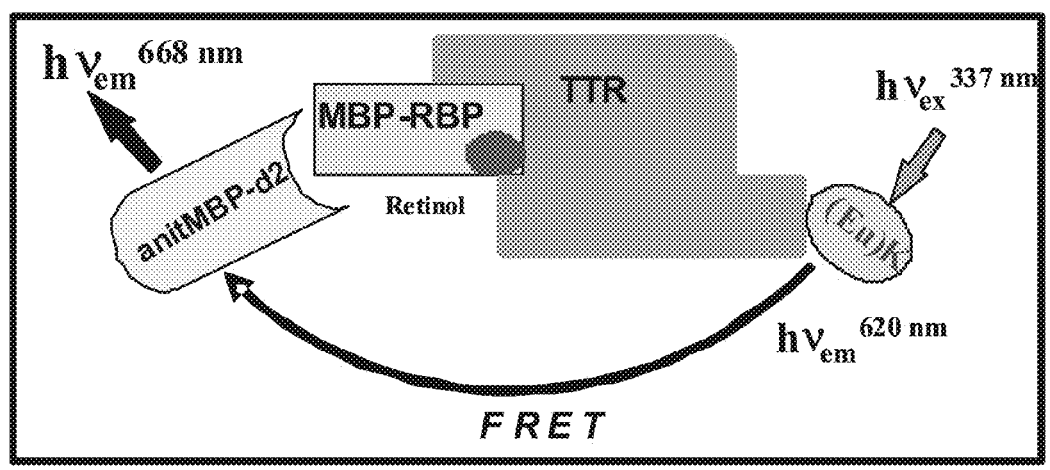
FIG. 7. Schematic depiction of the HTRF-based assay format for characterization of RBP4 antagonists disrupting retinol-induced RBP4-TTR interaction.

Binding of a desired RBP4 antagonist displaces retinol and induces hindrance for RBP4-TTR interaction resulting in the decreased FRET signal (FIG. 7). Bacterially expressed MBP-RBP4 and untagged TTR were used in this assay. For the use in the TR-FRET assay the maltose binding protein (MBP)-tagged human RBP4 fragment (amino acids 19-201) was expressed in the Gold(DE3)pLysS E. coli strain (Stratagene) using the pMAL-c4x vector. Following cell lysis, recombinant RBP4 was purified from the soluble fraction using the ACTA FPLC system (GE Healthcare) equipped with the 5-ml the MBP Trap HP column. Human untagged TTR was purchased from Calbiochem. Untagged TTR was labeled directly with $Eu^{3+}$ Cryptate-NHS using the HTRF Cryptate Labeling kit from CisBio following the manufacturer's recommendations. HTRF assay was performed in white low volume 384 well plates (Greiner-Bio) in a final assay volume of 16 µl per well. The reaction buffer contained 10 mM Tris-HCl pH 7.5, 1 mM DTT, 0.05% NP-40, 0.05% Prionex, 6% glycerol, and 400 mM KF. Each reaction contained 60 nM MBP-RBP4 and 2 nM TTR-Eu along with 26.7 nM of anti-MBP antibody conjugated with d2 (Cisbio). Titration of test compounds in this assay was conducted in the presence of 1 µM retinol. All reactions were assembled in the dark under dim red light and incubated overnight at +4° C. wrapped in aluminum foil. TR-FRET signal was measured in the SpectraMax M5e Multimode Plate Reader (Molecular Device). Fluorescence was excited at 337 nm and two readings per well were taken: Reading 1 for time-gated energy transfer from Eu(K) to d2 (337 nm excitation, 668 nm emission, counting delay 75 microseconds, counting window 100 microseconds) and Reading for Eu(K) time-gated fluorescence (337 nm excitation, 620 nm emission, counting delay 400 microseconds, counting window 400 microseconds). The TR-FRET signal was expressed as the ratio of fluorescence intensity: $Flu_{665}/Flu_{620} \times 10,000$.

Scintillation Proximity RBP4 Binding Assay

Untagged human RBP4 purified from urine of tubular proteinuria patients was purchased from Fitzgerald Industries International. It was biotinylated using the EZ-Link Sulfo-NHS-LC-Biotinylation kit from Pierce following the manufacturer's recommendations. Binding experiments were performed in 96-well plates (OptiPlate, PerkinElmer) in a final assay volume of 100 µl per well in SPA buffer (1×PBS, pH 7.4, 1 mM EDTA, 0.1% BSA, 0.5% CHAPS). The reaction mix contained 10 nM $^3$H-Retinol (48.7 Ci/mmol; PerkinElmer), 0.3 mg/well Streptavidin-PVT beads, 50 nM biotinylated RBP4 and a test compound. Nonspecific binding was determined in the presence of 20 µM of unlabeled retinol. The reaction mix was assembled in the dark under dim red light. The plates were sealed with clear tape (TopSeal-A: 96-well microplate, PerkinElmer), wrapped in the aluminum foil, and allowed to equilibrate 6 hours at room temperature followed by overnight incubation at +4° C. Radiocounts were measured using a TopCount NXT counter (Packard Instrument Company).

General Procedure (GP) for Preparing Intermediates for Synthesis of Piperidine Compounds

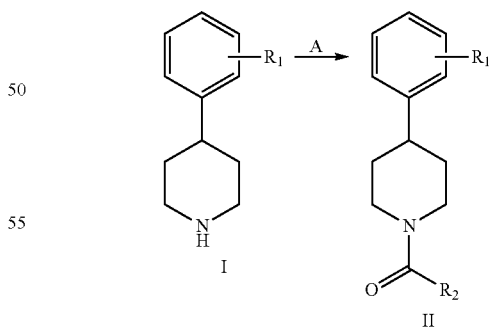

Conditions: A1) carboxylic acid, HBTU, $Et_3N$, DMF; A2) carboxylic acid, EDCI, HOBt, i-$Pr_2NEt$, DMF; A3) acid chloride, $Et_3N$, $CH_2Cl_2$.

General Procedure (GP-A1) for carboxamide formation: A mixture of amine I (1 equiv), desired carboxylic acid (1 equiv), triethylamine ($Et_3N$) (3 equiv), and 2-(1H-benzotriazole-1-yl)-1,1,3,3-tetramethyluronium hexafluorophosphate (HBTU) (1.5 equiv) in DMF (0.25 M) was stirred at room temperature until the reaction was complete by LC-MS. The mixture was diluted with $H_2O$ and extracted with EtOAc. The combined organic extracts were washed with $H_2O$, brine, dried over $Na_2SO_4$, filtered and concentrated under reduced pressure. The resulting residue was purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) to afford the desired carboxamide II. The product structure was verified by $^1H$ NMR and by mass analysis.

General Procedure (GP-A2) for carboxamide formation: A mixture of amine I (1 equiv), desired carboxylic acid (1 equiv), N, N-diisopropylethylamine (i-$Pr_2NEt$) (3 equiv), 1-ethyl-3-(3-dimethylaminopropyl)carbodiimide (EDCI) (1.5 equiv) and hydroxybenzotriazole (HOBt) (1.5 equiv) in DMF (0.25 M) was stirred at room temperature until the reaction was complete by LC-MS. The mixture was diluted with $H_2O$ and extracted with EtOAc. The combined organic extracts were washed with $H_2O$, brine, dried over $Na_2SO_4$, filtered and concentrated under reduced pressure. The resulting residue was purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) to afford the desired carboxamide II. The product structure was verified by $^1H$ NMR and by mass analysis.

General Procedure (GP-A3) for carboxamide formation: A mixture of amine I (1 equiv), $Et_3N$ (3 equiv), and acid chloride (1 equiv) in $CH_2Cl_2$ (0.25 M) was stirred at ambient temperature until the reaction was complete by LC-MS. The mixture was washed with $H_2O$, brine, dried over $Na_2SO_4$, filtered and concentrated under reduced pressure. The resulting residue was purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) to afford the desired carboxamides II. The product structure was verified by $^1H$ NMR and by mass analysis.

General Procedures for Preparing (4-Phenylpiperidin-1-yl)(4,5,6,7-tetrahydro-1H-pyrazolo[4,3-c]pyridin-3-yl)methanone Carboxamides IV

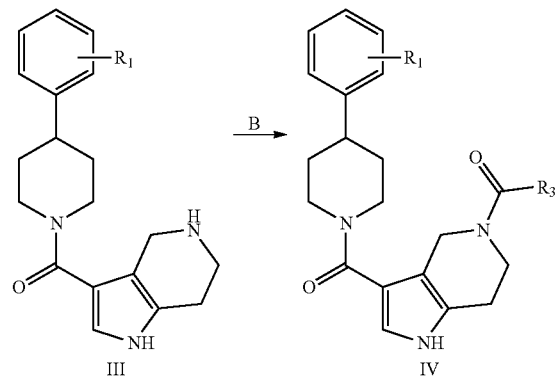

Conditions: B) acid chloride, $Et_3N$, $CH_2Cl_2$.

General Procedure (GP-B) for carboxamide formation: A mixture of amine III (1 equiv), desired acid chloride (1 equiv) and triethylamine ($Et_3N$) (3 equiv) in $CH_2Cl_2$ (0.25 M) was stirred from 0° C. to room temperature until the reaction was complete by LC-MS. The mixture was diluted with $H_2O$ and extracted with $CH_2Cl_2$. The combined organic extracts were washed with $H_2O$, brine, dried over $Na_2SO_4$, filtered and concentrated under reduced pressure. The resulting residue was purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) to afford the desired carboxamides IV. The product structure was verified by $^1H$ NMR and by mass analysis.

General Procedures for Preparing (4-Phenylpiperidin-1-yl)(4,5,6,7-tetrahydro-1H-pyrazolo[4,3-c]pyridin-3-yl)methanone Sulfonamides V

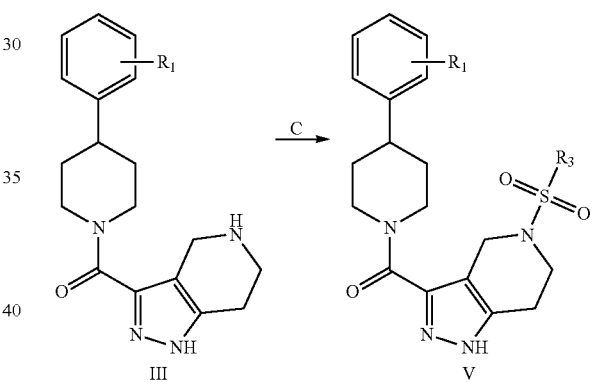

Conditions: C) sulfonyl chloride, i-$Pr_2NEt$, $CH_2Cl_2$.

General Procedure (GP-C) for sulfonamide formation: A mixture of amine III (1 equiv), desired sulfonyl chloride (1 equiv) and i-$Pr_2NEt$ (3 equiv) in $CH_2Cl_2$ (0.25 M) was stirred from 0° C. to room temperature until the reaction was complete by LC-MS. The mixture was diluted with $H_2O$ and extracted with $CH_2Cl_2$. The combined organic extracts were washed with $H_2O$, brine, dried over $Na_2SO_4$, filtered and concentrated under reduced pressure. The resulting residue was purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) to afford the desired sulfonamides V. The product structure was verified by $^1H$ NMR and by mass analysis.

General Procedures for Preparing Alkylated (4-Phenylpiperidin-1-yl)(4,5,6,7-tetrahydro-1H-pyrazolo[4,3-c]pyridin-3-yl)methanones VI

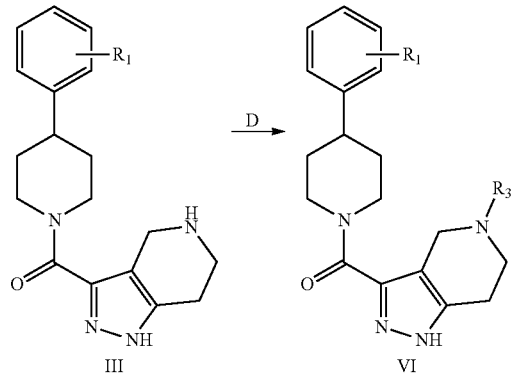

Conditions: D) aldehyde or ketone, NaBH(OAc)$_3$, CH$_2$Cl$_2$.

General Procedure (GP-D) for sulfonamide formation: A mixture of amine III (1 equiv), desired aldehyde or ketone (1.5 equiv) and HOAc (6 equiv) in CH$_2$Cl$_2$ (0.25 M) was stirred for 16 hours at room temperature. To this was added sodium triacetoxyborohydride (NaBH(OAc)$_3$) and the mixture stirred at room temperature until the reaction was complete by LC-MS. The mixture was diluted with aqueous, saturated NaHCO$_3$ solution and extracted with CH$_2$Cl$_2$. The combined organic extracts were washed with H$_2$O, brine, dried over Na$_2$SO$_4$, filtered and concentrated under reduced pressure. The resulting residue was purified by silica gel chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) to afford the desired amines VI. The product structure was verified by $^1$H NMR and by mass analysis.

General Procedure for Preparing (4-Phenylpiperidin-1-yl)(4,5,6,7-tetrahydro-1H-pyrazolo[3,4-c]pyridin-3-yl)methanone Carboxamides VIII

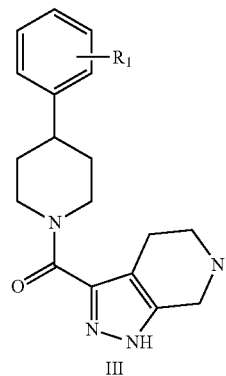

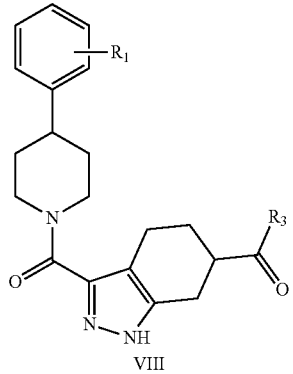

Conditions: E) acid chloride, Et$_3$N, CH$_2$Cl$_2$.

General Procedure (GP-E) for carboxamide formation: A mixture of amine VII (1 equiv), desired acid chloride (1 equiv) and triethylamine (Et$_3$N) (3 equiv) in CH$_2$Cl$_2$ (0.25 M) was stirred from 0° C. to room temperature until the reaction was complete by LC-MS. The mixture was diluted with H$_2$O and extracted with CH$_2$Cl$_2$. The combined organic extracts were washed with H$_2$O, brine, dried over Na$_2$SO$_4$, filtered and concentrated under reduced pressure. The resulting residue was purified by silica gel chromatography (typical eluents included either a mixture of or hexanes and EtOAc or a mixture of CH$_2$Cl$_2$ and a 90:9:1 mixture of CH$_2$Cl$_2$/CH$_3$OH/concentrated NH$_4$OH) to afford the desired carboxamides VIII. The product structure was verified by $^1$H NMR and by mass analysis.

General Procedures for Preparing (4-Phenylpiperidin-1-yl)(4,5,6,7-tetrahydro-1H-pyrazolo[3,4-c]pyridin-3-yl)methanone Sulfonamides IX

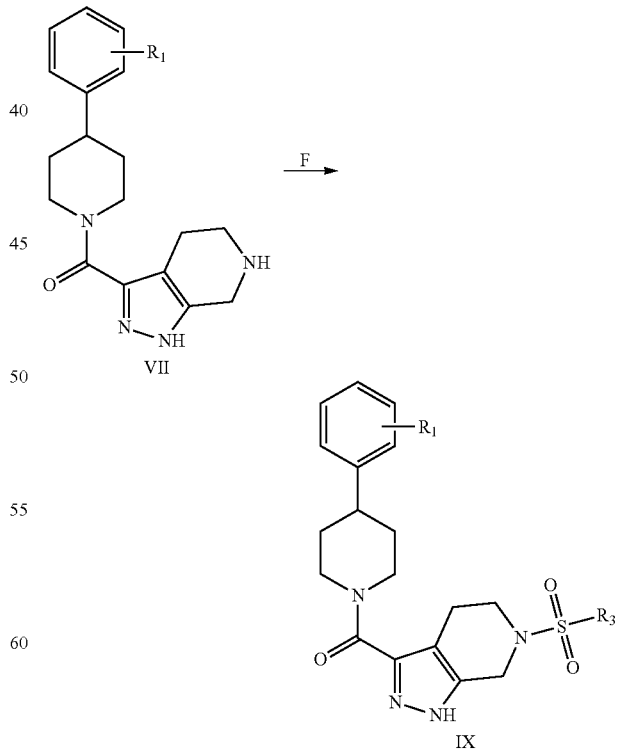

Conditions: F) sulfonyl chloride, i-Pr$_2$NEt, CH$_2$Cl$_2$.

General Procedure (GP-F) for sulfonamide formation: A mixture of amine VII (1 equiv), desired sulfonyl chloride (1 equiv) and i-Pr₂NEt (3 equiv) in CH₂Cl₂ (0.25 M) was stirred from 0° C. to room temperature until the reaction was complete by LC-MS. The mixture was diluted with H₂O and extracted with CH₂Cl₂. The combined organic extracts were washed with H₂O, brine, dried over Na₂SO₄, filtered and concentrated under reduced pressure. The resulting residue was purified by silica gel chromatography (typical eluents included either a mixture of or hexanes and EtOAc or a mixture of CH₂Cl₂ and a 90:9:1 mixture of CH₂Cl₂/CH₃OH/ concentrated NH₄OH) to afford the desired sulfonamides IX. The product structure was verified by ¹H NMR and by mass analysis.

General Procedures for Preparing Alkylated (4-Phenylpiperidin-1-yl)(4,5,6,7-tetrahydro-1H-pyrazolo[3,4-c]pyridin-3-yl)methanones X

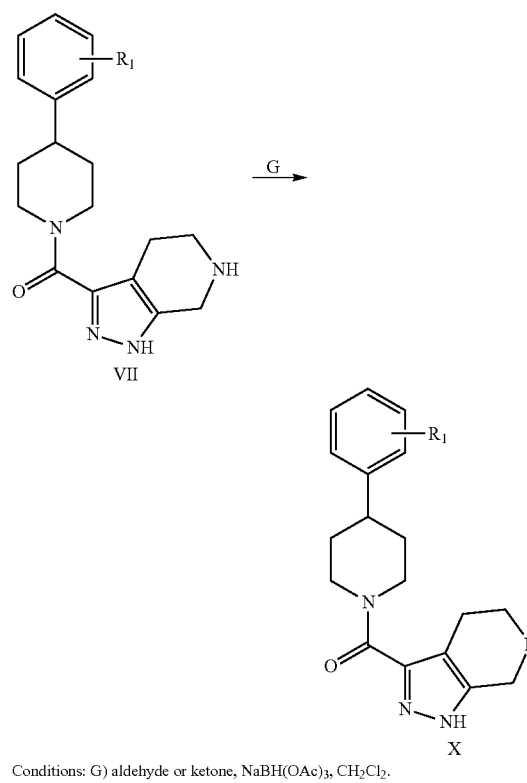

Conditions: G) aldehyde or ketone, NaBH(OAc)₃, CH₂Cl₂.

General Procedure (GP-G) for sulfonamide formation: A mixture of amine VII (1 equiv), desired aldehyde or ketone (1.5 equiv) and HOAc (6 equiv) in CH₂Cl₂ (0.25 M) was stirred for 16 hours at room temperature. To this was added sodium triacetoxyborohydride (NaBH(OAc)₃) and the mixture stirred at room temperature until the reaction was complete by LC-MS. The mixture was diluted with aqueous, saturated NaHCO₃ solution and extracted with CH₂Cl₂. The combined organic extracts were washed with H₂O, brine, dried over Na₂SO₄, filtered and concentrated under reduced pressure. The resulting residue was purified by silica gel chromatography (typical eluents included either a mixture of or hexanes and EtOAc or a mixture of CH₂Cl₂ and a 90:9:1 mixture of CH₂Cl₂/CH₃OH/concentrated NH₄OH) to afford the desired amines X. The product structure was verified by ¹H-NMR and by mass analysis.

General Procedures for Preparing (4-Phenylpiperidin-1-yl)(1,4,5,6-tetrahydropyrrolo[3,4-c]pyrazol-3-yl)methanone Carboxamides XII

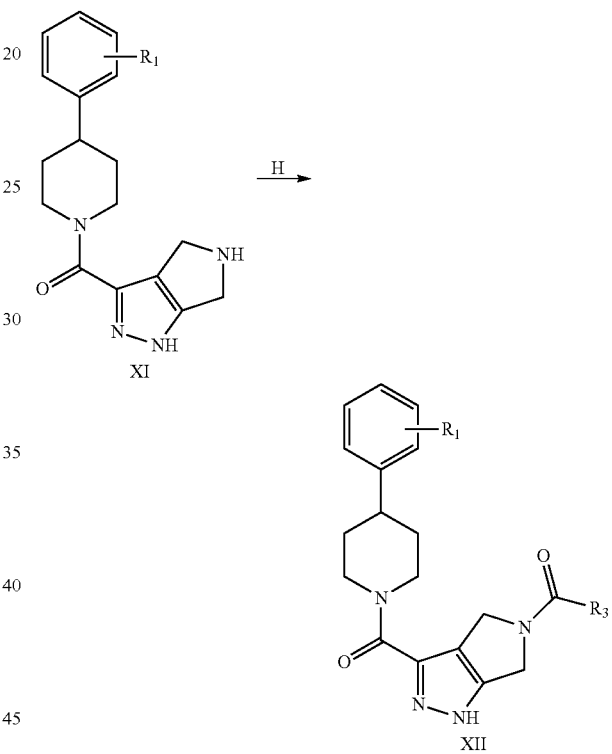

Conditions: H) acid chloride, Et₃N, CH₂Cl₂.

General Procedure (GP-H) for carboxamide formation: A mixture of amine XI (1 equiv), desired acid chloride (1 equiv) and triethylamine (Et₃N) (3 equiv) in CH₂Cl₂ (0.25 M) was stirred from 0° C. to room temperature until the reaction was complete by LC-MS. The mixture was diluted with H₂O and extracted with CH₂Cl₂. The combined organic extracts were washed with H₂O, brine, dried over Na₂SO₄, filtered and concentrated under reduced pressure. The resulting residue was purified by silica gel chromatography (typical eluents included either a mixture of or hexanes and EtOAc or a mixture of CH₂Cl₂ and a 90:9:1 mixture of CH₂Cl₂/CH₃OH/concentrated NH₄OH) to afford the desired carboxamides XII. The product structure was verified by ¹H NMR and by mass analysis.

General Procedures for Preparing (4-Phenylpiperidin-1-yl)(1,4,5,6-tetrahydropyrrolo[3,4-c]pyrazol-3-yl)methanone Sulfonamides XIII

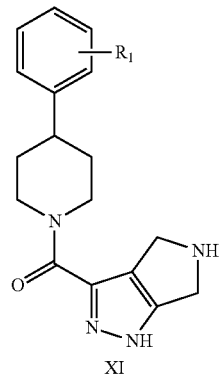

XI

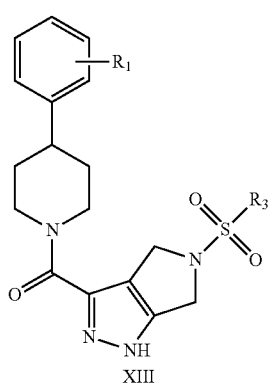

XIII

Conditions: I) sulfonyl chloride, i-Pr₂NEt, CH₂Cl₂.

General Procedure (GP-I) for sulfonamide formation: A mixture of amine XI (1 equiv), desired sulfonyl chloride (1 equiv) and i-Pr₂NEt (3 equiv) in CH₂Cl₂ (0.25 M) was stirred from 0° C. to room temperature until the reaction was complete by LC-MS. The mixture was diluted with H₂O and extracted with CH₂Cl₂. The combined organic extracts were washed with H₂O, brine, dried over Na₂SO₄, filtered and concentrated under reduced pressure. The resulting residue was purified by silica gel chromatography (typical eluents included either a mixture of or hexanes and EtOAc or a mixture of CH₂Cl₂ and a 90:9:1 mixture of CH₂Cl₂/CH₃OH/concentrated NH₄OH) to afford the desired sulfonamides XIII. The product structure was verified by ¹H NMR and by mass analysis.

General Procedures for Preparing Alkylated (4-Phenylpiperidin-1-yl)(1,4,5,6-tetrahydropyrrolo[3,4-c]pyrazol-3-yl)methanone XIV

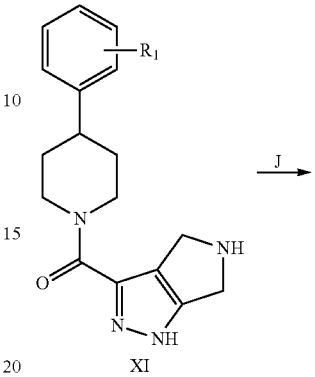

XI

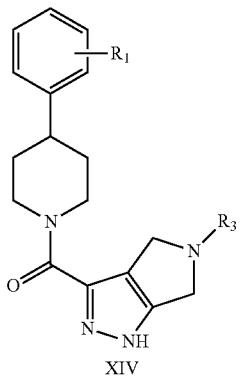

XIV

Conditions: J) aldehyde or ketone, NaBH(OAc)₃, CH₂Cl₂.

General Procedure (GP-J) for sulfonamide formation: A mixture of amine XI (1 equiv), desired aldehyde or ketone (1.5 equiv) and HOAc (6 equiv) in CH₂Cl₂ (0.25 M) was stirred for 16 hours at room temperature. To this was added sodium triacetoxyborohydride (NaBH(OAc)₃) and the mixture stirred at room temperature until the reaction was complete by LC-MS. The mixture was diluted with aqueous, saturated NaHCO₃ solution and extracted with CH₂Cl₂. The combined organic extracts were washed with H₂O, brine, dried over Na₂SO₄, filtered and concentrated under reduced pressure. The resulting residue was purified by silica gel chromatography (typical eluents included either a mixture of or hexanes and EtOAc or a mixture of CH₂Cl₂ and a 90:9:1 mixture of CH₂Cl₂/CH₃OH/concentrated NH₄OH) to afford the desired amines XIV. The product structure was verified by ¹H NMR and by mass analysis.

Preparation
4-(3-Fluoro-2-(trifluoromethyl)phenyl)piperidine Hydrochloride (5)

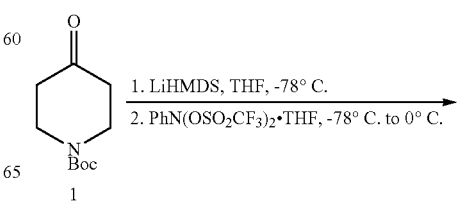

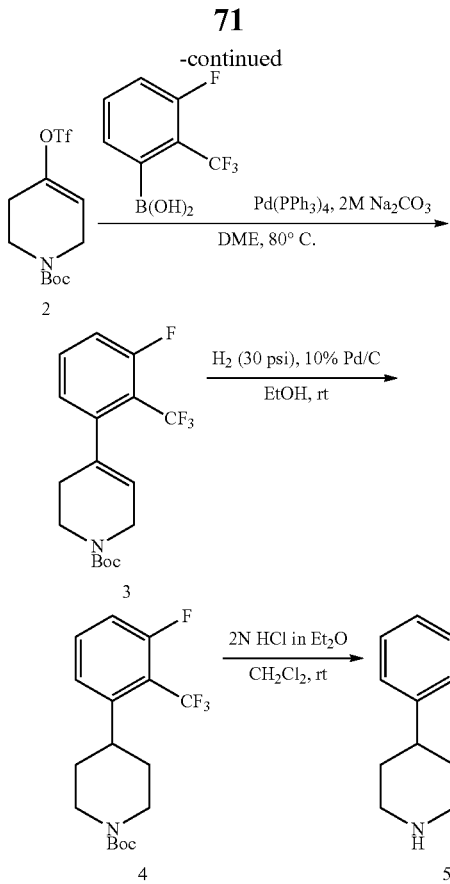

MHz, DMSO-$d_6$) δ 7.75-7.61 (m, 1H), 7.49-7.36 (m, 1H), 7.17 (d, J=7.8 Hz, 1H), 5.63-5.54 (m, 1H), 3.97-3.86 (m, 2H), 3.57-3.45 (m, 2H), 2.31-2.18 (m, 2H), 1.42 (s, 9H).

Step C: A mixture of tert-butyl 4-(3-fluoro-2-(trifluoromethyl) phenyl)-5,6-dihydropyridine-1(2H)-carboxylate (3, 4.7 g, 13.6 mmol) and 10% Pd/C (1.0 g) in EtOH (100 mL) was placed under an atmosphere of $H_2$ (30 psi) at ambient temperature for 18 h. the mixture was filtered through a Celite, and the filtrate was concentrated under reduced pressure to give tert-butyl 4-(3-fluoro-2-(trifluoromethyl) phenyl)piperidine-1-carboxylate (4) as a clear oil (4.80 g, >99%): $^1$H NMR (300 MHz, DMSO-$d_6$) δ 7.72-7.60 (m, 1H), 7.46 (d, J=8.1 Hz, 1H), 7.30 (dd, J=12.3, 8.1 Hz, 1H), 4.18-4.00 (m, 2H), 3.11-2.95 (m, 1H), 2.92-2.64 (m, 2H), 1.76-1.51 (m, 4H), 1.42 (s, 9H).

Step D: To a solution of tert-butyl 4-(3-fluoro-2(trifluoromethyl)phenyl)piperidine-1-carboxylate (4, 4.70 g, 13.6 mmol) in $CH_2Cl_2$ (40 mL) was added 2 N HCl (2.0 M in $Et_2O$, 40 mL). The mixture stirred at ambient temperature for 18 h and was diluted with $Et_2O$ (100 mL). The resulting precipitate was collected by filtration to give 4-(3-fluoro-2-(trifluoromethyl)phenylpiperidine hydrochloride as a white powder (5, 3.69 g, 96%): $^1$H NMR (300 MHz, DMSO-$d_6$) δ 9.09-8.80 (m, 2H), 7.83-7.70 (m, 1H), 7.44-7.29 (m, 2H), 3.42-3.31 (m, 2H), 3.29-3.15 (m, 1H), 3.14-2.95 (m, 2H), 2.11-1.91 (m, 2H), 1.89, 1.76 (m, 2H); ESI MS m/z 248 [M+H]+.

Preparation 4-(3,4-Difluoro-2-(trifluoromethyl)phenyl)piperidine (8)

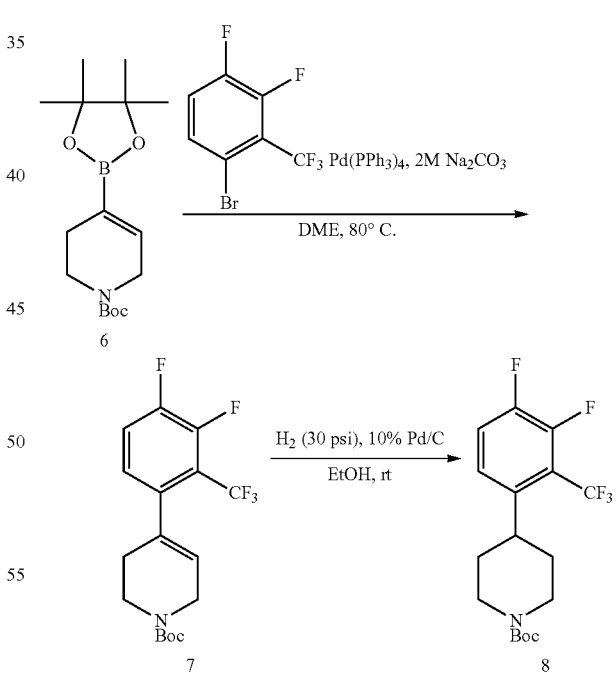

Step A: A mixture of tert-butyl 4-oxopiperidine-1-carboxylate (1, 1.0 g, 5.02 mmol) in THF (30 mL) was cooled to −78° C. LiHMDS (1.0 M solution in THF, 6.52 mL) was added dropwise over 30 min. The reaction was stirred at −78° C. for 1 h, then a solution of N-phenyl-bis(trifluoromethanesulfonimide) (2.52 g, 7.05 mmol) in THF (5.0 mL) was added dropwise over 30 min. The mixture stirred at 0° C. for 3 h, and was then concentrated under reduced pressure. The residue was chromatographed over silica gel (Isco CombiFlash Rf unit, 24 g Redisep column, 0% to 100% EtOAc in hexanes) to provide tert-butyl 4-(((trifluoromethyl)sulfonyl)oxy)-5,6-dihydropyridine-1(2H)-carboxylate (2) as a light yellow oil (1.50 g, 90%): $^1$H NMR (300 MHz, CDCl$_3$) δ 5.75 (br s, 1H), 4.05-4.02 (m, 2H), 3.64-3.60 (m, 2H), 2.44-2.42 (m, 2H), 1.46 (s, 9H).

Step B: A mixture of tert-butyl 4-(((trifluoromethyl)sulfonyl)oxy)-5,6-dihydropyridine-1(2H)-carboxylate (2, 3.50 g, 10.6 mmol), 3-fluoro-(2-trifluoromethyl)phenyl boronic acid (2.19 g, 10.6 mmol), Pd(PPh$_3$)$_4$ (1.22 g, 1.06 mmol), and 2 M Na$^2$CO$^3$ (62 mL) in DME (120 mL) was heated to 80° C. for 6 h. The mixture cooled to ambient temperature and was diluted with 5% aqueous LiCl solution (100 mL). The mixture was extracted with EtOAc (3×50 mL), and the combined organic extracts were washed with brine (2×50 mL) and concentrated under reduced pressure. The residue was diluted in $CH_2Cl_2$ (100 mL) and sent through a 300 mL silica gel plug, eluting with 10% EtOAc in hexanes (800 mL). The resulting filtrate was concentrated under reduced pressure and was chromatographed over silica gel (Isco CombiFlash R$^f$ unit, 80 g Redisep column, 0% to 50% EtOAc in hexanes) to provide tert-butyl 4-(3-fluoro-2-(trifluoromethyl)phenyl)-5,6-dihydropyridine-1(2H)-carboxylate (3) as a light yellow oil (2.39 g, 69%): $^1$H NMR (300

Step A: A mixture of tert-butyl 4-(4,4,5,5-tetramethyl-1,3,2-dioxaborolan-2-yl)-5,6-dihydropyridine-1(2H)-carboxylate (6, 57.4 g, 185 mmol), 3 1-bromo-3,4-difluoro-2-(trifluoromethyl)benzene (48.5 g, 185 mmol), Pd(PPh$_3$)$_4$ (21.5 g, 18.5 mmol), and 2 M Na$_2$CO$_3$ (150 mL) in DME (500 mL) was heated to 80° C. for 16 h. The mixture cooled to ambient temperature and was diluted with 5% aqueous LiCl solution (100 mL). The mixture was extracted with EtOAc (3×200 mL), and the combined organic extracts were washed with brine (2×200 mL) and concentrated under reduced pressure. The residue was diluted in $CH_2Cl_2$ (100 mL) and sent through a 300 mL silica gel plug, eluting with 10% EtOAc in hexanes (800 mL). The resulting filtrate was concentrated under reduced pressure and was chromatographed over silica gel (Isco CombiFlash Rf unit, 3×330 g Redisep columns, 0% to 50% EtOAc in hexanes) to provide tert-butyl 4-(3,4-difluoro-2-(trifluoromethyl) phenyl)-5,6-dihydropyridine-1(2H)-carboxylate (7) as a white solid (59.0 g, 92%): $^1$H NMR (300 MHz, $CDCl_3$) δ 7.34-7.28 (m, 1H), 6.93 (m, 1H), 5.55 (br, 1H), 4.01 (br, 2H), 3.60 (m, 2H), 2.30 (m, 2H), 1.50 (s, 9H); MS (ESI+) m/z 308 [M+H—$C_4H_8$]+.

Step B: A mixture of tert-butyl 4-(3,4-difluoro-2-(trifluoromethyl) phenyl)-5,6-dihydropyridine-1(2H)-carboxylate (7, 59.0 g, 162.3 mmol) and 10% Pd/C (5.0 g) in EtOH (200 mL) was placed under an atmosphere of $H_2$ (30 psi) at ambient temperature for 72 h. the mixture was filtered through a Celite, and the filtrate was concentrated under reduced pressure to give tert-butyl 4-(3,4-difluoro-2-(trifluoromethyl)phenyl)piperidine-1-carboxylate (8) as a white solid (57.9 g, 97%): $^1$H NMR (300 MHz, $CDCl_3$) δ 7.36-7.28 (m, 1H), 7.12 (m, 1H), 4.24 (br, 2H), 3.06 (m, 1H), 2.80 (m, 2H), 1.78-1.52 (m, 4H), 1.48 (s, 9H); MS (ESI+) m/z 310 [M+H—$C_4H_8$]+.

Preparation
4-(5-Fluoro-2-(trifluoromethyl)phenyl)piperidine Hydrochloride (11)

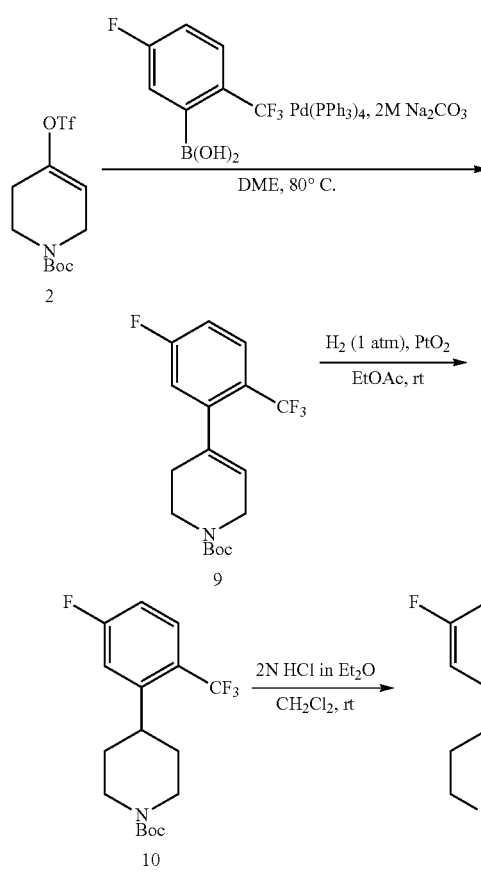

Step A: A mixture of tert-butyl 4-(((trifluoromethyl)sulfonyl)oxy)-5,6-dihydropyridine-1(2H)-carboxylate (2, 1.10 g, 3.32 mmol), 5-fluoro-(2-trifluoromethyl)phenyl boronic acid (0.69 g, 3.32 mmol), Pd(PPh$_3$)$_4$ (0.384 g, 0.332 mmol), and 2 M $Na_2CO_3$ (20 mL) in DME (50 mL) was heated at 80° C. for 6 h. The mixture cooled to ambient temperature, and the resulting solids were removed by filtration through a Celite pad. The filtrate was washed brine solution (4×50 mL) and concentrated under reduced pressure. The resulting residue was chromatographed over silica gel (Isco CombiFlash Rf unit, 40 g Redisep column, 0% to 80% EtOAc in hexanes) to provide tert-butyl 4-(5-fluoro-2-(trifluoromethyl)phenyl)-5,6-dihydropyridine-1(2H)-carboxylate (9) as a clear oil (0.542 g, 48%): $^1$H NMR (300 MHz, DMSO-$d_6$) δ 7.80 (dd, J=8.4, 6.0 Hz, 1H), 7.42-7.27 (m, 2H), 5.62 (br s, 1H), 3.97-3.87 (m, 2H), 3.51 (t, J=5.7 Hz, 2H), 2.34-2.23 (m, 2H), 1.42 (s, 9H).

Step B: A mixture of tert-butyl 4-(5-fluoro-2-(trifluoromethyl) phenyl)-5,6-dihydropyridine-1(2H)-carboxylate (9, 0.542 g, 1.58 mmol) and HCl (2 N solution in Et$_2$O, 10 mL) in $CH_2Cl_2$ (20 mL) stirred at ambient temperature for 18 h. The reaction mixture was diluted with Et$_2$O (30 mL), and the resulting precipitate was collected by filtration to provide 4-(5-fluoro-2-(trifluoromethyl) phenyl)-1,2,3,6-tetrahydropyridine hydrochloride (10) as a white solid (0.393 g, 88%): $^1$H NMR (300 MHz, DMSO-$d_6$) δ 9.26-9.00 (m, 2H), 7.84 (dd, J=8.7, 5.4 Hz, 1H), 7.46-7.36 (m, 1H), 7.24 (dd, J=9.3, 2.4 Hz, 1H), 5.67 (br s, 1H), 3.76-3.64 (m, 2H), 3.27 (t, J=5.1 Hz, 2H), 2.70-2.40 (m, 2H).

Step C: A mixture of 4-(5-fluoro-2-(trifluoromethyl)phenyl)-1,2,3,6-tetrahydropyridine hydrochloride (10, 0.393 g, 1.41 mmol) and PtO$_2$ (0.095 mg, 0.42 mmol) in EtOAc (14 mL) was stirred at ambient temperature for 18 h under a balloon of $H_2$. The mixture was filtered over Celite, and the filtrate was concentrated under reduced pressure and dissolved in $CH_2Cl_2$ (4 mL). To this solution was added HCl (2 N in Et$_2$O, 4.0 mL) and the resulting mixture stirred at ambient temperature for 20 min. The resulting suspension was diluted with Et$_2$O (20 mL) and the solids were collected by filtration to provide 4-(5-fluoro-2-(trifluoromethyl)phenyl)piperidine hydrochloride (11) as a white solid (309 mg, 78%): $^1$H NMR (300 MHz, DMSO-$d_6$) δ 8.81 (br s, 2H), 7.80 (dd, J=9.3, 6.0 Hz, 1H), 7.39-7.26 (m, 2H), 3.43-3.30 (m, 1H, overlaps with H$_2$O), 3.24-2.97 (m, 3H), 2.11-1.90 (m, 2H), 1.88-1.75 (m, 2H); ESI MS m/z 248 [M+H]+.

Preparation 4-(2-Chloro-3-fluorophenyl)piperidine Hydrochloride (14)

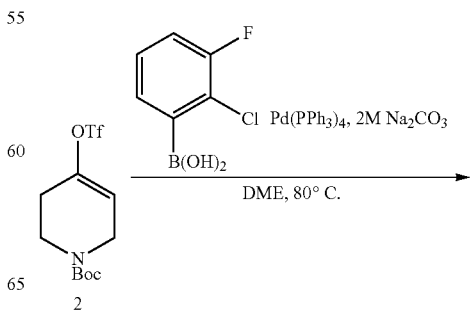

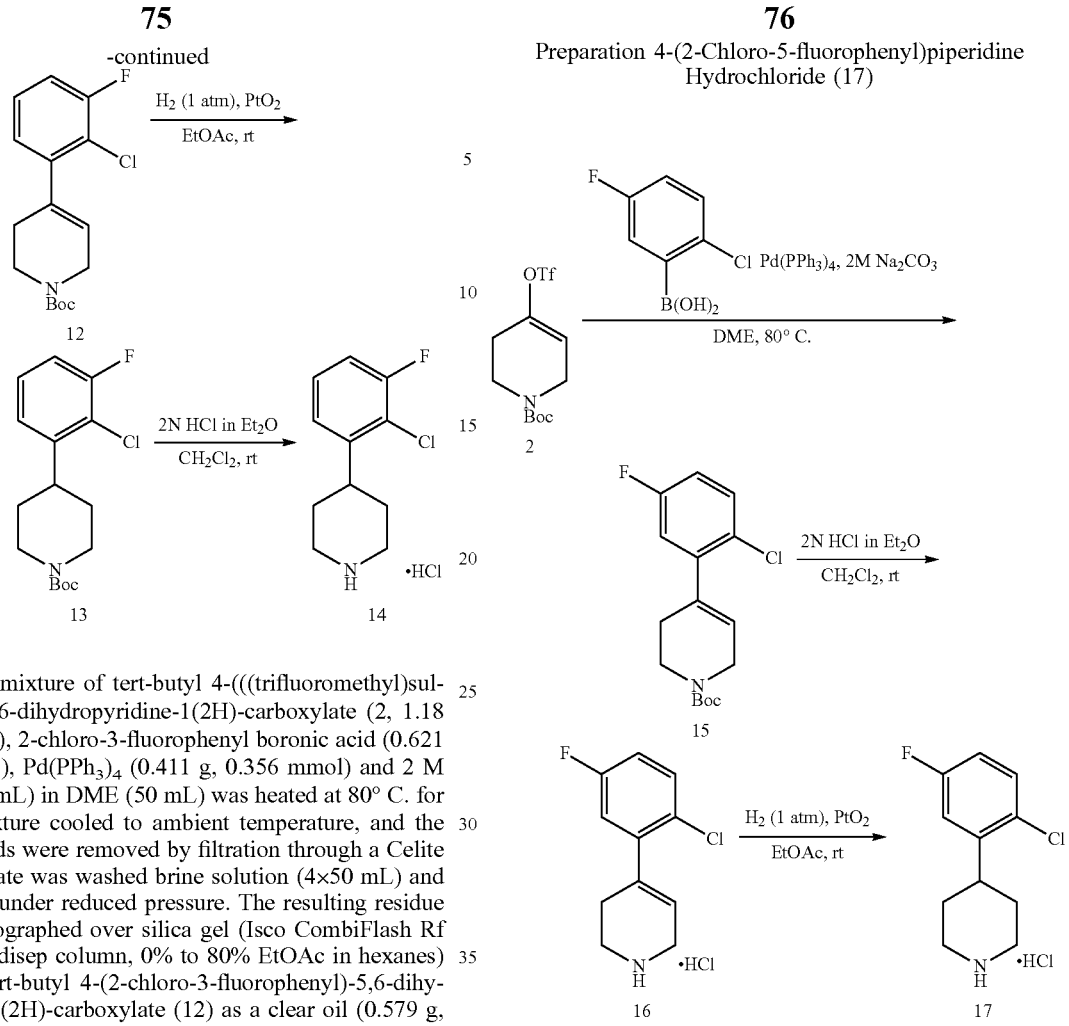

Preparation 4-(2-Chloro-5-fluorophenyl)piperidine Hydrochloride (17)

Step A: A mixture of tert-butyl 4-(((trifluoromethyl)sulfonyl)oxy)-5,6-dihydropyridine-1(2H)-carboxylate (2, 1.18 g, 3.56 mmol), 2-chloro-3-fluorophenyl boronic acid (0.621 g, 3.56 mmol), Pd(PPh$_3$)$_4$ (0.411 g, 0.356 mmol) and 2 M Na$_2$CO$_3$ (20 mL) in DME (50 mL) was heated at 80° C. for 6 h. The mixture cooled to ambient temperature, and the resulting solids were removed by filtration through a Celite pad. The filtrate was washed brine solution (4×50 mL) and concentrated under reduced pressure. The resulting residue was chromatographed over silica gel (Isco CombiFlash Rf unit, 40 g Redisep column, 0% to 80% EtOAc in hexanes) to provide tert-butyl 4-(2-chloro-3-fluorophenyl)-5,6-dihydropyridine-1(2H)-carboxylate (12) as a clear oil (0.579 g, 52%): $^1$H NMR (300 MHz, DMSO-d$_6$) δ 7.43-7.31 (m, 2H), 7.16-7.10 (m, 1H), 5.81-5.72 (m, 1H), 4.03-3.93 (m, 2H), 3.53 (t, J=5.7 Hz, 2H), 2.41-2.31 (m, 2H), 1.43 (s, 9H).

Step B: A mixture of tert-butyl 4-(2-chloro-3-fluorophenyl)-5,6-dihydropyridine-1(2H)-carboxylate (12, 0.488 g, 1.41 mmol) and PtO$_2$ (0.109 g, 0.48 mmol) in EtOAc (15 mL) was stirred at ambient temperature for 18 h under a balloon of H$_2$. The mixture was filtered over Celite, and the filtrate was concentrated under reduced pressure and dissolved in CH$_2$Cl$_2$ (4 mL). To this solution was added HCl (2 N in Et$_2$O, 4.0 mL) and the resulting mixture stirred at ambient temperature for 20 min. The resulting suspension was diluted with Et$_2$O (20 mL) and the solids were collected by filtration to provide tert-butyl-4-(2-chloro-3-fluorophenyl)piperidine-1 carboxylate (13) as a clear semi-solid (0.471 g, 95%): $^1$H NMR (300 MHz, DMSO-d$_6$) δ 7.43-7.19 (m, 3H), 4.17-4.01 (m, 2H), 3.20-3.03 (m, 1H), 2.95-2.68 (m, 2H), 1.79-1.65 (m, 2H), 1.58-1.45 (m, 2H), 1.41 (s, 9H).

Step C: To a solution of tert-butyl 4-(2-chloro-3-fluorophenyl) piperidine-1-carboxylate (13, 0.520 g, 1.66 mmol) in CH$_2$Cl$_2$ (10 mL) under an atmosphere of N$_2$ was added HCl (2 N in Et$_2$O, 10 mL) solution was stirred at ambient temperature for 18 h. The reaction mixture was diluted with Et$_2$O (20 mL). The resulting precipitate was collected by filtration and washed with Et$_2$O to provide 4-(2-chloro-3-fluorophenyl)piperidine hydrochloride (14) as a white solid (309 mg, 74%): $^1$H NMR (300 MHz, DMSO-d$_6$) δ 8.81-8.55 (m, 2H), 7.47-7.37 (m, 1H), 7.36-7.27 (m, 1H), 7.21-7.13 (m, 1H), 3.43-3.20, (m, 3H), 3.17-2.97 (m, 2H), 2.00-1.73 (m, 4H).

Step A: A mixture of tert-butyl 4-(((trifluoromethyl)sulfonyl)oxy)-5,6-dihydropyridine-1(2H)-carboxylate (2, 1.10 g, 3.3 mmol), 2-chloro-5-fluorophenyl boronic acid (0.58 g, 3.3 mmol), Pd(PPh$_3$)$_4$ (0.38 g, 0.33 mmol), and 2 M Na$_2$CO$_3$ (20 mL) in DME (50 mL) was heated at 80° C. for 6 h. The mixture cooled to ambient temperature, and the resulting solids were removed by filtration through a Celite pad. The filtrate was washed brine solution (4×50 mL) and concentrated under reduced pressure. The resulting residue was chromatographed over silica gel (Isco CombiFlash Rf unit, 40 g Redisep column, 0% to 80% EtOAc in hexanes) to provide tert-butyl 4-(2-chloro-5 fluorophenyl)-5,6-dihydropyridine-1(2H)-carboxylate (15) as a clear oil (0.57 g, 55%): $^1$H NMR (300 MHz, DMSO-d$_6$) δ 7.53-7.46 (m, 1H), 7.23-7.14 (m, 2H), 5.79-5.74 (m, 1H), 4.00-3.92 (m, 2H), 3.52 (t, J=5.7 Hz, 2H), 2.40-2.32 (m, 2H), 1.43 (s, 9H).

Step B: To a solution of tert-butyl 4-(2-chloro-5-fluorophenyl)-5,6-dihydropyridine-1(2H)-carboxylate (15, 0.573 g, 1.84 mmol) in CH$_2$Cl$_2$ (11 mL) was added HCl (2.0 N solution in Et$_2$O, 11.0 mL) and the mixture stirred at ambient temperature for 18 h. The reaction mixture was diluted with Et$_2$O (30 mL), and the resulting precipitate was collected by filtration to provide 4-(2-chloro-5-fluorophenyl)-1,2,3,6-tetrahydropyridine hydrochloride (16) as a white solid (0.267 g, 80%): $^1$H NMR (300 MHz, DMSO-d$_6$) δ 9.15 (br s, 2H), 7.54 (dd, J=9.0, 5.4 Hz, 1H), 7.29-7.17 (m, 1H), 7.14 (dd, J=9.3, 3.0 Hz, 1H), 5.84-5.79 (m, 1H), 3.76-3.68 (m, 2H), 3.28 (t, J=5.7 Hz, 2H), 2.62-2.53 (m, 2H); ESI MS m/z 212 [M+H]+.

Step C: A mixture of 4-(5-fluoro-2-(trifluoromethyl)phenyl)-1,2,3,6-tetrahydropyridine hydrochloride (16, 0.310 g, 1.31 mmol) PtO$_2$ (0.085 g, 0.37 mmol), and HOAc (71 µL, 1.31 mmol) in EtOAc (12 mL) stirred at ambient temperature for 18 under an atmosphere of H$_2$ (1 atm). The reaction mixture was diluted with EtOAc (50 mL) and CH$_3$OH (5 mL) and filtered over Celite and the filtrate was concentrated under reduced pressure and dissolved in CH$_2$Cl$_2$ (5 mL). To this solution was added HCl (2.0 N solution in Et$_2$O, 2.0 mL) and the mixture stirred at ambient temperature for 5 min. The resulting suspension was diluted with Et$_2$O (20 mL) and the solids collected by filtration to give 4-(2-chloro-5 fluorophenyl) piperidine hydrochloride (17) as an off-white solid (215 mg, 48%): $^1$H NMR (300 MHz, DMSO-d$_6$) δ 8.93-8.20 (m, 2H), 7.58-7.48 (m, 1H), 7.22-7.12 (m, 1H), 7.11-7.01 (m, 1H), 3.43-3.30 (m, 2H), 3.29-3.16 (m, 1H), 3.14-2.89 (m, 2H), 2.01-1.68 (m, 4H); ESI MS m/z 214 [M+H]+.

Preparation 4-(3,5-Bis(trifluoromethyl) phenyl) piperidine Hydrochloride (20)

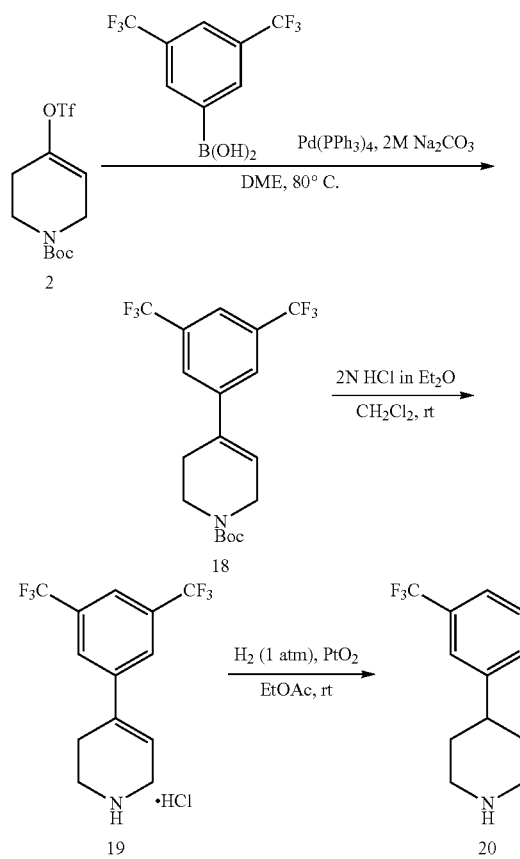

Step A: A solution of tert-butyl 4-(((trifluoromethyl)sulfonyl)oxy)-5,6-dihydropyridine-1(2H)-carboxylate (2, 1.10 g, 3.32 mmol) and (3,5-bis(trifluoromethyl)phenyl)boronic acid (1.42 g, 3.32 mmol), Pd(PPh$_3$)$_4$ (0.38 g, 0.33 mmol) and 2 M Na$_2$CO$_3$ (20 mL) in DME (50 mL) was heated at 80° C. for 6 h. The mixture cooled to ambient temperature, and the resulting solids were removed by filtration through a Celite pad. The filtrate was washed brine solution (4×50 mL) and concentrated under reduced pressure. The\ resulting residue was chromatographed over silica gel (Isco Combi-Flash Rf unit, 40 g Redisep column, 0% to 80% EtOAc in hexanes) to provide tert-butyl 4-(3,5-bis(trifluoromethyl)phenyl)-5,6-dihydropyridine-1(2H)-carboxylate (18) as a yellow oil (0.891 g, 68%): $^1$H NMR (300 MHz, DMSO-d$_6$) δ 8.09-8.04 (m, 2H), 8.00-7.96 (m, 1H), 6.53-6.42 (m, 1H), 4.09-4.00 (m, 2H), 3.55 (t, J=5.7 Hz, 2H), 2.60-2.52 (m, 2H), 1.43 (s, 9H).

Step B: To a solution of tert-butyl 4-(3,5 bis(trifluoromethyl) phenyl)-5,6-dihydropyridine-1(2H)-carboxylate (18, 0.891 g, 2.25 mmol) in CH$_2$Cl$_2$ (13.5 mL) in CH$_2$Cl$_2$ (11 mL) was added HCl (2.0 N solution in Et$_2$O, 11.0 mL) and the mixture stirred at ambient temperature for 18 h. The reaction mixture was diluted with Et$_2$O (30 mL), and the resulting precipitate was collected by filtration to provide 4-(3,5-bis(trifluoromethyl)phenyl)-1,2,3,6-tetrahydropyridine hydrochloride (19) as a white solid (0.452 g, 60%): $^1$H NMR (300 MHz, DMSO-d$_6$) δ 9.34 (br s, 2H), 8.14-8.09 (m, 2H), 8.08-8.04 (m, 1H), 6.59-6.53 (m, 1H), 3.83-3.74 (m, 2H), 3.38-3.25 (m, 2H), 2.83-2.71 (m, 2H); ESI MS m/z 296 [M+H]+.

Step C: A mixture of 4-(3,5-bis(trifluoromethyl)phenyl)-1,2,3,6-tetrahydropyridine hydrochloride (19, 452 mg, 1.37 mmol), ammonium formate (0.863 g, 13.7 mmol), and 10% Pd/C (0.332 g) in CH$_3$OH (10 mL) was heated at reflux for 7 h. The mixture was cooled to ambient temperature and was filtered over Celite. The filtrate was concentrated and the resulting residue was diluted in CH$_2$Cl$_2$ (8 mL) and CH$_3$OH (2 mL). To this solution was added HCl (2.0 N solution in Et$_2$O, 6 mL). The resulting solids were collected by filtration to give 4-(3,5-bis(trifluoromethyl)phenyl)piperidine hydrochloride (20) as a white solid (376 mg, 82%): $^1$H NMR (300 MHz, DMSO-d$_6$) δ 9.05-8.58 (m, 2H), 8.03-7.97 (m, 1H), 7.95-7.87 (m, 2H), 3.44-3.29 (m, 2H, overlaps with H$_2$O), 3.19-2.88 (m, 3H), 2.09-1.80 (m, 4H); ESI MS m/z 298 [M+H]+.

Preparation 4-(2-Fluoro-6-(trifluoromethyl) phenyl) piperidine Hydrochloride (23)

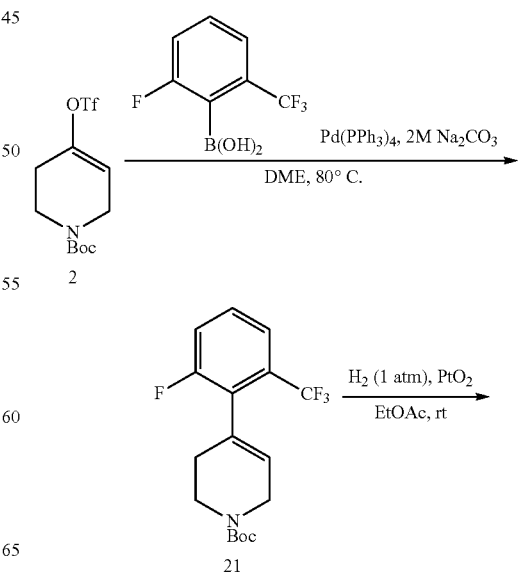

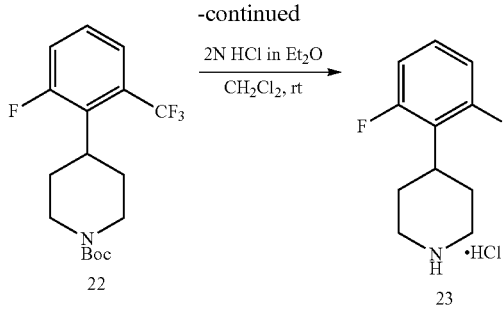

Preparation 4-(3,5-Difluoro-2-(trifluoromethyl)phenyl)piperidine Hydrochloride (28)

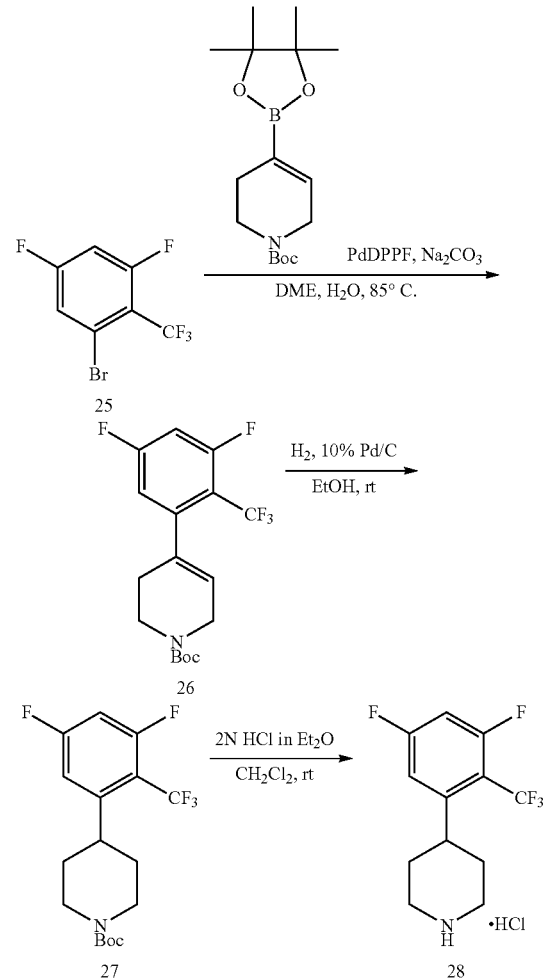

Step A: A mixture of tert-butyl 4-(((trifluoromethyl)sulfonyl)oxy)-5,6-dihydropyridine-1(2H)-carboxylate (2, 1.20 g, 3.62 mmol), and 6-fluoro-(2-trifluoromethyl)phenyl boronic acid (0.528 g, 2.53 mmol), Pd(PPh₃)₄ (0.292 g, 0.253 mmol), and 2 M Na₂CO₃ (20 mL) in DME (30 mL) was heated to 80° C. for 4 h. The mixture cooled to ambient temperature, was diluted with EtOAc (50 mL), and filtered through a Celite pad. The organic filtrate was washed with saturated sodium bicarbonate solution (2×30 mL), H₂O (30 ml), and concentrated to under reduced pressure. The resulting residue was chromatographed over silica gel (Isco CombiFlash Companion unit, 40 g Redisep column, 0% to 10% EtOAc in hexanes) to provide tert-butyl 4-(2-fluoro-6-(trifluoromethyl) phenyl)-5,6-dihydropyridine-1(2H)-carboxylate (21) as a clear oil (0.479 g, 39%): $^1$H NMR (300 MHz, DMSO-d₆) δ 7.66-7.51 (m, 3H), 5.68 (s, 1H), 4.04-3.82 (m, 2H), 3.67-3.39 (m, 2H), 2.39-2.02 (m, 2H), 1.43 (s, 9H).

Step B: A mixture of tert-butyl 4-(2-fluoro-6-(trifluoromethyl) phenyl)-5,6-dihydropyridine-1(2H)-carboxylate (21, 0.479 g, 1.41 mmol) and PtO₂ (0.095 g, 0.42 mmol) in EtOAc (15 mL) and HOAc (82 µL, 1.4 mmol) stirred at ambient temperature for 72 h under an atmosphere of H₂ (1 atm). The mixture was diluted with EtOAc (50 mL) and filtered over Celite. The filtrate was concentrated and the residue was chromatographed over silica gel (Isco CombiFlash Companion unit, 24 g Redisep column, 0% to 15% EtOAc in hexanes) to provide tert-butyl 4-(2-fluoro-6-(trifluoromethyl)phenyl)piperidine-1-carboxylate (22) as a white solid (0.219 g, 45%): $^1$H NMR (300 MHz, DMSO-d₆) δ 7.62-7.48 (m, 3H), 4.15-3.94 (m, 1H), 3.10-2.94 (m, 2H), 2.93-2.67 (m, 2H), 2.00-1.79 (m, 2H), 1.67-1.55 (m, 2H), 1.42 (s, 9H).

Step C: To a solution of tert-butyl 4-(2-fluoro-6-(trifluoromethyl) phenyl)piperidine-1-carboxylate (22, 0.219 g, 0.63 mmol) in CH₂Cl₂ (4 mL) was added 2 N HCl (2.0 N solution in Et₂O, 4 mL), and the mixture was stirred at ambient temperature for 4 h. The reaction mixture was diluted with Et₂O (50 mL) and the solids were collected by filtration to give 4-(2-fluoro-6-(trifluoromethyl)phenyl) piperidine hydrochloride (23) as an offwhite solid (158 mg, 88%): $^1$H NMR (300 MHz, DMSO-d₆) δ 8.82 (br s, 1H), 8.50 (br s, 1H), 7.66-7.48 (m, 3H), 3.42-3.33 (m, 2H), 3.24-2.95 (m, 3H), 2.35-2.15 (m, 2H), 1.87-1.74 (m, 2H); ESI MS m/z 248 [M+H]+.

Step A: A suspension of 3,5-difluoro-2-(trifluoromethyl) aniline (24, 1.0 g, 5.07 mmol) in a 48% aqueous HBr (8 mL) and H₂O (8 mL) was stirred at −5° C. for 5 min. To the suspension, NaNO₂ (350 mg, 5.07 mmol) was added in a 10 mL aqueous solution dropwise maintaining −5° C. The resulting mixture was stirred at −5° C. for 1 h then CuBr (1.09 g, 7.63 mmol) was added portion-wise and the resulting suspension was allowed to slowly warm to ambient temperature. After 4 hours, the resulting solution was extracted with hexanes (3×75 mL). The combined organics were dried over Na₂SO₄, filtered, and concentrated under reduced pressure. The resulting residue was chromatographed over silica gel (40 g Redisep column, pure hexanes) to afford 1-bromo-3,5-difluoro-2-(trifluoromethyl)benzene (25) as a light yellow liquid (1.01 g, 68%). $^1$H NMR (300 MHz, CDCl₃) δ 7.34-7.28 (m, 1H), 6.99-6.85 (m, 1H).

Step B: A mixture of 1-bromo-3,5-difluoro-2-(trifluoromethyl)benzene (25, 0.200 g, 0.76 mmol) and tert-butyl 4-(4,4,5,5-tetramethyl-1,3,2-dioxaborolan-2-yl)-5,6-dihydropyridine-1(2H)-carboxylate (0.237 g, 0.76 mmol), Pd(dppf) (0.056 g, 0.077 mmol), and 2 N $Na_2CO_3$ (2 mL, 4 mmol) in DME (3 mL) was heated to 85° C. for 5 h. The mixture was diluted with $H_2O$ (50 mL) and extracted with $CH_2Cl_2$ (3×75 mL). The combined organics were dried over $Na_2SO_4$, concentrated under reduced pressure, and the resulting residue was chromatographed over silica gel (24 g Redisep column, 0-25% EtOAc in hexanes) to afford tert-butyl 4-(3,5-difluoro-2-(trifluoromethyl)phenyl)-5,6-dihydropyridine-1(2H)-carboxylate (26) as a light yellow oil (0.325 g, 90%). $^1$H NMR (300 MHz, $CDCl_3$) δ 6.92-6.80 (m, 1H), 6.78-6.68 (m, 1H), 5.58 (s, 1H), 4.06-3.94 (m, 2H), 3.69-3.53 (m, 2H), 2.36-1.24 (m, 2H), 1.50 (s, 9H).

Step C: A mixture of tert-butyl 4-(3,5-difluoro-2-(trifluoromethyl) phenyl)-5,6-dihydropyridine-1(2H)-carboxylate (26, 0.750 g, 2.11 mmol) and 10% Pd/C (1.0 g) in EtOH (50 mL) stirred at ambient temperature under an atmosphere of $H_2$ for 24 h. The mixture was filtered through Celite and the filtrate concentrated under reduced pressure to afford tert-butyl 4-(3,5-difluoro-2-(trifluoromethyl) phenyl)piperidine-1-carboxylate (27) as a white solid (535 mg, 82%). $^1$H NMR (300 MHz, $CDCl_3$) δ 6.97-6.85 (m, 1H), 6.85-6.69 (m, 1H), 4.37-4.16 (m, 2H), 3.23-3.05 (m, 2H), 2.89-2.71 (m, 2H), 1.86-1.51 (m, 4H), 1.48 (s, 9H).

Step D: A solution of tert-butyl 4-(3,5-difluoro-2-(trifluoromethyl)phenyl)piperidine-1-carboxylate (27, 0.590 g, 1.61 mmol) in $CH_2Cl_2$ (10 mL) and HCl (2.0 N solution in $Et_2O$, 10 mL) stirred at ambient temperature for 18 h. The resulting solids were filtered to afford 4-(3,5-difluoro-2-(trifluoromethyl)phenyl)piperidine hydrochloride (28) as a white solid (0.309 g, 63%). $^1$H NMR (300 MHz, $CDCl_3$) δ 7.01-6.94 (m, 1H), 6.94-6.76 (m, 1H), 3.82-3.60 (m, 2H), 3.42-3.02 (m, 3H), 2.22-1.99 (m, 4H).

Preparation (4-(3-Fluoro-2-(trifluoromethyl)phenyl) piperidin-1-yl)(4,5,6,7-tetrahydro-1H-pyrazolo[3,4-c]pyridin-3-yl)methanone Hydrochloride (30)

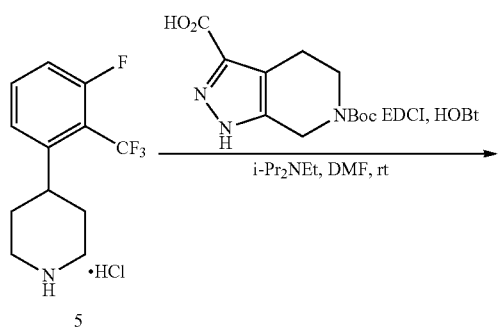

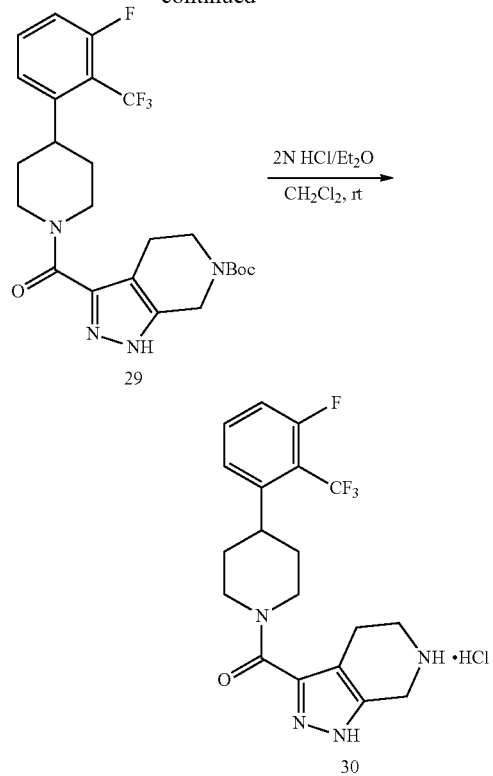

Step A: To a solution of 4-(3-fluoro-2-trifluoromethyl) phenylpiperidine hydrochloride (5, 0.080 g, 0.28 mmol), 6-(tert-butoxycarbonyl)-4,5,6,7-tetrahydro-1H-pyrazolo[3,4-c]pyridine-3-carboxylic acid (0.098 g, 0.67 mmol), and diisopropylethylamine (0.15 mL, 0.85 mmol) in DMF (5.3 mL) was added EDCI (0.065 mg, 0.34 mmol) and HOBt (46 mg, 0.34 mmol), and the mixture stirred at ambient temperature for 24 h. The mixture was diluted with $H_2O$ (30 mL) and extracted with EtOAc (4×30 mL). The combined organic extracts were washed with a saturated brine solution (4×30 mL) and concentrated to dryness under reduced pressure. The obtained residue was chromatographed over silica gel (Isco CombiFlash Rf unit, 12 g Redisep column, 0% to 10% $CH_3OH$ in $CH_2Cl_2$ with 0.1% $NH_4OH$ in $CH_2Cl_2$) to provide tert-butyl 3-(4-(3-fluoro-2-(trifluoromethyl)phenyl) piperidine-1-carbonyl)-4,5-dihydro-1H-pyrazolo[3,4-c]pyridine-6(7H)-carboxylate (29) as a white solid (66 mg, 47%): $^1$H NMR (300 MHz, DMSO-$d_6$) δ 13.20-12.78 (m, 1H), 7.73-7.59 (m, 1H), 7.46 (d, J=7.2 Hz, 1H), 7.37-7.24 (m, 1H), 4.90-4.60 (m, 2H), 4.53-4.43 (m, 2H), 3.60-3.48 (m, 2H), 3.28-2.98 (m, 2H), 2.85-2.69 (m, 1H), 2.65-2.50 (m, 2H, overlaps with solvent), 1.87-1.56 (m, 4H), 1.42 (s, 9H); ESI MS m/z 497 [M+H]+.

Step B: To a solution of tert-butyl 3-(4-(3-fluoro-2-(trifluoromethyl)phenyl)piperidine-1-carbonyl)-4,5-dihydro-1H-pyrazolo[3,4-c]pyridine-6(7H)-carboxylate (29, 0.066 g, 0.13 mmol) in $CH_2Cl_2$ (2 mL) was added HCl (2 mL, 2.0 N solution in $Et_2O$). The mixture stirred at ambient temperature for 18 h, was diluted with $Et_2O$ (30 mL), and the resulting solids were collected by filtration to give (4-(3-fluoro-2-(trifluoromethyl) phenyl)piperidin-1-yl)(4,5,6,7-tetrahydro-1H-pyrazolo[3,4-c]pyridin-3-yl)methanone hydrochloride (30) as a white solid (0.027 g, 47%): $^1$H NMR (300 MHz, DMSO-$d_6$) δ 9.46-9.20 (m, 2H), 7.74-7.61 (m, 1H), 7.46 (d, J=8.1 Hz, 1H), 7.37-7.25 (m, 1H), 4.70-4.44

(m, 2H), 4.34-4.22 (m, 2H), 3.50-3.10 (m, 4H), 2.93-2.76 (m, 3H), 1.86-1.60 (m, 4H); ESI MS m/z 468 [M+H]+.

Preparation ((4-(3-Fluoro-2-(trifluoromethyl)phenyl) piperidin-1-yl) (4,5,6,7-tetrahydro-1H-pyrazolo[4,3-c]pyridin-3-yl)methanone Hydrochloride (32)

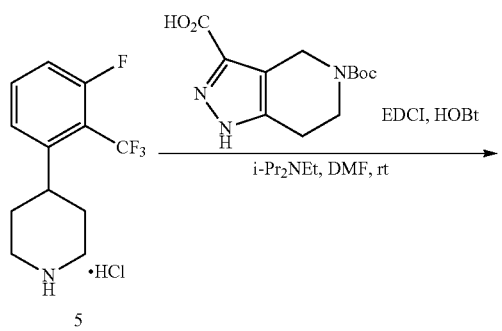

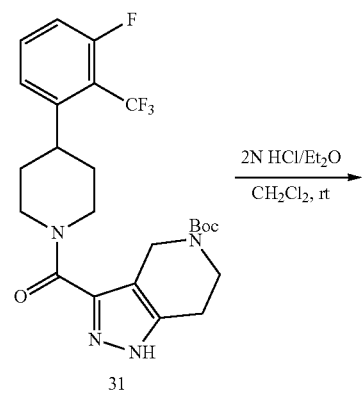

Step A: To a solution of 4-(3-fluoro-2-trifluoromethyl) phenylpiperidine hydrochloride (5, 0.080 g, 0.28 mmol), 5-(tert-butoxycarbonyl)-4,5,6,7-tetrahydro-1H-pyrazolo[3,4-c]pyridine-3-carboxylic acid (0.098 g, 0.67 mmol), and diisopropylethylamine (0.15 mL, 0.85 mmol) in DMF (5.3 mL) was added EDCI (0.065 mg, 0.34 mmol) and HOBt (46 mg, 0.34 mmol), and the mixture stirred at ambient temperature for 24 h. The mixture was diluted with H₂O (30 mL) and extracted with EtOAc (4×30 mL). The combined organic extracts were washed with a saturated brine solution (4×30 mL) and concentrated to dryness under reduced pressure. The obtained residue was chromatographed over silica gel (Isco CombiFlash Rf unit, 12 g Redisep column, 0% to 10% CH₃OH in CH₂Cl₂ with 0.1% NH₄OH in CH₂Cl₂) to provide tert-butyl 3-(4-(3-fluoro-2-(trifluoromethyl)phenyl) piperidine-1-carbonyl)-6,7-dihydro-1H-pyrazolo[4,3-c] pyridine-5(4H)-carboxylate (31) as a white solid (0.109 g, 77%): ¹H NMR (300 MHz, DMSO-d₆) δ 13.20-12.78 (m, 1H), 7.73-7.59 (m, 1H), 7.46 (d, J=7.2 Hz, 1H), 7.37-7.24 (m, 1H), 4.90-4.60 (m, 2H), 4.53-4.43 (m, 2H), 3.60-3.48 (m, 2H), 3.28-2.98 (m, 2H), 2.85-2.69 (m, 1H), 2.65-2.50 (m, 2H, overlaps with solvent), 1.87-1.56 (m, 4H), 1.42 (s, 9H); ESI MS m/z 497 [M+H]+.

Step B: To a solution of tert-butyl 3-(4-(3-fluoro-2-(trifluoromethyl)phenyl)piperidine-1-carbonyl)-6,7-dihydro-1H-pyrazolo[4,3-c]pyridine-5(4H)-carboxylate (31, 0.148 g, 0.30 mmol) in CH₂Cl₂ (2 mL) was added HCl (2 mL, 2.0 N solution in Et₂O). The mixture stirred at ambient temperature for 18 h, was diluted with Et₂O (30 mL), and the resulting solids were collected by filtration to give (4-(3-fluoro-2-(trifluoromethyl)phenyl)piperidin-1-yl) (4,5,6,7-tetrahydro-1H-pyrazolo[4,3-c]pyridin-3-yl)methanone hydrochloride (32) as a white solid (0.097 g, 75%): ¹H NMR (300 MHz, DMSO-d₆) δ 9.46-9.20 (m, 2H), 7.74-7.61 (m, 1H), 7.46 (d, J=8.1 Hz, 1H), 7.37-7.25 (m, 1H), 4.70-4.44 (m, 2H), 4.34-4.22 (m, 2H), 3.50-3.10 (m, 4H), 2.93-2.76 (m, 3H), 1.86-1.60 (m, 4H); ESI MS m/z 468 [M+H]+.

Preparation ((4-(3,4-Difluoro-2-(trifluoromethyl) phenyl)piperidin-1-yl)(4,5,6,7-tetrahydro-1H-pyrazolo[3,4-c]pyridin-3-yl)methanone Trifluoroacetic Acid Salt (34)

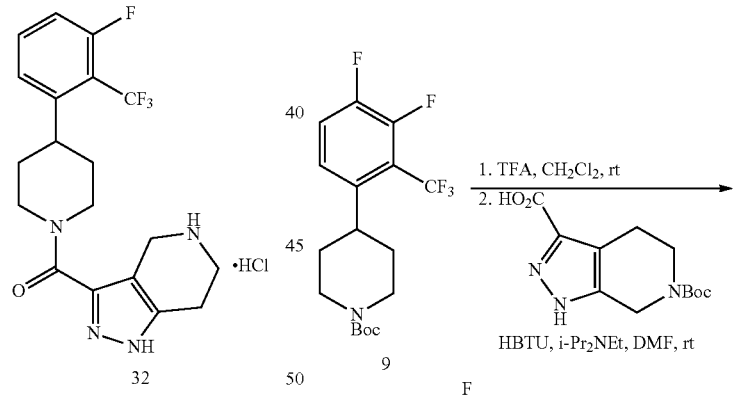

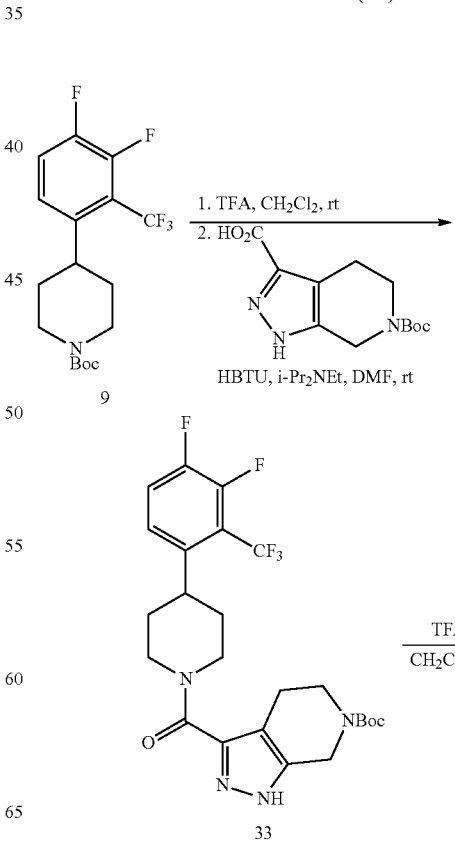

-continued

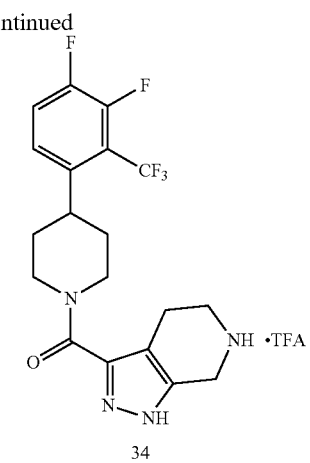

34

Step A: To a solution of tert-butyl 4-(3,4-difluoro-2-(trifluoromethyl)phenyl)piperidine-1-carboxylate (9, 41.1 g, 113 mmol) in CH$_2$Cl$_2$ (50 mL) was added TFA (50 mL). The mixture was stirred at ambient temperature for 1 h and was concentrated under reduced pressure. The residue was dissolved in DMF (240 mL) and to this solution was added N,N-diisopropylethylamine (72.4 g, 560 mmol), followed by 6-(tert-butoxycarbonyl)-4,5,6,7-tetrahydro-1H-pyrazolo[3,4-c]pyridine-3-carboxylic acid (30.1 g, 113 mmol), and HBTU (74.7 g, 169 mmol). The mixture stirred at ambient temperature for 16 h, was diluted with EtOAc (1 L) and washed with H$_2$O (1.4 L). The organic layer was washed with brine (3×600 mL), dried over Na$_2$SO$_4$, filtered, and concentrated under reduced pressure. The resulting residue was chromatographed over silica gel (30-80% EtOAc in hexanes) to give tert-butyl 3-(4-(3,4-difluoro-2-(trifluoromethyl)phenyl)piperidine-1-carbonyl)-4,5-dihydro-1H-pyrazolo[3,4-c]pyridine-6(7H)-carboxylate (33) as a white solid (41.2 g, 71%): $^1$H NMR (300 MHz, CDCl$_3$) δ 10.47 (br, 1H), 7.37-7.29 (m, 1H), 7.15 (m, 1H), 4.74 (br, 2H), 4.60 (s, 2H), 3.66 (br, 2H), 3.23 (m, 1H), 3.02 (br, 2H), 2.72 (m, 2H), 1.91-1.65 (m, 4H), 1.89-1.66 (m, 4H), 1.49 (s, 9H); MS (ESI+) m/z 515 [M+H]+.

Step B: To a solution of tert-butyl 3-(4-(3,4-difluoro-2-(trifluoro-methyl) phenyl) piperidine-1-carbonyl)-4,5-dihydro-1H-pyrazolo [3,4-c]pyridine-6(7H)-carboxylate (33, 41.2 g, 80.0 mmol) in CH$_2$Cl$_2$ (150 mL) was added TFA (70 mL). The mixture stirred at ambient temperature for 16 h and was then concentrated under reduced pressure to give ((4-(3,4-difluoro-2-(trifluoromethyl)phenyl) piperidin-1-yl) (4,5,6,7-tetrahydro-1H-pyrazolo[3,4-c]pyridin-3-yl)methanone TFA salt (34) as an off-white solid (40.0 g, >99%). The material was used as is without spectral characterization.

Preparation (4-(3,4-Difluoro-2-(trifluoromethyl) phenyl)piperidin-1-yl)(4,5,6,7-tetrahydro-1H-pyrazolo[4,3-c]pyridin-3-yl)methanone Trifluoroacetic Acid Salt (36)

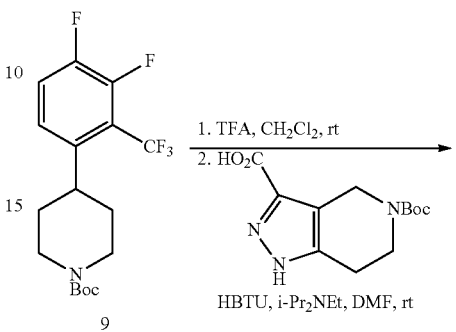

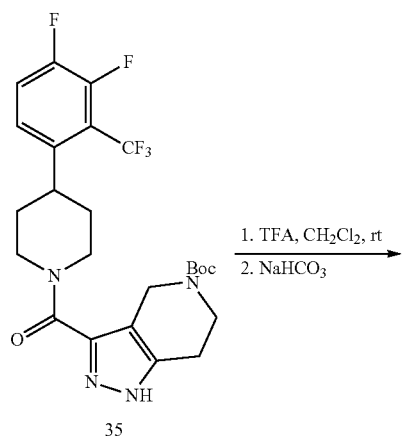

35

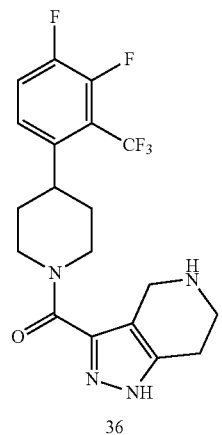

36

Step A: To a solution of tert-butyl 4-(3,4-difluoro-2-(trifluoromethyl)phenyl)piperidine-1-carboxylate (9, 41.1 g, 113 mmol) in CH$_2$Cl$_2$ (50 mL) was added TFA (50 mL). The mixture was stirred at ambient temperature for 1 h and was concentrated under reduced pressure. The residue was dissolved in DMF (240 mL) and to this solution was added N,N-diisopropylethylamine (72.4 g, 560 mmol), followed by 5-(tert-butoxycarbonyl)-4,5,6,7-tetrahydro-1H-pyrazolo[3,4-c]pyridine-3-carboxylic acid (30.1 g, 113 mmol), and HBTU (74.7 g, 169 mmol). The mixture stirred at ambient temperature for 16 h, was diluted with EtOAc (1 L) and washed with H$_2$O (1.4 L). The organic layer was washed with brine (3×600 mL), dried over Na$_2$SO$_4$, filtered, and concentrated under reduced pressure. The resulting residue was chromatographed over silica gel (30-80% EtOAc in hexanes) to give tert-butyl 3-(4-(3,4-difluoro-2-(trifluoromethyl) phenyl)piperidine-1-carbonyl)-6,7-dihydro-1H-pyrazolo[4,3-c] pyridine-5(4H)-carboxylate (35) as a white solid (0.068 g, 80%): $^1$H NMR (300 MHz, CDCl$_3$) δ 10.23 (br, 1H), 7.36-7.28 (m, 1H), 7.15 (m, 1H), 4.86 (br, 2H), 4.62 (s, 2H), 3.72 (br, 2H), 3.27-2.74 (m, 5H), 1.90-1.64 (m, 4H), 1.48 (s, 9H); MS (ESI+) m/z 515 [M+H]+.

Step B: To a mixture of tert-butyl 3-(4-(3,4-difluoro-2-(trifluoromethyl) phenyl) piperidine-1-carbonyl)-6,7-dihydro-1H-pyrazolo[4,3-c]pyridine-5(4H)-carboxylate (35, 41.2 g, 80.0 mmol) and CH$_2$Cl$_2$ (150 mL) was added TFA (70 mL). The mixture was stirred at ambient temperature for 16 h and was concentrated under reduced pressure. The residue was dissolved in CH$_2$Cl$_2$ and the solution washed with saturated NaHCO$_3$, dried over Na$_2$SO$_4$, filtered, and concentrated under reduced pressure. The resulting residue was chromatographed over silica gel (0-20% CH$_3$OH in CH$_2$Cl$_2$) to give (4-(3,4-difluoro-2-(trifluoromethyl) phenyl) piperidin-1-yl) (4,5,6,7-tetrahydro-1H-pyrazolo[4,3-c]pyridin-3-yl)methanone (36) as a white solid (0.052 g, 95%): $^1$H NMR (300 MHz, CDCl$_3$) δ 7.36-7.27 (m, 1H), 7.14 (m, 1H), 4.92 (m, 2H), 4.04 (s, 2H), 3.27-2.69 (m, 7H), 1.89-1.65 (m, 4H); MS (ESI+) m/z 415 [M+H]+.

Preparation (4-(3,4-Difluoro-2-(trifluoromethyl) phenyl)piperidin-1-yl)(1,4,5,6-tetrahydropyrrolo[3,4-c]pyrazol-3-yl)methanone Hydrochloride (38)

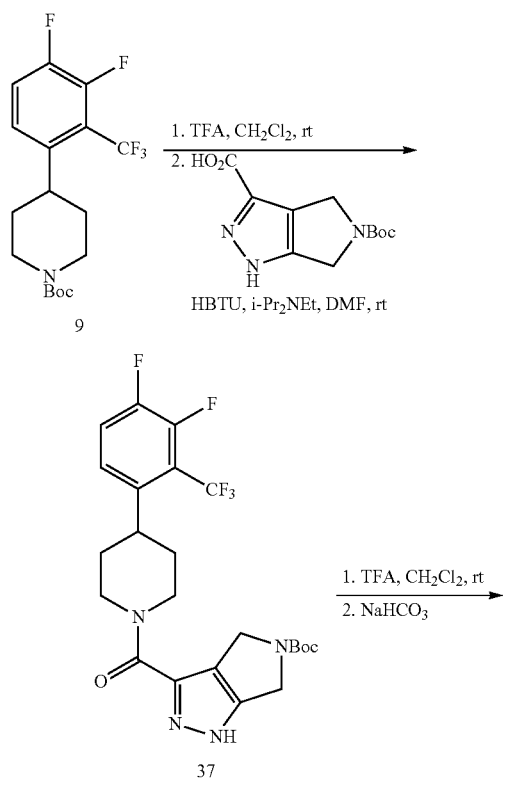

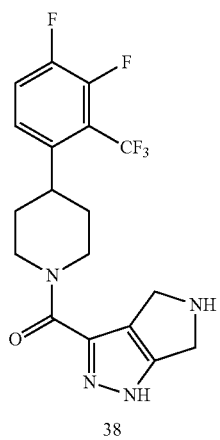

Step A: To a solution of tert-butyl 4-(3,4-difluoro-2-(trifluoromethyl)phenyl)piperidine-1-carboxylate (9, 0.100 g, 0.27 mmol) in CH$_2$Cl$_2$ (10 mL) was added TFA (2 mL). The mixture was stirred at ambient temperature for 1 h and was concentrated under reduced pressure. The residue was dissolved in DMF (2 mL) and to this solution was added 5-(tert-butoxycarbonyl)-1,4,5,6-tetrahydropyrrolo[3,4-c]pyrazole-3-carboxylic acid (0.073 g, 0.28 mmol), HBTU (0.191 g, 0.43 mmol), and N,N-diisopropylethylamine (0.11 g, 0.864 mmol). The mixture stirred at ambient temperature for 16 h and was diluted with EtOAc, washed with brine, dried over Na$_2$SO$_4$, filtered, and concentrated under reduced pressure. The resulting residue was chromatographed over silica gel (0-90% EtOAc in hexanes) to give tert-butyl 3-(4-(3,4-difluoro-2-(trifluoromethyl)phenyl)piperidine-1-carbonyl)-4,6-dihydropyrrolo[3,4-c]pyrazole-5(1H)-carboxylate (37) as a white solid (0.132 g, 91%): $^1$H NMR (300 MHz, CDCl$_3$) δ 10.39 (br, 1H), 7.38-7.30 (m, 1H), 7.15-7.08 (m, 1H), 4.80-4.26 (m, 6H), 3.26-3.20 (m, 2H), 2.92 (br, 1H), 1.96-1.66 (m, 4H), 1.51 (s, 9H); MS (ESI+) m/z 501 [M+H]+.

Step B: To a mixture of tert-butyl 3-(4-(3,4-difluoro-2-(trifluoro-methyl)phenyl) piperidine-1-carbonyl)-4,6-dihydropyrrolo [3,4-c] pyrazole-5(1H)-carboxylate (37, 0.132 g, 0.26 mmol) and CH$_2$Cl$_2$ (1 mL) was added TFA (1 mL). The mixture stirred at ambient temperature for 2 h and was concentrated under reduced pressure. The residue was dissolved in CH$_2$Cl$_2$ and the solution was washed with saturated NaHCO$_3$, dried over Na$_2$SO$_4$, filtered, and concentrated under reduced pressure. The resulting residue was chromatographed over silica gel (0-20% CH$_3$OH in CH$_2$Cl$_2$) to give (4-(3,4-difluoro-2-(trifluoromethyl)phenyl) piperidin-1-yl) (1,4,5,6-tetrahydropyrrolo [3,4-c]pyrazol-3-yl) methanone (38) as a white solid (0.070 g, 66%): $^1$H NMR (500 MHz, CDCl$_3$) δ 7.36-7.31 (m, 1H), 7.12 (m, 1H), 4.82 (br, 1H), 4.38 (br, 1H), 4.11 (s, 2H), 4.09 (s, 2H), 3.24 (m, 2H), 2.89 (br, 1H), 1.93-1.68 (m, 4H); MS (ESI+) m/z 401 [M+H]+.

Preparation (4-(2-Chloro-3-fluorophenyl)piperidin-1-yl)(4,5,6,7-tetrahydro-1Hpyrazolo[3,4-c]pyridin-3-yl)methanone Hydrochloride (40)

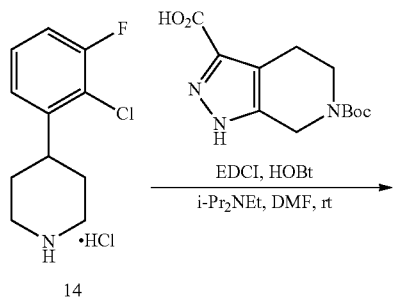

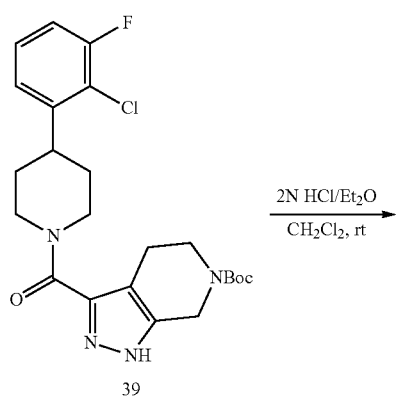

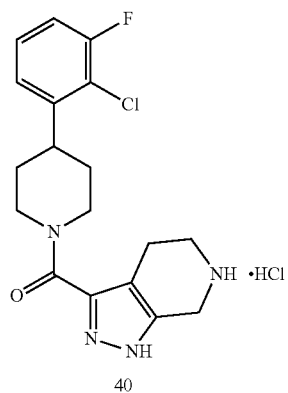

Step A: To a mixture of 4-(2-chloro-3-fluorophenyl)piperidine hydrochloride (14, 0.796 g, 3.18 mmol), 6-(tert-butoxycarbonyl)-4,5,6,7-tetrahydro-1H-pyrazolo[3,4-c]pyridine-3-carboxylic acid (0.935 g, 3.50 mmol), and diisopropylethylamine (1.7 mL, 9.76 mmol) in DMF (30 mL) was added EDCI (0.853 g, 4.45 mmol) and HOBt (0.601 g, 4.45 mmol). The mixture stirred at ambient temperature for 120 h, was concentrated under reduced pressure, and the obtained residue was chromatographed over silica gel (Isco CombiFlash Rf unit, 40 g Redisep column, 0% to 100% ethyl acetate in hexanes) to provide tert-butyl 3-(4-(2-chloro-3-(fluorophenyl)piperidine-1-carbonyl)-4,5-dihydro-1H-pyrazolo[3,4-c]pyridine-6(7H)-carboxylate (39) as a white solid (0.694 g, 47%): $^1$H NMR (300 MHz, CDCl$_3$) δ 7.24-7.18 (m, 1H), 7.06-7.00 (m, 2H), 4.93-4.42 (m, 3H), 3.67-3.65 (m, 2H), 3.39-3.01 (m, 3H), 2.73-2.70 (m, 2H), 2.14-1.94 (m, 2H), 1.71-1.68 (m, 2H), 1.49-1.44 (m, 11H); ESI MS m/z 463 [M+H]+.

Step B: To a solution of tert-butyl 3-(4-(2-chloro-3-(fluorophenyl)piperidine-1-carbonyl)-4,5-dihydro-1H-pyrazolo[3,4-c]pyridine-6(7H)-carboxylate (39, 0.694 g, 1.50 mmol) in CH$_2$Cl$_2$ (7 mL) was added 2 M HCl in Et$_2$O (16 mL). The mixture stirred at ambient temperature for 6 h, was diluted with Et$_2$O (30 mL), and the resulting solids were collected by filtration to give (4-(2-chloro-3-fluorophenyl)piperidin-1-yl)(4,5,6,7-tetrahydro-1H-pyrazolo[4,3-c] pyridin-3-yl)methanone hydrochloride (40) as an off-white solid (0.509 g, 94%): $^1$H NMR (300 MHz, DMSO-d$_6$) δ 13.18 (br s, 1H), 9.31 (br s, 2H), 7.38-7.23 (m, 3H), 4.69-4.65 (m, 2H), 4.49-4.21 (m, 2H), 3.39-3.11 (m, 4H), 2.99-2.84 (m, 3H), 1.94-1.54 (m, 4H); ESI MS m/z 363 [M+H]+.

Preparation (4-(2-Chloro-3-fluorophenyl)piperidin-1-yl)(4,5,6,7-tetrahydro-1Hpyrazolo[4,3-c]pyridin-3-yl)methanone Hydrochloride (42)

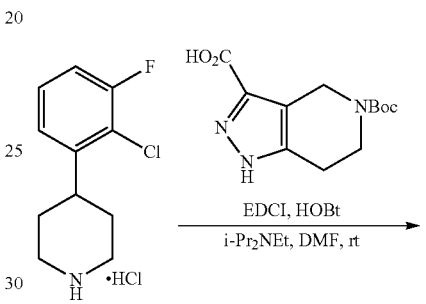

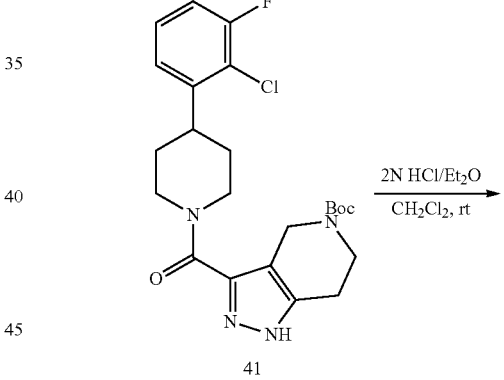

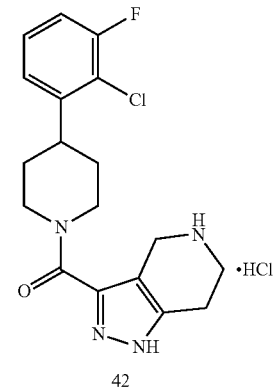

Step A: To a solution of 4-(2-chloro-3-fluorophenyl) piperidine hydrochloride (14, 90 mg, 0.36 mmol), 5-(tert-butoxycarbonyl)-4,5,6,7-tetrahydro-1H-pyrazolo[4,3-c] pyridine-3-carboxylic acid (96 mg, 0.36 mmol), and diisopropylethylamine (0.19 mL, 1.08 mmol) in DMF (7.8 mL) was added EDCI (83 mg, 0.43 mmol) and HOBt (58 mg, 0.43 mmol). The resulting solution was stirred at ambient temperature for 24 h. The reaction mixture was diluted with H$_2$O (30 mL), and the resulting precipitate was collected by filtration. The obtained solids were chromatographed over silica gel (Isco CombiFlash Rf unit, 12 g Redisep column, 0% to 5% CH$_3$OH in CH$_2$Cl$_2$ with 0.1% NH$_4$OH in CH$_2$Cl$_2$) to provide tert-butyl 3-(4-(2-chloro-3-fluorophenyl)piperidine-1-carbonyl)-6,7-dihydro-1Hpyrazolo[4,3-c]pyridine-5(4H)-carboxylate (41) as a white foam (139 mg, 82%): $^1$H NMR (500 MHz, DMSO-d$_6$) δ 13.11-12.91 (m, 1H), 7.39-7.32 (m, 1H), 7.30-7.22 (m, 2H), 5.28-5.13 (m, 1H), 4.75-4.60 (m, 1H), 4.49-4.36 (m, 2H), 3.65-3.53 (m, 2H), 3.33-3.25 (m, 1H, overlaps with H$_2$O), 3.24-3.08 (m, 1H), 2.91-276 (m, 1H), 2.67 (t, J=5.5 Hz, 2H), 1.91-1.75 (m, 2H), 1.67-1.50 (m, 2H), 1.41 (s, 9H); ESI MS m/z 463 [M+H]+.

Step B: To a solution of tert-butyl 3-(4-(2-chloro-3-fluorophenyl)piperidine-1-carbonyl)-6,7-dihydro-1H-pyrazolo[4,3-c]pyridine-5(4H)-carboxylate (41, 125 mg, 0.27 mmol) in CH$_2$Cl$_2$ (2 mL) was added HCl (2.0 N solution in Et$_2$O, 2 mL). The mixture was stirred for 18 h at ambient temperature. The reaction mixture was diluted with Et$_2$O (20 mL) and the resulting solids were collected by filtration to give (4-(2-chloro-3-fluorophenyl)piperidin-1-yl)(4,5,6,7-tetrahydro-1H-pyrazolo[4,3-c]pyridin-3-yl)methanone hydrochloride as a white solid (42, 93 mg, 86%): $^1$H NMR (300 MHz, DMSO-d$_6$) δ 9.37 (br s, 2H), 7.42-7.21 (m, 3H), 5.31-5.13 (m, 1H), 4.74-4.57 (m, 1H), 4.25-4.14 (m, 2H), 3.44-3.14 (m, 4H, overlaps with H$_2$O), 3.00-2.75 (m, 3H), 1.93-1.77 (m, 2H), 1.70-1.47 (m, 2H) missing N—H pyrazole; ESI MS m/z 363 [M+H]+.

Preparation (4-(5-Fluoro-2-(trifluoromethyl)phenyl) piperidin-1-yl)(4,5,6,7-tetrahydro-1H-pyrazolo[3,4-c]pyridin-3-yl)methanone Hydrochloride (44)

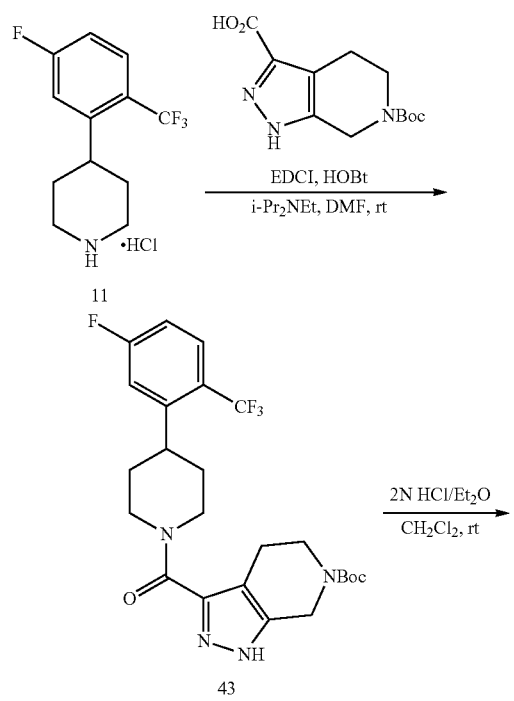

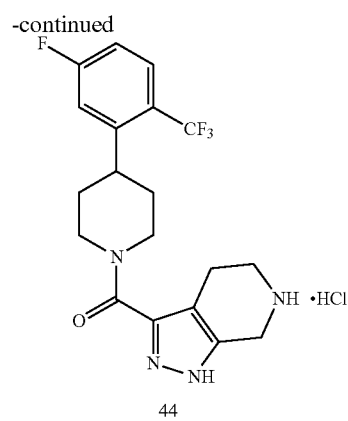

Step A: To a solution of 4-(5-fluoro-2-(trifluoromethyl) phenyl)piperidine hydrochloride (11, 93 mg, 0.33 mmol), 6-(tert-butoxycarbonyl)-4,5,6,7-tetrahydro-1H-pyrazolo[3,4-c]pyridine-3-carboxylic acid (88 mg, 0.33 mmol), and diisopropylethylamine (0.17 mL, 0.99 mmol) in DMF (6.0 mL) was added EDCI (76 mg, 0.40 mmol) and HOBt (54 mg, 0.40 mmol). The resulting solution was stirred at ambient temperature for 24 h. The reaction mixture was diluted with H$_2$O (10 mL) and extracted with EtOAc (3×30 mL). The combined organic extracts were washed with a saturated brine solution (4×20 mL) and concentrated to dryness under reduced pressure. The obtained residue was chromatographed over silica gel (Isco CombiFlash Rf unit, 12 g Redisep column, 0% to 5% MeOH in CH$_2$Cl$_2$ with 0.1% NH$_4$OH in CH$_2$Cl$_2$) to provide tert-butyl 3-(4-(5-fluoro-2-(trifluoromethyl) phenyl) piperidine-1-carbonyl)-4,5-dihydro-1H-pyrazolo[3,4-c]pyridine-6(7H)-carboxylate (43) as a white film (110 mg, 67%): $^1$H NMR (300 MHz, DMSO-d$_6$) δ 13.16-12.76 (m, 1H), 7.82-7.71 (m, 1H), 7.62-7.50 (m, 1H), 7.33-7.18 (m, 1H), 4.92-4.76 (m, 1H), 4.74-4.59 (m, 1H), 4.53-4.39 (m, 2H), 3.54 (t, J=5.7 Hz, 2H), 3.21-3.01 (m, 2H), 2.86-2.69 (m, 1H), 2.66-2.53 (m, 2H), 1.83-1.62 (m, 4H), 1.42 (s, 9H); ESI MS m/z 497 [M+H]+.

Step B: To a solution of tert-butyl 3-(4-(5-fluoro-2-(trifluoromethyl) phenyl) piperidine-1-carbonyl)-4,5-dihydro-1H-pyrazolo[3,4-c]pyridine-6(7H)-carboxylate (43, 107 mg, 0.21 mmol) in CH$_2$Cl$_2$ (2 mL) was added HCl (2N in Et$_2$O, 2 mL). The mixture stirred for 18 h at ambient temperature. The reaction mixture was diluted with Et$_2$O (20 mL) and the resulting solids were collected by filtration to provide (4-(5-fluoro-2-(trifluoromethyl) phenyl)piperidin-1-yl) (4,5,6,7-tetrahydro-1H-pyrazolo [3,4-c] pyridin-3-yl) methanone hydrochloride (44) as a white solid (66 mg, 71%): $^1$H NMR (500 MHz, DMSO-d$_6$) δ 13.52-13.13 (m, 1H), 9.41 (br s, 2H), 7.77 (dd, J=9.0, 5.7 Hz, 1H), 7.62-7.50 (m, 1H), 7.32-7.21 (m, 1H), 5.00-4.83 (m, 1H), 4.75-4.58 (m, 1H), 4.37-4.19 (m, 2H), 3.41-3.24 (m, 2H, overlaps with H$_2$O), 3.22-3.04 (m, 2H), 2.94-2.73 (m, 3H), 1.86-1.64 (m, 4H); ESI MS m/z 397 [M+H]+.

Preparation (4-(5-Fluoro-2-(trifluoromethyl)phenyl)piperidin-1-yl)(4,5,6,7-tetrahydro-1H-pyrazolo[4,3-c]pyridin-3-yl)methanone Hydrochloride (46)

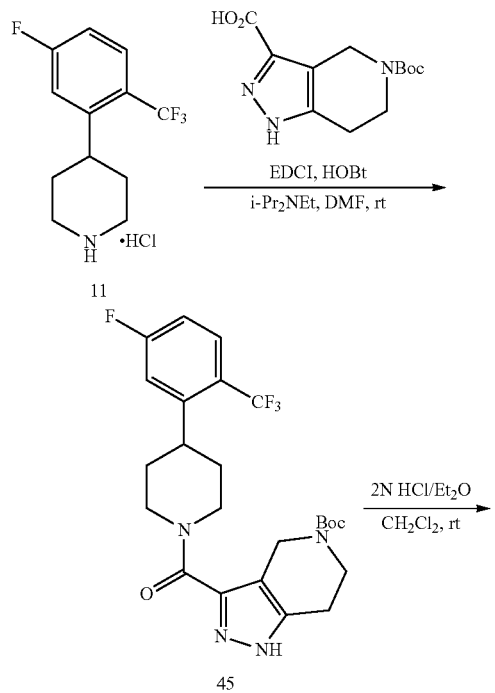

Step A To a solution of 4-(5-fluoro-2-trifluoromethyl)phenylpiperidine hydrochloride (11, 90 mg, 0.32 mmol), 5-(tert-butoxycarbonyl)-4,5,6,7-tetrahydro-1H-pyrazolo[4,3-c]pyridine-3-carboxylic acid (85 mg, 0.32 mmol), and diisopropylethylamine (0.17 mL, 0.96 mmol) in DMF (5.8 mL) was added EDCI (74 mg, 0.38 mmol) and HOBt (52 mg, 0.38 mmol). The resulting solution was stirred at ambient temperature for 24 h. The reaction mixture was diluted with $H_2O$ (10 mL) and extracted with EtOAc (3×30 mL). The combined organic extracts were washed with a saturated brine solution (4×20 mL) and concentrated to dryness under reduced pressure. The obtained residue was chromatographed over silica gel (Isco CombiFlash Rf unit, 12 g Redisep column, 0% to 5% MeOH in $CH_2Cl_2$ with 0.1% $NH_4OH$ in $CH_2Cl_2$) to provide tert-butyl 3-(4-(5-fluoro-2-(trifluoromethyl)phenyl) piperidine-1-carbonyl)-6,7-dihydro-1H-pyrazolo[4,3-c]pyridine-5(4H)-carboxylate (45) as a white film (120 mg, 80%): $^1$H NMR (300 MHz, DMSO-$d_6$) δ 12.96 (br s, 1H), 7.76 (dd, J=9.0, 5.7 Hz, 1H), 7.61-7.51 (m, 1H), 7.30-7.18 (m, 1H), 5.34-5.16 (m, 1H), 4.76-4.58 (m, 1H), 4.53-4.38 (m, 2H), 3.65-3.52 (m, 2H), 3.22-3.01 (m, 2H), 2.60-2.43 (m, 3H, overlaps with solvent), 1.83-1.65 (m, 4H), 1.42 (s, 9H); ESI MS m/z 497 [M+H]+.

Step B: To a solution of tert-butyl 3-(4-(5-fluoro-2-(trifluoromethyl)phenyl)piperidine-1-carbonyl)-6,7-dihydro-1H-pyrazolo[4,3-c]pyridine-5(4H)-carboxylate (45, 120 mg, 0.24 mmol) in $CH_2Cl_2$ (2 mL) was added HCl (2N in $Et_2O$, 2 mL). The mixture stirred for 18 h at ambient temperature. Additional HCl (2N in $Et_2O$, 1 mL) was added and the mixture was stirred at ambient temperature for 3 h. The reaction mixture was diluted with $Et_2O$ (20 mL) and the resulting solids were collected by filtration to provide (4-(5-fluoro-2-(trifluoromethyl)phenyl)piperidin-1-yl)(4,5,6,7-tetrahydro-1H-pyrazolo [4,3-c]pyridin-3-yl)methanone hydrochloride (46) as a white solid (104 mg, 99%): $^1$H NMR (300 MHz, DMSO-$d_6$) δ 9.54-9.19 (m, 2H), 7.84 (dd, J=9.0, 5.7 Hz, 1H), 7.60-7.51 (m, 1H), 7.32-7.20 (m, 1H), 5.32-5.12 (m, 1H), 4.78-4.60 (m, 1H), 4.29-4.16 (m, 2H), 3.43-3.30 (m, 2H, overlaps with $H_2O$), 3.26-3.06 (m, 2H), 2.95 (t, J=5.4 Hz, 2H), 2.89-2.72 (m, 1H), 1.84-1.65 (m, 4H) missing N—H pyrazole; ESI MS m/z 397 [M+H]+.

Preparation (4-(2-Chloro-5-fluorophenyl)piperidin-1-yl)(4,5,6,7-tetrahydro-1H-pyrazolo[3,4-c]pyridin-3-yl)methanone Hydrochloride (48)

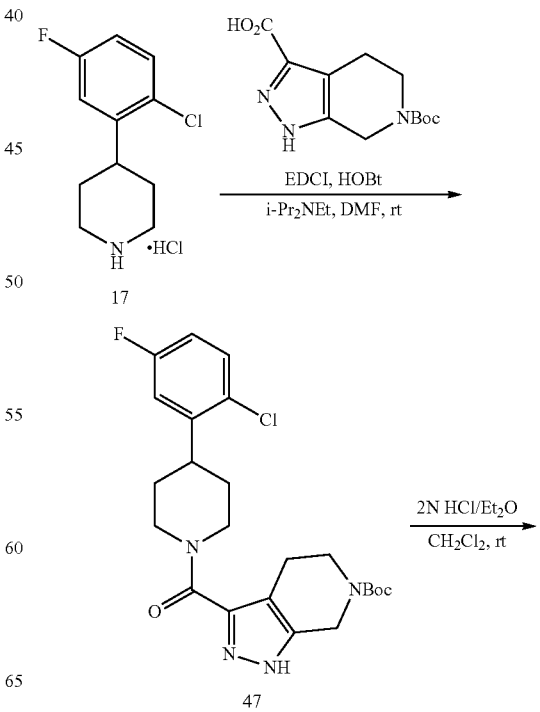

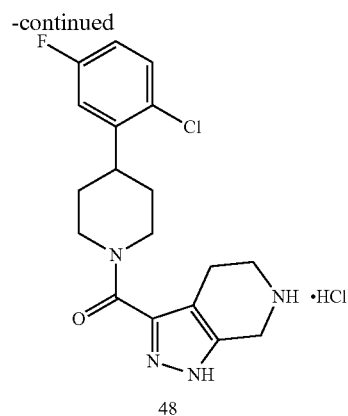

48

Step A: To a solution of 4-(2-chloro-5-fluorophenyl)piperidine hydrochloride (17, 70 mg, 0.28 mmol), 6-(tert-butoxycarbonyl)-4,5,6,7-tetrahydro-1H-pyrazolo[3,4-c]pyridine-3-carboxylic acid (104 mg, 0.39 mmol), and diisopropylethylamine (0.15 mL, 0.84 mmol) in DMF (5.4 mL) was added EDCI (65 mg, 0.34 mmol) and HOBt (45 mg, 0.34 mmol). The resulting solution was stirred at ambient temperature for 18 h. The reaction mixture was diluted with H$_2$O (20 mL) and extracted with EtOAc (4×20 mL). The combined organic extracts were washed with a saturated brine solution (9×20 mL), H$_2$O (2×20 mL) and concentrated to dryness under reduced pressure. The obtained residue was chromatographed over silica gel (Isco CombiFlash Rf unit, 12 g Redisep column, 0% to 100% EtOAc in hexanes) to provide tert-butyl 3-(4-(2-chloro-5-fluorophenyl)piperidine-1-carbonyl)-4,5-dihydro-1H-pyrazolo[3,4-c]pyridine-6(7H)-carboxylate (47) as a white solid (57 mg, 44%): $^1$H NMR (300 MHz, DMSO-d$_6$) δ 13.16-12.78 (m, 1H), 7.48 (dd, J=9.0, 5.7 Hz, 1H), 7.28 (dd, J=10.5, 3.3 Hz, 1H), 7.17-7.05 (m, 1H), 4.90-4.59 (m, 2H), 4.53-4.40 (m, 2H), 3.62-3.48 (m, 2H), 3.28-3.07 (m, 2H), 2.92-2.73 (m, 1H), 2.64-2.50 (m, 2H, overlaps with solvent), 1.93-1.69 (m, 2H), 1.68-1.49 (m, 2H), 1.42 (S, 9H); ESI MS m/z 463 [M+H]+.

Step B: To a solution of tert-butyl 3-(4-(2-chloro-5-fluorophenyl) piperidine-1-carbonyl)-4,5-dihydro-1H-pyrazolo[3,4-c] pyridine-6(7H)-carboxylate (47, 57 mg, 0.12 mmol) in CH$_2$Cl$_2$ (2 mL) was added HCl (2N in Et$_2$O, 2 mL). The mixture stirred for 18 h at ambient temperature. The reaction mixture was concentrated under reduced pressure to yield (4-(2-chloro-5-fluorophenyl)piperidin-1-yl)(4,5,6,7-tetrahydro-1H-pyrazolo[3,4-c]pyridin-3-yl)methanone hydrochloride (48) as a white solid (43 mg, 87%): $^1$H NMR (300 MHz, DMSO-d$_6$) δ 9.42 (br s, 2H), 7.49 (dd, J=8.7, 5.4 Hz, 1H), 7.28 (dd, J=10.2, 3.0 Hz, 1H), 7.16-7.07 (m, 1H), 4.71-4.43 (m, 2H), 4.32-4.23 (m, 2H), 3.38-3.14 (m, 4H, overlaps with H$_2$O), 2.91-2.72 (m, 3H), 1.89-1.73 (m, 2H), 1.69-1.50 (m, 2H), missing N—H pyrazole; ESI MS m/z 363 [M+H]+.

Preparation (4-(2-Chloro-5-fluorophenyl)piperidin-1-yl)(4,5,6,7-tetrahydro-1Hpyrazolo[4,3-c]pyridin-3-yl)methanone Hydrochloride (50)

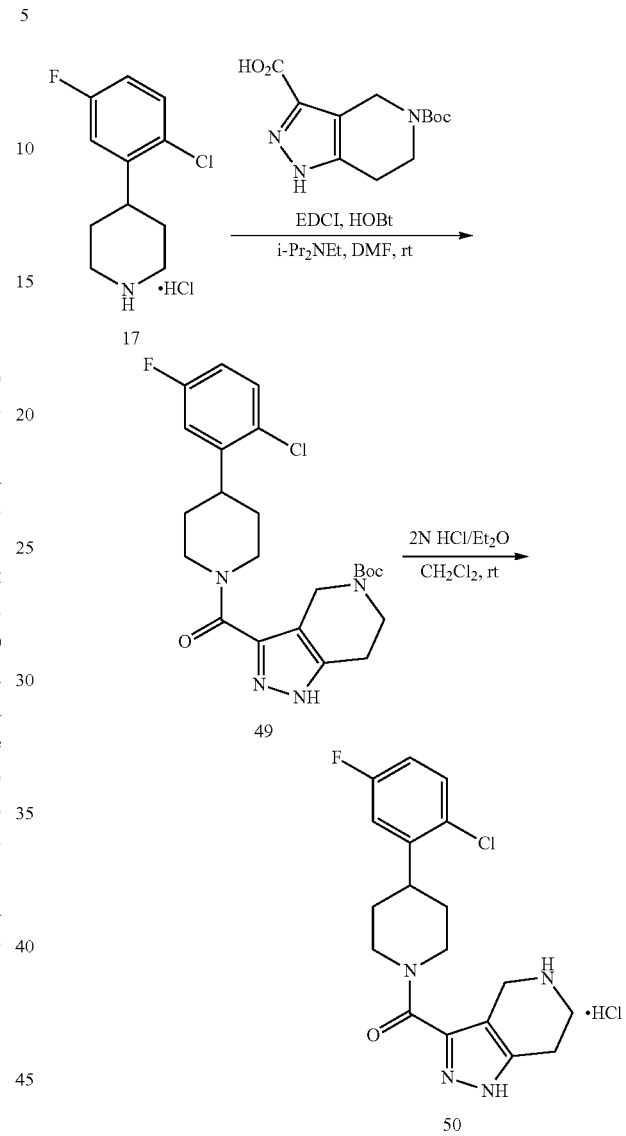

Step A: To a solution of 4-(2-chloro-5-fluorophenyl)piperidine hydrochloride (17, 70 mg, 0.28 mmol), 5-(tert-butoxycarbonyl)-4,5,6,7-tetrahydro-1H-pyrazolo[4,3-c]pyridine-3-carboxylic acid (89 mg, 0.34 mmol), and diisopropylethylamine (0.15 mL, 0.84 mmol) in DMF (5.4 mL) was added EDCI (64 mg, 0.34 mmol) and HOBt (45 mg, 0.34 mmol). The resulting solution was stirred at ambient temperature for 24 h. The reaction mixture was diluted with H$_2$O (20 mL) and extracted with EtOAc (4×20 mL). The combined organic extracts were washed with a saturated brine solution (8×20 mL), H$_2$O (20 mL), and concentrated to dryness under reduced pressure. The obtained residue was chromatographed over silica gel (Isco CombiFlash Rf unit, 12 g Redisep column, 0% to 100% EtOAc in hexanes) to give tert-butyl 3-(4-(2-chloro-5-fluorophenyl)piperidine-1-carbonyl)-6,7-dihydro-1H-pyrazolo[4,3-c]pyridine-5(4H)-carboxylate (49) as a white solid (78 mg, 60%): $^1$H NMR (300 MHz, DMSO-d$_6$) δ 12.96 (s, 1H), 7.48 (dd, J=8.7, 5.4 Hz, 1H), 7.34-7.21 (m, 1H), 7.16-7.06 (m, 1H), 5.28-5.11 (m, 1H), 4.77-4.57 (m, 1H), 4.53-4.38 (m, 2H), 3.66-3.52 (m, 2H), 3.30-3.04 (m, 2H, overlaps with H₂O), 2.92-2.61 (m, 3H), 1.92-1.74 (m, 2H), 1.69-1.49 (m, 2H), 1.41 (s, 9H); ESI MS m/z 462 [M+H]+.

Step B: To a solution of tert-butyl 3-(4-(2-chloro-5-fluorophenyl)piperidine-1-carbonyl)-6,7-dihydro-1H-pyrazolo[4,3-c]pyridine-5(4H)-carboxylate (49, 78 mg, 0.17 mmol) in CH₂Cl₂ (2 mL) was added HCl (2N in Et₂O, 2 mL). The mixture stirred for 18 h at ambient temperature. The reaction mixture was concentrated under reduced pressure to yield (4-(2-chloro-5-fluorophenyl)piperidin-1-yl)(4,5,6,7-tetrahydro-1H-pyrazolo[4,3-c]pyridin-3-yl)methanone hydrochloride (50) as a white solid (64 mg, 94%): ¹H NMR (300 MHz, DMSO-d₆) δ 9.19 (br s, 2H), 7.49 (dd, J=8.7, 5.4 Hz, 1H), 7.27 (dd, J=10.2, 3.0 Hz, 1H), 7.17-7.07 (m, 1H), 5.34-5.05 (m, 1H), 4.79-4.56 (m, 1H), 4.38-4.19 (m, 2H), 3.44-3.07 (m, 4H, overlaps with H₂O), 3.01-2.76 (m, 3H), 1.92-1.73 (m, 2H), 1.71-1.50 (m, 2H), missing N—H pyrazole; ESI MS m/z 363 [M+H]+.

Preparation ((4-(3,5-Bis(trifluoromethyl)phenyl) piperidin-1-yl) (4,5,6,7-tetrahydro-1H-pyrazolo[3,4-c]pyridin-3-yl)methanone Hydrochloride (52)

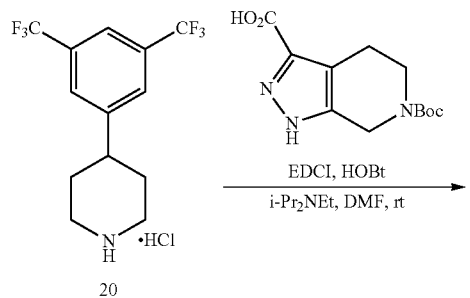

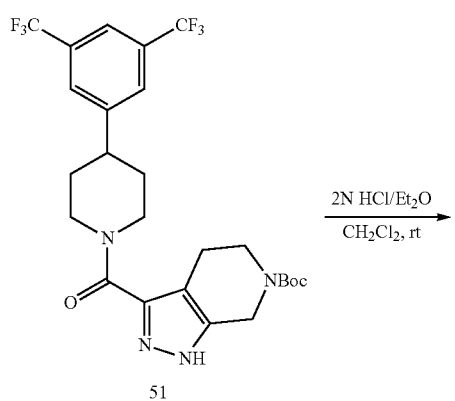

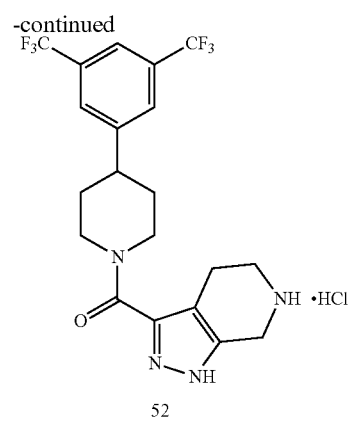

Step A: To a solution of 4-(3,5-bis(trifluoromethyl)phenyl)piperidine hydrochloride (20, 100 mg, 0.31 mmol), 6-(tert-butoxycarbonyl)-4,5,6,7-tetrahydro-1H-pyrazolo[3,4-c]pyridine-3-carboxylic acid (96 mg, 0.36 mmol), and diisopropylethylamine (0.16 mL, 0.90 mmol) in DMF (5.6 mL) was added EDCI (69 mg, 0.36 mmol) and HOBt (49 mg, 0.36 mmol). The resulting solution was stirred at ambient temperature for 18 h. The reaction mixture was diluted with H₂O (30 mL) and extracted with EtOAc (3×30 mL). The combined organic extracts were washed with a saturated brine solution (4×30 mL) and concentrated to dryness under reduced pressure. The obtained residue was chromatographed over silica gel (Isco CombiFlash Rf unit, 12 g Redisep column, 0% to 5% CH₃OH in CH₂Cl₂ with 0.1% NH₄OH in CH₂Cl₂) to provide tert-butyl 3-(4-(3,5-bis(trifluoromethyl)phenyl)piperidine-1-carbonyl)-4,5-dihydro-1H-pyrazolo[3,4-c]pyridine-6(7H)-carboxylate (51) as a white film (76 mg, 45%): ¹H NMR (300 MHz, DMSO-d₆) δ 13.13-12.77 (m, 1H), 8.02-7.98 (m, 2H), 7.96-7.91 (m, 1H), 4.91-4.59 (m, 2H), 4.53-4.41 (m, 2H), 3.60-3.46 (m, 2H), 3.21-3.03 (m, 2H), 2.85-2.69 (m, 1H), 2.63-2.54 (m, 2H, overlaps with solvent), 1.97-1.78 (m, 2H), 1.77-1.58 (m, 2H), 1.42 (s, 9H); ESI MS m/z 547 [M+H]+.

Step B: To a solution of tert-butyl 3-(4-(3,5-bis (trifluoromethyl)phenyl)piperidine-1-carbonyl)-4,5-dihydro-1H-pyrazolo[3,4-c]pyridine-6(7H)-carboxylate (51, 75 mg, 0.14 mmol) in CH₂Cl₂ (1 mL) was added HCl (2N in Et₂O, 1 mL). The mixture stirred for 18 h at ambient temperature. The reaction mixture was diluted with Et₂O (50 mL) and concentrated to yield (4-(3,5-bis(trifluoromethyl)phenyl)piperidin-1-yl)(4,5,6,7-tetrahydro-1H-pyrazolo[3,4-c]pyridin-3-yl)methanone hydrochloride (52) as a yellow solid (79 mg, >99%): ¹H NMR (300 MHz, DMSO-d₆) δ 9.37 (br s, 2H), 8.05-7.86 (m, 3H), 4.75-4.44 (m, 2H), 4.39-4.18 (m, 2H), 3.42-3.25 (m, 2H, overlaps with H₂O), 3.20-3.03 (m, 2H), 2.95-2.75 (m, 3H), 2.03-1.80 (m, 2H), 1.79-1.62 (m, 2H), missing N—H pyrazole; ESI MS m/z 447 [M+H]+.

Preparation (4-(3,5-Bis(trifluoromethyl)phenyl)piperidin-1-yl)(4,5,6,7-tetrahydro-1H-pyrazolo[4,3-c]pyridin-3-yl)methanone Hydrochloride (54)

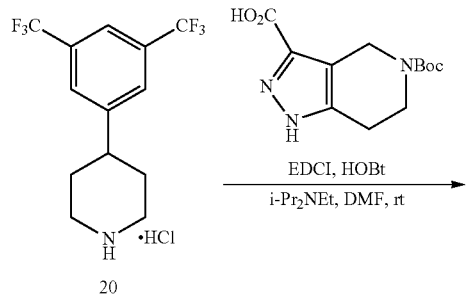

Step A: To a solution of 4-(3,5-bis(trifluoromethyl)phenyl)piperidine hydrochloride (20, 100 mg, 0.30 mmol), 5-(tert-butoxycarbonyl)-4,5,6,7-tetrahydro-1H-pyrazolo[4,3-c]pyridine-3-carboxylic acid (81 mg, 0.30 mmol), and diisopropylethylamine (0.18 mL, 0.90 mmol) in DMF (5.6 mL) was added EDCI (69 mg, 0.36 mmol) and HOBt (49 mg, 0.36 mmol). The resulting solution was stirred at ambient temperature for 18 h. The reaction mixture was diluted with H$_2$O (30 mL). The resulting precipitate was collected by filtration to yield tert-butyl 3-(4-(3,5-bis(trifluoromethyl)phenyl)piperidine-1-carbonyl)-6,7-dihydro-1H-pyrazolo[4,3-c]pyridine-5(4H)-carboxylate (53) as a white solid (142 mg, 86%): $^1$H NMR (300 MHz, DMSO-d$_6$) δ 12.95 (s, 1H), 8.03-7.97 (m, 2H), 7.95-7.90 (m, 1H), 5.31-5.13 (m, 1H), 4.76-4.58 (m, 1H), 4.52-4.39 (m, 2H), 3.64-3.53 (m, 2H), 3.20-3.03 (m, 2H), 2.87-2.61 (m, 3H), 1.97-1.81 (m, 2H), 1.78-1.58 (m, 2H), 1.41 (s, 9H); ESI MS m/z 547 [M+H]+.

Step B: To a solution of tert-butyl 3-(4-(3,5-bis(trifluoromethyl)phenyl)piperidine-1-carbonyl)-6,7-dihydro-1H-pyrazolo[4,3-c]pyridine-5(4H)-carboxylate (53, 142 mg, 0.26 mmol) in 1:1 MeOH/CH$_2$Cl$_2$ (2 mL) was added HCl (2N in Et$_2$O, 2 mL). The mixture was stirred for 18 h at ambient temperature. The reaction mixture was diluted with Et$_2$O (20 mL) and the resulting solids were collected by filtration to give (4-(3,5-bis(trifluoromethyl)phenyl)piperidin-1-yl)(4,5,6,7-tetrahydro-1H-pyrazolo[4,3-c]pyridin-3-yl)methanone hydrochloride (54) as an off-white solid (127 mg, >99%): $^1$H NMR (500 MHz, DMSO-d$_6$) δ 9.28 (br s, 2H), 8.02-7.98 (m, 2H), 7.96-7.92 (m, 1H), 5.30-5.09 (m, 1H), 4.78-4.55 (m, 1H), 4.28-4.14 (m, 2H), 3.43-3.28 (m, 2H, overlaps with H$_2$O), 3.26-3.07 (m, 2H), 3.02-2.90 (m, 2H), 2.89-2.75 (m, 1H), 2.00-1.82 (m, 2H), 1.80-1.61 (m, 2H), missing N—H pyrazole; ESI MS m/z 447 [M+H]+.

Preparation (4-(2-Fluoro-6-(trifluoromethyl)phenyl)piperidin-1-yl) (4,5,6,7-tetrahydro-1H-pyrazolo[3,4-c]pyridin-3-yl)methanone Hydrochloride (56)

Step A: To a solution of 4-(2-fluoro-6-(trifluoromethyl)phenyl)piperidine hydrochloride (20, 83 mg, 0.29 mmol), 6-(tert-butoxycarbonyl)-4,5,6,7-tetrahydro-1H-pyrazolo[3,4-c]pyridine-3-carboxylic acid (78 mg, 0.29 mmol), and diisopropylethylamine (0.15 mL, 0.88 mmol) in DMF (6.3 mL) was added EDCI (67 mg, 0.35 mmol) and HOBt (47 mg, 0.35 mmol). The resulting solution was stirred at ambient temperature for 18 h. The reaction mixture was diluted with H$_2$O (20 mL) and resulting solids were collected by filtration. The obtained solids were chromatographed over silica gel (Isco CombiFlash Rf unit, 12 g Redisep column, 0% to 5% MeOH in CH$_2$Cl$_2$ with 0.1% NH$_4$OH in CH$_2$Cl$_2$) to provide tert-butyl 3-(4-(2-fluoro-6-(trifluoromethyl) phenyl) piperidine-1-carbonyl)-4,5-dihydro-1H-pyrazolo[3,4-c]pyridine-6(7H)-carboxylate (55) as a clear film (95 mg, 65%): $^1$H NMR (300 MHz, DMSO-d$_6$) δ 13.27-12.72 (m, 1H), 7.63-7.45 (m, 3H), 4.86-4.56 (m, 2H), 4.55-4.38 (m, 2H), 3.63-3.43 (m, 2H), 3.27-3.00 (m, 2H), 2.92-2.41 (m, 3H, overlaps with solvent), 2.13-1.84 (m, 2H), 1.80-1.61 (m, 2H), 1.42 (s, 9H); ESI MS m/z 496 [M+H]+.

Step B: To a solution of tert-butyl 3-(4-(2-fluoro-6-(trifluoromethyl)phenyl)piperidine-1-carbonyl)-4,5-dihydro-1H pyrazolo [3,4-c]pyridine-6(7H)-carboxylate (55, 94 mg, 0.19 mmol) in CH$_2$Cl$_2$ (3 mL) was added HCl (2N in Et$_2$O, 3 mL). The mixture was stirred for 18 h at ambient temperature. The reaction mixture was diluted with Et$_2$O (20 mL) and the mixture concentrated under reduced pressure to yield (4-(2-fluoro-6-(trifluoromethyl)phenyl)piperidin-1-yl) (4,5,6,7-tetrahydro-1H-pyrazolo[3,4-c]pyridin-3-yl)methanone hydrochloride (56) as a white solid (80 mg, 97%): $^1$H NMR (300 MHz, DMSO-d$_6$) δ 9.39-9.26 (m, 2H), 7.63-7.47 (m, 3H), 4.76-4.40 (m, 1H), 4.35-4.25 (m, 2H), 3.78-3.39 (m, 4H), 3.25-3.08 (m, 2H), 2.91-2.78 (m, 3H), 2.11-1.88 (m, 2H), 1.81-1.66 (m, 2H); ESI MS m/z 397 [M+H]+.

Preparation (4-(2-Fluoro-6-(trifluoromethyl)phenyl) piperidin-1-yl)(4,5,6,7-tetrahydro-1H-pyrazolo[4,3-c]pyridin-3-yl)methanone Hydrochloride (58)

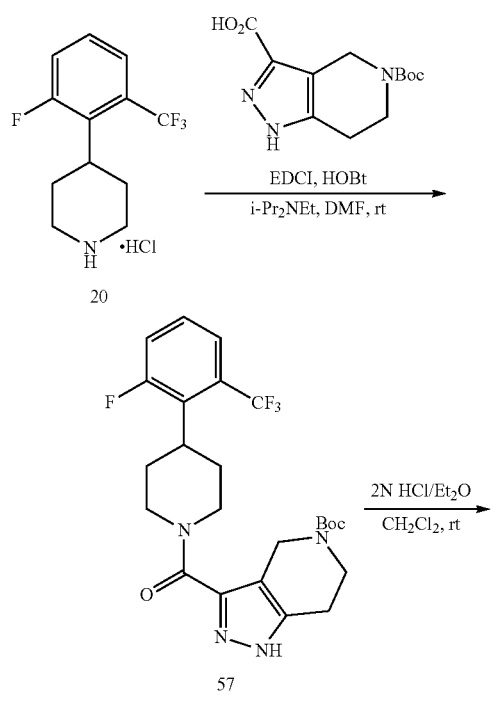

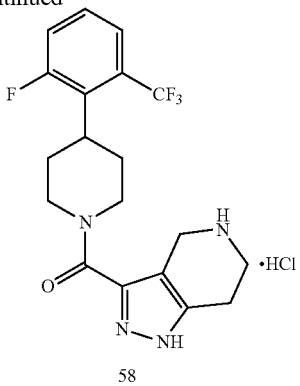

Step A: To a solution of 4-(3,5-bis(trifluoromethyl)phenyl)piperidine hydrochloride (20, 100 mg, 0.30 mmol), 5-(tert-butoxycarbonyl)-4,5,6,7-tetrahydro-1H-pyrazolo[4,3-c]pyridine-3-carboxylic acid (81 mg, 0.30 mmol), and diisopropylethylamine (0.18 mL, 0.90 mmol) in DMF (5.6 mL) was added EDCI (69 mg, 0.36 mmol) and HOBt (49 mg, 0.36 mmol). The resulting solution was stirred at ambient temperature for 18 h. The reaction mixture was diluted with H$_2$O (30 mL). The resulting precipitate was collected by filtration to yield tert-butyl 3-(4-(3,5-bis(trifluoromethyl)phenyl)piperidine-1-carbonyl)-6,7-dihydro-1H-pyrazolo[4,3-c]pyridine-5(4H)-carboxylate (53) as a white solid (142 mg, 86%): $^1$H NMR (300 MHz, DMSO-d$_6$) δ 12.95 (s, 1H), 8.03-7.97 (m, 2H), 7.95-7.90 (m, 1H), 5.31-5.13 (m, 1H), 4.76-4.58 (m, 1H), 4.52-4.39 (m, 2H), 3.64-3.53 (m, 2H), 3.20-3.03 (m, 2H), 2.87-2.61 (m, 3H), 1.97-1.81 (m, 2H), 1.78-1.58 (m, 2H), 1.41 (s, 9H); ESI MS m/z 547 [M+H]+.

Step B: To a solution of tert-butyl 3-(4-(3,5-bis (trifluoromethyl)phenyl)piperidine-1-carbonyl)-6,7-dihydro-1H-pyrazolo[4,3-c]pyridine-5(4H)-carboxylate (53, 142 mg, 0.26 mmol) in 1:1 MeOH/CH$_2$Cl$_2$ (2 mL) was added HCl (2N in Et$_2$O, 2 mL). The mixture was stirred for 18 h at ambient temperature. The reaction mixture was diluted with Et$_2$O (20 mL) and the resulting solids were collected by filtration to give (4-(3,5-bis(trifluoromethyl) phenyl)piperidin-1-yl)(4,5,6,7-tetrahydro-1H-pyrazolo[4,3-c]pyridin-3-yl)methanone hydrochloride (54) as an off-white solid (127 mg, >99%): $^1$H NMR (500 MHz, DMSO-d$_6$) δ 9.28 (br s, 2H), 8.02-7.98 (m, 2H), 7.96-7.92 (m, 1H), 5.30-5.09 (m, 1H), 4.78-4.55 (m, 1H), 4.28-4.14 (m, 2H), 3.43-3.28 (m, 2H, overlaps with H$_2$O), 3.26-3.07 (m, 2H), 3.02-2.90 (m, 2H), 2.89-2.75 (m, 1H), 2.00-1.82 (m, 2H), 1.80-1.61 (m, 2H), missing N—H pyrazole; ESI MS m/z 447 [M+H]+.

Preparation (4-(3,5-Difluoro-2-(trifluoromethyl)
phenyl)piperidin-1-yl) (4,5,6,7-tetrahydro-1H-pyra-
zolo[3,4-c]pyridin-3-yl)methanone Hydrochloride
(60)

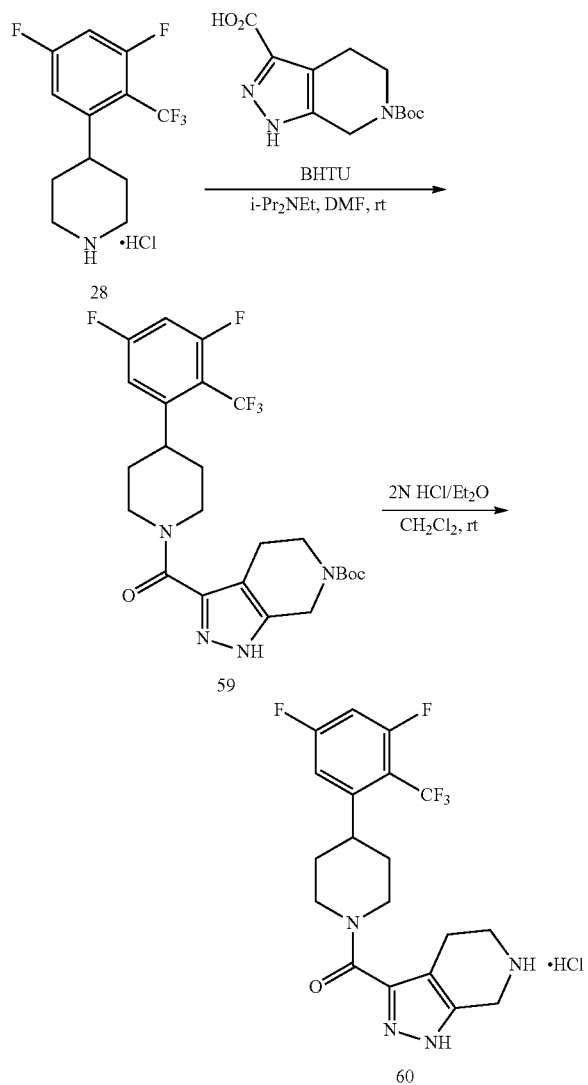

Step A: To a suspension of 4-(3,5-difluoro-2-(trifluoromethyl) phenyl)piperidine hydrochloride (28, 500 mg, 1.66 mmol), 6-(tert-butoxycarbonyl)-4,5,6,7-tetrahydro-1Hpyrazolo[3,4-c]pyridine-3-carboxylic acid (443 mg, 1.66 mmol), and diisopropylethylamine (36 μL, 2.04 mmol) in DMF (5 mL) was added HBTU (1.10 g, 2.49 mmol). The resulting mixture was stirred at ambient temperature for 18 h. the reaction was diluted in H₂O (50 mL) and extracted with EtOAc (3×75 mL). The combined organic extracts were dried over Na₂SO₄, filtered, and concentrated under reduced pressure. The resulting residue was chromatographed over silica gel (40 g Redisep column, 0-100% EtOAc in hexanes) to afford tert-butyl 3-(4-(3,5-difluoro-2-(trifluoromethyl) phenyl)piperidine-1-carbonyl)-4,5 dihydro-1H-pyrazolo[3, 4-c]pyridine-6(7H)-carboxylate (59) as a white solid (200 mg, 23%). ¹H NMR (300 MHz, CDCl₃) δ 7.017-6.876 (m, 1H), 6.876-6.741 (m, 1H), 5.306 (s, 1H), 4.632 (s, 2H), 3.776-3.581 (m, 2H), 2.762-2.631 (m, 2H), 1.986-1.653 (m, 4H), 1.500 (s, 9H), 1.399-1.189 (m, 4H).

Step B: To a solution of tert-butyl 3-(4-(3,5-difluoro-2-(trifluoro-methyl)phenyl)piperidine-1-carbonyl)-4,5-di-hydro-1H-pyrazolo[3,4-c]pyridine-6(7H)-carboxylate (59, 94 mg, 0.19 mmol) in CH₂Cl₂ (3 mL) was added HCl (2.0 N solution in Et₂O, 3 mL). The mixture was stirred for 18 h at ambient temperature. The reaction mixture was diluted with Et₂O (20 mL) and the mixture concentrated under reduced pressure to yield (4-(3,5-difluoro-2-(trifluoromethyl)phenyl) piperidin-1-yl) (4,5,6,7-tetrahydro-1H-pyrazolo [3,4-c] pyridin-3-yl)methanone hydrochloride (60) as a white solid (80 mg, 97%).

Preparation (4-(3,5-Difluoro-2-(trifluoromethyl)
phenyl)piperidin-1-yl)(4,5,6,7-tetrahydro-1H-pyra-
zolo[4,3-c]pyridin-3-yl)methanone (62)

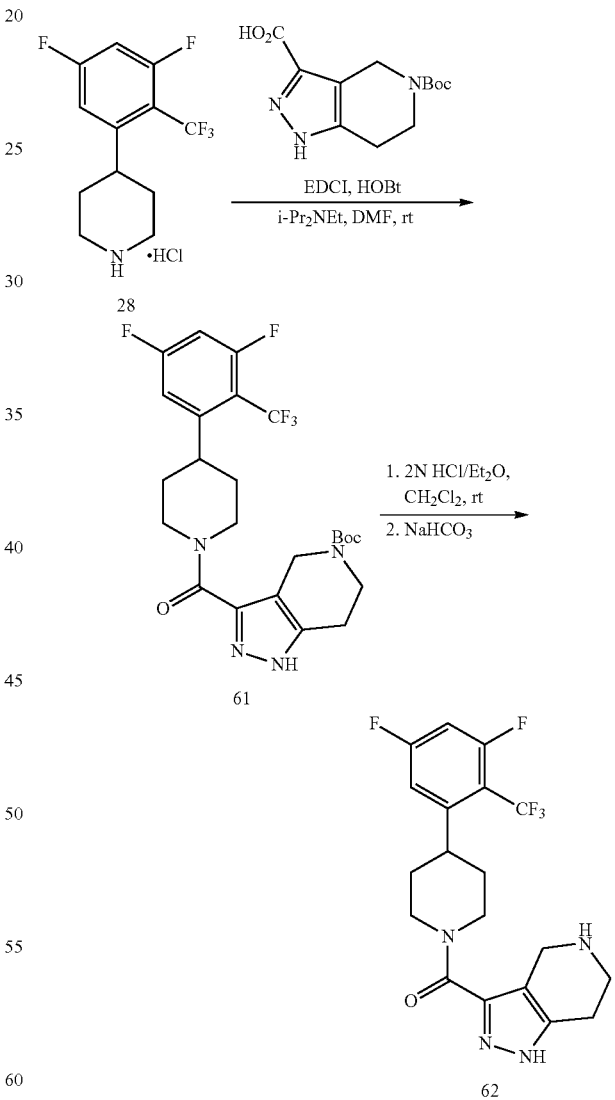

Step A: To a suspension of 4-(3,5-difluoro-2-(trifluoromethyl) phenyl)piperidine hydrochloride (28, 500 mg, 1.66 mmol), 5-(tert-butoxycarbonyl)-4,5,6,7-tetrahydro-1Hpyrazolo[3,4-c]pyridine-3-carboxylic acid (443 mg, 1.66 mmol), and diisopropylethylamine (36 μL, 2.04 mmol) in DMF (5 mL) was added HBTU (1.10 g, 2.49 mmol). The resulting mixture was stirred at ambient temperature for 18 h. the reaction was diluted in H$_2$O (50 mL) and extracted with EtOAc (3×75 mL). The combined organic extracts were dried over Na$_2$SO$_4$, filtered, and concentrated under reduced pressure. The resulting residue was chromatographed over silica gel (40 g Redisep column, 0-100% EtOAc in hexanes) to afford tert-butyl 3-(4-(3,5-difluoro-2-(trifluoromethyl) phenyl)piperidine-1-carbonyl)-6,7-dihydro-1H-pyrazolo[4, 3-c]pyridine-5(4H)-carboxylate (61) as a white solid (200 mg, 23%).

Step B: To a solution of tert-butyl 3-(4-(3,5-difluoro-2-(trifluoromethyl) phenyl) piperidine-1-carbonyl)-6,7-dihydro-1H pyrazolo[4,3-c]pyridine-5(4H)-carboxylate (61, 94 mg, 0.19 mmol) in CH$_2$Cl$_2$ (3 mL) was added HCl (2.0 N solution in Et$_2$O, 3 mL). The mixture was stirred for 18 h at ambient temperature. The reaction mixture was diluted with Et$_2$O (20 mL), washed with saturated NaHCO$_3$ solution, and the concentrated under reduced pressure to yield (4-(3,5-difluoro-2-(trifluoromethyl) phenyl)piperidin-1-yl) (4,5,6,7-tetrahydro-1H-pyrazolo [4,3-c]pyridin-3-yl)methanone (62) as a white solid (80 mg, 97%): $^1$H NMR (500 MHz, DMSO-d$_6$) δ 12.73 (s, 1H), 7.487-7.336 (m, 2H), 5.193-5.008 (m, 1H), 4.76-4.58 (br s, 1H), 3.75 (s, 2H), 3.25-3.04 (m, 2H), 2.94-2.84 (m, 1H), 2.84-2.71 (br s, 1H), 2.60-2.53 (m, 2H), 1.89-1.58 (m, 4H); ESI MS m/z 415.1 [M+H]+.

EXAMPLE 1

Preparation of 1-(3-(4-(3-Fluoro-2-(trifluoromethyl) phenyl)piperidine-1-carbonyl)-4,5-dihydro-1H-pyrazolo[3,4-c]pyridin-6(7H)-yl)ethanone (63)

Step A: Following general procedure GP-E1, ((4-(3-fluoro-2-(trifluoromethyl)phenyl)piperidin-1-yl)(4,5,6,7-tetrahydro-1H-pyrazolo[3,4-c]pyridin-3-yl)methanone hydrochloride (30) and acetyl chloride were converted to 1-(3-(4-(3-fluoro-2-(trifluoromethyl) phenyl)piperidine-1-carbonyl)-4,5-dihydro-1H-pyrazolo[3,4-c]pyridin-6(7H)-yl) ethanone as a white solid (20 mg, 73%): $^1$H NMR (500 MHz, DMSO-d$_6$) δ 13.18-12.83 (m, 1H), 7.73-7.60 (m, 1H), 7.46 (d, J=8.0 Hz, 1H), 7.35-7.26 (m, 1H), 4.91-4.49 (m, 4H), 3.71-3.57 (m, 2H), 3.25-3.06 (m, 2H), 2.85-2.48 (m, 3H, overlaps with solvent), 2.12-2.05 (m, 3H), 1.83-1.66 (m, 4H); ESI MS m/z 439 [M+H]+.

EXAMPLE 2

Preparation of (4-(3-Fluoro-2-(trifluoromethyl)phenyl) piperidin-1-yl)(5-(methylsulfonyl)-4,5,6,7-tetrahydro-1H-pyrazolo [4,3-c]pyridin-3-yl)methanone (64)

Step A: Following general procedure GP-C, (4-(3-fluoro-2-(trifluoromethyl)phenyl)piperidin-1-yl)(4,5,6,7-tetrahydro-1H-pyrazolo[4,3-c]pyridin-3-yl)methanone hydrochloride (32) and methanesulfonyl chloride were converted to (4-(3-fluoro-2-(trifluoromethyl)phenyl)piperidin-1-yl) (5-(methylsulfonyl)-4,5,6,7-tetrahydro-1H-pyrazolo[4,3-c] pyridin-3-yl)methanone as a white solid (23 mg, 41%): mp 243-246° C.; $^1$H NMR (500 MHz, DMSO-d$_6$) δ 13.03 (br s, 1H), 7.69-7.60 (m, 1H), 7.46 (d, J=7.5 Hz, 1H), 7.33-7.26 (m, 1H), 5.30-5.21 (m, 1H), 4.72-4.62 (m, 1H), 4.41-4.24 (m, 2H), 3.52-3.39 (m, 2H), 3.27-3.09 (m, 2H), 2.95 (s, 3H), 2.85-2.74 (m, 3H), 1.85-1.61 (m, 4H); ESI MS m/z 475 [M+H]+.

EXAMPLE 3

Preparation of 3-(4-(3-Fluoro-2-(trifluoromethyl) phenyl) piperidine-1-carbonyl)-[1,2,4]triazolo[4,3-a] pyridine-6-carbonitrile (65)

Step A: To a solution of ethyl 6-bromo-[1,2,4]triazolo[4, 3-a]pyridine-3-carboxylate (75 mg, 0.28 mmol) in THF (2.3 mL) was added a solution of LiOH.H$_2$O (23 mg, 0.56 mmol) in H$_2$O (1.5 mL). The mixture was stirred for 20 min and was neutralized with 2N HCl. The mixture was concentrated under reduced pressure. The obtained residue was diluted in DMF (3.0 mL) under an atmosphere of N$_2$. To this mixture was added 4-(3-fluoro-2-trifluoromethyl)phenylpiperidine hydrochloride (5, 78 mg, 0.28 mmol), benzotriazole-1-yl-oxy-tris-(dimethylamino)-phosphonium hexafluorophosphate (245 mg, 0.556 mmol), and diisopropylethylamine (107 mg, 0.834 mmol). The mixture was stirred at ambient temperature for 18 h. The resulting mixture was diluted with H$_2$O (20 mL). The mixture was extracted with EtOAc (4×30 mL). The combined organic layers were washed with 5% lithium chloride solution (4×20 mL) and concentrated under reduced pressure. The resulting residue was chromatographed over silica gel (Isco CombiFlash Rf unit, 12 g Redisep column, 0% to 50% EtOAc in hexanes) to provide (6-bromo-[1,2,4]triazolo[4,3-a]pyridin-3-yl)(4-(3-fluoro-2-(trifluoromethyl)phenyl)piperidin-1-yl)methanone as an orange film (87 mg, 66%): $^1$H NMR (300 MHz, DMSO-d$_6$) δ 9.13-9.10 (m, 1H), 7.75-7.62 (m, 2H), 7.52-7.46 (m, 1H), 7.38-7.25 (m, 1H), 5.30-5.17 (m, 1H), 4.78-4.64 (m, 1H), 3.42-3.28 (m, 3H, overlaps with H$_2$O), 3.11-2.92 (m, 1H), 1.98-1.70 (m, 4H); ESI MS m/z 471 [M+H]+.

Step B: A solution of (6-bromo-[1,2,4]triazolo[4,3-a]pyridin-3-yl) (4-(3-fluoro-2-(trifluoromethyl)phenyl)piperidin-1-yl)methanone (87 mg, 0.19 mmol) and zinc cyanide (43 mg, 037 mmol) in DMF (2.0 mL) was sparged with Ar for 10 min. To the solution was added Pd(PPh$_3$)$_4$ (21 mg, 0.019 mmol) the vessel was sealed and heated to 130° C. with microwaves for 30 min. The mixture was diluted with saturated sodium bicarbonate solution (30 mL) and extracted with EtOAc (3×30 mL). The combined organic extracts were concentrated to dryness under reduced pressure. The resulting residue was chromatographed over silica gel (Isco CombiFlash Rf unit, 12 g Redisep column, 0% to 70% EtOAc in hexanes) and freeze dried to provide 3-(4-(3-fluoro-2-(trifluoromethyl)phenyl)piperidine-1-carbonyl)-[1, 2,4]triazolo[4,3-a] pyridine-6-carbonitrile as a white solid (52 mg, 67%): mp 188-190° C.; $^1$H NMR (500 MHz, DMSO-d$_6$) δ 9.54-9.51 (m, 1H), 8.13 (dd, J=9.5, 1.0 Hz, 1H), 7.81 (dd, J=9.5, 1.5 Hz, 1H), 7.71-7.65 (m, 1H), 7.48 (d, J=8.0 Hz, 1H), 7.32 (dd, J=12.5, 8.5 Hz, 1H), 5.17-5.09 (m, 1H), 4.78-4.70 (m, 1H), 3.44-3.28 (m, 2H, overlaps with H$_2$O), 3.09-3.00 (m, 1H), 1.97-1.75 (m, 4H); ESI MS m/z 418 [M+H]+.

EXAMPLE 4

Preparation of 3-(4-(3-Fluoro-2-(trifluoromethyl) phenyl) piperidine-1-carbonyl)-N-methyl-6,7-dihydro-1H-pyrazolo[4,3-c]pyridine-5(4H)-carboxamide (66)

Step A: Following general procedure GP-E2, ((4-(3-fluoro-2-(trifluoromethyl)phenyl)piperidin-1-yl)(4,5,6,7-tetrahydro-1H-pyrazolo[3,4-c]pyridin-3-yl)methanone hydrochloride (30) and methyl isocyanate were converted to 3-(4-(3-fluoro-2-(trifluoromethyl) phenyl)piperidine-1-carbonyl)-N-methyl-6,7-dihydro-1Hpyrazolo[4,3-c] pyridine-5 (4H)-carboxamide as a white solid (32 mg, 41%): mp 165-170° C.; $^1$H NMR (500 MHz, DMSO-d6) δ 13.03-12.85 (m, 1H), 7.70-7.62 (m, 1H), 7.46 (d, J=8.0 Hz, 1H), 7.30 (dd, J=12.0, 8.0 Hz, 1H), 6.58-6.49 (m, 1H), 5.19-5.06 (m, 2H), 4.76-4.62 (m, 2H), 3.63-3.50 (m, 2H), 3.27-3.09 (m, 2H), 2.86-2.72 (m, 1H), 2.64 (t, J=5.5 Hz, 2H), 2.59-2.54 (m, 3H), 1.84-1.59 (m, 4H); ESI MS m/z 454 [M+H]+.

EXAMPLE 5

Preparation of (5-ethyl-4,5,6,7-tetrahydro-1H-pyrazolo[4,3-c]pyridin-3-yl)(4-(3-fluoro-2-(trifluoromethyl) phenyl) piperidin-1-yl)methanone (67)

Step A: Following general procedure GP-D, (4-(3-fluoro-2-(trifluoro-methyl) phenyl)piperidin-1-yl)(4,5,6,7-tetrahydro-1H-pyrazolo[4,3-c]pyridin-3-yl)methanone hydrochloride (32) and acetaldehyde were converted (5-ethyl-4,5,6,7-tetrahydro-1H-pyrazolo[4,3-c]pyridin-3-yl)(4-(3-fluoro-2-(trifluoromethyl) phenyl) piperidin-1-yl)methanone as a white solid (2.5 mg, 2%): $^1$H NMR (500 MHz, CD$_3$OD) δ7.64-7.53 (m, 1H), 7.38 (d, J=8.0 Hz, 1H), 7.13 (dd, J=12.0, 8.5 Hz, 1H), 4.90-4.72 (m, 2H, overlaps with H$_2$O), 3.62 (br s, 2H), 3.34-3.17 (m, 2H, overlaps with solvent), 2.92-2.78 (m, 5H), 2.68 (q, J=7.0 Hz, 2H), 1.96-1.74 (m, 4H), 1.20 (t, J=7.5 Hz, 3H) missing NH-pyrazole; ESI MS m/z 425 [M+H]+.

EXAMPLE 6

Preparation of 3-(4-(3-Fluoro-2-(trifluoromethyl) phenyl) piperidine-1-carbonyl)-6,7-dihydro-1H-pyrazolo[4,3-c]pyridine-5(4H)-carboxylate (68)

Step A: Following general procedure GP-B1, (4-(3-fluoro-2-(trifluoro-methyl)phenyl)piperidin-1-yl)(4,5,6,7-tetrahydro-1H-pyrazolo[4,3-c] pyridin-3-yl)methanone hydrochloride (32) and methyl chloroformate were converted to 3-(4-(3-fluoro-2-(trifluoromethyl) phenyl) piperidine-1-carbonyl)-6,7-dihydro-1H-pyrazolo[4,3-c] pyridine-5(4H)-carboxylate as a white solid (62 mg, 60%): $^1$H NMR (500 MHz, DMSO-d$_6$) δ 13.11-12.94 (m, 1H), 7.68-7.61 (m, 1H), 7.46 (d, J=8.0 Hz, 1H), 7.29 (dd, J=12.5, 8.5 Hz, 1H), 5.33-5.16 (m, 1H), 4.74-4.60 (m, 1H), 4.56-4.41 (m, 2H), 3.68-3.58 (m, 5H), 3.26-3.08 (m, 2H), 2.85-2.74 (m, 1H), 2.70 (t, J=5.5 Hz, 2H), 1.85-1.59 (m, 4H); ESI MS m/z 455 [M+H]+.

EXAMPLE 7

Preparation of (5-(Cyclopropylmethyl)-4,5,6,7-tetrahydro-1Hpyrazolo[4,3-c]pyridin-3-yl)(4-(3-fluoro-2-(trifluoromethyl) phenyl)piperidin-1-yl)methanone (69)

Step A: Following general procedure GP-D1, (4-(3-fluoro-2-(trifluoro-methyl) phenyl)piperidin-1-yl)(4,5,6,7-tetrahydro-1H-pyrazolo [4,3-c]pyridin-3-yl)methanone hydrochloride (32) and cyclopropane carboxaldehyde were converted (5-(cyclopropylmethyl)-4,5,6,7-tetrahydro-1H-pyrazolo[4,3-c]pyridin-3-yl) (4-(3-fluoro-2-(trifluoromethyl) phenyl)piperidin-1-yl)methanone as a white solid (33 mg, 81%): $^1$H NMR (500 MHz, DMSO-d$_6$) δ 12.92-12.73 (m, 1H), 7.69-7.61 (m, 1H), 7.45 (d, J=8.0 Hz, 1H), 7.29 (dd, J=12.0, 8.5 Hz, 1H), 5.13-5.00 (m, 1H), 4.73-4.60 (m, 1H), 3.60-3.46 (m, 2H), 3.25-3.03 (m, 2H), 2.83-2.64 (m, 5H), 2.41-2.33 (m, 2H), 1.85-1.59 (m, 4H), 0.94-0.83 (m, 1H), 0.52-0.44 (m, 2H), 0.14-0.08 (m, 2H); ESI MS m/z 451 [M+H]+.

EXAMPLE 8

Preparation of 3-(4-(3-Fluoro-2-(trifluoromethyl) phenyl) piperidine-1-carbonyl)-6,7-dihydro-1H-pyrazolo[4,3-c]pyridine-5(4H)-carbonitrile (70)

Step A: Following general procedure GP-D2, (4-(3-fluoro-2-(trifluoro methyl) phenyl) piperidin-1-yl) (4,5,6,7-tetrahydro-1H-pyrazolo[4,3-c]pyridin-3-yl)methanone hydrochloride (32) and cyanogen bromide were converted to 3-(4-(3-fluoro-2-(trifluoromethyl)phenyl)piperidine-1-carbonyl)-6,7-dihydro-1H-pyrazolo[4,3-c]pyridine-5(4H)-carbonitrile as a white solid (35 mg, 70%): $^1$H NMR (500 MHz, DMSO-d$_6$) δ 13.26-13.05 (m, 1H), 7.68-7.61 (m, 1H), 7.61 (d, J=8.0 Hz, 1H), 7.32 (dd, J=12.5, 8.5 Hz, 1H), 5.32-5.20 (m, 1H), 4.71-4.61 (m, 1H), 4.44-4.29 (m, 2H), 3.46 (t, J=5.5 Hz, 2H), 3.27-3.09 (m, 2H), 2.87-2.73 (m, 3H), 1.85-1.59 (m, 4H); ESI MS m/z 422 [M+H]+.

EXAMPLE 9

Preparation of (4-(3-Fluoro-2-(trifluoromethyl)phenyl) piperidin-1-yl)(5-(2,2,2-trifluoroethyl)-4,5,6,7-tetrahydro-1H-pyrazolo[4,3-c]pyridin-3-yl)methanone (71)

Step A: Following general procedure GP-D2, (4-(3-fluoro-2-(trifluoro methyl) phenyl) piperidin-1-yl) (4,5,6,7-tetrahydro-1H-pyrazolo[4,3-c]pyridin-3-yl)methanone hydrochloride (32) and 2,2,2-trifluoroethyl trifluoromethanesulfonate were converted to (4-(3-fluoro-2-(trifluoromethyl)phenyl)piperidin-1-yl) (5-(2,2,2-trifluoroethyl)-4,5,6,7-tetrahydro-1H-pyrazolo[4,3-c]pyridin-3-yl) methanone as a white solid (71 mg, 64%): mp 144-151° C.; $^1$H NMR (500 MHz, DMSO-d$_6$) δ 12.99-12.81 (m, 1H), 7.68-7.61 (m, 1H), 7.45 (d, J=8.0 Hz, 1H), 7.38-7.26 (m, 1H), 5.20-5.08 (m, 1H), 4.69-4.61 (m, 1H), 3.82-3.69 (m, 2H), 3.50-3.30 (m, 2H, overlaps with H$_2$O), 3.24-3.06 (m, 2H), 2.92 (t, J=6.5 Hz, 2H), 2.83-2.73 (m, 1H), 2.70 (t, J=5.5 Hz, 2H), 1.86-1.58 (m, 4H); ESI MS m/z 479 [M+H]+.

EXAMPLE 10

Preparation of (4-(3-Fluoro-2-(trifluoromethyl)phenyl) piperidin-1-yl)(5-(3,3,3-trifluoropropyl)-4,5,6,7-tetrahydro-1H-pyrazolo[4,3-c]pyridin-3-yl)methanone (72)

Step A: Following general procedure GP-D2, (4-(3-fluoro-2-(trifluoromethyl) phenyl) piperidin-1-yl) (4,5,6,7-tetrahydro-1H-pyrazolo[4,3-c]pyridin-3-yl)methanone hydrochloride (32) and 3-bromo-1,1,1-trifluoropropane were converted to (4-(3-fluoro-2-(trifluoromethyl) phenyl) piperidin-1-yl) (5-(3,3,3-trifluoropropyl)-4,5,6,7-tetrahydro-1H-pyrazolo[4,3-c]pyridin-3-yl)methanone as a white solid (26 mg, 32%): mp 152-159° C.; $^1$H NMR (500 MHz, DMSO-d$_6$) δ 12.93-12.75 (m, 1H), 7.69-7.61 (m, 1H), 7.47-7.43 (m, 1H), 7.29 (dd, J=12.0, 8.5 Hz, 1H), 5.11-5.00 (m, 1H), 4.71-4.62 (m, 1H), 3.58-3.44 (m, 2H), 3.25-3.06 (m, 2H), 2.83-2.61 (m, 7H), 2.58-2.46 (m, 1H, overlaps with solvent), 1.84-1.59 (m, 4H); ESI MS m/z 493 [M+H]+.

EXAMPLE 11

Preparation of (4-(3-Fluoro-2-(trifluoromethyl)phenyl) piperidin-1-yl)(5-(2-methoxyethyl)-4,5,6,7-tetrahydro-3aH-pyrazolo 4,3-c]pyridin-3-yl)methanone (73)

Step A: Following general procedure GP-G2, ((4-(3-fluoro-2-(trifluoro methyl)phenyl)piperidin-1-yl)(4,5,6,7-tetrahydro-1H-pyrazo [3,4-c]pyridin-3-yl)methanone hydrochloride (30) and bromoethylmethyl ether were converted to 4-(3-fluoro-2-(trifluoromethyl)phenyl) piperidine-1-yl)(5-(2-methoxyethyl)-4,5,6,7-tetrahydro-3aH-pyrazolo [4,3-c]pyridin-3-yl)methanone as an off-white solid (28 mg, 56%): mp 147-151° C.; $^1$H NMR (300 MHz, DMSO-$d_6$) δ 2.82 (br s, 1H), 7.65-7.27 (m, 3H), 5.18-5.09 (m, 1H), 4.75-4.60 (m, 1H), 3.51-3.45 (m, 2H), 3.27-3.11 (m, 6H), 2.84-2.70 (m, 8H), 1.87-1.63 (m, 4H); ESI MS m/z 475 [M+H]+.

EXAMPLE 12

Preparation of 4-(3-Fluoro-2-(trifluoromethyl)phenyl) piperidine-1-yl)(5-(oxetan-3-yl)-4,5,6,7-tetrahydro-1H-pyrazolo[4,3-c]pyridin-3-yl)methanone (74)

Step A: Following general procedure GP-D1, (4-(3-fluoro-2-(trifluoromethyl) phenyl)piperidin-1-yl)(4,5,6,7-tetrahydro-1H-pyrazo [4,3-c]pyridin-3-yl)methanone hydrochloride (32) and 3-oxetanone were converted to 4-(3-fluoro-2-(trifluoromethyl)phenyl) piperidine-1-yl)(5-(oxetan-3-yl)-4,5,6,7-tetrahydro-1Hpyrazolo[4,3-c]pyridin-3-yl)methanone as a white foam (30 mg, 29%): $^1$H NMR (300 MHz, CDCl$_3$) δ 10.04 (br s, 1H), 7.48-7.42 (m, 1H), 7.20-7.17 (m, 1H), 7.06-7.02 (m, 1H), 5.22-4.81 (m, 2H), 4.74 (d, J=6.6 Hz, 4H), 3.89-3.81 (m, 1H), 3.62 (br s, 2H), 3.31-3.24 (m, 1H), 3.21-2.68 (m, 5H), 1.91-1.72 (m, 5H); ESI MS m/z 453 [M+H]+.

EXAMPLE 13

Preparation of (6-Ethyl-4,5,6,7-tetrahydro-1H-pyrazolo [3,4-c]pyridin-3-yl)(4-(3-fluoro-2-(trifluormethyl)phenyl)piperidin-1-yl)methanone (75)

Step A: Following general procedure GP-G1, ((4-(3-fluoro-2-(trifluoromethyl) phenyl) piperidin-1-yl) (4,5,6,7-tetrahydro-1H-pyrazolo[3,4-c]pyridin-3-yl)methanone hydrochloride (30) and acetaldehyde were converted to (6-ethyl-4,5,6,7-tetrahydro-1H-pyrazolo[3,4-c]pyridin-3-yl)(4-(3-fluoro-2-(trifluormethyl) phenyl) piperidin-1-yl) methanone as a white solid (21 mg, 31%): $^1$H NMR (300 MHz, DMSO-$d_6$) δ 12.74 (br s, 1H), 7.72-7.65 (m, 1H), 7.48-7.27 (m, 2H), 4.92-4.63 (m, 2H), 3.68-3.04 (m, 4H), 2.90-2.39 (m, 7H), 1.74-1.55 (m, 4H), 1.18-1.02 (m, 3H); ESI MS m/z 425 [M+H]+.

EXAMPLE 14

Preparation of (4-(3-Fluoro-2-(trifluoromethyl)phenyl) piperidin-1-yl)(6-(3,3,3-trifluoropropyl)-4,5,6,7-tetrahydro-1H-pyrazolo[3,4-c]pyridin-3-yl)methanone (76)

Step A: Following general procedure GP-G1, ((4-(3-fluoro-2-(trifluoromethyl) phenyl) piperidin-1-yl) (4,5,6,7-tetrahydro-1H-pyrazolo[3,4-c]pyridin-3-yl)methanone hydrochloride (30) and bromotrifluoromethyl propane were converted to 4-(3-fluoro-2-(trifluoromethyl) phenyl) piperidin-1-yl) (6-(3,3,3-trifluoropropyl)-4,5,6,7-tetrahydro-1H-pyrazolo[3,4-c]pyridin-3-yl)methanone as a white solid (19 mg, 15%): mp 162-166° C.; $^1$H NMR (300 MHz, DMSO-$d_6$) δ 12.78 (br s, 1H), 7.72-7.65 (m, 1H), 7.48-7.27 (m, 2H), 4.92-4.63 (m, 2H), 3.57-3.53 (m, 2H), 3.27-3.09 (m, 2H), 2.88-2.39 (m, 9H), 1.77-1.72 (m, 4H); ESI MS m/z 493 [M+H]+.

EXAMPLE 15

Preparation of (4-(3-Fluoro-2-(trifluoromethyl)phenyl) piperidin-1-yl)(6-(2-methoxyethyl)-4,5,6,7-tetrahydro-3aH-pyrazolo [3,4-c]pyridin-3-yl)methanone (77)

Step A: Following general procedure GP-G1, ((4-(3-fluoro-2-(trifluoromethyl)phenyl) piperidin-1-yl) (4,5,6,7-tetrahydro-1H-pyrazolo[3,4-c]pyridin-3-yl)methanone hydrochloride (30) and bromoethylmethyl ether were converted 4-(3-fluoro-2-(trifluoromethyl)phenyl)piperidine-1-yl)(6-(2-methoxyethyl)-4,5,6,7-tetrahydro-3aH-pyrazolo[3,4-c]pyridin-3-yl)methanone as a white solid (23 mg, 30%): $^1$H NMR (300 MHz, DMSO-$d_6$) δ 12.72 (br s, 1H), 7.67-7.62 (m, 1H), 7.46 (d, J=8.1 Hz, 1H), 7.33-7.27 (m, 1H), 4.92-4.63 (m, 2H), 3.57-3.48 (m, 4H), 3.27-3.05 (m, 5H), 2.81-2.49 (m, 7H), 1.77-1.72 (m, 4H); ESI MS m/z 455 [M+H]+.

EXAMPLE 16

Preparation of 3-(4-(3-Fluoro-2-(trifluoromethyl) phenyl) piperidine-1-carbonyl)-4,5-dihydro-1H-pyrazolo[3,4-c]pyridine-6(7H)-carbonitrile (78)

Step A: Following general procedure GP-G2, ((4-(3-fluoro-2-(trifluoromethyl) phenyl)piperidin-1-yl) (4,5,6,7-tetrahydro-1H-pyrazolo [3,4-c]pyridin-3-yl)methanone hydrochloride (30) and cyanogen bromide were converted to 3-(4-(3-fluoro-2-(trifluormethyl) phenyl)piperidine-1-carbonyl)-4,5-dihydro-1H-pyrazolo[3,4-c] pyridine-6(7H)-carbonitrile as a white solid (38 mg, 53%): mp 194-198° C.; $^1$H NMR (300 MHz, DMSO-$d_6$) δ 12.98 (br s, 1H), 7.68-7.65 (m, 1H), 7.47 (d, J=7.8 Hz, 1H), 7.34-7.27 (m, 1H), 4.92-4.63 (m, 2H), 4.48-4.40 (m, 2H), 3.43-3.38 (m, 2H), 3.27-3.05 (m, 2H), 2.88-2.71 (m, 3H), 1.77-1.72 (m, 4H); ESI MS m/z 422 [M+H]+.

EXAMPLE 17

Preparation of (4-(3-fluoro-2-(trifluoromethyl)phenyl) piperidin-1-yl)(6-oxetan-3-yl)-4,5,6,7-tetrahydro-1H-pyrazolo[3,4-c]pyridine-3-yl)methanone (79)

Step A: Following general procedure GP-G1, ((4-(3-fluoro-2-(trifluoromethyl)phenyl)piperidin-1-yl)(4,5,6,7-tetrahydro-1H-pyrazolo [3,4-c]pyridin-3-yl)methanone hydrochloride (30) and oxetan-3-one were converted to (4-(3-fluoro-2-(trifluormethyl)piperidine-1-yl) (6-oxetan-3-yl)-4,5,6,7-tetrahydro-1H-pyrazolo[3,4-c] pyridine-3-yl) methanone as a white solid (30 mg, 39%): mp 148-151° C.; $^1$H NMR (300 MHz, DMSO-$d_6$) δ 12.77 (br s, 1H), 7.70-7.63 (m, 1H), 7.47 (d, J=8.1 Hz, 1H), 7.34-7.27 (m, 1H), 4.91-4.47 (m, 6H), 3.71-3.66 (m, 1H), 3.47-3.34 (m, 2H), 3.28-3.06 (m, 2H), 2.93-2.78 (m, 1H), 2.74-2.53 (m, 2H), 1.91-1.78 (m, 2H), 1.89-1.55 (m, 4H); ESI MS m/z 453 [M+H]+.

EXAMPLE 18

Preparation of (6-(cyclopropylmethyl)-4,5,6,7-tetrahydro-1H-pyrazolo[3,4-c]pyridin-3-yl)(4-(3-fluoro-2-(trifluoromethyl) phenyl)piperidin-1-yl)methanone (80)

Step A: Following general procedure GP-G1, ((4-(3-fluoro-2-(trifluoro-methyl)phenyl)piperidin-1-yl) (4,5,6,7-tetrahydro-1H-pyrazolo[3,4-c]pyridin-3-yl)methanone hydrochloride (30) and cyclopropane carbaldehyde were converted to (6-ethyl-4,5,6,7-tetrahydro-1H-pyrazolo[3,4-c]pyridin-3-yl) (4-(3-fluoro-2-(trifluormethyl) phenyl) piperidin-1-yl)methanone as a white solid (23 mg, 34%): $^1$H NMR (300 MHz, DMSO-$d_6$) δ 12.74 (br s, 1H), 7.72-7.65 (m, 1H), 7.47 (d, J=7.8 Hz, 1H), 7.34-7.27 (m, 1H), 4.92-4.63 (m, 2H), 3.59-3.53 (m, 2H), 3.32-3.09 (m, 2H), 2.90-2.39 (m, 7H), 1.81-1.62 (m, 4H), 0.92-0.85 (m, 1H), 0.52-0.48 (m, 2H), 0.14-0.10 (m, 2H); ESI MS m/z 451 [M+H]+.

EXAMPLE 19

1-(3-(4-(3,4-Difluoro-2-(trifluoromethyl)phenyl) piperidine-1-carbonyl)-4,5-dihydro-1H-pyrazolo[3,4-c]pyridin-6(7H)-yl)ethanone (81)

Step A: Following general procedure GP-G1, (4-(3,4-difluoro-2-(trifluoromethyl) phenyl) piperidin-1-yl) (4,5,6,7-tetrahydro-1H-pyrazolo [3,4-c]pyridin-3-yl)methanone TFA salt (34) and acetyl chloride were converted to give 1-(3-(4-(3,4-difluoro-2-(trifluoromethyl)phenyl)piperidine-1-carbonyl)-4,5-dihydro-1H-pyrazolo[3,4-c]pyridin-6(7H)-yl)ethanone as a white solid (29.2 g, 80%): $^1$H NMR (500 MHz, CDCl$_3$) δ 10.59 (br, 1H), 7.36-7.29 (m, 1H), 7.15 (m, 1H), 4.81 (br, 2H), 4.77 and 4.65 (s, 2H), 3.85 (br, 1H), 3.68 (m, 1H), 3.26-2.69 (m, 5H), 2.21 and 2.19 (s, 3H), 1.89-1.73 (m, 4H) MS (ESI+) m/z 457 [M+H]+.

EXAMPLE 20

1-(3-(4-(3,4-Difluoro-2-(trifluoromethyl)phenyl) piperidine-1-carbonyl)-6,7-dihydro-1H-pyrazolo[4,3-c]pyridin-5(4H)-yl)ethanone (82)

Step A: Following general procedure GP-B1, (4-(3,4-difluoro-2-(trifluoromethyl)phenyl)piperidin-1-yl)(4,5,6,7-tetrahydro-1H-pyrazolo[4,3-c]pyridin-3-yl)methanone (36) and acetyl chloride were converted to 1-(3-(4-(3,4-difluoro-2-(trifluoromethyl)phenyl) piperidine-1-carbonyl)-6,7-dihydro-1H-pyrazolo[4,3-c]pyridin-5(4H)-yl)ethanone as a white solid (0.046 g, 85%): $^1$H NMR (300 MHz, CDCl$_3$) δ 10.15 (br, 1H), 7.36-7.27 (m, 1H), 7.15 (m, 1H), 5.33-4.72 (m, 4H), 3.90-3.73 (m, 2H), 3.30-2.76 (m, 5H), 2.20 (s, 3H), 1.89-1.70 (m, 4H); MS (ESI+) m/z 457 [M+H]+.

EXAMPLE 21

1-(3-(4-(3,4-Difluoro-2-(trifluoromethyl)phenyl) piperidine-1-carbonyl)pyrrolo[3,4-c]pyrazol-5(1H,4H,6H)-yl)ethanone (83)

Step A: Following general procedure GP-B1, (4-(3,4-difluoro-2-(trifluoromethyl)phenyl)piperidin-1-yl)(1,4,5,6-tetrahydropyrrolo [3,4-c]pyrazol-3-yl)methanone (38) and acetyl chloride were converted to 1-(3-(4-(3,4-difluoro-2-(trifluoromethyl) phenyl) piperidine-1-carbonyl)pyrrolo[3,4-c]pyrazol-5(1H,4H,6H)-yl)ethanone as a white solid (0.045 g, 72%): $^1$H NMR (500 MHz, CDCl$_3$) δ 10.92 (br, 1H), 7.37-7.32 (m, 1H), 7.12 (m, 1H), 4.81-4.21 (m, 6H), 3.29-2.88 (m, 3H), 2.18 and 2.16 (s, 3H), 1.97-1.70 (m, 4H); MS (ESI+) m/z 443 [M+H]+

EXAMPLE 22

Preparation of 1-(3-(4-(3,4-difluoro-2-(trifluoro methyl)phenyl)piperidine-1-carbonyl)pyrrolo[3,4-c] pyrazol-5 (1H,4H,6H)-yl)propan-1-one (84)

Step A: Following general procedure GP-H1, (4-(3,4-difluoro-2-(trifluoromethyl)phenyl)piperidin-1-yl)(1,4,5,6-tetrahydropyrrolo [3,4-c]pyrazol-3-yl)methanone (38) and propionyl chloride were converted to 1-(3-(4-(3,4-difluoro-2-(trifluoromethyl)phenyl) piperidine-1-carbonyl)pyrrolo[3,4-c]pyrazol-5(1H,4H,6H)-yl)propan-1-one as a white solid (37 mg, 51%): mp>260° C.; $^1$H NMR (500 MHz, CDCl$_3$) δ 7.38-7.30 (m, 1H), 7.13-7.10 (m, 1H), 4.99-4.61 (m, 5.5H), 4.46-4.19 (m, 0.5H), 3.46-2.72 (m, 3H), 2.42-2.35 (m, 2H), 1.99-1.92 (m, 2H), 1.82-1.57 (m, 2H), 1.35-1.16 (m, 3H), missing N—H pyrazole; ESI MS m/z 457 [M+H]+.

EXAMPLE 23

Preparation of 1-(3-(4-(3,4-difluoro-2-(trifluoro methyl)phenyl)piperidine-1-carbonyl)pyrrolo[3,4-c] pyrazol 5(1H,4H,6H)-yl)-2-methylpropan-1-one (85)

Step A: Following general procedure GP-H1, (4-(3,4-difluoro-2-(trifluoromethyl)phenyl)piperidin-1-yl) (1,4,5,6-tetrahydropyrrolo [3,4-c]pyrazol-3-yl)methanone (38) and isobutyryl chloride were converted to 1-(3-(4-(3,4-difluoro-2-(trifluoromethyl) phenyl) piperidine-1-carbonyl)pyrrolo [3,4-c]pyrazol-5(1H,4H,6H)-yl)-2-methyl propan-1-one as a white solid (29 mg, 38%): mp 249-253° C.; $^1$H NMR (500 MHz, DMSO-$d_6$) δ 13.21, (br s, 1H), 7.81-7.68 (m, 1H), 7.57-7.47 (m, 1H), 4.83-3.65 (m, 6H), 3.29-2.67 (m, 4H), 1.82-1.61 (m, 4H), 1.05 (d, J=9 Hz, 6H); ESI MS m/z 471 [M+H]+.

EXAMPLE 24

Preparation of 1-(3-(4-(3,4-difluoro-2-(trifluorom ethyl) phenyl)piperidine-1-carbonyl)pyrrolo[3,4-c] pyrazol-5(1H,4H,6H)-yl)-3-methylbutan-1-one (86)

Step A: Following general procedure GP-H1, (4-(3,4-difluoro-2-(trifluoromethyl)phenyl)piperidin-1-yl)(1,4,5,6-tetrahydropyrrolo [3,4-c]pyrazol-3-yl)methanone (38) and isovaleryl chloride were converted to 1-(3-(4-(3,4-difluoro-2-(trifluoromethyl)phenyl) piperidine-1-carbonyl)pyrrolo[3,4-c]pyrazol-5(1H,4H,6H)-yl)-3-methylbutan-1-one as a white solid (42 mg, 54%): $^1$H NMR (500 MHz, CDCl$_3$) δ 7.37-7.28 (m, 1H), 7.17-7.08 (m, 1H), 4.95-4.53 (m, 5.5H), 4.43-3.90 (m, 0.5H), 3.34-2.70 (m, 3H), 2.30-2.19 (m, 3H), 1.98-1.89 (m, 2H), 1.80-1.58 (m, 2H), 1.05-0.94 (m, 6H) missing N—H pyrazole; ESI MS m/z 485 [M+H]+.

EXAMPLE 25

Preparation of (4-(3,4-difluoro-2-(trifluoromethyl) phenyl)piperidin-1-yl) (5-ethyl-4,5,6,7-tetrahydro-1H-pyrazolo[4,3-c]pyridin-3-yl)methanone (87)

Step A: Following general procedure GP-D1, (4-(3,4-difluoro-2-(trifluoromethyl) phenyl) piperidin-1-yl) (4,5,6,7-tetrahydro-1H-pyrazolo [4,3-c] pyridin-3-yl) methanone (36) and acetaldehyde were converted to (4-(3,4-difluoro-2-(trifluoromethyl)phenyl)piperidin-1-yl) (5-ethyl-4,5,6,7-tetrahydro-1H-pyrazolo [4,3-c]pyridin-3-yl) methanone as a white solid (35 mg, 36%): mp 185-190° C.; $^1$H NMR (300 MHz, DMSO-$d_6$) δ 12.793 (s, 1H), 7.903-7.609 (m, 1H), 7.60-7.40 (m, 1H), 5.24-4.93 (m, 1H), 4.85-4.49 (m, 1H), 3.45 (s, 2H), 3.13 (s, 2H), 2.96-2.71 (m, 1H), 2.61 (s, 4H), 2.58-2.52 (m, 1H), 1.84-1.57 (br s, 4H), 1.19-0.97 (t, 3H); ESI MS m/z 433.1 [M+H]+.

EXAMPLE 26

Preparation of (5-(cyclopropylmethyl)-4,5,6,7-tetrahydro-1Hpyrazolo[4,3-c]pyridin-3-yl)(4-(3,4-difluoro-2-(trifluoromethyl) phenyl)piperidin-1-yl) methanone (88)

Step A: Following general procedure GP-D1, (4-(3,4-difluoro-2-(trifluoromethyl)phenyl)piperidin-1-yl) (4,5,6,7-tetrahydro-1H-pyrazolo[4,3-c]pyridin-3-yl)methanone (36) and cyclopropane carboxaldehyde were converted to (5-(cyclopropylmethyl)-4,5,6,7-tetrahydro-1H-pyrazolo[4,3-c]pyridin-3-yl) (4-(3,4-difluoro-2-(tri-fluoromethyl)phenyl)piperidin-1-yl)methanone as a white solid (38 mg, 37%): No clear melt observed; $^1$H NMR (500 MHz, DMSO-$d_6$) δ 12.80 (s, 1H), 7.80-7.66 (m, 1H), 7.54-7.45 (m, 1H), 5.19-5.03 (br s, 1H), 4.73-4.58 (m, 1H), 3.66-3.46 (br s, 1H), 3.22-3.05 (br s, 2H), 2.85-2.63 (m, 4H), 1.83-1.59 (br s, 4H), 0.99-0.82 (br s, 1H), 0.58-0.43 (m, 2H), 0.21-0.07 (br s, 2H); ESI MS m/z 469.2 [M+H]+.

EXAMPLE 27

Preparation of (4-(3,4-difluoro-2-(trifluoromethyl) phenyl) piperidin-1-yl)(5-(oxetan-3-yl)-4,5,6,7-tetrahydro-1H-pyrazolo [4,3-c]pyridin-3-yl)methanone (89)

Step A: Following general procedure GP-D1, (4-(3,4-difluoro-2-(trifluoromethyl)phenyl)piperidin-1-yl)(4,5,6,7-tetrahydro-1H-pyrazolo[4,3-c]pyridin-3-yl)methanone (36) and 3-oxetanone were converted to (4-(3,4-difluoro-2-(trifluoromethyl)phenyl)piperidin-1-yl) (5-(oxetan-3-yl)-4,5,6,7-tetrahydro-1Hpyrazolo[4,3-c]pyridin-3-yl)methanone as a white solid (28 mg, 27%): mp 212-215° C.; $^1$H NMR (300 MHz, DMSO-$d_6$) δ 12.847 (s, 1H), 7.796-7.684 (m, 1H), 7.546-7.458 (m, 1H), 5.151 (d, 1H), 4.737-4.554 (m, 3H), 4.554-4.423 (m, 2H), 3.755-3.600 (m, 1H), 3.379 (s, 2H), 3.222-3.050 (br s, 2H), 2.844-2.643 (m, 3H), 1.898-1.515 (br s, 4H); ESI MS m/z 471.2 [M H]+.

EXAMPLE 28

Preparation of (4-(3,4-difluoro-2-(trifluoromethyl) phenyl) piperidin-1-yl) (5-neopentyl-4,5,6,7-tetrahydro-1H-pyrazolo[4,3-c]pyridin-3-yl)methanone methanone (90)

Step A: Following general procedure GP-D1, (4-(3,4-difluoro-2-(trifluoromethyl) phenyl) piperidin-1-yl) (4,5,6,7-tetrahydro-1H-pyrazolo[4,3-c]pyridin-3-yl)methanone (36) and pivaldehyde were converted to (4-(3,4-difluoro-2-(trifluoromethyl)phenyl)piperidin-1-yl)(5-neopentyl-4,5,6,7-tetrahydro-1H-pyrazolo[4,3-c]pyridin-3-yl) methanone methanone as a white solid (11 mg, 10%): mp 203-210° C.; $^1$H NMR (500 MHz, DMSO-$d_6$) δ 12.789 (s, 1H), 7.821-7.681 (m, 1H), 7.553-7.424 (m, 1H), 5.216-5.064 (br s, 1H), 4.755-4.579 (br s, 1H), 3.686-3.546 (m, 2H), 3.172-3.070 (m, 2H), 2.845-2.710 (m, 1H), 2.249 (s, 2H), 1.799-1.612 (m, 4H), 0.864 (s, 9H); ESI MS m/z 485.2 [M H]+.

EXAMPLE 29

Preparation of methyl 3-(4-(3,4-difluoro-2-(trifluoromethyl) phenyl)piperidine-1-carbonyl)-6,7-dihydro-1H-pyrazolo[4,3-c]pyridine-5(4H)-carboxylate (91)

Step A: Following general procedure GP-B1, (4-(3,4-difluoro-2-(trifluoromethyl) phenyl)piperidin-1-yl)(4,5,6,7-tetrahydro-1H-pyrazolo[4,3-c]pyridin-3-yl)methanone (36) and methyl chloroformate were converted to methyl 3-(4-(3,4-difluoro-2-(trifluoromethyl) phenyl) piperidine-1-carbonyl)-6,7-dihydro-1H-pyrazolo[4,3-c] pyridine-5(4H)-carboxylate as a white solid (21 mg, 20%): mp 248-252° C.; $^1$H NMR (500 MHz, DMSO-$d_6$) δ 12.924 (s, 1H), 7.763-7.692 (m, 1H), 7.540-7.472 (m, 1H), 5.358-5.152 (br s, 1H), 4.754-4.605 (br s, 1H), 4.650-4.418 (m, 2H), 3.705-3.581 (m, 6H), 3.119-3.100 (m, 3H), 2.860-2.731 (m, 4H), 1.296-1.237 (m, 6H); ESI MS m/z 473.1 [M+H]+.

EXAMPLE 30

Preparation of 3-(4-(3,4-difluoro-2 (trifluoromethyl) phenyl)piperidine-1-carbonyl)-N-methyl-6,7-dihydro-1H-pyrazolo[4,3-c]pyridine-5(4H)-carboxamide (92)

Step A: Following general procedure GP-B2, (4-(3,4-difluoro-2-(trifluoromethyl)phenyl)piperidin-1-yl) (4,5,6,7-tetrahydro-1H-pyrazolo[4,3-c]pyridin-3-yl)methanone (36) and methyl isocyanate were converted to 3-(4-(3,4-difluoro-2-(trifluoromethyl)phenyl) piperidine-1-carbonyl)-N-methyl-6,7-dihydro-1H-pyrazolo[4,3-c]pyridine-5(4H)-carboxamide as a white solid (28 mg, 36%): No clear melt observed; $^1$H NMR (500 MHz, DMSO-$d_6$) δ 12.895 (s, 1H), 7.780-7.692 (m, 1H), 7.538-7.472 (m, 1H), 6.579-6.490 (m, 1H), 5.202-5.086 (m, 1H), 4.743-4.622 (m, 1H), 4.465-4.332 (m, 2H), 3.630-3.499 (m, 2H), 3.209-3.095 (m, 2H), 2.849-2.730 (m, 1H), 2.673-2.602 (m, 2H), 2.602-2.542 (m, 3H), 1.912-1.588 (m, 5H); ESI MS m/z 472.2 [M+H]+.

EXAMPLE 31

Preparation of (4-(3,4-difluoro-2-(trifluoromethyl) phenyl)piperidin-1-yl)(5-(3,3,3-trifluoropropyl)-4,5,6,7-tetrahydro-1H-pyrazolo[4,3-c]pyridin-3-yl) methanone (93)

Step A: Following general procedure GP-D2, (4-(3,4-difluoro-2-(trifluoromethyl)phenyl)piperidin-1-yl)(4,5,6,7-tetrahydro-1H-pyrazolo[4,3-c]pyridin-3-yl)methanone (36) and 1,1,1-trifluoro-3-bromopropane were converted to (4-(3,4-difluoro-2-(trifluoromethyl) phenyl)piperidin-1-yl)(5-(3,3,3-trifluoropropyl)-4,5,6,7-tetrahydro-1H-pyrazolo[4,3-c]pyridin-3-yl)methanone as a white solid (24 mg, 21%): mp 190-195° C.; $^1$H NMR (500 MHz, DMSO-$d_6$) δ 12.939-

12.764 (m, 1H), 7.847-7.665 (m, 1H), 7.591-7.417 (m, 1H), 5.213-4.965 (m, 1H), 4.729-4.555 (m, 1H), 3.637-3.456 (m, 2H), 3.223-3.039 (br s, 2H), 2.853-2.698 (m, 5H), 2.698-2.623 (m, 2H), 2.596-2.522 (m, 1H), 1.859-1.589 (m, 4H); ESI MS m/z 511.1 [M+H]+.

EXAMPLE 32

Preparation of (4-(3,4-difluoro-2-(trifluoromethyl) phenyl)piperidin-1-yl)(5-(2-methoxyethyl)-4,5,6,7-tetrahydro-1H-pyrazolo[4,3-c]pyridin-3-yl)methanone (94)

Step A: Following general procedure GP-D2, (4-(3,4-difluoro-2-(trifluoromethyl) phenyl) piperidin-1-yl)(4,5,6,7-tetrahydro-1H-pyrazolo [4,3-c]pyridin-3-yl)methanone (36) and 2-methoxybromoethane were converted to (4-(3,4-difluoro-2-(trifluoromethyl)phenyl) piperidin-1-yl)(5-(2-methoxyethyl)-4,5,6,7-tetrahydro-1H-pyrazolo [4,3-c]pyridin-3-yl)methanone as a white solid (24 mg, 23%): mp 179-182° C.; $^1$H NMR (500 MHz, DMSO-d$_6$) δ 12.805 (s, 1H), 7.824-7.654 (m, 1H), 7.563-7.438 (m, 1H), 5.085 (s, 1H), 4.660 (s, 1H), 3.517 (s, 4H), 3.268 (s, 3H), 3.187-3.063 (m, 2H), 2.906-2.604 (m, 6H), 1.885-1.550 (m, 4H); ESI MS m/z 473.2 [M+H]+.

EXAMPLE 33

Preparation of 3-(4-(3,4-difluoro-2-(trifluoromethyl) phenyl)piperidine-1-carbonyl)-6,7-dihydro-1H-pyrazolo[4,3-c]pyridine-5(4H)-carbonitrile (95)

Step A: Following general procedure GP-D2, (4-(3,4-difluoro-2-(trifluoromethyl)phenyl)piperidin-1-yl)(4,5,6,7-tetrahydro-1H-pyrazolo[4,3-c]pyridin-3-yl)methanone (36) and cyanogen bromide were converted to 3-(4-(3,4-difluoro-2-(trifluoromethyl)phenyl) piperidine-1-carbonyl)-6,7-dihydro-1H-pyrazolo[4,3-c]pyridine-5(4H)-carbonitrile as a white solid (95 mg, quant.): No clear melt observed; $^1$H NMR (500 MHz, DMSO-d$_6$) δ 13.115 (s, 1H), 7.833-7.627 (m, 1H), 7.627-7.409 (m, 1H), 5.188-5.067 (m, 1H), 4.558-4.469 (m, 1H), 4.374 (s, 2H), 3.538-3.404 (m, 2H), 3.074-2.98 (br s, 2H), 2.877-2.805 (m, 2H), 1.801-1.694 (br s, 4H); ESI MS m/z 440 [M+H]+.

EXAMPLE 34

Preparation of (4-(3,4-difluoro-2(trifluoromethyl) phenyl) piperidin-1-yl)(5-ethyl-1,4,5,6-tetrahydropyrrolo[3,4-c]pyrazol-3-yl)methanone (96)

Step A: Following general procedure GP-J1, (4-(3,4-difluoro-2-(trifluoromethyl)phenyl)piperidin-1-yl)(1,4,5,6-tetrahydropyrrolo [3,4-c]pyrazol-3-yl)methanone (38) and acetaldehyde were converted to (4-(3,4-difluoro-2-(trifluoromethyl)phenyl)piperidin-1-yl) (5-ethyl-1,4,5,6-tetrahydropyrrolo[3,4-c]pyrazol-3-yl)methanone as a white solid (36 mg, 76%): No clear melt observed; $^1$H NMR (500 MHz, DMSO-d$_6$) δ 13.140-12.832 (m, 1H), 7.879-7.669 (m, 1H), 7.669-7.408 (m, 1H), 5.271-3.901 (m, 2H), 3.901-3.559 (m, 4H), 3.216-3.013 (m, 2H), 2.960-2.684 (m, 3H), 1.854-1.569 (m, 4H), 1.162-1.005 (m, 3H); ESI MS m/z 429.2 [M+H]+.

EXAMPLE 35

Preparation of (5-(cyclopropylmethyl)-1,4,5,6-tetrahydro pyrrolo[3,4-c]pyrazol-3-yl)(4-(3,4-difluoro-2-(trifluoromethyl) phenyl)piperidin-1-yl)methanone (97)

Step A: Following general procedure GP-J1, (4-(3,4-difluoro-2-(trifluoromethyl) phenyl)piperidin-1-yl) (1,4,5,6-tetrahydropyrrolo [3,4-c]pyrazol-3-yl)methanone (38) and cyclopropropane carboxaldehyde were converted to ((5-(cyclopropylmethyl)-1,4,5,6-tetrahydropyrrolo [3,4-c]pyrazol-3-yl) (4-(3,4-difluoro-2-(trifluoromethyl) phenyl) piperidin-1-yl)methanone as a white solid (36 mg, 76%): No clear melt observed; $^1$H NMR (500 MHz, DMSO-d$_6$) δ 13.101-12.818 (m, 1H), 7.887-7.665 (m, 1H), 7.665-7.423 (m, 1H), 5.223-3.923 (m, 2H), 3.923-3.594 (m, 4H), 3.258-3.667 (m, 3H), 2.667-2.533 (m, 2H), 1.827-1.606 (m, 4H), 0.988-0.793 (m, 1H), 0.598-0.417 (m, 2H), 0.235-0.087 (m, 2H); ESI MS m/z 455.1 [M+H]+.

EXAMPLE 36

Preparation of (5-(cyclopropylmethyl)-1,4,5,6-tetrahydropyrrolo[3,4-c]pyrazol-3-yl)(4-(3,4-difluoro-2-(trifluoromethyl)phenyl)piperidin-1-yl)methanone (98)

Step A: Following general procedure GP-J1, (4-(3,4-difluoro-2-(trifluoromethyl) phenyl) piperidin-1-yl)(1,4,5,6-tetrahydropyrrolo [3,4-c]pyrazol-3-yl)methanone (38) and 3-oxetanone were converted to (4-(3,4-difluoro-2-(trifluoromethyl)phenyl) piperidin-1-yl) (5-(oxetan-3-yl)-1,4,5,6-tetrahydropyrrolo[3,4-c]pyrazol-3-yl) methanone as a white solid (39 mg, 74%): No clear melt observed; $^1$H NMR (500 MHz, DMSO-d$_6$) δ 13.105-12.925 (m, 1H), 7.874-7.651 (m, 1H), 7.602-7.442 (m, 1H), 5.250-4.509 (m, 1H), 4.245-3.601 (m, 5H), 3.221-3.074 (m, 1H), 3.016-2.723 (m, 3H), 2.596-2.518 (m, 2H), 1.854-1.610 (m, 4H); ESI MS m/z 457.1 [M+H]+.

EXAMPLE 37

Preparation of (4-(3,4-difluoro-2-(trifluoromethyl) phenyl) piperidin-1-yl)(5-neopentyl-1,4,5,6-tetrahydropyrrolo[3,4-c]pyrazol-3-yl)methanone (99)

Step A: Following general procedure GP-J1, (4-(3,4-difluoro-2-(trifluoromethyl) phenyl) piperidin-1-yl)(1,4,5,6-tetrahydropyrrolo [3,4-c]pyrazol-3-yl)methanone (38) and pivaldehyde were converted to (4-(3,4-difluoro-2-(trifluoromethyl)phenyl)piperidin-1-yl) (5-neopentyl-1,4,5,6-tetrahydropyrrolo[3,4-c]pyrazol-3-yl)methanone as a white solid (25 mg, 46%): No clear melt observed; $^1$H NMR (500 MHz, DMSO-d$_6$) δ 13.060-12.840 (m, 1H), 7.840-7.440 (m, 2H), 5.315-4.473 (m, 1H), 4.210-3.642 (m, 5H), 3.272-2.728 (m, 3H), 2.555 (s, 2H), 1.867-1.597 (m, 4H), 0.905 (s, 9H); ESI MS m/z 471.2 [M+H]+.

EXAMPLE 38

Preparation of 3-(4-(3,4-difluoro-2-(trifluoromethyl) phenyl)piperidine-1-carbonyl)-N-methyl-4,6-dihydropyrrolo[3,4-c] pyrazole-5(1H)-carboxamide (100)

Step A: Following general procedure GP-H2, (4-(3,4-difluoro-2-(trifluoromethyl)phenyl)piperidin-1-yl)(1,4,5,6- tetrahydropyrrolo [3,4-c]pyrazol-3-yl)methanone (38) and methyl isocyanate were converted to 3-(4-(3,4-difluoro-2-(trifluoromethyl)phenyl) piperidine-1-carbonyl)-N-methyl-4,6-dihydropyrrolo[3,4-c]pyrazole-5(1H) carboxamide as a white solid (55 mg, 53%): mp>260° C.; $^1$H NMR (300 MHz, DMSO-d$_6$) δ 13.449-12.960 (m, 1H), 7.719-7.620 (m, 1H), 7.620-7.379 (m, 1H), 6.272 (s, 1H), 5.454-3.850 (m, 6H), 3.240-2.737 (m, 3H), 2.623 (s, 3H), 1.979-1.523 (m, 4H; ESI MS m/z 458.1 [M+H]+.

EXAMPLE 39

Preparation of methyl 3-(4-(3,4-difluoro-2-(trifluoromethyl)phenyl)piperidine-1-carbonyl)-4,6-dihydropyrrolo [3,4-c]pyrazole-5(1H)-carboxylate (101)

Step A: Following general procedure GP-H1, (4-(3,4-difluoro-2-(trifluoromethyl)phenyl)piperidin-1-yl)(1,4,5,6-tetrahydropyrrolo [3,4-c]pyrazol-3-yl)methanone (38) and methyl chloroformate were converted to methyl 3-(4-(3,4-difluoro-2-(trifluoromethyl) phenyl)piperidine-1-carbonyl)-4,6-dihydropyrrolo[3,4-c]pyrazole-5 (1H)-carboxylate as a white solid (30 mg, 55%): No clear melt observed; $^1$H NMR (500 MHz, DMSO-d$_6$) δ 13.503-13.110 (br s, 1H), 7.310-7.721 (m, 1H), 7.587-7.471 (m, 1H), 4.808-4.531 (br s, 1H), 4.531-4.370 (m, 4H), 3.673 (s, 3H), 3.277-3.102 (m, 2H), 3.012-2.722 (br s, 1H), 1.851-1.621 (m, 4H); ESI MS m/z 459.2 [M+H]+.

EXAMPLE 40

Preparation of (5-benzoyl-1,4,5,6-tetrahydropyrrolo [3,4-c]pyrazol-3-yl)(4-(3,4-difluoro-2-(trifluoromethyl)phenyl)piperidin-1-yl)methanone (102)

Step A: Following general procedure GP-H1, (4-(3,4-difluoro-2-(trifluoromethyl) phenyl) piperidin-1-yl)(1,4,5,6-tetrahydropyrrolo [3,4-c]pyrazol-3-yl)methanone (38) and benzoyl chloride were converted to (5-benzoyl-1,4,5,6-tetrahydropyrrolo[3,4-c]pyrazol-3-yl) (4-(3,4-difluoro-2-(trifluoromethyl) phenyl) piperidin-1-yl) methanone as a white solid (30 mg, 55%): mp>260° C.; $^1$H NMR (500 MHz, DMSO-d$_6$) δ 13.697-13.007 (m, 1H), 7.867-7.668 (m, 1H), 7.668-7.545 (m, 2H), 7.545-7.384 (m, 4H), 5.416-3.891 (m, 6H), 3.248-2.620 (m, 3H), 1.923-1.524 (m, 4H); ESI MS m/z 505 [M+H]+.

EXAMPLE 41

Preparation of (4-(3,4-difluoro-2(trifluoromethyl) phenyl) piperidin-1-yl)(5-picolinoyl-1,4,5,6-tetrahydropyrrolo[3,4-c]pyrazol-3-yl)methanone (103)

Step A: Following general procedure GP-H1, (4-(3,4-difluoro-2-(trifluoromethyl) phenyl) piperidin-1-yl)(1,4,5,6-tetrahydropyrrolo [3,4-c]pyrazol-3-yl)methanone (38) and picolinoyl chloride were converted to (4-(3,4-difluoro-2-(trifluoromethyl) phenyl) piperidin-1-yl) (5-picolinoyl-1,4,5,6-tetrahydropyrrolo[3,4-c]pyrazol-3-yl) methanone as a white solid (13 mg, 22%): No clear melt observed; $^1$H NMR (300 MHz, DMSO-d$_6$) δ 13.632-13.061 (m, 1H), 8.722-8.139 (m, 1H), 8.140-7.908 (m, 1H), 7.908-7.684 (m, 2H), 7.684-7.398 (m, 2H), 5.115-4.428 (m, 5H), 3.316-2.598 (m, 3H), 1.927-1.133 (m, 5H); ESI MS m/z, 506.1 [M+H]+.

EXAMPLE 42

Preparation of (4-(3,4-difluoro-2-(trifluoromethyl) phenyl) piperidin-1-yl)(5-nicotinoyl-1,4,5,6-tetrahydropyrrolo[3,4-c]pyrazol-3-yl)methanone (104)

Step A: Following general procedure GP-H1, (4-(3,4-difluoro-2-(trifluoromethyl)phenyl)piperidin-1-yl)(1,4,5,6-tetrahydropyrrolo [3,4-c] pyrazol-3-yl)methanone (38) and nicotinoyl chloride were converted to (4-(3,4-difluoro-2-(trifluoromethyl)phenyl)piperidin-1-yl)(5-nicotinoyl-1,4,5,6-tetrahydropyrrolo[3,4-c]pyrazol-3-yl)methanone as a white solid (34 mg, 59%): No clear melt observed; $^1$H NMR (500 MHz, DMSO-d$_6$) δ 13.589-13.123 (br s, 1H), 8.807 (s, 1H), 8.140-7.991 (m, 1H), 7.843-7.678 (m, 1H), 7.628-7.364 (m, 2H), 5.433-3.721 (m, 6H), 3.257-2.701 (m, 3H), 1.933-1.522 (m, 4H); ESI MS m/z 506.1 [M+H]+.

EXAMPLE 43

Preparation of (4-(3,4-difluoro-2(trifluoromethyl) phenyl) piperidin-1-yl)(5-isonicotinoyl-1,4,5,6-tetrahydropyrrolo[3,4-c] pyrazol-3-yl)methanone (105)

Step A: Following general procedure GP-H1, (4-(3,4-difluoro-2-(trifluoromethyl) phenyl) piperidin-1-yl) (1,4,5,6-tetrahydropyrrolo [3,4-c] pyrazol-3-yl)methanone (38) and isonicotinoyl chloride were converted to (4-(3,4-difluoro-2-(trifluoromethyl)phenyl)piperidin-1-yl) (5-isonicotinoyl-1,4,5,6-tetrahydropyrrolo [3,4-c] pyrazol-3-yl) methanone as a white solid (14 mg, 24%): mp>260° C.; $^1$H NMR (500 MHz, DMSO-d$_6$) δ 13.420-13.120 (m, 1H), 8.770-8.620 (m, 2H), 7.833-7.679 (m, 1H), 7.612-7.369 (m, 3H), 5.410-3.820 (m, 6H), 3.240-3.060 (m, 2H), 1.860-1.530 (m, 4H), 1.290-1.190 (m, 1H); ESI MS m/z 506.1 [M+H]+.

EXAMPLE 44

Preparation of (4-(3,4-difluoro-2-(trifluoromethyl) phenyl)piperidin-1-yl)(5-(pyrrolidine-1-carbonyl)-1, 4,5,6-tetrahydropyrrolo [3,4-c]pyrazol-3-yl)methanone (106)

Step A: Following general procedure GP-H2, (4-(3,4-difluoro-2-(trifluoromethyl) phenyl) piperidin-1-yl) (1,4,5, 6-tetrahydropyrrolo [3,4-c]pyrazol-3-yl)methanone (38) and 1-pyrolocarbamoyl chloride were converted to (4-(3,4-difluoro-2-(trifluoromethyl)phenyl) piperidin-1-yl)(5-(pyrrolidine-1-carbonyl)-1,4,5,6-tetrahydropyrrolo [3,4-c]pyrazol-3-yl)methanone as a white solid (22 mg, 38%): mp>260° C.; $^1$H NMR (500 MHz, DMSO-d$_6$) δ 13.389-13.022 (m, 1H), 7.858-7.407 (m, 2H), 5.439-3.846 (m, 6H), 3.412-3.326 (m, 4H), 3.253-2.742 (m, 3H), 1.868-1.638 (m, 8H); ESI MS m/z 498.2 [M+H]+.

EXAMPLE 45

Preparation of 4-(3,4-difluoro-2-(trifluoromethyl) phenyl) piperidin-1-yl)(5-(2,2,2-trifluoroethyl)-1,4, 5,6-tetrahydropyrrolo [3,4-c]pyrazol-3-yl)methanone (107)

Step A: Following general procedure GP-J2, (4-(3,4-difluoro-2-(trifluoromethyl) phenyl)piperidin-1-yl) (1,4,5,6-tetrahydropyrrolo [3,4-c]pyrazol-3-yl)methanone (38) and 2,2,2-trifluoroethyl trifluoromethanesulfonate were converted to (4-(3,4-difluoro-2-(trifluoromethyl) phenyl) piperidin-1-yl) (5-(2,2,2-trifluoroethyl)-1,4,5,6-tetrahydropyrrolo[3,4-c]pyrazol-3-yl)methanone as a white solid (16 mg, 28%): No clear melt observed; $^1$H NMR (500 MHz, DMSO-$d_6$) δ 13.274-12.902 (m, 1H), 7.343-7.681 (m, 1H), 7.601-7.441 (m, 1H), 5.368-3.811 (m, 6H), 3.695-3.520 (m, 2H), 3.273-2.71 (m, 3H), 1.906-1.571 (m, 4H); ESI MS m/z 483.1 [M+H]+.

EXAMPLE 46

Preparation of (4-(3,4-difluoro-2(trifluoromethyl) phenyl) piperidin-1-yl)(5-(3,3,3-trifluoropropyl)-1,4,5,6-tetrahydropyrrolo [3,4-c]pyrazol-3-yl)methanone (108)

Step A: Following general procedure GP-J2, (4-(3,4-difluoro-2-(trifluoromethyl)phenyl)piperidin-1-yl)(1,4,5,6-tetrahydropyrrolo [3,4-c]pyrazol-3-yl)methanone (38) and 1,1,1-trifluoro-3-bromopropane were converted to (4-(3,4-difluoro-2-(trifluoromethyl)phenyl) piperidin-1-yl) (5-(3,3,3-trifluoropropyl)-1,4,5,6-tetrahydro-pyrrolo[3,4-c]pyrazol-3-yl)methanone as a white solid (13 mg, 22%): No clear melt observed; $^1$H NMR (500 MHz, DMSO-$d_6$) δ 13.091-12.860 (m, 1H), 7.837-7.651 (m, 1H), 7.638-7.430 (m, 1H), 5.271-4.038 (m, 7H), 3.899-3.673 (m, 4H), 3.210-3.059 (m, 2H), 2.955-2.681 (br s, 1H), 1.869-1.558 (m, 4H); ESI MS m/z 497 [M+H]+.

EXAMPLE 47

Preparation of (4-(3,4-difluoro-2(trifluoromethyl) phenyl) piperidin-1-yl)(5-(2-methoxyethyl)-1,4,5,6-tetrahydropyrrolo[3,4-c]pyrazol-3-yl)methanone (109)

Step A: Following general procedure GP-J2, (4-(3,4-difluoro-2-(trifluoromethyl) phenyl)piperidin-1-yl)(1,4,5,6-tetrahydropyrrolo [3,4-c] pyrazol-3-yl)methanone (38) and 2-methoxy-bromoethane were converted to (4-(3,4-difluoro-2-(trifluoromethyl)phenyl)piperidin-1-yl)(5-(2-methoxyethyl)-1,4,5,6-tetrahydropyrrolo[3,4-c]pyrazol-3-yl) methanone as a white solid (14 mg, 22%): No clear melt observed; $^1$H NMR (300 MHz, DMSO-$d_6$) δ 13.070-12.860 (m, 1H), 7.852-7.648 (m, 1H), 7.616-7.449 (m, 1H), 5.365-3.596 (m, 6H), 3.560-3.413 (m, 2H), 3.298-3.219 (m, 4H), 3.219-3.047 (m, 2H), 2.937-2.832 (m, 3H), 1.843-1.576 (m, 5H); ESI MS m/z 459.2 [M+H]+.

EXAMPLE 48

Preparation of 3-(4-(3,4-difluoro-2-(trifluoromethyl) phenyl) piperidine-1-carbonyl)-4,6-dihydropyrrolo [3,4-c]pyrazole-5(1H)-carbonitrile (110)

Step A: Following general procedure GP-J2, (4-(3,4-difluoro-2-(trifluoromethyl)phenyl)piperidin-1-yl)(1,4,5,6-tetrahydropyrrolo [3,4-c]pyrazol-3-yl)methanone (38) and cyanogen bromide were converted to -(4-(3,4-difluoro-2-(trifluoromethyl)phenyl)piperidine-1-carbonyl)-4,6-dihydropyrrolo[3,4-c]pyrazole-5(1H)-carbonitrile as a white solid (23 mg, 79%): No clear melt observed; $^1$H NMR (500 MHz, DMSO-$d_6$) δ 13.623-13.172 (m, 1H), 7.850-7.664 (m, 1H), 7.664-7.470 (m, 1H), 5.552-3.846 (m, 6H), 3.271-2.652 (m, 3H), 2.042-1.503 (m, 4H); ESI MS m/z 426 [M+H]+.

EXAMPLE 49

Preparation of (4-(3,4-Difluoro-2-(trifluoromethyl) phenyl) piperidin-1-yl)(6-ethyl-4,5,6,7-tetrahydro-1H-pyrazolo[3,4-c]pyridin-3-yl)methanone (111)

Step A: Following general procedure GP-G1, (4-(3,4-difluoro-2-(trifluoromethyl) phenyl)piperidin-1-yl) (4,5,6,7-tetrahydro-1H-pyrazolo[3,4-c]pyridin-3-yl)methanone TFA salt (34) and acetaldehyde were converted to (4-(3,4-difluoro-2-(trifluoromethyl)phenyl) piperidin-1-yl) (6-ethyl-4,5,6,7-tetrahydro-1H-pyrazolo [3,4-c] pyridin-3-yl)methanone as a white solid (13 mg, 21%): mp 207-210° C.; $^1$H NMR (500 MHz, DMSO-$d_6$) δ 12.90 (br s, 0.25H), 12.71 (br s, 0.75H), 7.78-7.70 (m, 1H), 7.50-7.49 (m, 1H), 4.87-4.85 (m, 1H), 4.68-4.66 (m, 1H), 3.48-3.45 (m, 2H), 3.14-3.13 (m, 2H), 2.78-2.77 (m, 1H), 2.61-2.55 (m, 6H, partially merged with DMSO peak), 1.76-1.70 (m, 4H), 1.07 (t, J=7.0 Hz, 3H); ESI MS m/z 443 [M+H]+.

EXAMPLE 50

Preparation of 3-(4-(3,4-Difluoro-2-(trifluoromethyl) phenyl)piperidine-1-carbonyl)-N-methyl-1,4,5,7-tetrahydro-6Hpyrazolo[3,4-c]pyridine-6-carboxamide (112)

Step A: Following general procedure GP-E2, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and isocyanatomethane were converted to 3-(4-(3,4-difluoro-2-(trifluoromethyl)phenyl) piperidine-1-carbonyl)-N-methyl-1,4,5,7-tetrahydro-6Hpyrazolo[3,4-c] pyridine-6-carboxamide as an off-white solid (6 mg, 27%): mp 220-225° C.; $^1$H NMR (500 MHz, DMSO-$d_6$) δ 13.05 (br s, 0.25H), 12.85 (br s, 0.75H), 7.79-7.70 (m, 1H), 7.51-7.48 (m, 1H), 6.61-6.60 (m, 0.75H), 6.55-6.54 (m, 0.25H), 4.86-4.84 (m, 1H), 4.68-4.65 (m, 1H), 4.47-4.42 (m, 2H), 3.54-3.50 (m, 2H), 3.14-3.13 (m, 2H), 2.78-2.77 (m, 1H), 2.59-2.56 (m, 5H, partially merged with DMSO peak), 1.76-1.67 (m, 4H); ESI MS m/z 472 [M+H]+.

EXAMPLE 51

Preparation of (4-(3,4-Difluoro-2-(trifluoromethyl) phenyl)piperidin-1-yl)(6-methyl-4,5,6,7-tetrahydro-1H-pyrazolo[3,4-c]pyridin-3-yl)methanone (113)

Step A: Following general procedure GP-G1, (4-(3,4-difluoro-2-(trifluoromethyl) phenyl) piperidin-1-yl)(4,5,6,7-tetrahydro-1H-pyrazolo[3,4-c]pyridin-3-yl)methanone TFA salt (34) and formaldehyde were converted to (4-(3,4-difluoro-2-(trifluoromethyl)phenyl) piperidin-1-yl) (6-methyl-4,5,6,7-tetrahydro-1H-pyrazolo [3,4-c] pyridin-3-yl)methanone as a white solid (18 mg, 55%): mp 210-211° C.; $^1$H NMR (500 MHz, DMSO-$d_6$) δ 12.91 (br s, 0.25H), 12.72 (br s, 0.75H), 7.79-7.70 (m, 1H), 7.50-7.49 (m, 1H), 4.88-4.86 (m, 1H), 4.67-4.65 (m, 1H), 3.43-3.40 (m, 2H), 3.15-3.13 (m, 2H), 2.77-2.76 (m, 1H), 2.65-2.60 (m, 4H), 2.36 (s, 3H), 1.76-1.69 (m, 4H); ESI MS m/z 429 [M+H]+.

EXAMPLE 52

Preparation of 3-(4-(3-Fluoro-2-(trifluoromethyl) phenyl) piperidine-1-carbonyl)-N-methyl-6,7-dihydro-1H-pyrazolo[4,3-c]pyridine-5(4H)-carboxamide (114)

Step A: Following general procedure GP-C, (4-(3-fluoro-2-(trifluoromethyl)phenyl)piperidin-1-yl)(4,5,6,7-tetrahydro-1H-pyrazolo[4,3-c]pyridin-3-yl)methanone hydrochloride (32) and methyl isocyanate were converted to 3-(4-(3-fluoro-2-(trifluoromethyl) phenyl)piperidine-1-carbonyl)-N-methyl-6,7-dihydro-1H-pyrazolo[4,3-c]pyridine-5(4H)-carboxamide as a white solid (32 mg, 41%): mp 165-170° C.; $^1$H NMR (500 MHz, DMSO-$d_6$) δ 13.03-12.85 (m, 1H), 7.70-7.62 (m, 1H), 7.46 (d, J=8.0 Hz, 1H), 7.30 (dd, J=12.0, 8.0 Hz, 1H), 6.58-6.49 (m, 1H), 5.19-5.06 (m, 2H), 4.76-4.62 (m, 2H), 3.63-3.50 (m, 2H), 3.27-3.09 (m, 1H), 2.86-2.72 (m, 1H), 2.64 (t, J=5.5 Hz, 2H), 2.59-2.54 (m, 3H), 1.84-1.59 (m, 4H); ESI MS m/z 454 [M+H]$^+$.

EXAMPLE 53

Preparation of 2-(3-(4-(3,4-Difluoro-2-(trifluoromethyl) phenyl)piperidine-1-carbonyl)-1,4,5,7-tetrahydro-6H-pyrazolo[3,4-c]pyridin-6-yl)acetic acid (115)

Step A: Following general procedure GP-G2, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and tert-butyl 2-bromoacetate were converted to provide tert-butyl 2-(3-(4-(3,4-difluoro-2-(trifluoromethyl)phenyl) piperidine-1-carbonyl)-1,4,5,7-tetrahydro-6H-pyrazolo[3,4-c]pyridin-6-yl)acetate as a clear, glassy solid (55 mg, 69%): $^1$H NMR (500 MHz, DMSO-$d_6$) δ 12.94 (br s, 0.25H), 12.71 (br s, 0.75H), 7.37-7.33 (m, 1H), 7.50-7.49 (m, 1H), 4.86-4.84 (m, 1H), 4.68-4.66 (m, 1H), 3.67-3.63 (m, 2H), 3.34-3.30 (m, 2H, partially merged with H$_2$O peak), 3.14-3.13 (m, 2H), 2.59-2.58 (m, 3H), 2.59-2.50 (m, 2H, partially merged with DMSO peak), 1.76-1.70 (m, 4H), 1.43 (s, 9H); ESI MS m/z 529 [M+H]+.

Step B: A solution tert-butyl 2-(3-(4-(3,4-difluoro-2-(trifluoromethyl) phenyl)piperidine-1-carbonyl)-1,4,5,7-tetrahydro-6H-pyrazolo[3,4-c]pyridin-6-yl)acetate (53 mg, 0.10 mmol) in anhydrous CH$_2$Cl$_2$ (3 mL) was treated with TFA (3 mL) and stirred under an atmosphere of N$_2$ at room temperature for 8 h. After this time, the mixture was concentrated to dryness under reduced pressure and solvent exchanged with CH$_2$Cl$_2$ (10 mL). The residue was diluted in anhydrous CH$_2$Cl$_2$ (10 mL), treated with MP-carbonate (0.50 g) and stirred at room temperature for 15 min. After this time, the solution was filtered and the resin washed with CH$_2$Cl$_2$ (2×10 mL). The filtrate was concentrated to dryness under reduced pressure to provide 2-(3-(4-(3,4-difluoro-2-(trifluoromethyl) phenyl) piperidine-1-carbonyl)-1,4,5,7-tetrahydro-6H-pyrazolo[3,4-c]pyridin-6-yl)acetic acid as an off-white solid (40 mg, 85%): mp 151-153° C.; $^1$H NMR (500 MHz, DMSO-$d_6$) δ 13.29 (br s, 0.25H), 12.89 (br s, 0.75H), 7.56-7.55 (m, 1H), 7.51-7.50 (m, 1H), 4.87-4.86 (m, 1H), 4.66-4.64 (m, 1H), 4.04-4.02 (m, 2H), 3.76-3.72 (m, 2H), 3.34-3.32 (m, 2H, partially merged with H$_2$O peak), 3.15-3.11 (m, 4H), 2.76-2.74 (m, 2H), 1.76-1.70 (m, 4H); ESI MS m/z 473 [M+H]+.

EXAMPLE 54

Preparation of Methyl 3-(4-(3,4-difluoro-2-(trifluoromethyl) phenyl)piperidine-1-carbonyl)-1,4,5,7-tetrahydro-6H-pyrazolo[3,4-c]pyridine-6-carboxylate (116)

Step A: Following general procedure GP-E1, (4-(3,4-difluoro-2-(trifluoromethyl) phenyl) piperidin-1-yl)(4,5,6,7-tetrahydro-1H-pyrazolo[3,4-c]pyridin-3-yl)methanone TFA salt (34) and methyl carbonochloridate were converted to 3-(4-(3,4-difluoro-2-(trifluoromethyl) phenyl) piperidine-1-carbonyl)-1,4,5,7-tetrahydro-6Hpyrazolo[3,4-c]pyridine-6-carboxylate as a light orange solid (30 mg, 60%): mp 238-240° C.; $^1$H NMR (500 MHz, DMSO-$d_6$) δ 13.13 (br s, 0.25H), 12.86 (br s, 0.75H), 7.78-7.70 (m, 1H), 7.51-7.48 (m, 1H), 4.82-4.80 (m, 1H), 4.67-4.65 (m, 1H), 4.54 (s, 1.5H), 4.50 (s, 0.5H), 3.64 (s, 3H), 3.60-3.57 (m, 2H), 3.15-3.13 (m, 2H), 2.79-2.78 (m, 1H), 2.64-2.59 (m, 2H), 1.76-1.68 (m, 4H); ESI MS m/z 473 [M+H]+.

EXAMPLE 55

Preparation of (4-(3,4-Difluoro-2-(trifluoromethyl) phenyl)piperidin-1-yl)(6-(oxetan-3-yl)-4,5,6,7-tetrahydro-1H-pyrazolo [3,4-c]pyridin-3-yl)methanone (117)

Step A: Following general procedure GP-G1, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and oxetan-3-one were converted to (4-(3,4-difluoro-2-(trifluoromethyl)phenyl) piperidin-1-yl)(6-(oxetan-3-yl)-4,5,6,7-tetrahydro-1Hpyrazolo[3,4-c] pyridin-3-yl)methanone as an off-white solid (32 mg, 500): mp 206-207° C.; $^1$H NMR (500 MHz, DMSO-$d_6$) δ 12.96 (br s, 0.25H), 12.76 (br s, 0.75H), 7.80-7.70 (m, 1H), 7.51-7.50 (m, 1H), 4.86-4.84 (m, 1H), 4.68-4.65 (m, 1H), 4.60 (apparent t, J=6.5 Hz, 2H), 4.50 (apparent t, J=6.0 Hz, 2H), 3.71-3.64 (m, 1H), 3.43-3.38 (m, 2H), 3.15-3.13 (m, 2H), 2.78-2.77 (m, 1H), 2.64-2.60 (m, 2H), 1.79-1.68 (m, 4H), CH$_2$ obscured by solvent peak; ESI MS m/z 471 [M+H]+.

EXAMPLE 56

Preparation of (6-(Cyclopropylmethyl)-4,5,6,7-tetrahydro-1Hpyrazolo[3,4-c]pyridin-3-yl)(4-(3,4-difluoro-2-(trifluoromethyl) phenyl)piperidin-1-yl) methanone (118)

Step A: Following general procedure GP-G1, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and cyclopropanecarbaldehyde were converted to (6-(cyclopropylmethyl)-4,5,6,7-tetrahydro-1H-pyrazolo[3,4-c]pyridin-3-yl) (4-(3,4-difluoro-2-(trifluoromethyl)phenyl)piperidin-1-yl)methanone as a white solid (30 mg, 58%): mp 184-185° C.; $^1$H NMR (500 MHz, CD3OD) δ 7.53 (dd, J=17.5, 9.0 Hz, 1H), 7.39 (dd, J=9.0, 4.0 Hz, 1H), 4.83-4.82 (m, 1H, partially merged with H$_2$O peak), 4.65-4.63 (m, 1H), 3.94-3.92 (m, 2H), 3.29-3.26 (m, 2H, partially merged with CH$_3$OH peak), 3.05-3.03 (m, 2H), 2.90-2.84 (m, 3H), 2.69-2.67 (m, 2H), 1.89-1.81 (m, 4H), 1.04-1.02 (m, 1H), 0.65 (d, J=7.0 Hz, 2H), 0.29-0.27 (m, 2H), NH proton not observed; ESI MS m/z 469 [M+H]+.

EXAMPLE 57

Preparation of (4-(3,4-Difluoro-2(trifluoromethyl) phenyl) piperidin-1-yl)(6-(3,3,3-trifluoropropyl)-4,5,6,7-tetrahydro-1H-pyrazolo[3,4-c]pyridin-3-yl) methanone (119)

Step A: Following general procedure GP-G1, (4-(3,4-difluoro-2-(trifluoromethyl) phenyl) piperidin-1-yl)(4,5,6,7-tetrahydro-1H-pyrazolo[3,4-c]pyridin-3-yl)methanone TFA salt (34) and 3,3,3-trifluoropropanal were converted to (4-(3,4-difluoro-2-(trifluoromethyl)phenyl)piperidin-1-yl)(6-

(3,3,3-trifluoropropyl)-4,5,6,7-tetrahydro-1H-pyrazolo[3,4-c]pyridin-3-yl)methanone as an off-white solid (18 mg, 36%): mp 194-195° C.; $^1$H NMR (500 MHz, DMSO-d$_6$) δ 12.94 (br s, 0.25H), 12.76 (br s, 0.75H), 7.79-7.70 (m, 1H), 7.50-7.49 (m, 1H), 4.87-4.85 (m, 1H), 4.68-4.66 (m, 1H), 3.57-3.53 (m, 2H), 3.15-3.13 (m, 2H), 2.75 (t, J=7.5 Hz, 2H), 2.69-2.67 (m, 2H), 2.58-2.50 (m, 5H, partially merged with DMSO peak), 1.76-1.68 (m, 4H); ESI MS m/z 511 [M+H]+.

EXAMPLE 58

Preparation of 3-(4-(3,4-Difluoro-2-(trifluoromethyl) phenyl) piperidine-1-carbonyl)-1,4,5,7-tetrahydro-6H-pyrazolo[3,4-c]pyridine-6-carbonitrile (120)

Step A: Following general procedure GP-G2, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and cyanogen bromide were converted to 3-(4-(3,4-difluoro-2-(trifluoromethyl) phenyl)piperidine-1-carbonyl)-1,4,5,7-tetrahydro-6H-pyrazolo[3,4-c] pyridine-6-carbonitrile as a white solid (36 mg, 83%): mp 248-250° C.; $^1$H NMR (500 MHz, DMSO-d$_6$) δ 13.26 (br s, 0.25H), 12.97 (br s, 0.75H), 7.78-7.75 (m, 1H), 7.51-7.49 (m, 1H), 4.85 (apparent d, J=8.0 Hz, 1H), 4.68-4.66 (m, 1H), 4.47-4.40 (m, 2H), 3.43-3.40 (m, 2H), 3.16-3.14 (m, 2H), 2.77-2.72 (m, 3H), 1.77-1.71 (m, 4H); ESI MS m/z 440 [M+H]+.

EXAMPLE 59

Preparation of 1-(3-(4-(3,4-Difluoro-2-(trifluoromethyl) phenyl)piperidine-1-carbonyl)-1,4,5,7-tetrahydro-6H-pyrazolo[3,4-c]pyridin-6-yl)-2-methylpropan-1-one (121)

Step A: Following general procedure GP-E1, (4-(3,4-difluoro-2-(trifluoromethyl) phenyl) piperidin-1-yl) (4,5,6,7-tetrahydro-1H-pyrazolo [3,4-c]pyridin-3-yl)methanone TFA salt (34) and isobutyryl chloride were converted to 1-(3-(4-(3,4-difluoro-2-(trifluoromethyl)phenyl)piperidine-1-carbonyl)-1,4,5,7-tetrahydro-6Hpyrazolo[3,4-c] pyridin-6-yl)-2-methylpropan-1-one as a white solid (29 mg, 62%): mp 228-229° C.; $^1$H NMR (500 MHz, DMSO-d$_6$) δ 13.12 (br s, 0.25H), 12.87 (br s, 0.75H), 7.79-7.70 (m, 1H), 7.50-7.48 (m, 1H), 4.88-4.86 (m, 1H), 4.68-4.56 (m, 3H), 3.70 (s, 2H), 3.15-3.13 (m, 2H), 2.99-2.97 (m, 1H), 2.79-2.77 (m, 1H), 2.70-2.64 (m, 2H), 1.76-1.68 (m, 4H), 1.04-1.01 (m, 6H); ESI MS m/z 485 [M+H]+.

EXAMPLE 60

Preparation of 1-(3-(4-(3,4-Difluoro-2-(trifluoromethyl) phenyl) piperidine-1-carbonyl)-1,4,5,7-tetrahydro-6H-pyrazolo[3,4-c]pyridin-6-yl)propan-1-one (122)

Step A: Following general procedure GP-E1, (4-(3,4-difluoro-2-(trifluoromethyl) phenyl) piperidin-1-yl) (4,5,6,7-tetrahydro-1H-pyrazolo [3,4-c]pyridin-3-yl)methanone TFA salt (34) and propionyl chloride were converted to 1-(3-(4-(3,4-difluoro-2-(trifluoromethyl)phenyl)piperidine-1-carbonyl)-1,4,5,7-tetrahydro-6Hpyrazolo[3,4-c]pyridin-6-yl)propan-1-one as a white solid (35 mg, 63%): mp 182-187° C.; $^1$H NMR (500 MHz, DMSO-d$_6$) δ 13.15-13.10 (m, 0.25H), 12.87 (br s, 0.75H), 7.76-7.72 (m, 1H), 7.51-7.49 (m, 1H), 4.85-4.83 (m, 1H), 4.68-4.57 (m, 3H), 3.69 (s, 0.5H), 3.63 (s, 1.5H), 3.15-3.13 (m, 2H), 2.79-2.77 (m, 1H), 2.68-2.55 (m, 2H, partially merged with DMSO peak), 2.46-2.38 (m, 2H), 1.76-1.71 (m, 4H), 1.02 (t, J=7.5 Hz, 3H); ESI MS m/z 471 [M+H]+.

EXAMPLE 61

Preparation of 1-(3-(4-(3,4-Difluoro-2-(trifluoromethyl)phenyl)piperidine-1-carbonyl)-1,4,5,7-tetrahydro-6H-pyrazolo[3,4-c]pyridin-6-yl)-3-methylbutan-1-one (123)

Step A: Following general procedure GP-E1, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and 3-methylbutanoyl chloride were converted to 1-(3-(4-(3,4-difluoro-2-(trifluoromethyl)phenyl)piperidine-1-carbonyl)-1,4,5,7-tetrahydro-6Hpyrazolo[3,4-c]pyridin-6-yl)-3-methylbutan-1-one as a white solid (37 mg, 63%): mp 184-188° C.; $^1$H NMR (500 MHz, DMSO-d$_6$) δ 13.13-13.11 (m, 0.25H), 12.87-12.84 (m, 0.75H), 7.79-7.70 (m, 1H), 7.51-7.49 (m, 1H), 4.89-4.86 (m, 1H), 4.67-4.57 (m, 3H), 3.67-3.64 (m, 2H), 3.15-3.13 (m, 2H), 2.79-2.77 (m, 1H), 2.68-2.64 (m, 2H), 2.55-2.51 (m, 1H, partially merged with DMSO peak), 2.02 (pent, J=7.0 Hz, 1H), 1.76-1.70 (m, 4H), 1.26 (t, J=7.0 Hz, 1H), 0.92-0.90 (m, 6H); ESI MS m/z 499 [M+H]+.

EXAMPLE 62

Preparation of (4-(3,4-Difluoro-2-(trifluoromethyl) phenyl)piperidin-1-yl)(6-(2-methoxyethyl)-4,5,6,7-tetrahydro-1H-pyrazolo[3,4-c]pyridin-3-yl)methanone (124)

Step A: Following general procedure GP-G2, (4-(3,4-difluoro-2-(trifluoromethyl) phenyl) piperidin-1-yl) (4,5,6,7-tetrahydro-1H-pyrazolo[3,4-c]pyridin-3-yl)methanone TFA salt (34) and 1-bromo-2-methoxyethane were converted to (4-(3,4-difluoro-2-(trifluoromethyl) phenyl)piperidin-1-yl) (6-(2-methoxyethyl)-4,5,6,7-tetrahydro-1H-pyrazolo[3,4-c]pyridin-3-yl)methanone as a white solid (33 mg, 48%): mp 171-173° C.; $^1$H NMR (500 MHz, DMSO-d$_6$) δ 12.91 (br s, 0.25H), 12.71 (br s, 0.75H), 7.78-7.70 (m, 1H), 7.51-7.48 (m, 1H), 4.85 (apparent d, J=11.0 Hz, 1H), 4.66 (apparent d, J=11.0 Hz, 1H), 3.57-3.49 (m, 4H), 3.25 (s, 3H), 3.16-3.11 (m, 2H), 2.77-2.58 (m, 7H), 1.76-1.68 (m, 4H); ESI MS m/z 473 [M+H]+.

EXAMPLE 63

Preparation of (4-(3,4-Difluoro-2-(trifluoromethyl) phenyl)piperidin-1-yl)(6-(2,2,2-trifluoroethyl)-4,5,6,7-tetrahydro-1H-pyrazolo[3,4-c]pyridin-3-yl)methanone (125)

Step A: Following general procedure GP-G2, (4-(3,4-difluoro-2-(trifluoromethyl) phenyl) piperidin-1-yl) (4,5,6,7-tetrahydro-1H-pyrazolo [3,4-c]pyridin-3-yl)methanone TFA salt (34) and 2,2,2-trifluoroethyl trifluoromethanesulfonate were converted to (4-(3,4-difluoro-2-(trifluoromethyl) phenyl) piperidin-1-yl) (6-(2,2,2-trifluoroethyl)-4,5,6,7-tetrahydro-1H-pyrazolo[3,4-c]pyridin-3-yl) methanone as an offwhite solid (39 mg, 72%): mp 192-193° C.; $^1$H NMR (500 MHz, DMSO-d$_6$) δ 13.00 (br s, 0.25H), 12.76 (br s, 0.75H), 7.80-7.70 (m, 1H), 7.50-7.48 (m, 1H), 4.85 (apparent d, J=11.0 Hz, 1H), 4.66 (apparent d, J=11.0 Hz, 1H), 3.79

(s, 1.5H), 3.75 (s, 0.5H), 3.42-3.35 (m, 2H), 3.15-3.13 (m, 2H), 2.87 (t, J=6.0 Hz, 2H), 2.78-2.76 (m, 1H), 2.64-2.62 (m, 2H), 1.79-1.68 (m, 4H); ESI MS m/z 497 [M+H]+.

EXAMPLE 64

Preparation of (4-(3,4-Difluoro-2(trifluoromethyl) phenyl) piperidin-1-yl) (6-neopentyl-4,5,6,7-tetrahydro-1H-pyrazolo[3,4-c]pyridin-3-yl)methanone (126)

Step A: Following general procedure GP-G1, (4-(3,4-difluoro-2-(trifluoromethyl)phenyl)piperidin-1-yl)(4,5,6,7-tetrahydro-1H-pyrazolo[3,4-c]pyridin-3-yl)methanone TFA salt (34) and pivalaldehyde were converted to (4-(3,4-difluoro-2-(trifluoromethyl)phenyl) piperidin-1-yl) (6-neopentyl-4,5,6,7-tetrahydro-1H-pyrazolo[3,4-c]pyridin-3-yl) methanone as a white solid (28 mg, 49%): mp 218-220° C.; $^1$H NMR (500 MHz, DMSO-$d_6$) δ12.90 (br s, 0.25H), 12.67 (br s, 0.75H), 7.75-7.70 (m, 1H), 7.49 (dd, J=8.0, 4.0 Hz, 1H), 4.88 (apparent d, J=12.0 Hz, 1H), 4.67 (apparent d, J=10.0 Hz, 1H), 3.61 (s, 1.5H), 3.59 (s, 0.5H), 3.15-3.13 (m, 2H), 2.78-2.76 (m, 1H), 2.71 (t, J=5.5 Hz, 2H), 2.64-2.58 (m, 2H), 2.25 (s, 2H), 1.79-1.68 (m, 4H), 0.88 (s, 9H); ESI MS m/z 485 [M+H]+.

EXAMPLE 65

Preparation of (4-(3,5-Difluoro-2-(trifluoromethyl) phenyl)piperidin-1-yl)(5-(2-methoxyethyl)-4,5,6,7-tetrahydro-1H-pyrazolo[4,3-c]pyridin-3-yl)methanone (127)

Step A: Following general procedure GP-G2, (4-(3,5-difluoro-2-(trifluoromethyl) phenyl)piperidin-1-yl) (4,5,6,7-tetrahydro-1H-pyrazolo[3,4-c]pyridin-3-yl) methanone hydrochloride (60) and bromoethylmethyl ether were converted to (4-(3,5-difluoro-2-(trifluoromethyl)phenyl)piperidin-1-yl) (5-(2-methoxyethyl)-4,5,6,7-tetrahydro-1H-pyrazolo[4,3-c]pyridin-3-yl)methanone as a white solid (32 mg, 41%): $^1$H NMR (500 MHz, DMSO-$d_6$) δ 12.85 (m, 1H), 7.48 (m, 2H), 5.12 (m, 1H), 4.67 (m, 1H), 3.50 (m, 4H), 3.01-3.32 (m, 5H), 2.73 (m, 7H), 3.63-3.50 (m, 2H), 1.62 (m, 4H); ESI MS m/z 473 [M+H]+.

EXAMPLE 66

Preparation of (4-(3,4-Difluoro-2-(trifluoromethyl) phenyl)piperidin-1-yl)(5-(piperidine-1-carbonyl)-1,4, 5,6 tetrahydropyrrolo[3,4-c]pyrazol-3-yl)methanone (128)

Step A: Following general procedure GP-H2, (4-(3,4-difluoro-2-(trifluoromethyl)phenyl) piperidin-1-yl)(1,4,5,6-tetrahydropyrrolo [3,4-c]pyrazol-3-yl)methanone (38) and piperidine-1-carbonyl chloride were converted to (4-(3,4-difluoro-2-(trifluoromethyl) phenyl) piperidin-1-yl) (5-(piperidine-1-carbonyl)-1,4,5,6-tetrahydropyrrolo [3,4-c]pyrazol-3-yl)methanone as a white solid (45 mg, 77%): mp 236-237° C.; $^1$H NMR (500 MHz, DMSO-$d_6$) δ 13.26 (br s, 0.6H), 13.06 (br s, 0.4H), 7.79-7.70 (m, 1H), 7.56-7.50 (m, 1H), 5.25-5.23 (m, 0.4H), 4.65-4.62 (m, 0.6H), 4.57 (s, 2H), 4.47 (s, 2H), 4.17-3.91 (m, 1H), 3.26-3.03 (m, 6H), 3.01-2.73 (m, 1H), 1.80-1.71 (m, 4H), 1.53-1.49 (m, 6H); ESI MS m/z 512 [M+H]+.

EXAMPLE 67

Preparation of (4-(3,5-Difluoro-2-(trifluoromethyl) phenyl)piperidin-1-yl)(5-(3,3,3-trifluoropropyl)-4,5, 6,7-tetrahydro-1H-pyrazolo[4,3-c]pyridin-3-yl) methanone (129)

Step A: Following general procedure GP-G2, (4-(3,5-difluoro-2-(trifluoromethyl)phenyl)piperidin-1-yl)(4,5,6,7-tetrahydro-1H-pyrazolo[3,4-c]pyridin-3-yl)methanone hydrochloride (60) and 3-bromo-1,1,1-trifluoropropane were converted to (4-(3,5-difluoro-2-(trifluoromethyl)phenyl)piperidin-1-yl)(5-(2-methoxyethyl)-4,5,6,7-tetrahydro-1H-pyrazolo[4,3-c]pyridin-3-yl)methanone as a white solid (41 mg, 51%): $^1$H NMR (500 MHz, DMSO-$d_6$) δ 12.83 (m, 1H), 7.43 (m, 2H), 5.12 (m, 1H), 4.67 (m, 1H), 3.53 (m, 2H), 2.50-3.12 (m, 11H), 1.68 (m, 4H); ESI MS m/z 511 [M+H]$^+$.

EXAMPLE 68

Preparation of Methyl 3-(4-(3,5-difluoro-2-(trifluoromethyl) phenyl)piperidine-1-carbonyl)-1,4,5,7-tetrahydro-6H-pyrazolo[3,4-c]pyridine-6-carboxylate (130)

Step A: Following general procedure GP-E2, (4-(3,5-bis (trifluoromethyl) phenyl) piperidin-1-yl) (4,5,6,7-tetrahydro-1H-pyrazolo[3,4-c]pyridin-3-yl)methanone hydrochloride (52) and methyl carbonochloridate were converted to methyl 3-(4-(3,5-difluoro-2-(trifluoromethyl) phenyl) piperidine-1-carbonyl)-1,4,5,7-tetrahydro-6H-pyrazolo[3,4-c] pyridine-6-carboxylate as an off-white solid (7 mg, 20%): mp 253-254° C.; $^1$H NMR (500 MHz, DMSO-$d_6$) δ 13.12 (br s, 0.25H), 12.86 (br s, 0.75H), 7.45-7.38 (m, 2H), 4.84-4.82 (m, 1H), 4.68-4.66 (m, 1H), 4.54-4.51 (m, 2H), 3.64 (s, 3H), 3.60-3.58 (m, 2H), 3.20-3.13 (m, 2H), 2.79-2.77 (m, 1H), 2.65-2.62 (m, 2H), 1.76-1.72 (m, 4H); ESI MS m/z 473 [M+H]+.

EXAMPLE 69

1-(3-(4-(3,5-Difluoro-2-(trifluoromethyl) phenyl) piperidine-1-carbonyl)-4,5-dihydro-1H-pyrazolo[3, 4-c]pyridin-6(7H)-yl)ethanone (131)

Step A: Following general procedure GP-E1, (4-(3,5-bis (trifluoromethyl)phenyl)piperidin-1-yl)(4,5,6,7-tetrahydro-1H-pyrazolo[3,4-c]pyridin-3-yl)methanone hydrochloride (52) and acetyl chloride were converted to 1-(3-(4-(3,5-difluoro-2-(trifluoromethyl) phenyl)piperidine-1-carbonyl)-4,5-dihydro-1H-pyrazolo[3,4-c]pyridin-6(7H)-yl)ethanone as a white solid (0.087 g, 41%): $^1$H NMR (300 MHz, CDCl$_3$) δ 11.01 (br, 1H), 6.93 (m, 1H), 6.78 (m, 1H), 4.84-4.66 (m, 4H), 3.85-3.67 (m, 2H), 3.34-2.68 (m, 5H), 2.22 and 2.19 (s, 3H), 1.89-1.66 (m, 4H); MS (ESI+) m/z 457 [M+H]+0.77 (m, 1H), 2.65-2.62 (m, 2H), 1.76-1.72 (m, 4H); ESI MS m/z 473 [M+H]+.

EXAMPLE 70

3-(4-(3,5-Difluoro-2-(trifluoromethyl)phenyl)piperidine-1-carbonyl)-[1,2,4]triazolo[4,3-a]pyridine-6-carbonitrile (132)

Step A: To a solution of tert-butyl 4-(3,5-difluoro-2-(trifluoromethyl)phenyl)piperidine-1-carboxylate (0.246 g, 0.675 mmol) in dichloromethane (5 mL) was added HCl (2

M in ether, 10 mL). The mixture was stirred for 6 h and evaporated to afford a solid that was dissolved in DMF (4 mL). In a separate flask, to a solution of ethyl 6-bromo-[1,2,4]triazolo[4,3-a]pyridine-3-carboxylate (0.182 g, 0.675 mmol) in THF (5 mL) was added a solution of lithium hydroxide hydrate (0.028 g, 0.675 mmol) in water (2 mL). The mixture was stirred for 20 min, acidified with 2 N HCl to pH 6 and evaporated to dryness. To this residue were added benzotriazole-1-yl-oxytris (dimethylamino) phosphonium hexafluorophosphate (0.448 g, 1.01 mmol), N,N-diisopropylethylamine (0.349 g, 2.70 mmol), and the DMF solution obtained from the first reaction. The mixture was stirred at ambient temperature for 16 h and poured into water. The mixture was extracted with ethyl acetate and the organic layer was washed with brine for three times, dried ($Na_2SO_4$), filtered, and concentrated under reduced pressure. The resulting residue was chromatographed over silica gel (0-60% EtOAc in hexanes) to give (6-bromo-[1,2,4]triazolo[4,3-a]pyridin-3-yl)(4-(3,5-difluoro-2-(trifluoromethyl)phenyl)piperidin-1-yl)methanone as an off-white solid (0.115 g, 34%): $^1$H NMR (300 MHz, $CDCl_3$) δ 9.37 (m, 1H), 7.79 (dd, J=9.6, 0.9 Hz, 1H), 7.50 (dd, J=9.6, 1.7 Hz, 1H), 6.96 (d, J=9.7 Hz, 1H), 6.84-6.77 (m, 1H), 5.77-5.72 (m, 1H), 5.00-4.95 (m, 1H), 3.44-3.29 (m, 2H), 3.01-2.92 (m, 1H), 2.01-1.69 (m, 4H); MS (ESI+) m/z 489 [M+H]+.

Step B: A mixture of (6-bromo-[1,2,4]triazolo[4,3-a]pyridin-3-yl) (4-(3,5-difluoro-2-(trifluoromethyl)phenyl)piperidin-1-yl) methanone (0.115 g, 0.235 mmol), zinc cyanide (0.055 g, 0.470 mmol), tetrakis(triphenylphosphine)palladium (0.027 g, 0.0235 mmol), and DMF (4 mL) was heated under microwave irradiation at 130° C. for 30 min. After cooling to ambient temperature, the mixture was diluted with water (80 mL) and extracted with EtOAc (80 mL). The extract was washed with brine (2×80 mL), dried ($Na_2SO_4$), filtered, and concentrated under reduced pressure. The resulting residue was chromatographed over silica gel (0-50% EtOAc in hexanes) to give 3-(4-(3,5-difluoro-2-(trifluoromethyl)phenyl)piperidine-1-carbonyl)-[1,2,4]triazolo[4,3-a]pyridine-6-carbonitrile as a white solid (0.050 g, 49%): $^1$H NMR (300 MHz, $CDCl_3$) δ 9.71 (m, 1H), 7.98 (dd, J=9.5, 1.0 Hz, 1H), 7.51 (dd, J=9.5, 1.6 Hz, 1H), 6.95 (d, J=9.5 Hz, 1H), 6.84-6.77 (m, 1H), 5.76 (m, 1H), 5.01-4.96 (m, 1H), 3.46-3.31 (m, 2H), 3.03-2.94 (m, 1H), 2.07-1.70 (m, 4H); MS (ESI+) m/z 436 [M+H]+.

EXAMPLE 71

Preparation of (4-(3,5-difluoro-2-(trifluoromethyl) phenyl)piperidin-1-yl)(5-ethyl-4,5,6,7-tetrahydro-1H-pyrazolo[4,3-c]pyridin-3-yl)methanone (133)

Step A: Following general procedure GP-G1, (4-(3,5-bis (trifluoromethyl) phenyl)piperidin-1-yl)(4,5,6,7-tetrahydro-1H-pyrazolo[3,4-c]pyridin-3-yl)methanone hydrochloride (52) and acetaldehyde were converted to (4-(3,5-difluoro-2-(trifluoromethyl) phenyl)piperidin-1-yl)(5-ethyl-4,5,6,7-tetrahydro-1H-pyrazolo[4,3-c]pyridin-3-yl)methanone as a white solid (29 mg, 67%): mp 149-155° C.; $^1$H NMR (500 MHz, DMSO-$d_6$) δ 12.766 (s, 1H), 7.481-7.353 (m, 1H), 5.196-5.049 (m, 1H), 4.765-4.569 (m, 1H), 3.558-3.378 (m, 2H), 3.263-3.048 (m, 2H), 2.850-2.715 (m, 1H), 2.664 (s, 4H), 2.575-2.515 (m, 2H), 1.858-1.606 (br s, 4H), 1.121-1.018 (m, 4H); ESI MS m/z 443.2 [M+H]+.

EXAMPLE 72

Preparation of (5-(cyclopropylmethyl)-4,5,6,7-tetrahydro-1H-pyrazolo[4,3-c]pyridin-3-yl)(4-(3,5-difluoro-2-(trifluoromethyl) phenyl)piperidin-1-yl) methanone (134)

Step A: Following general procedure GP-G1, (4-(3,5-bis (trifluoromethyl) phenyl) piperidin-1-yl) (4,5,6,7-tetrahydro-1H-pyrazolo [3,4-c]pyridin-3-yl)methanone hydrochloride (52) and cyclopropyl acetaldehyde were converted to (5-(cyclopropylmethyl)-4,5,6,7-tetrahydro-1H-pyrazolo [4,3-c] pyridin-3-yl) (4-(3,5-difluoro-2-(trifluoromethyl) phenyl)piperidin-1-yl)methanone as a white solid (29 mg, 67%): No clear melt observed; $^1$H NMR (500 MHz, DMSO-$d_6$) δ 12.764 (s, 1H), 7.522-7.347 (m, 2H), 5.225-5.016 (br s, 1H), 4.766-4.580 (br s, 1H), 3.673-3.444 (m, 2H), 3.258-3.034 (m, 2H), 2.868-2.601 (m, 5H), 2.443-2.334 (m, 2H), 1.858-1.620 (br s, 4H), 0.995-0.829 (m, 1H), 0.551-0.410 (m, 2H), 0.195-0.075 (m, 2H); ESI MS m/z 469.1 [M+H]+.

EXAMPLE 73

Preparation of (4-(3,5-difluoro-2-(trifluoromethyl) phenyl)piperidin-1-yl)(5-(oxetan-3-yl)-4,5,6,7-tetrahydro-1H-pyrazolo[4,3-c]pyridin-3-yl)methanone (135)

Step A: Following general procedure GP-G1, (4-(3,5-bis (trifluoromethyl)phenyl)piperidin-1-yl)(4,5,6,7-tetrahydro-1H-pyrazolo[3,4-c]pyridin-3-yl)methanone hydrochloride (52) and 3-oxetanone were converted to (4-(3,5-difluoro-2-(trifluoromethyl) phenyl)piperidin-1-yl)(5-(oxetan-3-yl)-4,5,6,7-tetrahydro-1H-pyrazolo[4,3-c]pyridin-3-yl)methanone as a white solid (35 mg, 67%): No clear melt observed; $^1$H NMR (300 MHz, DMSO-$d_6$) δ 12.843 (s, 1H), 7.483-7.346 (m, 1H), 5.234-5.065 (br s, 1H), 4.731-4.627 (br s, 1H), 4.627-4.562 (m, 2H), 4.562-4.452 (m, 2H), 3.714-3.643 (m, 1H), 3.473-3.337 (br s, 2H), 3.260-3.058 (m, 2H), 2.850-2.724 (m, 1H), 2.724-2.658 (m, 2H), 2.582-2.516 (m, 2H), 1.876-1.586 (br s, 4H); ESI MS m/z 471 [M+H]+.

EXAMPLE 74

Preparation of 3-(4-(3,5-difluoro-2-(trifluoromethyl) phenyl)piperidine-1-carbonyl)-6,7-dihydro-1H-pyrazolo[4,3-c]pyridine-5(4H)-carbonitrile (136)

Step A: Following general procedure GP-G2, (4-(3,5-bis (trifluoromethyl) phenyl)piperidin-1-yl) (4,5,6,7-tetrahydro-1H-pyrazolo[3,4-c]pyridin-3-yl)methanone hydrochloride (52) and cyanogen bromide were converted to 3-(4-(3,5-difluoro-2-(trifluoromethyl) phenyl) piperidine-1-carbonyl)-6,7-dihydro-1H-pyrazolo[4,3-c] pyridine-5(4H)-carbonitrile as a white solid (16 mg, 55%): No clear melt observed; $^1$H NMR (500 MHz, DMSO-$d_6$) δ 13.146-13.060 (m, 1H), 7.508-7.356 (m, 2H), 5.402-4.584 (m, 2H), 4.433-4.327 (m, 2H), 3.536-3.412 (m, 2H), 3.261-3.092 (m, 2H), 2.905-2.728 (m, 3H), 1.884-1.608 (m, 4H); ESI MS m/z 440 [M+H]+.

EXAMPLE 75

Preparation of (4-(3,5-difluoro-2-(trifluoromethyl) phenyl)piperidin-1-yl)(5-(2,2,2-trifluoroethyl)-4,5,6,7-tetrahydro-1H-pyrazolo[4,3-c]pyridin-3-yl)methanone (137)

Step A: Following general procedure GP-G2, (4-(3,5-bis (trifluoromethyl) phenyl)piperidin-1-yl)(4,5,6,7-tetrahydro- 1H-pyrazolo [3,4-c]pyridin-3-yl)methanone hydrochloride (52) and 2,2,2-trifluoroethyl trifluoromethanesulfonate were converted to (4-(3,5-difluoro-2-(trifluoromethyl) phenyl) piperidin-1-yl) (5-(2,2,2-trifluoroethyl)-4,5,6,7-tetrahydro-1H-pyrazolo[4,3-c]pyridin-3-yl) methanone as a white solid (16 mg, 55%): No clear melt observed; $^1$H NMR (500 MHz, DMSO-$d_6$) δ 13.033-12.768 (m, 1H), 7.506-7.333 (m, 2H), 5.290-4.578 (m, 2H), 3.894-3.657 (m, 2H), 3.447-3.320 (m, 2H), 3.256-3.037 (m, 2H), 2.937 (s, 2H), 2.709 (s, 3H), 1.906-1.605 (br s, 4H); ESI MS m/z 497 [M+H]+.

EXAMPLE 76

Preparation of Methyl 3-(4-(3,5-difluoro-2-(trifluoro-methyl)phenyl)piperidine-1-carbonyl)-6,7-dihydro-1H-pyrazolo[4,3-c] pyridine-5(4H)-carboxylate (138)

Step A: Following general procedure GP-B2, (4-(3,5-difluoro-2-(trifluoromethyl) phenyl) piperidin-1-yl)(4,5,6,7-tetrahydro-1H-pyrazolo[3,4-c]pyridin-3-yl)methanone hydrochloride (60) and methyl chloroformate were converted to methyl 3-(4-(3,5-difluoro-2-(trifluoromethyl) phenyl) piperidine-1-carbonyl)-6,7-dihydro-1H-pyrazolo[4,3-c] pyridine-5(4H)-carboxylate as a white solid (16 mg, 55%): $^1$H NMR (300 MHz, DMSO-$d_6$) 5♦ 13.11-12.93 (m, 1H), 7.56-7.32 (m, 2H), 5.40-5.16 (m, 1H), 4.81-4.59 (m, 1H), 4.59-4.40 (m, 2H), 3.64 (s, 5H), 3.28-3.03 (br s, 2H), 2.89-2.62 (m, 3H), 1.94-1.61 (br s, 4H); ESI MS m/z 472 [M+H]$^+$.

EXAMPLE 77

Preparation of 3-(4-(3,5-difluoro-2-(trifluoromethyl) phenyl)piperidine-1-carbonyl)-N-methyl-6,7-dihydro-1H-pyrazolo[4,3-c]pyridine-5(4H)-carboxamide (139)

Step A: Following general procedure GP-E2, (4-(3,5-bis (trifluoromethyl) phenyl)piperidin-1-yl)(4,5,6,7-tetrahydro-1H-pyrazolo[3,4-c]pyridin-3-yl)methanone hydrochloride (52) and methyl isocyanate were converted to 3-(4-(3,5-difluoro-2-(trifluoromethyl) phenyl) piperidine-1-carbonyl)-N-methyl-6,7-dihydro-1Hpyrazolo[4,3-c] pyridine-5(4H)-carboxamide as a white solid (16 mg, 55%): No clearmelt; $^1$H NMR (500 MHz, DMSO-$d_6$) δ 13.043-12.777 (m, 1H), 7.523-7.348 (m, 2H), 6.536 (s, 1H), 5.275-4.595 (m, 2H), 4.536-4.296 (m, 2H), 3.561 (s, 2H), 3.273-3.076 (m, 2H), 2.891-2.706 (br s, 1H), 2.706-2.614 (m, 2H), 2.576 (s, 3H), 1.906-1.585 (m, 4H); ESI MS m/z 472 [M+H]+.

EXAMPLE 78

Preparation of 1-(3-(4-(5-fluoro-2-(trifluoromethyl) phenyl)piperidine-1-carbonyl)-4,5-dihydro-1H-pyrazolo[3,4-c]pyridin-6(7H)-yl)ethanone (140)

Step A: Following general procedure GP-E1, (4-(5-fluoro-2-(trifluoromethyl) phenyl) piperidin-1-yl) (4,5,6,7-tetrahydro-1H-pyrazolo[3,4-c]pyridin-3-yl)methanone hydrochloride (44) and acetyl chloride were converted to 1-(3-(4-(5-fluoro-2-(trifluoromethyl) phenyl) piperidine-1-carbonyl)-4,5-dihydro-1H-pyrazolo[3,4-c] pyridine-6(7H)-yl)ethanone as a white solid (27 mg, 41%): mp 190-195° C.; $^1$H NMR (500 MHz, DMSO-$d_6$) δ 13.17-12.85 (m, 1H), 7.79-7.73 (m, 1H), 7.57-7.52 (m, 1H), 7.30-7.22 (m, 1H), 4.94-4.77 (m, 1H), 4.74-4.63 (m, 1H), 4.62-4.51 (m, 2H), 3.73-3.56 (m, 2H), 3.19-3.06 (m, 2H), 2.83-2.53 (m, 3H), 2.14-2.05 (m, 3H), 1.80-1.64 (m, 4H); ESI MS m/z 439 [M+H]+.

EXAMPLE 79

Preparation of (4-(5-fluoro-2-(trifluoromethyl)phenyl) piperidin-1-yl)(5-(methylsulfonyl)-4,5,6,7-tetrahydro-1H-pyrazolo[4,3-c]pyridin-3-yl)methanone (141)

Step A: Following general procedure GP-C, (4-(5-fluoro-2-(trifluoromethyl) phenyl)piperidin-1-yl)(4,5,6,7-tetrahydro-1H-pyrazolo[4,3-c]pyridin-3-yl)methanone hydrochloride (46) and methane sulfonyl chloride were converted to (4-(5-fluoro-2-(trifluoromethyl)phenyl)piperidin-1-yl)(5-(methylsulfonyl)-4,5,6,7-tetrahydro-1H-pyrazolo[4,3-c] pyridin-3-yl)methanone as a white solid (105 mg, 60%): mp>260° C.; $^1$H NMR (500 MHz, DMSO-$d_6$) δ 13.03 (s, 1H), 7.76 (dd, J=9.0, 6.0 Hz, 1H), 7.55 (dd, J=10.5, 2.5 Hz, 1H), 7.28-7.21 (m, 1H), 5.34-5.23 (m, 1H), 4.72-4.64 (m, 1H), 4.43-4.26 (m, 2H), 3.54-3.39 (m, 2H), 3.22-3.09 (m, 2H), 2.94 (s,3H), 2.86-2.72 (m, 3H), 1.83-1.67 (m, 4H); ESI MS m/z 475 [M+H]+.

EXAMPLE 80

Preparation of 3-(4-(5-fluoro-2-(trifluoromethyl) phenyl)piperidine-1-carbonyl)-[1,2,4]triazolo[4,3-a] pyridine-6-carbonitrile (142)

Step A: To a solution of ethyl 6-bromo-[1,2,4]triazolo[4,3-a]pyridine-3-carboxylate (85 mg, 0.32 mmol) in THF (2.6 mL) was added a solution of LiOH monohydrate (15 mg, 0.35 mmol) in H$_2$O (1.8 mL). The mixture stirred for 20 min and was neutralized with 2 N HCl. The mixture was concentrated under reduced pressure. The obtained residue was diluted in DMF (3.0 mL) under an atmosphere of N2. To this mixture was added 4-(5-fluoro-2-trifluoromethyl)phenylpiperidine hydrochloride (11, 89 mg, 0.32 mmol), benzotriazole-1-yl-oxy-tris-(dimethylamino)-phosphonium hexafluorophosphate (280 mg, 0.63 mmol), and diisopropylethylamine (0.17 mL, 0.95 mmol). The mixture was stirred at ambient temperature for 18 h. The resulting mixture was diluted with H$_2$O (20 mL). The solution was extracted with EtOAc (3×20 mL). The combined organic layers were washed with a saturated brine solution (3×20 mL) and concentrated under reduced pressure. The resulting residue was chromatographed over silica gel (Isco CombiFlash Rf unit, 12 g Redisep column, 0% to 50% EtOAc in hexanes) to provide to provide (6-bromo-[1,2,4]triazolo[4,3-a]pyridin-3-yl) (4-(5-fluoro-2-(trifluoromethyl)phenyl)piperidin-1-yl)methanone as a white solid (97 mg, 65%): $^1$H NMR (500 MHz, DMSO-$d_6$) δ 9.16-9.14 (m, 1H), 7.98 (dd, J=10.0, 1.0 Hz, 1H), 7.77 (dd, J=8.5, 5.5 Hz, 1H), 7.72 (dd, J=9.5, 1.5 Hz, 1H), 7.52 (dd, J=11.0, 3.5 Hz, 1H), 7.29-7.23 (m, 1H), 5.31-5.24 (m, 1H), 4.76-4.70 (m, 1H), 3.42-3.32 (m, 1H), 3.27-3.19 (m, 1H), 3.06-2.96 (m, 1H), 1.98-1.75 (m, 4H).

Step B: A solution of (6-bromo-[1,2,4]triazolo[4,3-a]pyridin-3-yl) (4-(5-fluoro-2-(trifluoromethyl)phenyl)piperidin-1-yl)methanone (97 mg, 0.21 mmol) in DMF (2.2 mL) was sparged with Ar for 20 min. Zinc cyanide (48 mg, 0.41 mmol) was added and the solution sparged with Ar for 10 min. To the solution was added Pd(PPh$_3$)$_4$ (24 mg, 0.021 mmol) and the vessel was sealed and heated to 130° C. with microwaves for 30 min. The mixture was diluted with saturated sodium bicarbonate solution (10 mL) and extracted with EtOAc (4×30 mL). The combined organic extracts were concentrated to dryness under reduced pressure. The resulting residue was chromatographed over silica gel (Isco CombiFlash Rf unit, 12 g Redisep column, 0% to 50% EtOAc in hexanes) and freeze dried to give 3-(4-(5-fluoro-2-(trifluoromethyl)phenyl)piperidine-1-carbonyl)-[1,2,4]triazolo[4,3-a]pyridine-6-carbonitrile as a white solid (35 mg, 41%): mp 190-197° C.; $^1$H NMR (500 MHz, DMSO-$d_6$) δ 9.54-9.53 (m, 1H), 8.14 (dd, J=9.5, 1.5 Hz, 1H), 7.82 (d, J=9.5, 1.5 Hz, 1H), 7.78 (dd, J=9.0, 6.0 Hz, 1H), 7.56 (dd, J=10.5, 2.5 Hz, 1H), 7.30-7.24 (m, 1H), 5.20-5.10 (m, 1H), 4.73-4.71 (m, 1H), 3.43-3.34 (m, 1H), 3.29-3.20 (m, 1H), 3.08-3.00 (m, 1H), 1.99-1.77 (m, 4H); ESI MS m/z 418 [M+H]+.

EXAMPLE 81

Preparation of 1-(3-(4-(2-chloro-5-fluorophenyl) piperidine-1-carbonyl)-4,5-dihydro-1H-pyrazolo[3, 4-c]pyridin-6(7H)-yl)ethanone (143)

Step A: Following general procedure GP-E1, ((4-(2-chloro-5-fluorophenyl)piperidin-1-yl)(4,5,6,7-tetrahydro-1H-pyrazolo[3,4-c] pyridin-3-yl)methanone hydrochloride (48) and acetyl chloride were converted to 1-(3-(4-(2-chloro-5-fluorophenyl)piperidine-1-carbonyl)-4,5-dihydro-1H-pyrazolo[3,4-c]pyridin-6(7H)-yl)ethanone as a white solid (27 mg, 63%): $^1$H NMR (500 MHz, DMSO-$d_6$) δ 13.99-12.18 (m, 1H), 7.48 (dd, J=9.0, 5.5 Hz, 1H), 7.72 (dd, J=10.5, 3.5 Hz, 1H), 7.15-7.08 (m, 1H), 4.90-4.74 (m, 1H), 4.73-4.53 (m, 3H), 3.71-3.55 (m, 2H), 3.28-3.10 (m, 2H), 2.87-2.50 (m, 3H, overlaps with solvent), 2.12-2.04 (m, 3H), 1.91-1.71 (m, 2H), 1.66-1.52 (m, 2H); ESI MS m/z 405 [M+H]+.

EXAMPLE 82

Preparation of (4-(2-chloro-5-fluorophenyl)piperidin-1-yl)(5-(methylsulfonyl)-4,5,6,7-tetrahydro-1H-pyrazolo[4,3-c]pyridin-3-yl)methanone (144)

Step A: Following general procedure GP-C, (4-(2-chloro-5-fluorophenyl)piperidin-1-yl)(4,5,6,7-tetrahydro-1H-pyrazolo[4,3-c]pyridin-3-yl)methanone hydrochloride (50) and methane sulfonyl chloride were converted to (4-(2-chloro-5-fluorophenyl)piperidin-1-yl) (5-(methylsulfonyl)-4,5,6,7-tetrahydro-1H-pyrazolo[4,3-c]pyridin-3-yl)methanone as a white solid (36 mg, 51%): mp 260-267° C.; $^1$H NMR (500 MHz, DMSO-$d_6$) δ 13.03 (s, 1H), 7.48 (dd, J=8.5, 5.0 Hz, 1H), 7.28 (dd, J=10.5, 3.5 Hz, 1H), 7.13-7.08 (m, 1H), 5.30-5.20 (m, 1H), 4.72-4.63 (m, 1H), 4.41-4.24 (m, 2H), 3.53-3.40 (m, 2H), 3.28-3.13 (m, 2H), 2.93 (s, 3H), 2.89-2.73 (m, 3H), 1.90-1.74 (m, 2H), 1.70-1.51 (m, 2H); ESI MS m/z 441 [M+H]+.

EXAMPLE 83

Preparation of 3-(4-(2-Chloro-5-fluorophenyl)piperidine-1-carbonyl)-[1,2,4]triazolo[4,3-a]pyridine-6-carbonitrile (145)

Step A: To a solution of ethyl 6-bromo-[1,2,4]triazolo[4,3-a]pyridine-3-carboxylate (73 mg, 0.27 mmol) in THF (2.2 mL) was added a solution of LiOH monohydrate (13 mg, 0.30 mmol) in H$_2$O (1.5 mL). The mixture stirred for 20 min and was neutralized with 2 N HCl. The mixture was concentrated under reduced pressure. The obtained residue was diluted in DMF (2.9 mL) under an atmosphere of N2. To this mixture was added 4-(2-chloro-5-fluorophenyl)piperidine hydrochloride (17, 68 mg, 0.27 mmol), benzotriazole-1-yl-oxy-tris-(dimethylamino)-phosphonium hexafluorophosphate (240 mg, 0.54 mmol), and diisopropylethylamine (0.14 mL, 0.81 mmol). The mixture was stirred at ambient temperature for 18 h. The resulting mixture was diluted with H$_2$O (20 mL) and the resulting precipitate was collected by filtration. The obtained solids were chromatographed over silica gel (Isco CombiFlash Rf unit, 12 g Redisep column, 0 to 50% EtOAc in hexanes) to provide (6-bromo-[1,2,4] triazolo[4,3-a]pyridin-3-yl) (4-(2-chloro-5-fluorophenyl)piperidin-1-yl)methanone as a white solid (50 mg, 42%): $^1$H NMR (500 MHz, DMSO-$d_6$) δ 9.13-9.11 (m, 1H), 7.98 (dd, J=9.5, 1.0 Hz, 1H), 7.71 (dd, J=9.5, 1.5 Hz, 1H), 7.50 (dd, J=9.0, 5.5 Hz, 1H), 7.28 (dd, J=25, 3.0 Hz, 1H), 7.15-7.10 (m, 1H), 5.28-5.20 (m, 1H), 4.76-4.70 (m, 1H), 3.42-3.29 (m, 2H, overlaps with H$_2$O), 3.07-2.98 (m, 1H), 1.96-1.65 (m, 4H).

Step B: A solution of (6-bromo-[1,2,4]triazolo[4,3-a]pyridin-3-yl)(4-(2-chloro-5-fluorophenyl)piperidin-1-yl)methanone (50 mg, 0.21 mmol) in DMF (2.0 mL) zinc cyanide (48 mg, 0.41 mmol) was sparged with Ar for 20 min. To the solution was added Pd(PPh$_3$)$_4$ (13 mg, 0.011 mmol) and the vessel was sealed and heated to 130° C. with microwaves for 30 min. The mixture was diluted with saturated sodium bicarbonate solution (10 mL) and extracted with EtOAc (4×30 mL). The combined organic extracts were concentrated to dryness under reduced pressure. The resulting residue was chromatographed over silica gel (Isco Combi-Flash Rf unit, 12 g Redisep column, 0% to 50% EtOAc in hexanes) and freeze dried to give 3-(4-(2-chloro-5-fluorophenyl)piperidine-1-carbonyl)-[1,2,4]triazolo[4,3-a]pyridine-6-carbonitrile as a white solid (21 mg, 54%): mp 211-214° C.; $^1$H NMR (500 MHz, DMSO-$d_6$) δ 9.52-9.50 (m, 1H), 8.13 (dd, J=9.5, 1.0 Hz, 1H), 7.81 (dd, J=9.5, 1.5 Hz, 1H), 7.50 (dd, J=9.0, 5.5 Hz, 1H), 7.28 (dd, J=10.5, 3.5 Hz, 1H), 7.16-7.11 (m, 1H), 5.16-5.11 (m, 1H), 4.78-4.71 (m, 1H), 3.46-3.30 (m, 2H, overlaps with H$_2$O), 3.11-3.01 (m, 1H), 1.99-1.70 (m, 4H); ESI MS m/z 384 [M+H]+.

EXAMPLE 84

Preparation of (4-(2-chloro-3-(fluorophenyl)piperidin-1-yl)(6-cyclopropylmethyl)-4,5,6,7-tetrahydro-1H-pyrazolo[3,4-c]pyridine-3-yl)methanone (146)

Step A: Following general procedure GP-G2, (4-(2-chloro-3-fluorophenyl)piperidin-1-yl) (4,5,6,7-tetrahydro-1H-pyrazolo[4,3-c]pyridin-3-yl)methanone hydrochloride (40) and cyclopropane carbaldehyde were converted to (4-(2-chloro-3-(fluorophenyl) piperidine-1-yl)(6-cyclopropylmethyl)-4,5,6,7-tetrahydro-1H-pyrazolo [3,4-c]pyridine-3-yl)methanone as a white solid (21 mg, 36%): mp 187-191° C.; $^1$H NMR (300 MHz, DMSO-$d_6$) δ 12.74 (br s, 1H), 7.38-7.24 (m, 3H), 4.96-4.55 (m, 2H), 3.57 (s, 2H), 3.28-3.17 (m, 2H), 2.91-2.38 (m, 7H), 1.91-1.79 (m, 2H), 1.64-1.56 (m, 2H), 0.92-0.85 (m, 1H), 0.52-0.48 (m, 2H), 0.16-0.08 (m, 2H); ESI MS m/z 417 [M+H]+.

EXAMPLE 85

Preparation of Methyl 3-(4-(2-chloro-3-fluorophenyl)piperidine-1-carbonyl)-4,5-dihydro-1H-pyrazolo [3,4-c]pyridine-6(7H)-carboxylate (147)

Step A: Following general procedure GP-E1, (4-(2-chloro-3-fluorophenyl)piperidin-1-yl)(4,5,6,7-tetrahydro- 1H-pyrazolo[4,3-c] pyridin-3-yl)methanone hydrochloride (40) and methyl chloroformate were converted to methyl 3-(4-(2-chloro-3-fluorophenyl)piperidine-1-carbonyl)-4,5-dihydro-1H-pyrazolo[3,4-c]pyridine-6(7H)-carboxylate as a white solid (30 mg, 65%): mp 182-185° C.; $^1$H NMR (300 MHz, DMSO-$d_6$) δ 12.88 (br s, 1H), 7.39-7.24 (m, 3H), 4.85-4.61 (m, 2H), 4.54-4.49 (m, 2H), 3.64-3.56 (m, 5H), 3.28-3.12 (m, 2H), 2.93-2.75 (m, 1H), 2.61-2.55 (m, 2H), 1.91-1.78 (m, 2H), 1.64-1.55 (m, 2H); ESI MS m/z 421 [M+H]+.

EXAMPLE 86

Preparation of 3-(4-(2-chloro-3-fluorophenyl)piperidine-1-carbonyl)-4,5-dihydro-1H-pyrazolo[3,4-c]pyridine-6(7H)-carbonitrile (148)

Step A: Following general procedure GP-G2, (4-(2-chloro-3-fluorophenyl)piperidin-1-yl)(4,5,6,7-tetrahydro-1H-pyrazolo[4,3-c]pyridin-3-yl)methanone hydrochloride (40) and cyanogen bromide were converted to 3-(4-(2-chloro-3-fluorophenyl)piperidine-1-carbonyl)-4,5-dihydro-1H-pyrazolo[3,4-c]pyridine-6(7H)-carbonitrile as a white solid (19 mg, 35%): mp 182-185° C.; $^1$H NMR (300 MHz, DMSO-$d_6$) δ 12.98 (br s, 1H), 7.37-7.24 (m, 3H), 4.91-4.65 (m, 2H), 4.47-4.40 (m, 2H), 3.43-3.12 (m, 4H), 2.93-2.69 (m, 3H), 1.91-1.78 (m, 2H), 1.76-1.55 (m, 2H); ESI MS m/z 388 [M+H]+.

EXAMPLE 87

Preparation of (4-(2-chloro-3-(fluorophenyl)piperidin-1-yl)(6-oxetan-3-yl)-4,5,6,7-tetrahydro-1H-pyrazolo[3,4-c]pyridin-3-yl)methanone (149)

Step A: Following general procedure GP-G1, (4-(2-chloro-3-fluorophenyl)piperidin-1-yl)(4,5,6,7-tetrahydro-1H-pyrazolo[4,3-c] pyridin-3-yl)methanone hydrochloride (40) and oxetan-3-one were converted to (4-(2-chloro-3-(fluorophenyl)piperidine-1-yl) (6-oxetan-3-yl)-4,5,6,7-tetrahydro-1H-pyrazolo[3,4-c]pyridin-3-yl)methanone as a white solid (17 mg, 31%): $^1$H NMR (300 MHz, DMSO-$d_6$) δ 12.77 (br s, 1H), 7.37-7.24 (m, 3H), 4.91-4.47 (m, 6H), 3.71-3.61 (m, 1H), 3.47-3.12 (m, 4H), 2.93-2.78 (m, 1H), 2.74-2.53 (m, 4H), 1.91-1.78 (m, 2H), 1.76-1.55 (m, 2H); ESI MS m/z 419 [M+H]+.

EXAMPLE 88

Preparation of 1-(3-(4-(2-chloro-3-fluorophenyl) piperidine-1-carbonyl)-4,5-dihydro-1H-pyrazolo [3,4-c]pyridin-6(7H)-yl)ethanone (150)

Step A: Following general procedure GP-E1, (4-(2-chloro-3-fluorophenyl)piperidin-1-yl)(4,5,6,7-tetrahydro-1H-pyrazolo[4,3-c] pyridin-3-yl)methanone hydrochloride (40) and acetyl chloride were converted to 1-(3-(4-(2-chloro-3-fluorophenyl)piperidine-1-carbonyl) -4,5-dihydro-1H-pyrazolo[3,4-c]pyridin-6(7H)-yl)ethanone as a white solid (14 mg, 25%): $^1$H NMR (500 MHz, DMSO-$d_6$) δ 13.18-12.83 (m, 1H), 7.41-7.31 (m, 1H), 7.30-7.22 (m, 2H), 4.87-4.74 (m, 1H), 4.73-4.63 (m, 1H), 4.62-4.53 (m, 2H), 3.71-3.58 (m, 2H), 3.31-3.24 (m, 1H, overlaps with H$_2$O), 3.20-3.12 (m, 1H), 2.90-2.76 (m, 1H), 2.74-2.52 (m, 2H), 2.11-2.07 (m, 3H), 1.89-1.72 (m, 2H), 1.65-1.52 (m, 2H); ESI MS m/z 405 [M+H]+; HPLC>99% purity (Method H). (m, 3H), 4.91-4.47 (m, 6H), 3.71-3.61 (m, 1H), 3.47-3.12 (m, 4H), 2.93-2.78 (m, 1H), 2.74-2.53 (m, 4H), 1.91-1.78 (m, 2H), 1.76-1.55 (m, 2H); ESI MS m/z 419 [M+H]+.

EXAMPLE 89

Preparation of (4-(2-chloro-3-fluorophenyl)piperidin-1-yl)(5-(methylsulfonyl)-4,5,6,7-tetrahydro-1H-pyrazolo[4,3-c]pyridin-3-ylmethanone (151)

Step A: Following general procedure GP-C, ((4-(2-chloro-3-fluorophenyl)piperidin-1-yl)(4,5,6,7-tetrahydro-1H-pyrazolo[4,3-c]pyridin-3-yl)methanone hydrochloride (40) and methanesulfonyl chloride were converted to 1-(3-(4-(2-chloro-3-fluorophenyl) piperidine-1-carbonyl)-4,5-dihydro-1H-pyrazolo[3,4-c(4-(2-chloro-3-fluorophenyl)piperidin-1-yl) (5-(methylsulfonyl)-4,5,6,7-tetrahydro-1H-pyrazolo[4,3-c]pyridin-3-ylmethanone as a white solid (21 mg, 34%): mp 247-253° C. decomp.; $^1$H NMR (500 MHz, DMSO-$d_6$) δ 13.03 (br s, 1H), 7.39-7.31 (m, 1H), 7.29-7.22 (m, 2H), 5.28-5.19 (m, 1H), 4.72-4.63 (m, 1H), 4.39-4.28 (m, 2H), 3.50-3.14 (m, 7H, overlaps with H$_2$O), 2.86-2.79 (m, 3H), 1.91-1.76 (m, 2H), 1.69-1.53 (m, 2H); ESI MS m/z 441 [M+H]+.

EXAMPLE 90

Preparation of (6-bromo-[1,2,4]triazolo[4,3-a]pyridin-3-yl)(4-(2-chloro-3-fluorophenyl)piperidin-1-yl) methanone (152)

Step A: To a solution of ethyl 6-bromo-[1,2,4]triazolo[4,3-a]pyridine-3-carboxylate (102 mg, 0.38 mmol) in THF (3.1 mL) was added a solution of LiOH monohydrate (16 mg, 0.38 mmol) in H$_2$O (2.0 mL). The mixture stirred for 20 min and was neutralized with 2 N HCl. The mixture was concentrated under reduced pressure. The obtained residue was diluted in DMF (4.0 mL) under an atmosphere of N2. To this mixture was added 4-(2-chloro-3-fluorophenyl)piperidine hydrochloride (14, 94 mg, 0.38 mmol), benzotriazole-1-yl-oxy-tris-(dimethylamino)-phosphonium hexafluorophosphate (334 mg, 0.76 mmol), and diisopropylethylamine (0.20 mL, 1.1 mmol). The mixture was stirred at ambient temperature for 18 h. The resulting mixture was diluted with H$_2$O (20 mL) and the resulting precipitate was collected by filtration. The obtained solids were chromatographed over silica gel (Isco CombiFlash Rf unit, 12 g Redisep column, 0 to 50% EtOAc in hexanes) to provide (6-bromo-[1,2,4] triazolo [4,3-a]pyridin-3-yl) (4-(2-chloro-3-fluorophenyl) piperidin-1-yl)methanone as a white solid (80 mg, 48%): $^1$H NMR (300 MHz, DMSO-$d_6$) δ 9.11 (br s, 1H), 8.03-7.95 (m, 1H), 7.71 (dd, J=9.6, 1.8 Hz, 1H), 7.43-7.23 (m, 3H), 5.27-5.17 (m, 1H), 4.80-4.69 (m, 1H), 3.48-3.34 (m, 2H), 3.12-2.96 (m, 1H), 2.02-1.59 (m, 4H); ESI MS m/z 438 [M+H]+.

Step B: A solution of (6-bromo-[1,2,4]triazolo[4,3-a]pyridin-3-yl) (4-(2-chloro-3-fluorophenyl)piperidin-1-yl)methanone (80 mg, 0.18 mmol) in DMF (2.0 mL) with zinc cyanide (43 mg, 0.65 mmol) was sparged with Ar for 20 min. To the solution was added Pd(PPh$_3$)$_4$ (21 mg, 0.018 mmol) and the vessel was sealed and heated to 130° C. with microwaves for 30 min. The mixture was diluted with H$_2$O (10 mL) and extracted with EtOAc (4×30 mL). The combined organic extracts were concentrated to dryness under reduced pressure. The resulting residue was chromatographed over silica gel (Isco CombiFlash Rf unit, 12 g Redisep column, 0% to 60% EtOAc in hexanes) and freeze dried to give 3-(4-(2-chloro-3-fluorophenyl)piperidine-1- carbonyl)-[1,2,4]triazolo[4,3-a]pyridine-6-carbonitrile as a white solid (38 mg, 55%): mp 158-163° C.; $^1$H NMR (500 MHz, DMSO-$d_6$) δ 9.51-9.50 (m, 1H), 8.12 (dd, J=9.5, 1.0 Hz, 1H), 7.81 (dd, J=9.5, 1.5 Hz, 1H), 7.41-7.34 (m, 1H), 7.31-7.24 (m, 2H), 5.16-5.09 (m, 1H), 4.78-4.71 (m, 1H), 3.47-3.37 (m, 2H), 3.12-3.03 (m, 1H), 2.00-1.64 (m, 4H); ESI MS m/z 384 [M+H]+.

Example 91

Preparation of 1-(3-(4-(3,5-bis(trifluoromethyl) phenyl)piperidine-1-carbonyl)-4,5-dihydro-1H-pyrazolo[3,4-c]pyridin-6(7H)-yl)ethanone (153)

Step A: Following general procedure GP-E1, 4-(3,5-bis (trifluoromethyl) phenyl) piperidin-1-yl) (4,5,6,7-tetrahydro-1H-pyrazolo[3,4-c]pyridin-3-yl)methanone hydrochloride (52) and acetyl chloride were converted to 1-(3-(4-(3,5-bis(trifluoromethyl)phenyl) piperidine-1-carbonyl)-4,5-dihydro-1H-pyrazolo[3,4-c]pyridin-6(7H)-yl) ethanone as a white solid (33 mg, 50%): mp 204-205° C.; $^1$H NMR (500 MHz, DMSO-$d_6$) δ 13.13-12.82 (m, 1H), 8.01-7.97 (m, 2H), 7.96-7.90 (m, 1H), 4.92-4.79 (m, 1H), 4.75-4.63 (m, 1H), 4.62-4.53 (m, 2H), 3.72-3.58 (m, 2H), 3.18-3.05 (m, 2H), 2.84-2.48 (m, 3H, overlaps with solvent), 2.12-2.05 (m, 3H), 1.97-1.78 (m, 2H), 1.76-1.61 (m, 2H); ESI MS m/z 489 [M+H]+.

EXAMPLE 92

Preparation of (4-(3,5-bis(trifluoromethyl)phenyl) piperidin-1-yl)(5-(methylsulfonyl)-4,5,6,7-tetrahydro-1H-pyrazolo [4,3-c]pyridin-3-yl)methanone (154)

Step A: Following general procedure GP-C, (4-(3,5-bis (trifluoromethyl)phenyl) piperidin-1-yl) (4,5,6,7-tetrahydro-1H-pyrazolo[4,3-c]pyridin-3-yl) methanone hydrochloride (52) and methanesulfonyl chloride were converted to (4-(3,5-bis (trifluoromethyl)phenyl) piperidin-1-yl-(5-(methylsulfonyl)-4,5,6,7-tetrahydro-1H-pyrazolo[4,3-c]pyridin-3-yl) methanone as a white solid (25 mg, 37%): $^1$H NMR (500 MHz, DMSO-$d_6$) δ 13.02 (s, 1H), 8.01-7.98 (m, 2H), 7.94-7.91 (m, 1H), 5.31-5.24 (m, 1H), 4.73-4.63 (m, 1H), 4.40-4.26 (m, 2H), 3.51-3.41 (m, 2H), 3.21-3.06 (m, 2H), 2.93 (s, 3H), 2.85-2.74 (m, 3H), 1.96-1.80 (m, 2H), 1.79-1.64 (m, 2H); ESI MS m/z 525 [M+H]+.

EXAMPLE 93

Preparation of (4-(3,5-bis(trifluoromethyl) phenyl) piperidin-1-yl)(5-(methylsulfonyl)-4,5,6,7-tetrahydro-1H-pyrazolo[4,3-c]pyridin-3-yl)methanone (155)

Step A: To a solution of ethyl 6-methoxy-[1,2,4]triazolo [4,3-a]pyridine-3-carboxylate (66 mg, 0.30 mmol) in THF (2.5 mL) was added a solution of LiOH monohydrate (25 mg, 0.60 mmol) in $H_2O$ (1.6 mL). The mixture stirred for 20 min and was neutralized with 2 N HCl. The mixture was concentrated under reduced pressure. The obtained residue was diluted in DMF (3.3 mL) under an atmosphere of $N_2$. To this mixture was added 4-(3,5-bis(trifluoromethyl)phenyl) piperidine hydrochloride (20, 100 mg, 0.30 mmol), benzotriazole-1-yl-oxy-tris-(dimethylamino)-phosphonium hexafluorophosphate (266 mg, 0.60 mmol), and diisopropylethylamine (0.16 mL, 0.90 mmol). The mixture was stirred at ambient temperature for 18 h. The resulting mixture was diluted with $H_2O$ (20 mL) and extracted with EtOAc (4×30 mL). The combined organic extracts were washed with a saturated brine solution (3×30 ml) and concentrated under reduced pressure. The obtained residue was chromatographed over silica gel (Isco CombiFlash Rf unit, 24 g Redisep column, 0% to 2% MeOH in $CH_2Cl_2$ with 0.1% $NH_4OH$ in $CH_2Cl_2$). The obtained residue was dissolved in $CH_2Cl_2$ (10 mL) and hexanes (100 mL). The solution was partially concentrated and the resulting solids were collected by filtration to provide (4-(3,5-bis(trifluoromethyl) phenyl) piperidin-1-yl) (6-methoxy-[1,2,4]triazolo[4,3-a]pyridin-3-yl) methanone as an off-white solid (80 mg, 56%): mp 146-149° C.; $^1$H NMR (500 MHz, DMSO-$d_6$) δ 8.55 (d, J=2.0 Hz, 1H), 8.03 (s, 2H), 7.95-7.89 (m, 2H), 7.38 (dd, J=10, 2.5 Hz, 1H), 5.40-5.33 (m, 1H), 4.81-4.73 (m, 1H), 3.85 (s, 3H), 3.39-3.31 (m, 1H, overlaps with $H_2O$), 3.26-3.16 (m, 1H), 3.02-2.93 (m, 1H), 2.03-1.77 (m, 4H); ESI MS m/z 473 [M+H]+.

EXAMPLE 94

Preparation of 1-(3-(4-(2-fluoro-6-(trifluoromethyl) phenyl)piperidine-1-carbonyl)-4,5-dihydro-1H-pyrazolo[3,4-c]pyridin-6(7H)-yl)ethanone (156)

Step A: Following general procedure GP-E1, (4-(2-fluoro-6-(trifluoromethyl) phenyl) piperidin-1-yl) (4,5,6,7-tetrahydro-1H-pyrazolo[3,4-c]pyridin-3-yl)methanone hydrochloride (56) and acetyl chloride were converted to 1-(3-(4-(2-fluoro-6-(trifluoromethyl) phenyl)piperidine-1-carbonyl)-4,5-dihydro-1H-pyrazolo[3,4-c]pyridin-6(7H)-yl) ethanone as a white solid (33 mg, 43%): $^1$H NMR (500 MHz, DMSO-$d_6$) δ 13.26-12.80 (m, 1H), 7.61-7.56 (m, 1H), 7.56-7.47 (m, 2H), 4.87-4.49 (m, 4H), 3.72-3.56 (m, 2H), 3.25-3.04 (m, 2H), 2.84-2.53 (m, 3H), 2.07-1.89 (m, 5H), 1.79-1.64 (m, 2H); ESI MS m/z 439 [M+H]+.

EXAMPLE 95

Preparation of 3-(4-(2-fluoro-6-(trifluoromethyl) phenyl) piperidine-1-carbonyl)-[1,2,4]triazolo[4,3-a] pyridine-6-carbonitrile (157)

Step A: To a solution of ethyl 6-bromo-[1,2,4]triazolo[4,3-a]pyridine-3-carboxylate (72 mg, 0.27 mmol) in THF (2.2 mL) was added a solution of LiOH monohydrate (12 mg, 0.29 mmol) in $H_2O$ (1.5 mL). The mixture stirred for 20 min and was neutralized with 2 N HCl. The mixture was concentrated under reduced pressure. The obtained residue was diluted in DMF (2.8 mL) under an atmosphere of $N_2$. To this mixture was added 4-(2-fluoro-6-(trifluoromethyl)phenyl) piperidine hydrochloride (23, mg, 0.27 mmol), benzotriazole-1-yl-oxy-tris-(dimethylamino)-phosphonium hexafluorophosphate (236 mg, 0.53 mmol), and diisopropylethylamine (0.14 mL, 0.80 mmol). The mixture was stirred at ambient temperature for 18 h. The resulting mixture was diluted with $H_2O$ (20 mL) and extracted with EtOAc (3×30 mL). The combined organic extracts were washed with a saturated brine solution (30 mL) and concentrated under reduced pressure. The obtained residue was chromatographed over silica gel (Isco CombiFlash Rf unit, 12 g Redisep column, 0 to 50% EtOAc in hexanes) to provide (6-bromo-[1,2,4]triazolo[4,3-a]pyridin-3-yl)(4-(2-fluoro-6-(trifluoromethyl)phenyl)piperidin-1-yl)methanone as a light orange film (80 mg, 64%): $^1$H NMR (300 MHz, DMSO-$d_6$) δ 9.12-9.10 (m, 1H), 8.00-7.95 (m, 1H), 7.74-

7.68 (m, 1H), 7.65-7.50 (m, 3H), 5.29-5.15 (m, 1H), 4.82-4.68 (m, 1H), 3.41-3.19 (m, 2H, overlaps with H$_2$O), 3.07-2.97 (m, 1H), 2.34-2.19 (m, 1H), 2.15-2.02 (m, 1H), 1.93-1.75 (m, 2H); ESI MS m/z 472 [M+H]+.

Step B: A solution of (6-bromo-[1,2,4]triazolo[4,3-a]pyridin-3-yl)(4-(2-fluoro-6-(trifluoromethyl)phenyl)piperidin-1-yl)methanone (80 mg, 0.17 mmol) in DMF (2.0 mL) with zinc cyanide (40 mg, 0.34 mmol) was sparged with Ar for 15 min. To the solution was added Pd(PPh$_3$)$_4$ (19 mg, 0.017 mmol) and the vessel was sealed and heated to 130° C. with microwaves for 30 min. The mixture was diluted with saturated sodium bicarbonate solution (20 mL) and extracted with EtOAc (3×30 mL). The combined organic extracts were washed with a saturated brine solution (2×30 mL) and concentrated to dryness under reduced pressure. The resulting residue was chromatographed over silica gel (Isco CombiFlash Rf unit, 12 g Redisep column, 0% to 50% EtOAc in hexanes) followed by HPLC (Phenomenex Luna C18 (2), 250.0×50.0 mm, 15 micron, H$_2$O with 0.05% TFA and CH$_3$CN with 0.05% TFA) and was washed with saturated sodium bicarbonate solution, and freeze dried to give 3-(4-(2-fluoro-6-(trifluoromethyl)phenyl)piperidine-1-carbonyl)-[1,2,4]triazolo[4,3-a]pyridine-6-carbonitrile as a white solid (23 mg, 33%): $^1$H NMR (500 MHz, DMSO-d$_6$) δ 9.54-9.52 (m, 1H), 8.14-8.11 (m, 1H), 7.82-7.78 (m, 1H), 7.64-7.59 (m, 1H), 7.57-7.50 (m, 2H), 5.17-5.10 (m, 1H), 4.79-4.72 (m, 1H), 3.40-3.24 (m, 2H, overlaps with H$_2$O), 3.07-2.98 127 (m, 1H), 2.30-2.19 (m, 1H), 2.14-2.03 (m, 1H), 1.91-1.79 (m, 2H); ESI MS m/z 418 [M+H]+.

EXAMPLE 96

Preparation of 1-(3-(4-(4-fluoro-2-(trifluoromethyl)phenyl)piperidine-1-carbonyl)-4,5-dihydro-1H-pyrazolo[3,4-c]pyridin-6(7H)-yl)ethanone (158)

Step A: A solution of tert-butyl 4-(((trifluoromethyl)sulfonyl)oxy)-5,6-dihydropyridine-1(2H)-carboxylate (1.50 g, 4.53 mmol) in 1,2-dimethoxyethane (25 mL) was sparged with N$_2$ for 30 min. 4-Fluoro-(2-trifluoromethyl)phenyl boronic acid (1.13 g, 5.43 mmol) was added followed by a 2 M solution of sodium carbonate (2.9 mL). The resulting mixture was sparged with N$_2$ for 10 min. Pd(PPh$_3$)$_4$ (260 mg, 0.225 mmol) was added and the resulting mixture was heated to 80° C. under an atmosphere of N$_2$. After 72 h, the resulting solution was cooled to ambient temperature and diluted with 5% lithium chloride solution (100 mL). The solution was extracted with EtOAc (3×50 mL). The combined organic extracts were washed with saturated brine (2×50 mL) and concentrated to dryness under reduced pressure. The residue was chromatographed over silica gel (Isco CombiFlash Rf unit, 24 g Redisep column, 0% to 100% EtOAc in hexanes) to provide tert-butyl 4-(4-fluoro-2-(trifluoromethyl) phenyl)-5,6-dihydropyridine-1(2H)-carboxylate as a brown oil (1.29 g, 83%): $^1$H NMR (300 MHz, CDCl$_3$) δ 7.37-7.08 (m, 3H), 5.57 (br s, 1H), 4.02-3.99 (m, 2H), 3.62-3.58 (m, 2H), 2.32 (br s, 2H), 1.46 (s, 9H).

Step B: A solution of tert-butyl 4 (4-fluoro 2 (trifluoromethyl) phenyl)-5,6-dihydropyridine-1(2H)-carboxylate (1.29 g, 3.74 mmol) in ethyl acetate (20 mL) and acetic acid (0.22 mL) was sparged with N$_2$. Platinum dioxide (84 mg) was added and the resulting suspension was sparged with N$_2$ for 5 min. The mixture was placed under an H$_2$ atmosphere at 1 atm. After 18 h the reaction was sparged with N$_2$ for 15 min, filtered through a diatomaceous earth pad, recharged with platinum dioxide (100 mg) and stirred under a 1 atm hydrogen atmosphere. The filtration and recharging of the reaction was repeated thrice over the next 64 h. The reaction was filtered through diatomaceous earth. The obtained filtrate was washed with sodium bicarbonate solution, dried (Na$_2$SO$_4$) and concentrated under reduced pressure. The residue was chromatographed over silica gel (Isco Combi-Flash Rf unit, 24 g Redisep column, 0% to 100% EtOAc in hexanes) to provide tert-butyl 4-(4-fluoro-2-(trifluoromethyl)phenyl)piperidine-1-carboxylate as a yellow oil (0.813 g, 63%): $^1$H NMR (300 MHz, CDCl$_3$) δ 7.37-7.20 (m, 3H), 4.27-4.22 (m, 2H), 3.07-2.99 (m, 1H), 2.85-2.75 (m, 2H), 2.04-1.46 (m, 13H).

Step C: To a solution of tert-butyl 4-(4-fluoro-2-(trifluoromethyl)phenyl)piperidine-1-carboxylate (0.813 g, 2.34 mmol) in diethyl ether (6 mL) was added 2 M HCl in diethyl ether (10 mL). The mixture stirred for 18 h at ambient temperature. The reaction mixture was concentrated under reduced pressure and the residue triturated with diethyl ether (10 mL). The solids were collected by filtration to give 4-(4-fluoro-2-(trifluoromethyl)phenylpiperidine hydrochloride as a white solid (0.244 g, 37%): $^1$H NMR (300 MHz, CDCl$_3$) δ 9.79 (br s, 1H), 7.59-7.54 (m, 1H), 7.37-7.24 (m, 2H), 3.68-3.64 (m, 2H), 3.27-3.03 (m, 4H), 2.39-2.27 (m, 2H), 2.01-1.96 (m, 2H); ESI MS m/z 248 [M+H]+.

Step D: To a solution of 4-(4-fluoro-2-trifluoromethyl) phenylpiperidine hydrochloride (75 mg, 0.26 mmol), 6-(tert-butoxycarbonyl)-4,5,6,7-tetrahydro-1H-pyrazolo[3,4-c]pyridine-3-carboxylic acid (75 mg, 0.29 mmol), and diisopropylethylamine (0.14 mL, 0.80 mmol) in DMF (3 mL) under an atmosphere of N$_2$ was added EDC (70 mg, 0.37 mmol) and HOBt (49 mg, 0.36 mmol). The resulting solution was stirred at ambient temperature for 24 h. The reaction mixture was diluted with H$_2$O (30 mL) and extracted with EtOAc (3×10 mL). The combined organic extracts were washed with brine (1×20 mL) and concentrated to dryness under reduced pressure. The obtained residue was chromatographed over silica gel (Isco Combi-Flash Rf unit, 12 g Redisep column, 0% to 100% ethyl acetate in hexanes) to provide tert-butyl 3-(4-(4-fluoro-2-(trifluoromethyl)phenyl)piperidine-1-carbonyl)-4,5-dihydro-1H-pyrazolo[3,4-c]pyridine-6(7H)-carboxylate as a white solid (75 mg, 58%): $^1$H NMR (300 MHz, DMSO-d$_6$) δ 12.04 (br s, 1H), 7.72-7.68 (m, 1H), 7.57-7.49 (m, 2H), 4.84-4.64 (m, 1H), 4.49-4.45 (m, 2H), 3.56-3.53 (m, 2H), 3.08 (br s, 2H), 2.78-2.50 (m, 4H), 1.75 (br s, 4H), 1.42 (s, 9H); ESI MS m/z 497 [M+H]+.

Step E: To a solution of tert-butyl 3-(4-(4-fluoro-2-(trifluoromethyl)phenyl)piperidine-1-carbonyl)-4,5-dihydro-1H-pyrazolo [3,4-c]pyridine-6(7H)-carboxylate (74 mg, 0.15 mmol) in CH$_2$Cl$_2$ (3 mL) and methanol (1 mL) was added 2 N HCl (2 mL, 2M in Et$_2$O). The mixture stirred for 4 h at ambient temperature. The reaction mixture was diluted with Et$_2$O (30 mL) and the resulting solids were collected by filtration to give (4-(4-fluoro-2-(trifluoromethyl) phenyl)piperidin-1-yl)(4,5,6,7-tetrahydro-1H-pyrazolo [3,4-c] pyridin-3-yl)methanone hydrochloride as a white solid (64 mg, 98%): $^1$H NMR (300 MHz, DMSO-d$_6$) δ 13.14 (s, 1H), 9.16 (br s, 2H), 7.73-7.68 (m, 1H), 7.59-7.50 (m, 2H), 4.84-4.69 (m, 1H), 4.32-4.25 (m, 2H), 3.26-3.03 (m, 2H), 2.89-2.81 (m, 2H), 2.68-2.48 (m, 4H), 1.73 (m, 4H); ESI MS m/z 397 [M+H]+.

Step F: To a solution of (4-(4-fluoro-2-(trifluoromethyl)phenyl)piperidin-1-yl)(4,5,6,7-tetrahydro-1H-pyrazolo[3,4-c]pyridin-3-yl)methanone hydrochloride (63 mg, 0.15 mmol) and diisopropylethylamine (70 µL, 0.40 mmol) in DMF (3.0 mL) was added acetyl chloride (11 µL, 0.15 mmol). The mixture was stirred for 16 hour. The solvent was removed under reduced pressure and the residue was diluted with H₂O (10 mL) and extracted with EtOAc (2×10 mL). The combined organic extracts were washed with saturated brine (1×20 mL), dried over Na₂SO₄ and concentrated to dryness under reduced pressure. The resulting residue was chromatographed over silica gel (Isco CombiFlash Rf unit, 12 g Redisep column, 0% to 100% (10% CH₃OH in CH₂Cl₂ with 0.01% NH₄OH) in CH₂Cl₂) and further purified by reverse phase chromatography (Isco CombiFlash Rf unit, 12 g Redisep c18 gold column, 0% to 100% acetonitrile in water) to give 1-(3-(4-(4-fluoro-2-(trifluoromethyl)phenyl) piperidine-1-carbonyl)-4,5-dihydro-1H-pyrazolo[3,4-c] pyridin-6(7H)-yl)ethanone as a white solid (20 mg, 94%): mp 176-180° C.; ¹H NMR (500 MHz, DMSO-d₆) δ 12.86 (s, 1H), 7.71-7.68 (m, 1H), 7.56-7.49 (m, 2H), 4.94-4.55 (m, 3H), 3.66-3.62 (m, 2H), 3.10 (br s, 2H), 2.85-2.48 (m, 4H), 2.10-2.08 (m, 3H), 1.73 (m, 4H); ESI MS m/z 439 [M+H]+.

EXAMPLE 97

Preparation of (4-(4-fluoro-2-(trifluoromethyl)phenyl) piperidin-1-yl) (5-(methylsulfonyl)-4,5,6,7-tetrahydro-1H-pyrazolo [4,3-c]pyridine-3-yl)methanone (159)

Step A: To a solution of 4-(4-fluoro-2-trifluoromethyl) phenylpiperidine hydrochloride (75 mg, 0.26 mmol), 5-(tert-butoxycarbonyl)-4,5,6,7-tetrahydro-1H-pyrazolo[4,3-c] pyridine-3-carboxylic acid (75 mg, 0.29 mmol), and diisopropylethylamine (0.14 mL, 0.80 mmol) in DMF (3.0 mL) under an atmosphere of N₂ was added EDCI (70 mg, 0.37 mmol) and HOBt (49 mg, 0.36 mmol). The resulting solution was stirred at ambient temperature for 16 h. The reaction mixture was diluted with H₂O (30 mL) and extracted with EtOAc (3×30 mL). The combined organic extracts were washed with brine (1×30 mL) and concentrated to dryness under reduced pressure. The obtained residue was chromatographed over silica gel (Isco CombiFlash Rf unit, 12 g Redisep column, 0% to 100% ethyl acetate in hexanes) to provide tert-butyl 3-(4-(4-fluoro-2-(trifluoromethyl)phenyl)piperidine-1-carbonyl)-6,7-dihydro-1H-pyrazolo[4,3-c]pyridine-5(4H)-carboxylate as a white solid (109 mg, 77%): ¹H NMR (300 MHz, DMSO-d₆) δ 12.96 (s, 1H), 7.70-7.68 (m, 1H), 7.57-7.49 (m, 2H), 5.32-5.13 (m, 1H), 4.74-4.64 (m, 1H), 4.47-4.45 (m, 2H), 3.59 (br s, 2H), 3.22-3.10 (m, 2H), 2.82-2.50 (m, 3H), 1.73 (br s, 4H), 1.42 (s, 9H); ESI MS m/z 497 [M+H]+.

Step B: To a solution of tert-butyl 3-(4-(4-fluoro-2-(trifluoromethyl phenyl)piperidine-1-carbonyl)-4,5-dihydro-1H-pyrazolo[3,4-c]-pyridine-5(4H)-carboxylate (85 mg, 0.17 mmol) in CH₂Cl₂ (3 mL) and methanol (1 mL) was added 2 N HCl (2 mL, 2M in Et₂O). The mixture stirred for 4 h at ambient temperature. The reaction mixture was diluted with Et₂O (30 mL) and the resulting solids were collected by filtration to give (4-(4-fluoro-2-(trifluoromethyl)phenyl)piperidin-1-yl)(4,5,6,7-tetrahydro-1H-pyrazolo[4,3-c]pyridin-3-yl)methanone hydrochloride as an off-white solid (78 mg, >99%): ¹H NMR (300 MHz, DMSO-d₆) δ 13.14 (br s, 1H), 9.13 (br s, 2H), 7.73-7.67 (m, 1H), 7.58-7.50 (m, 2H), 5.32-4.69 (m, 3H), 4.24 (s, 2H), 3.38 (br s, 2H), 3.21 3.07 (m, 2H), 2.96-2.72 (m, 3H), 1.75 (m, 4H); ESI MS m/z 397 [M+H]+.

Step C: To a solution of (4-(4-fluoro-2-(trifluoromethyl) phenyl) piperidin-1-yl)(4,5,6,7-tetrahydro-1H-pyrazolo[4,3-c]pyridin-3-yl)methanone hydrochloride (38 mg, 0.088 mmol) and diisopropylethylamine (35 µL, 0.20 mmol) in DMF (2.0 mL) was added methanesulfonyl chloride (9 µL, 0.12 mmol). The mixture was stirred for 16 h at ambient temperature. The solvent was removed under reduced pressure and the residue diluted with H₂O (10 mL) and extracted with ethyl acetate (3×10 mL). The combined organic extracts were dried (Na₂SO₄) and concentrated under reduced pressure. The obtained solids were chromatographed over silica gel (Isco CombiFlash Rf unit, 12 g Redisep column, 0% to 100% (10% CH₃OH in CH₂Cl₂ with 0.01% NH₄OH) in CH₂Cl₂) and freeze dried to give (4-(4-fluoro-2-(trifluoromethyl)phenyl)piperidin-1-yl) (5-(methylsulfonyl)-4,5,6,7-tetrahydro-1H-pyrazolo[4,3-c]pyridin-3-yl)methanone as a white solid (4 mg, 10%): ¹H NMR (300 MHz, DMSO-d₆) δ 13.05 (s, 1H), 7.73-7.69 (m, 1H), 7.57-7.46 (m, 2H), 5.28-5.24 (m, 1H), 4.70-4.65 (m, 1H), 4.38-4.33 (m, 2H), 3.51-3.45 (m, 2H), 3.22-3.10 (m, 2H), 2.94 (s, 3H), 2.84-2.70 (m, 3H), 1.73 (br s, 4H); ESI MS m/z 475 [M+H]+.

EXAMPLE 98

Preparation of 3-(4-(4-fluoro-2-(trifluoromethyl) phenyl)piperidine-1-carbonyl)-[1,2,4]triazolo[4,3-a] pyridine-6-carbonitrile (160)

Step A: To a solution of ethyl 6-bromo-[1,2,4]triazolo[4, 3-a]pyridine-3-carboxylate (81 mg, 0.30 mmol) in THF (2.5 mL) was added a solution of LiOH monohydrate (14 mg, 0.30 mmol) in H₂O (1.7 mL). The mixture stirred for 20 min and was neutralized with 2 N HCl. The mixture was concentrated under reduced pressure. The obtained residue was diluted in DMF (3.2 mL) under an atmosphere of N₂. To this mixture was added 4-(4-fluoro-2-(trifluoromethyl)phenyl) piperidine hydrochloride (85 mg, 0.30 mmol), benzotriazole-1-yl-oxy-tris-(dimethylamino)-phosphonium hexafluorophosphate (267 mg, 0.60 mmol), and diisopropylethylamine (0.15 mL, 0.91 mmol). The mixture was stirred at ambient temperature for 18 h. The resulting mixture was diluted with H₂O (20 mL) and the resulting precipitate was collected by filtration. The obtained solids were chromatographed over silica gel (Isco CombiFlash Rf unit, 12 g Redisep column, 0 to 50% EtOAc in hexanes) to provide (6-bromo-[1,2,4]triazolo[4,3-a]pyridin-3-yl) (4-(4-fluoro-2-(trifluoromethyl)phenyl)piperidin-1-yl)methanone as an orange film (92 mg, 64%): ¹H NMR (300 MHz, DMSO-d₆) δ 9.13 (dd, J=1.7, 0.9 Hz 1H), 7.98 (dd, J=10, 0.9 Hz, 1H), 7.77-7.69 (m, 2H), 7.60-7.47 (m, 2H), 5.30-5.18 (m, 1H), 4.77-4.68 (m, 1H), 3.43-3.34 (m, 1H), 3.28-3.12 (m, 1H), 3.11-2.90 (m, 1H), 1.97-1.69 (m, 4H); ESI MS m/z 472 [M+H]+.

Step B: A solution of (6-bromo-[1,2,4]triazolo[4,3-a]pyridin-3-yl)(4-(4-fluoro-2-(trifluoromethyl)phenyl)piperidin-1-yl)methanone (90 mg, 0.19 mmol) in DMF (2.2 mL) zinc cyanide (45 mg, 0.38 mmol) was sparged with Ar for 15 min. To the solution was added Pd(PPh₃)₄ (22 mg, 0.019 mmol) and the vessel was sealed and heated to 130° C. microwaves for 30 min. The mixture was diluted with saturated sodium bicarbonate solution (10 mL) and extracted with EtOAc (3×20 mL). The combined organic extracts were washed with saturated brine solution (30 mL) and concentrated to dryness under reduced pressure. The resulting residue was chromatographed over silica gel (Isco CombiFlash Rf unit, 12 g Redisep column, 0% to 50% EtOAc in hexanes) followed by HPLC (Phenomenex Luna C18 (2), 250.0×50.0 mm, 15 micron, H₂O with 0.05% TFA and CH₃CN with 0.05% TFA) and was washed with saturated sodium bicarbonate solution (3×30 mL) then freeze dried to provide 3-(4-(4-fluoro-2-(trifluoromethyl)phenyl)piperidine-1-carbonyl)-[1,2,4]triazolo[4,3-a]pyridine-6-carbonitrile as a white solid (32 mg, 40%): mp 158-162° C.; $^1$H NMR (300 MHz, DMSO-d$_6$) δ 9.53 (s, 1H), 8.14 (dd, J=9.0, 0.9 Hz, 1H), 7.82 (dd, J=9.6, 1.5 Hz, 1H), 7.77-7.67 (m, 1H), 7.61-7.47 (m, 2H), 5.19-5.04 (m, 1H), 4.80-4.67 (m, 1H), 3.46-3.14 (m, 2H, overlaps with H$_2$O), 3.12-2.94 (m, 1H), 2.02-1.70 (m, 4H); ESI MS m/z 418 [M+H]+.

EXAMPLE 99

Preparation of 3-(3-(4-(5-Chloro-2-(trifluoromethyl) phenyl) piperidine-1-carbonyl)-[1,2,4]triazolo[4,3-a] pyridine-6-carbonitrile (161)

Step A: A mixture of (5-chloro-2-(trifluoromethyl)phenyl) boronic acid (0.453 g, 2.02 mmol), tert-butyl 4-(((trifluoromethyl)sulfonyl)oxy)-5,6-dihydropyridine-1(2H)-carboxylate (0.669 g, 2.02 mmol), tetrakis(triphenylphosphine)palladium (0.117 g, 0.1 mmol), sodium carbonate (2 M, 5 mL), and 1,2-dimethoxyethane (10 mL) was heated at 80° C. under microwave irradiation for 1.5 h. After cooling to ambient temperature, the mixture was diluted with water (80 mL) and extracted with ethyl acetate (80 mL). The extract was washed with brine (2×50 mL), dried over Na$_2$SO$_4$, filtered, and concentrated under reduced pressure. The resulting residue was chromatographed over silica gel (0-25% EtOAc in hexanes) to give tert-butyl 4-(5-chloro-2-(trifluoromethyl)phenyl)-5,6-dihydropyridine-1(2H)-carboxylate as colorless oil (0.614 g, 84%): $^1$H NMR (300 MHz, CDCl$_3$) δ 7.59 (d, J=8.5 Hz, 1H), 7.37-7.22 (m, 1H), 7.22 (d, J=1.68 Hz, 1H), 5.60 (br. 1H), 4.02 (br, 2H), 3.61 (br, 2H), 2.34 (br, 2H), 1.50 (s, 9H); MS (ESI+) m/z 306 [M+H]+.

Step B: A mixture of tert-butyl 4-(5-chloro-2-(trifluoromethyl) phenyl)-5,6-dihydropyridine-1(2H)-carboxylate (0.614 g, 1.70 mmol), platinum oxide (0.200 g, 0.881 mmol), acetic acid (1 mL), and ethyl acetate (15 mL) was hydrogenated using a balloon of H$_2$ for 16 h and filtered. After concentration, the residue was chromatographed over silica gel (0-30% EtOAc in hexanes) to give tert-butyl 4-(5-chloro-2-(trifluoromethyl)phenyl)piperidine-1-carboxylate as colorless thick oil (0.302 g, 48%): $^1$H NMR (300 MHz, CDCl$_3$) δ 7.56 (d, J=8.5 Hz, 1H), 7.38 (s, 1H), 7.29 (d, J=1.3 Hz, 1H), 4.26 (br, 2H), 3.04 (m, 1H), 2.80 (m, 2H), 1.80-1.55 (m, 4H), 1.49 (s, 9H); MS (ESI+) m/z 308 [M+H]+.

Step C: To a solution of tert-butyl 4-(5-chloro-2-(trifluoromethyl)phenyl)piperidine-1-carboxylate (0.302 g, 0.830 mmol) in dichloromethane (5 mL) was added HCl solution (2 M in ether, 5 mL). The mixture was stirred for 4 h and evaporated to afford a solid that was dissolved in DMF (8 mL). In a separate flask, to a solution of ethyl 6-bromo-[1,2,4]triazolo[4,3-a]pyridine-3-carboxylate (0.224 g, 0.830 mmol) in THF (5 mL) was added a solution of lithium hydroxide hydrate (0.035 g, 0.830 mmol) in water (2 mL). The mixture was stirred for 20 min, acidified with 2 N HCl to PH 6 and evaporated to dryness. To this residue were added benzotriazole-1-yl-oxytris(dimethylamino)phosphonium hexafluorophosphate (0.550 g, 1.25 mmol), N,N-diisopropylethylamine (0.646 g, 5.00 mmol), and the DMF solution obtained from the first reaction. The mixture was stirred at ambient temperature for 16 h and poured into water. The mixture was extracted with ethyl acetate and the organic layer was washed with brine for three times, dried over Na$_2$SO$_4$, filtered and concentrated under reduced pressure. The resulting residue was chromatographed over silica gel (0-60% EtOAc in hexanes) to give (6-bromo-[1,2,4] triazolo[4,3-a]pyridin-3-yl)(4-(5-chloro-2-(trifluoromethyl) phenyl) piperidin-1-yl)methanone as a solid (0.205 g, 50%): $^1$H NMR (300 MHz, CDCl$_3$) δ 9.38 (m, 1H), 7.79 (dd, J=9.6, 0.9 Hz, 1H), 7.60 (d, J=8.5 Hz, 1H), 7.50 (dd, J=9.6, 1.7 Hz, 1H), 7.42 (d, J=1.4 Hz, 1H), 7.31 (dd, J=8.5, 1.3 Hz, 1H), 5.76-5.71 (m, 1H), 5.01-4.95 (m, 1H), 3.38-3.26 (m, 2H), 3.02-2.92 (m, 1H), 2.01-1.82 (m, 4H); MS (ESI+) m/z 489 [M+H]+.

Step D: A mixture of (6-bromo-[1,2,4]triazolo[4,3-a]pyridin-3-yl)(4-(5-chloro-2-(trifluoromethyl)phenyl)piperidin-1-yl)methanone (0.205 g, 0.42 mmol), zinc cyanide (0.099 g, 0.840 mmol), tetrakis (triphenylphosphine)palladium (0.048 g, 0.042 mmol), and DMF (4 mL) was heated under microwave irradiation at 130° C. for 30 min. After cooling to ambient temperature, the mixture was diluted with water (80 mL) and extracted with ethyl acetate (80 mL). The extract was washed with brine (2×80 mL), dried (Na$_2$SO$_4$), filtered, and concentrated under reduced pressure. The resulting residue was chromatographed over silica gel (0-60% EtOAc in hexanes) to give 3-(4-(5-chloro-2-(trifluoromethyl) phenyl) piperidine-1-carbonyl)-[1,2,4]triazolo [4,3-a]pyridine-6-carbonitrile as a white solid (0.115 g, 63%): $^1$H NMR (300 MHz, CDCl$_3$) δ 9.72 (s, 1H), 7.98 (dd, J=9.5, 1.1 Hz, 1H), 7.60 (d, J=8.5 Hz, 1H), 7.51 (dd, J=9.5, 1.6 Hz, 1H), 7.41 (s, 1H), 7.31 (dd, J=8.5, 1.3 Hz, 1H), 5.77-5.72 (m, 1H), 5.02-4.96 (m, 1H), 3.40 (m, 2H), 3.04-2.94 (m, 1H), 2.06-1.80 (m, 4H); MS (ESI+) m/z 434 [M+H]+.

EXAMPLE 100

Preparation of 3-(4-(3-Chloro-2-(trifluoromethyl) phenyl) piperidine-1-carbonyl)-[1,2,4]triazolo[4,3-a] pyridine-6-carbonitrile (162)

Step A: A mixture of (3-chloro-2-(trifluoromethyl)phenyl) boronic acid (0.453 g, 2.02 mmol), tert-butyl 4-(((trifluoromethyl)sulfonyl)oxy)-5,6-dihydropyridine-1(2H)-carboxylate (0.669 g, 2.02 mmol), tetrakis(triphenylphosphine) palladium (0.117 g, 0.1 mmol), sodium carbonate (2 M, 5 mL), and 1,2-dimethoxyethane (10 mL) was heated at 80° C. under microwave irradiation for 1 h. After cooling to ambient temperature, the mixture was diluted with water (80 mL) and extracted with ethyl acetate (80 mL). The extract was washed with brine (2×50 mL), dried (Na$_2$SO$_4$), filtered, and concentrated under reduced pressure. The resulting residue was chromatographed over silica gel (0-30% EtOAc in hexanes) to give tert-butyl 4-(3-chloro-2-(trifluoromethyl) phenyl)-5,6-dihydropyridine-1(2H)-carboxylate as colorless oil (0.438 g, 60%): $^1$H NMR (300 MHz, CDCl$_3$) δ 7.44-7.34 (m, 2H), 7.09 (m, 1H), 5.49 (br. 1H), 4.01 (br, 2H), 3.60 (br, 2H), 2.30 (br, 2H), 1.50 (s, 9H); MS (ESI+) m/z 306 [M+H]+.

Step B: A mixture of tert-butyl 4-(3-chloro-2-(trifluoromethyl) phenyl)-5,6-dihydropyridine-1(2H)-carboxylate (0.438 g, 1.21 mmol), platinum oxide (0.082 g, 0.363 mmol), acetic acid (0.073 g, 1.21 mmol), and ethyl acetate (20 mL) was hydrogenated using a balloon for 20 h and filtered. The material was re-submitted to hydrogenation at 80° C. for 16 h and filtered. After concentration, the residue was chromatographed over silica gel (0-30% EtOAc in hexanes) to give tert-butyl 4-(3-chloro-2-(trifluoromethyl) phenyl) piperidine-1-carboxylate as colorless thick oil (0.115 g, 26%): $^1$H NMR (300 MHz, CDCl$_3$) δ 7.42-7.30 (m, 3H), 4.25 (br, 2H), 3.21 (m, 1H), 2.81 (m, 2H), 1.80-1.60 (m, 4H), 1.49 (s, 9H); MS (ESI+) m/z 308 [M+H]+.

Step C: To a solution of tert-butyl 4-(3-chloro-2-(trifluoromethyl) phenyl)piperidine-1-carboxylate (0.115 g, 0.316 mmol) in dichloromethane (3 mL) was added HCl (2 M in ether, 3 mL). The mixture was stirred for 3 h and evaporated to afford a solid that was dissolved in DMF (3 mL). In a separate flask, to a solution of ethyl 6-bromo-[1,2,4]triazolo [4,3-a]pyridine-3-carboxylate (0.094 g, 0.348 mmol) in THF (3 mL) was added a solution of lithium hydroxide hydrate (0.015 g, 0.348 mmol) in water (1 mL). The mixture was stirred for 20 min, acidified with 2 N HCl to PH 6 and evaporated. To the residue were added benzotriazole-1-yl-oxy-tris(dimethylamino)phosphonium hexafluorophosphate (0.210 g, 0.474 mmol), N,N-diisopropylethylamine (0.163 g, 1.26 mmol), and the DMF solution obtained from the first reaction. The mixture was stirred at ambient temperature for 16 h and poured into water. The mixture was extracted with ethyl acetate and the organic layer was washed with brine for three times, dried ($Na_2SO_4$), filtered, and concentrated under reduced pressure. The resulting residue was chromatographed over silica gel (0-60% EtOAc in hexanes) to give (6-bromo-[1,2,4]triazolo[4,3-a]pyridin-3-yl)(4-(3-chloro-2-(trifluoromethyl)phenyl)piperidin-1-yl)methanone as a solid (0.076 g, 49%): $^1$H NMR (300 MHz, $CDCl_3$) δ 9.36 (m, 1H), 7.78 (dd, J=9.6, 0.9 Hz, 1H), 7.50-7.34 (m, 4H), 5.73-5.68 (m, 1H), 5.00-4.94 (m, 1H), 3.52-3.28 (m, 2H), 2.97 (m, 1H), 2.01-1.74 (m, 4H); MS (ESI+) m/z 489 [M+H]+.

Step D: A mixture of (6-bromo-[1,2,4]triazolo[4,3-a]pyridin-3-yl)(4-(3-chloro-2-(trifluoromethyl)phenyl)piperidin-1-yl)methanone (0.076 g, 0.156 mmol), zinc cyanide (0.037 g, 0.312 mmol), palladium tetrakis(triphenylphosphine) (0.018 g, 0.0156 mmol), and DMF (2 mL) was heated under microwave irradiation at 130° C. for 30 min. After cooling to ambient temperature, the mixture was diluted with water (50 mL) and extracted with ethyl acetate (50 mL). The extract was washed with brine (2×50 mL), dried over $Na_2SO_4$, filtered, and concentrated under reduced pressure. The resulting residue was chromatographed over silica gel (0-60% EtOAc in hexanes) to give 3-(4-(3-chloro-2-(trifluoromethyl) phenyl) piperidine-1-carbonyl)-[1,2,4] triazolo [4,3-a]pyridine-6-carbonitrile as a white solid (0.026 g, 38%): $^1$H NMR (300 MHz, $CDCl_3$) δ 9.70 (s, 1H), 7.97 (dd, J=9.5, 1.0 Hz, 1H), 7.52-7.32 (m, 4H), 5.74-5.69 (m, 1H), 5.00-4.95 (m, 1H), 3.52-3.31 (m, 2H), 2.99 (m, 1H), 2.06-1.75 (m, 4H); MS (ESI+) m/z 434 [M+H]+.

EXAMPLE 101

Preparation of (4-(2-Chloro-3-fluorophenyl)piperidin-1-yl)(5-ethyl-4,5,6,7-tetrahydro-1H-pyrazolo[4,3-c]pyridin-3-yl)methanone (163)

Step A: Following general procedure GP-D1, (4-(2-chloro-3-fluorophenyl)piperidin-1-yl)(4,5,6,7-tetrahydro-1H-pyrazolo[4,3-c]pyridin-3-yl)methanone hydrochloride (42) and formaldehyde were converted to (4-(2-Chloro-3-fluorophenyl)piperidin-1-yl) (5-ethyl-4,5,6,7-tetrahydro-1H-pyrazolo[4,3-c]pyridin-3-yl)methanone as a white solid (25 mg, 32%): $^1$H NMR (300 MHz, DMSO-$d_6$) δ 12.93 (m, 1H), 7.56-7.32 (m, 3H), 5.16 (m, 1H), 4.81 (m, 1H), 2.61-3.42 (m, 9H), 1.94-1.61 (m, 4H); ESI MS m/z 391 [M+H]+.

EXAMPLE 102

Preparation of (4-(2-Chloro-3-fluorophenyl) piperidin-1-yl)(5-(cyclopropylmethyl)-4,5,6,7-tetrahydro-1H-pyrazolo[4,3-c]pyridin-3-yl)methanone (164)

Step A: Following general procedure GP-D1, (4-(2-chloro-3-fluorophenyl) piperidin-1-yl) (4,5,6,7-tetrahydro-1H-pyrazolo[4,3-c]pyridin-3-yl)methanone hydrochloride (42) and cyclopropyl-carboxaldehyde were converted to (4-(2-chloro-3-fluorophenyl) piperidin-1-yl)(5-(cyclopropylmethyl)-4,5,6,7-tetrahydro-1H-pyrazolo [4,3-c]pyridin-3-yl)methanone as a white solid (41 mg, 65%): $^1$H NMR (300 MHz, DMSO-$d_6$) δ 12.91 (m, 1H), 7.56-7.39 (m, 3H), 5.15 (m, 1H), 4.85 (m, 1H), 3.53 (m, 2H), 3.12 (m, 1H), 2.62-2.35 (m, 5H), 2.43 (m, 2H), 1.87 (m, 2H), 1.63 (m, 2H), 0.98 (m, 1H), 0.55 (m, 2H), 0.021 (m, 2H); ESI MS m/z 417 [M+H]+.

EXAMPLE 103

Preparation of (4-(2-Chloro-3-fluorophenyl) piperidin-1-yl)(5-(oxetan-3-yl)-4,5,6,7-tetrahydro-1H-pyrazolo[4,3-c]pyridin-3-yl)methanone (165)

Step A: Following general procedure GP-D1, (4-(2-chloro-3-fluorophenyl) piperidin-1-yl) (4,5,6,7-tetrahydro-1H-pyrazolo[4,3-c]pyridin-3-yl)methanone hydrochloride (42) and 3-oxetanone were converted to (4-(2-chloro-3-fluorophenyl) piperidin-1-yl) (5-(oxetan-3-yl)-4,5,6,7-tetrahydro-1H-pyrazolo[4,3-c]pyridin-3-yl)methanone as a white solid (53 mg, 62%): $^1$H NMR (300 MHz, DMSO-$d_6$) δ 12.91 (m, 1H), 7.56-7.39 (m, 3H), 5.15 (m, 1H), 4.52-4.85 (m, 5H), 3.53 (m, 1H), 3.12-3.40 (m, 3H), 2.82-265 (m, 3H), 1.72 (m, 2H), 1.53 (m, 2H); ESI MS m/z 419 [M+H]+.

EXAMPLE 104

Preparation of (4-(2-Chloro-3-fluorophenyl) piperidin-1-yl)(5-(2,2,2-trifluoroethyl)-4,5,6,7-tetrahydro-1H-pyrazolo[4,3-c]pyridin-3-yl)methanone (166)

Step A: Following general procedure GP-D2, (4-(2-chloro-3-fluorophenyl) piperidin-1-yl) (4,5,6,7-tetrahydro-1H-pyrazolo[4,3-c]pyridin-3-yl)methanone hydrochloride (42) and 2,2,2-trifluoroethyl trifluoromethanesulfonate were converted to (4-(2-chloro-3-fluorophenyl) piperidin-1-yl) (5-(2,2,2-trifluoroethyl)-4,5,6,7-tetrahydro-1H-pyrazolo[4, 3-c]pyridin-3-yl)methanone as a white solid (56 mg, 62%): $^1$H NMR (300 MHz, DMSO-$d_6$) δ 12.91 (m, 1H), 7.56-7.39 (m, 3H), 5.15 (m, 1H), 4.73 (m, 1H), 3.82 (m, 2H), 3.32 (m, 1H), 2.89 (m, 2H), 2.65 (m, 2H), 1.89 (m, 2H), 1.56 (m, 2H); ESI MS m/z 445 [M+H]+.

EXAMPLE 105

Preparation of (4-(2-Chloro-3-fluorophenyl)piperidin-1-yl) (5-(3,3,3-trifluoropropyl)-4,5,6,7-tetrahydro-1H-pyrazolo[4,3-c]pyridin-3-yl)methanone (167)

Step A: Following general procedure GP-D2, (4-(2-chloro-3-fluorophenyl)piperidin-1-yl) (4,5,6,7-tetrahydro-1H-pyrazolo [4,3-c]pyridin-3-yl)methanone hydrochloride (42) 3-bromo-1,1,1-trifluoropropane were converted to (4-(2-chloro-3-fluorophenyl) piperidin-1-yl) (5-(3,3,3-trifluoropropyl)-4,5,6,7-tetrahydro-1H-pyrazolo[4,3-c]pyridin-3-yl)methanone as a white solid (36 mg, 43%): $^1$H NMR (300 MHz, DMSO-$d_6$) δ 13.01 (m, 1H), 7.56-7.39 (m, 3H), 5.15

(m, 1H), 4.52 (m, 2H), 3.41 (m, 2H), 2.82 (m, 3H), 1.89 (m, 2H), 1.56 (m, 2H); ESI MS m/z 459 [M+H]$^+$.

EXAMPLE 106

Preparation of (4-(2-Chloro-3-fluorophenyl) piperidin-1-yl)(5-(2-methoxyethyl)-4,5,6,7-tetrahydro-1H-pyrazolo[4,3-c]pyridin-3-yl)methanone (168)

Step A: Following general procedure GP-D2, (4-(2-chloro-3-fluorophenyl) piperidin-1-yl) (4,5,6,7-tetrahydro-1H-pyrazolo[4,3-c]pyridin-3-yl)methanone hydrochloride (42) bromoethylmethyl ether were converted to (4-(2-chloro-3-fluorophenyl)piperidin-1-yl) (5-(2-methoxyethyl)-4,5,6,7-tetrahydro-1H-pyrazolo[4,3-c] pyridin-3-yl) methanone as a white solid (53 mg, 45%): $^1$H NMR (300 MHz, DMSO-d$_6$) δ 12.89 (m, 1H), 7.56-7.39 (m, 3H), 5.15 (m, 1H), 4.52 (m, 2H), 3.51 (m, 4H), 3.23 (m, 4H), 2.72 (m, 6H), 1.89 (m, 2H), 1.56 (m, 2H); ESI MS m/z 421 [M+H]$^+$.

EXAMPLE 107

Preparation of (4-(3,4-Difluoro-2-(trifluoromethyl) phenyl)piperidin-1-yl)(5-(piperazine-1-carbonyl)-1, 4,5,6-tetrahydropyrrolo[3,4-c]pyrazol-3-yl)methanone (169)

Step A: A solution of tert-butyl piperazine-1-carboxylate (210 mg, 1.13 mmol) and pyridine (137 mg, 1.73 mmol) in anhydrous CH$_2$Cl$_2$ (2 mL) was cooled to 0° C. under an atmosphere of N$_2$, treated with a solution of triphosgene (402 mg, 1.35 mmol) in anhydrous CH$_2$Cl$_2$ (2 mL) and stirred at 0° C. for 1 h. The cooling bath was then removed and the reaction stirred at room temperature for a further 1 h. After this time, the mixture was diluted with 1 M hydrochloric acid (25 mL) and extracted with CH$_2$Cl$_2$ (3×20 mL). The combined organic extracts were washed with brine (20 mL), dried over Na$_2$SO$_4$ and the drying agent removed by filtration. The filtrate was concentrated to dryness under reduced pressure to provide tert-butyl 4-(chlorocarbonyl)piperazine-1-carboxylate as a white solid (280 mg, 100%): $^1$H NMR (500 MHz, CDCl$_3$) δ 10.76 (br s, 1H), 7.33 (dd, J=17.0, 9.0 Hz, 1H), 7.11 (dd, J=9.0, 4.0 Hz, 1H), 4.88-4.52 (m, 2H), 4.69 (br s, 2H), 4.62 (s, 2H), 3.49 (apparent t, J=4.5 Hz, 4H), 3.32 (apparent t, J=4.5 Hz, 4H), 3.25 (apparent t, J=12.5 Hz, 1H), 3.14-2.88 (m, 2H), 1.94 (d, J=12.5 Hz, 2H), 1.72-1.66 (m, 2H), 1.48 (s, 9H).

Step B: A solution of (4-(3,4-difluoro-2-(trifluoromethyl) phenyl)piperidin-1-yl)(1,4,5,6-tetrahydropyrrolo[3,4-c] pyrazol-3-yl) methanone hydrochloride salt (50 mg, 0.11 mmol), N,N,N-diisopropylethylamine (0.05 mL, 0.3 mmol) and DMAP (0.5 mg, 0.004 mmol) in anhydrous CH$_2$Cl$_2$ (1 mL) was cooled to 0° C. under an atmosphere of N$_2$, treated with tert-butyl 4-(chlorocarbonyl)piperazine-1-carboxylate (30 mg, 0.12 mmol) and stirred at 0° C. for 1 h. The cooling bath was then removed and the reaction stirred at room temperature for a further 4 h. After this time, the mixture was chromatographed over silica gel (Isco CombiFlash Rf unit, 12 g Redisep gold column, 0% to 10% CH$_3$OH in CH$_2$Cl$_2$) to provide tert-butyl 4-(3-(4-(3,4-difluoro-2-(trifluoromethyl)phenyl)piperidine-1-carbonyl)-1,4,5,6-tetrahydropyrrolo[3,4-c]pyrazole-5-carbonyl)piperazine-1-carboxylate as a white solid (48 mg, 71%): $^1$H NMR (500 MHz, CDCl$_3$) δ 10.76 (br s, 1H), 7.33 (dd, J=17.0, 9.0 Hz, 1H), 7.11 (dd, J=9.0, 4.0 Hz, 1H), 4.88-4.52 (m, 2H), 4.69 (br s, 2H), 4.62 (s, 2H), 3.49 (apparent t, J=4.5 Hz, 4H), 3.32 (apparent t, J=4.5 Hz, 4H), 3.25 (apparent t, J=12.5 Hz, 1H), 3.14-2.88 (m, 2H), 1.94 (d, J=12.5 Hz, 2H), 1.72-1.66 (m, 2H), 1.48 (s, 9H).

Step C: A solution of tert-butyl 4-(3-(4-(3,4-difluoro-2-(trifluoro-methyl)phenyl)piperidine-1-carbonyl)-1,4,5,6-tetrahydro-pyrrolo[3,4-c]pyrazole-5-carbonyl)piperazine-1-carboxylate (47 mg, 0.077 mmol) in anhydrous CH$_2$Cl$_2$ (1.5 mL) was cooled to 0° C. under an atmosphere of N2 and treated with TFA (1.5 mL). When the addition was complete, the cooling bath was removed and the reaction stirred at room temperature for 1 h. After this time, the mixture was concentrated to dryness under reduced pressure, diluted in CH$_2$Cl$_2$ (100 mL) and washed with 2 M aqueous NaOH (2×50 mL). The organic layer was dried over Na$_2$SO$_4$ and the drying agent removed by filtration. The filtrate was concentrated to dryness under reduced pressure and the resulting residue chromatographed over silica gel (Isco CombiFlash Rf unit, 120 g Redisep column, 0% to 40% CH$_3$OH in CH$_2$Cl$_2$). The combined column fractions were concentrated to dryness under reduced pressure and found to contain residual TFA (~17%). The resulting residue (21 mg) was diluted in a mixture of CH$_2$Cl$_2$ (5 mL) and CH$_3$OH (1 mL), treated with MP-carbonate and stirred at room temperature for 2 h. After this time the mixture was filtered and the filtrate concentrated to dryness under reduced pressure to provide (4-(3,4-difluoro-2-(trifluoromethyl)phenyl)piperidin-1-yl) (5-(piperazine-1-carbonyl)-1,4,5,6-tetrahydropyrrolo[3,4-c]pyrazol-3-yl)methanone as a white solid (13 mg, 33%): mp 153-155° C.; $^1$H NMR (500 MHz, DMSO-d$_6$) δ 13.20 (br s, 1H), 7.75 (dd, J=18.0, 9.0 Hz, 1H), 7.55-7.52 (m, 1H), 4.65-4.51 (m, 6H), 3.24-3.22 (m, 2H), 3.14 (t, J=5.0 Hz, 4H), 2.96-2.80 (m, 1H), 2.70-2.68 (m, 3H), 2.32-2.22 (m, 1H), 1.79-1.70 (m, 4H), 1 proton not readily observed; ESI MS m/z 513 [M+H]$^+$.

EXAMPLE 108

RPB4 Binding of Substituted Piperidine Compounds

The compounds listed in Table 1 were tested in two in vitro assays, RBP4 binding (SPA) and retinol-dependent RBP4-TTR interaction (HTRF). The compounds binded to RBP4 and/or antagonized retinol-dependent RBP4-TTR interaction (Table 2). This activity indicated that the compounds reduce the levels of serum RBP4 and retinol.

TABLE 1

| Compound | Structure |
| --- | --- |
| 30 | 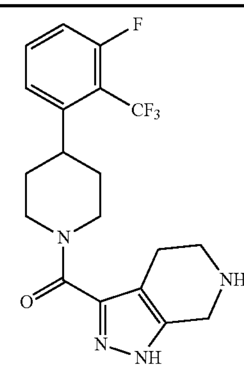 |

TABLE 1-continued

| Compound | Structure |
|----------|-----------|
| 32 | 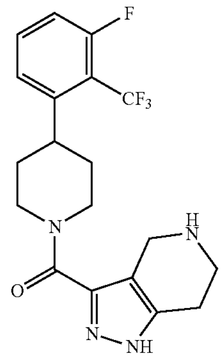 [SMILES: O=C(c1n[nH]c2c1CNCC2)N1CCC(c2cccc(F)c2C(F)(F)F)CC1] |
| 34 | 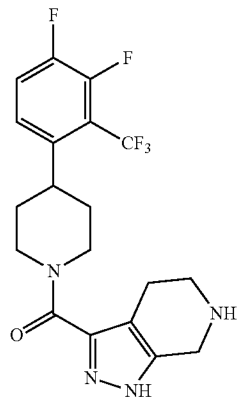 [SMILES: O=C(c1n[nH]c2c1CCNC2)N1CCC(c2ccc(F)c(F)c2C(F)(F)F)CC1] |
| 36 | 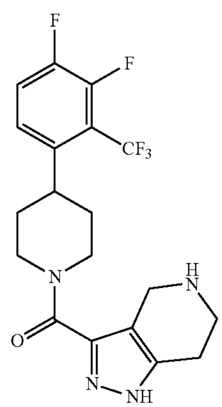 [SMILES: O=C(c1n[nH]c2c1CNCC2)N1CCC(c2ccc(F)c(F)c2C(F)(F)F)CC1] |
| 38 | 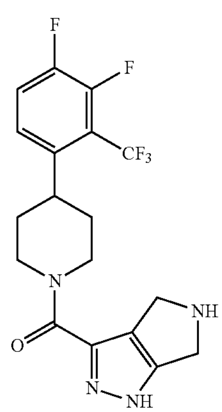 [SMILES: O=C(c1n[nH]c2c1CNC2)N1CCC(c2ccc(F)c(F)c2C(F)(F)F)CC1] |
| 40 | |
| 42 | |
| 63 | |
| 64 | |

TABLE 1-continued

| Compound | Structure |
|---|---|
| 65 | 3-{[4-(3-fluoro-2-(trifluoromethyl)phenyl)piperidin-1-yl]carbonyl}-[1,2,4]triazolo[4,3-a]pyridine-6-carbonitrile |
| 66 | N-methyl-3-{[4-(3-fluoro-2-(trifluoromethyl)phenyl)piperidin-1-yl]carbonyl}-1,4,6,7-tetrahydro-5H-pyrazolo[4,3-c]pyridine-5-carboxamide |
| 67 | {5-ethyl-3-[(4-(3-fluoro-2-(trifluoromethyl)phenyl)piperidin-1-yl)carbonyl]-4,5,6,7-tetrahydro-1H-pyrazolo[4,3-c]pyridine} |
| 68 | methyl 3-{[4-(3-fluoro-2-(trifluoromethyl)phenyl)piperidin-1-yl]carbonyl}-1,4,6,7-tetrahydro-5H-pyrazolo[4,3-c]pyridine-5-carboxylate |
| 69 | {5-(cyclopropylmethyl)-3-[(4-(3-fluoro-2-(trifluoromethyl)phenyl)piperidin-1-yl)carbonyl]-4,5,6,7-tetrahydro-1H-pyrazolo[4,3-c]pyridine} |
| 70 | 3-{[4-(3-fluoro-2-(trifluoromethyl)phenyl)piperidin-1-yl]carbonyl}-1,4,6,7-tetrahydro-5H-pyrazolo[4,3-c]pyridine-5-carbonitrile |
| 71 | {3-[(4-(3-fluoro-2-(trifluoromethyl)phenyl)piperidin-1-yl)carbonyl]-5-(2,2,2-trifluoroethyl)-4,5,6,7-tetrahydro-1H-pyrazolo[4,3-c]pyridine} |
| 72 | {3-[(4-(3-fluoro-2-(trifluoromethyl)phenyl)piperidin-1-yl)carbonyl]-5-(3,3,3-trifluoropropyl)-4,5,6,7-tetrahydro-1H-pyrazolo[4,3-c]pyridine} |

TABLE 1-continued

| Compound | Structure |
|---|---|
| 73 | (structure) |
| 74 | (structure) |
| 75 | (structure) |
| 76 | (structure) |
| 77 | (structure) |
| 77 | (structure) |
| 78 | (structure) |
| 79 | (structure) |

TABLE 1-continued

| Compound | Structure |
|---|---|
| 80 | 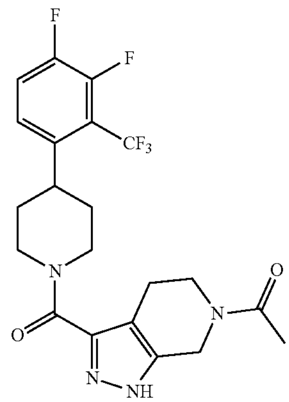 [SMILES: CC(=O)N1CCc2c(C(=O)N3CCC(c4ccc(F)c(F)c4C(F)(F)F)CC3)n[nH]c2C1] |
| 81 | 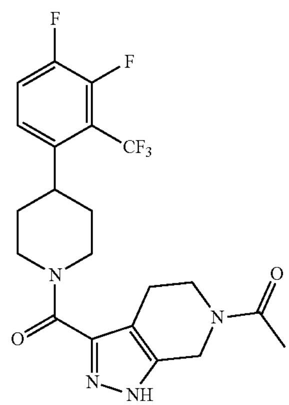 [SMILES: CC(=O)N1CCc2c(C(=O)N3CCC(c4ccc(F)c(F)c4C(F)(F)F)CC3)n[nH]c2C1] |
| 82 | 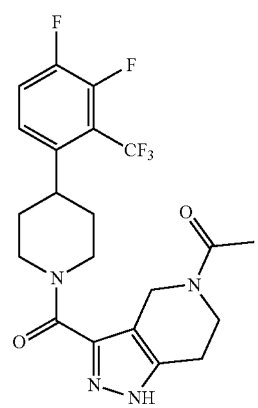 [SMILES: CC(=O)N1CCc2[nH]nc(C(=O)N3CCC(c4ccc(F)c(F)c4C(F)(F)F)CC3)c2C1] |
| 83 | 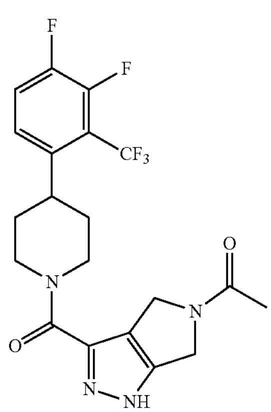 [SMILES: CC(=O)N1Cc2[nH]nc(C(=O)N3CCC(c4ccc(F)c(F)c4C(F)(F)F)CC3)c2C1] |
| 84 | |
| 85 | |
| 86 | |

TABLE 1-continued

| Compound | Structure |
|---|---|
| 87 | (structure) |
| 88 | (structure) |
| 89 | (structure) |
| 90 | (structure) |
| 91 | (structure) |
| 92 | (structure) |
| 93 | (structure) |

TABLE 1-continued

| Compound | Structure |
|---|---|
| 94 | (4-(3,4-difluoro-2-(trifluoromethyl)phenyl)piperidin-1-yl)(5-(2-methoxyethyl)-1,4,5,6-tetrahydropyrrolo[3,4-c]pyrazol-3-yl)methanone |
| 95 | 3-(4-(3,4-difluoro-2-(trifluoromethyl)phenyl)piperidine-1-carbonyl)-1,4,6,7-tetrahydro-5H-pyrazolo[4,3-c]pyridine-5-carbonitrile |
| 96 | (4-(3,4-difluoro-2-(trifluoromethyl)phenyl)piperidin-1-yl)(5-ethyl-1,4,5,6-tetrahydropyrrolo[3,4-c]pyrazol-3-yl)methanone |
| 97 | (5-(cyclopropylmethyl)-1,4,5,6-tetrahydropyrrolo[3,4-c]pyrazol-3-yl)(4-(3,4-difluoro-2-(trifluoromethyl)phenyl)piperidin-1-yl)methanone |
| 98 | (4-(3,4-difluoro-2-(trifluoromethyl)phenyl)piperidin-1-yl)(5-(oxetan-3-yl)-1,4,5,6-tetrahydropyrrolo[3,4-c]pyrazol-3-yl)methanone |
| 99 | (4-(3,4-difluoro-2-(trifluoromethyl)phenyl)piperidin-1-yl)(5-neopentyl-1,4,5,6-tetrahydropyrrolo[3,4-c]pyrazol-3-yl)methanone |
| 100 | 3-(4-(3,4-difluoro-2-(trifluoromethyl)phenyl)piperidine-1-carbonyl)-N-methyl-1,4,6,7-tetrahydro-5H-pyrazolo[3,4-c]pyrrole-5-carboxamide |

TABLE 1-continued

| Compound | Structure |
|---|---|
| 101 | 4-(3,4-difluoro-2-(trifluoromethyl)phenyl)piperidin-1-yl coupled via carbonyl to 3-position of 1H-pyrrolo[3,4-c]pyrazole with 5-methoxycarbonyl |
| 102 | 4-(3,4-difluoro-2-(trifluoromethyl)phenyl)piperidin-1-yl coupled via carbonyl to 3-position of 1H-pyrrolo[3,4-c]pyrazole with 5-benzoyl |
| 103 | 4-(3,4-difluoro-2-(trifluoromethyl)phenyl)piperidin-1-yl coupled via carbonyl to 3-position of 1H-pyrrolo[3,4-c]pyrazole with 5-(pyridin-2-ylcarbonyl) |
| 104 | 4-(3,4-difluoro-2-(trifluoromethyl)phenyl)piperidin-1-yl coupled via carbonyl to 3-position of 1H-pyrrolo[3,4-c]pyrazole with 5-(pyridin-3-ylcarbonyl) |
| 105 | 4-(3,4-difluoro-2-(trifluoromethyl)phenyl)piperidin-1-yl coupled via carbonyl to 3-position of 1H-pyrrolo[3,4-c]pyrazole with 5-(pyridin-4-ylcarbonyl) |
| 106 | 4-(3,4-difluoro-2-(trifluoromethyl)phenyl)piperidin-1-yl coupled via carbonyl to 3-position of 1H-pyrrolo[3,4-c]pyrazole with 5-(pyrrolidin-1-ylcarbonyl) |
| 107 | 4-(3,4-difluoro-2-(trifluoromethyl)phenyl)piperidin-1-yl coupled via carbonyl to 3-position of 1H-pyrrolo[3,4-c]pyrazole with 5-(2,2,2-trifluoroethyl) |

TABLE 1-continued

| Compound | Structure |
|---|---|
| 108 | 4-(3-(trifluoromethyl)-4,5-difluorophenyl)piperidin-1-yl carbonyl pyrrolo[3,4-c]pyrazole with N-(3,3,3-trifluoropropyl) substituent |
| 109 | 4-(3-(trifluoromethyl)-4,5-difluorophenyl)piperidin-1-yl carbonyl pyrrolo[3,4-c]pyrazole with N-(2-methoxyethyl) substituent |
| 110 | 4-(3-(trifluoromethyl)-4,5-difluorophenyl)piperidin-1-yl carbonyl pyrrolo[3,4-c]pyrazole with N-CN substituent |
| 111 | 4-(3-(trifluoromethyl)-4,5-difluorophenyl)piperidin-1-yl carbonyl tetrahydropyrazolo[3,4-c]pyridine with N-ethyl substituent |
| 112 | 4-(3-(trifluoromethyl)-4,5-difluorophenyl)piperidin-1-yl carbonyl tetrahydropyrazolo[3,4-c]pyridine with N-C(O)NHCH₃ substituent |
| 113 | 4-(3-(trifluoromethyl)-4,5-difluorophenyl)piperidin-1-yl carbonyl tetrahydropyrazolo[3,4-c]pyridine with N-methyl substituent |
| 114 | 4-(3-(trifluoromethyl)-2-fluorophenyl)piperidin-1-yl carbonyl tetrahydropyrazolo[3,4-c]pyridine with N-C(O)NHCH₃ substituent |
| 115 | 4-(3-(trifluoromethyl)-4,5-difluorophenyl)piperidin-1-yl carbonyl tetrahydropyrazolo[3,4-c]pyridine with N-CH₂COOH substituent |

TABLE 1-continued
| Compound | Structure |
|---|---|
| 116 | 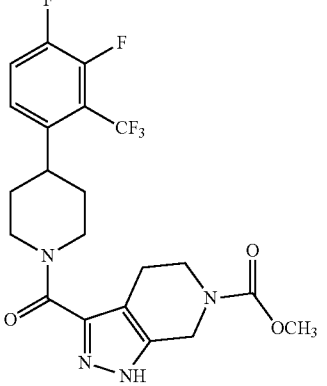 |
| 117 | 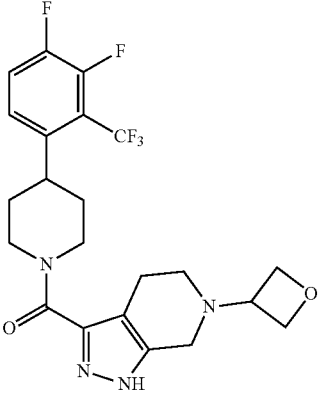 [SMILES: O=C(c1n[nH]c2c1CCN(C1COC1)C2)N1CCC(c2ccc(F)c(F)c2C(F)(F)F)CC1] |
| 118 | 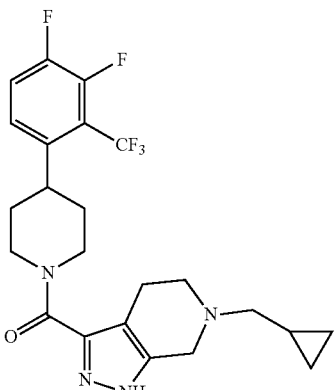 |
| 119 | 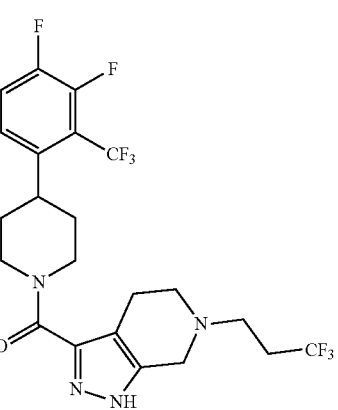 |
| 120 | 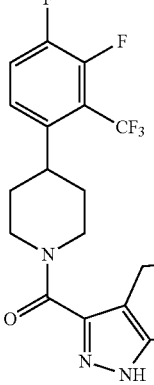 |
| 121 | 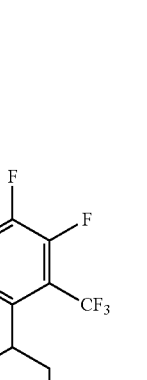 |
| 122 | 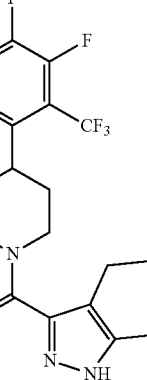 |

TABLE 1-continued

| Compound | Structure |
|---|---|
| 123 | (structure) |
| 124 | (structure) |
| 125 | (structure) |
| 126 | (structure) |
| 127 | (structure) |
| 128 | (structure) |
| 129 | (structure) |
| 130 | (structure) |

TABLE 1-continued

| Compound | Structure |
|---|---|
| 131 | (structure) |
| 132 | (structure) |
| 133 | (structure) |
| 134 | (structure) |
| 135 | (structure) |
| 136 | (structure) |
| 137 | (structure) |
| 138 | (structure) |

TABLE 1-continued
| Compound | Structure |
|---|---|
| 139 | 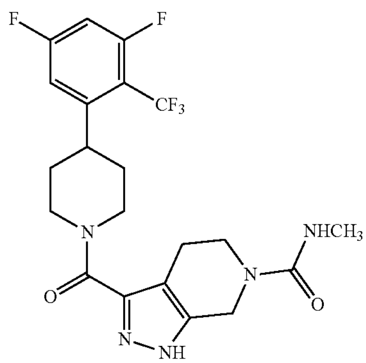 [SMILES: CNC(=O)N1CCc2c(C(=O)N3CCC(c4cc(F)cc(F)c4C(F)(F)F)CC3)n[nH]c2C1] |
| 140 | 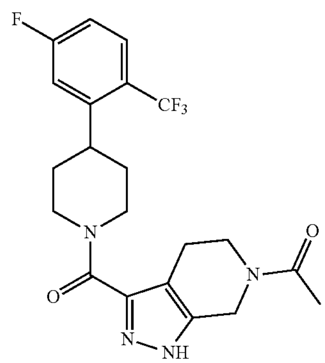 [SMILES: CC(=O)N1CCc2c(C(=O)N3CCC(c4cc(F)ccc4C(F)(F)F)CC3)n[nH]c2C1] |
| 141 | 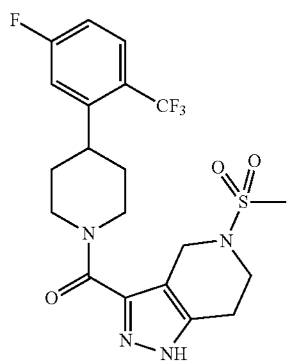 [SMILES: CS(=O)(=O)N1CCc2[nH]nc(C(=O)N3CCC(c4cc(F)ccc4C(F)(F)F)CC3)c2C1] |
| 142 | 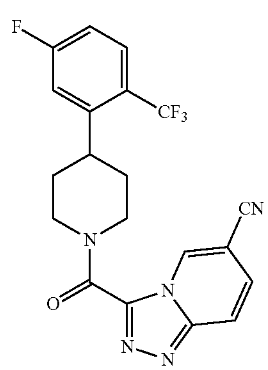 |
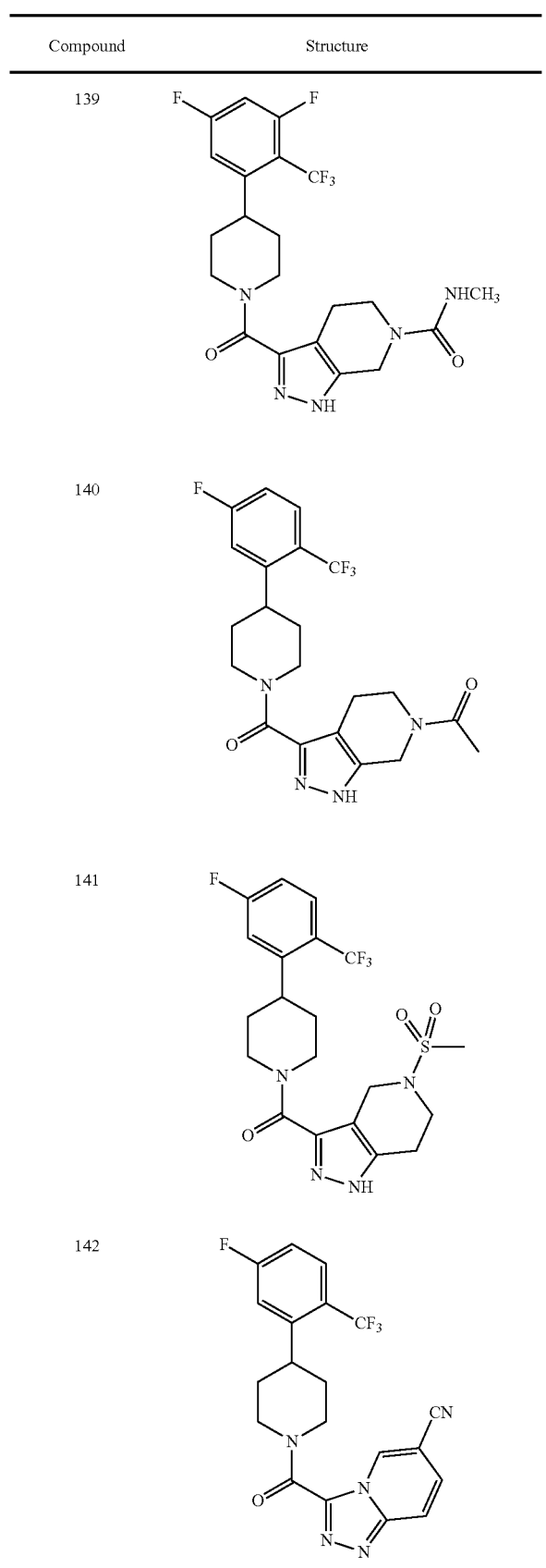
TABLE 1-continued
| Compound | Structure |
|---|---|
| 143 | 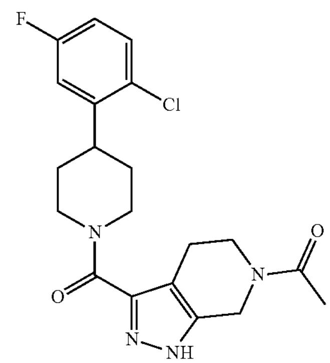 [SMILES: CC(=O)N1CCc2c(C(=O)N3CCC(c4cc(F)ccc4Cl)CC3)n[nH]c2C1] |
| 144 | 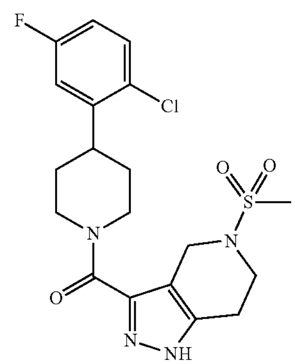 [SMILES: CS(=O)(=O)N1CCc2[nH]nc(C(=O)N3CCC(c4cc(F)ccc4Cl)CC3)c2C1] |
| 145 | 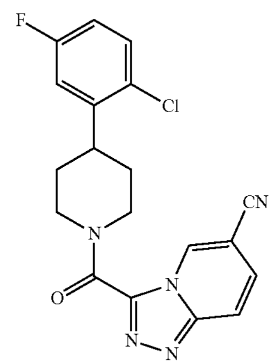 [SMILES: N#Cc1ccc2nnc(C(=O)N3CCC(c4cc(F)ccc4Cl)CC3)n2c1] |
| 146 | 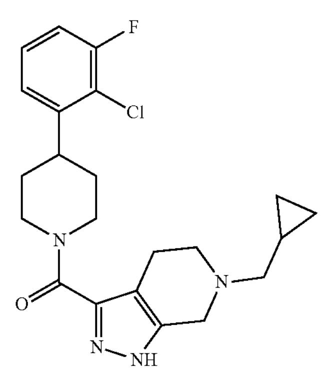 [SMILES: O=C(c1n[nH]c2c1CCN(CC1CC1)C2)N1CCC(c2cccc(F)c2Cl)CC1] |
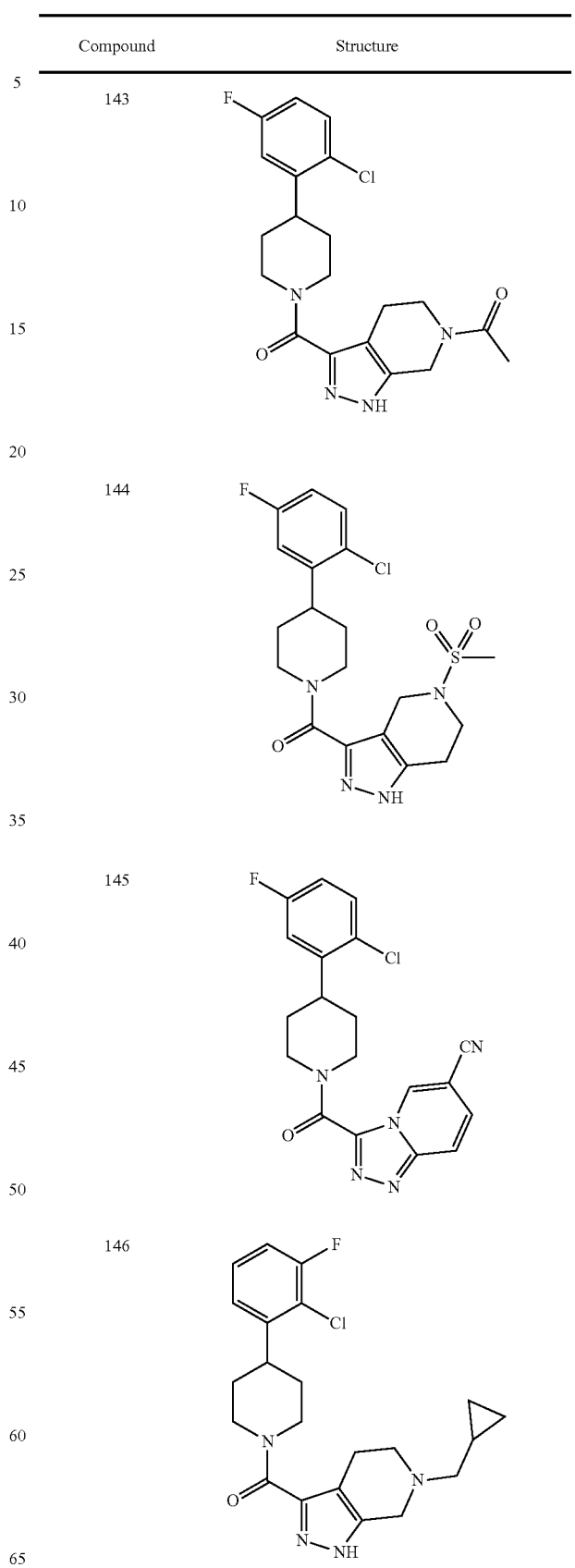

TABLE 1-continued

| Compound | Structure |
|---|---|
| 147 | 3-fluoro-2-chlorophenyl piperidine linked via carbonyl to 4,5,6,7-tetrahydro-1H-pyrazolo[3,4-c]pyridine with N-C(O)OCH3 |
| 148 | 3-fluoro-2-chlorophenyl piperidine linked via carbonyl to 4,5,6,7-tetrahydro-1H-pyrazolo[3,4-c]pyridine with N-CN |
| 149 | 3-fluoro-2-chlorophenyl piperidine linked via carbonyl to 4,5,6,7-tetrahydro-1H-pyrazolo[3,4-c]pyridine with N-oxetanyl |
| 150 | 3-fluoro-2-chlorophenyl piperidine linked via carbonyl to 4,5,6,7-tetrahydro-1H-pyrazolo[3,4-c]pyridine with N-acetyl |
| 151 | 3-fluoro-2-chlorophenyl piperidine linked via carbonyl to 4,5,6,7-tetrahydro-1H-pyrazolo[3,4-c]pyridine with N-SO2CH3 |
| 152 | 3-fluoro-2-chlorophenyl piperidine linked via carbonyl to [1,2,4]triazolo[4,3-a]pyridine with CN |
| 153 | 3,5-bis(trifluoromethyl)phenyl piperidine linked via carbonyl to 4,5,6,7-tetrahydro-1H-pyrazolo[3,4-c]pyridine with N-acetyl |
| 154 | 3,5-bis(trifluoromethyl)phenyl piperidine linked via carbonyl to 4,5,6,7-tetrahydro-1H-pyrazolo[3,4-c]pyridine with N-SO2CH3 |

TABLE 1-continued
| Compound | Structure |
|---|---|
| 155 | 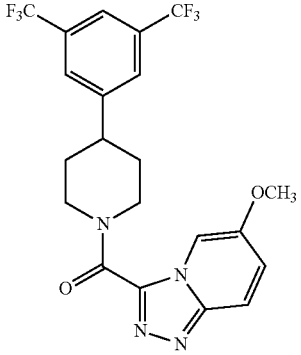 [SMILES: COc1ccc2nnc(C(=O)N3CCC(c4cc(C(F)(F)F)cc(C(F)(F)F)c4)CC3)n2c1] |
| 156 | 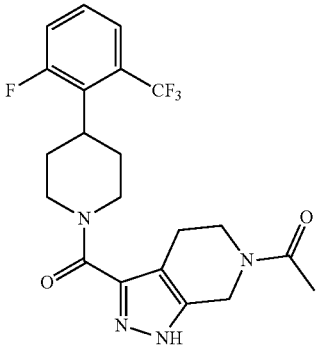 [SMILES: CC(=O)N1CCc2c(C(=O)N3CCC(c4c(F)cccc4C(F)(F)F)CC3)n[nH]c2C1] |
| 157 | 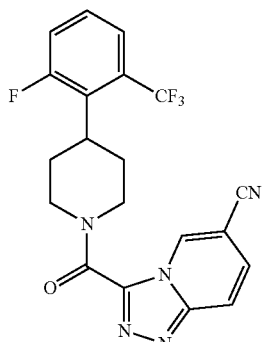 |
| 158 | 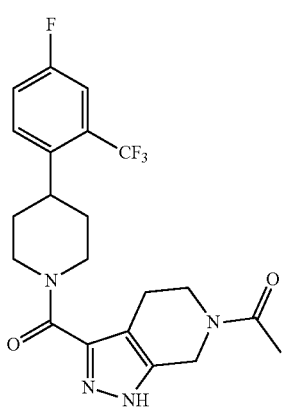 [SMILES: CC(=O)N1CCc2c(C(=O)N3CCC(c4ccc(F)cc4C(F)(F)F)CC3)n[nH]c2C1] |
| 159 | 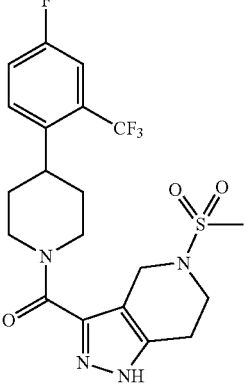 |
| 160 | 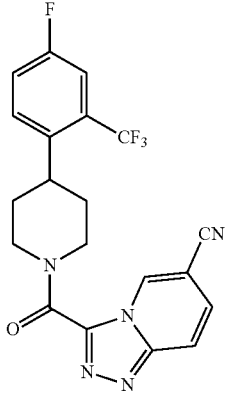 [SMILES: N#Cc1ccc2nnc(C(=O)N3CCC(c4ccc(F)cc4C(F)(F)F)CC3)n2c1] |
| 161 | 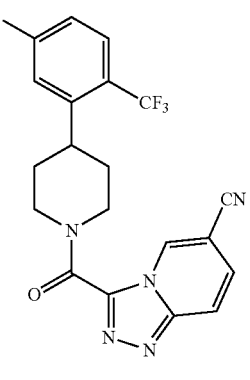 |
| 162 | 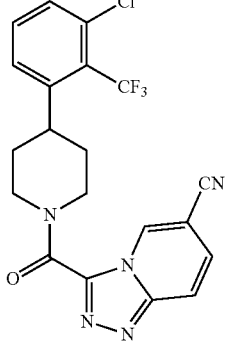 |

TABLE 1-continued

| Compound | Structure |
|---|---|
| 163 | (4-(3-fluoro-2-chlorophenyl)piperidin-1-yl)(5-ethyl-4,5,6,7-tetrahydro-1H-pyrazolo[4,3-c]pyridin-3-yl)methanone |
| 164 | (4-(3-fluoro-2-chlorophenyl)piperidin-1-yl)(5-(cyclopropylmethyl)-4,5,6,7-tetrahydro-1H-pyrazolo[4,3-c]pyridin-3-yl)methanone |
| 165 | (4-(3-fluoro-2-chlorophenyl)piperidin-1-yl)(5-(oxetan-3-yl)-4,5,6,7-tetrahydro-1H-pyrazolo[4,3-c]pyridin-3-yl)methanone |
| 166 | (4-(3-fluoro-2-chlorophenyl)piperidin-1-yl)(5-(2,2,2-trifluoroethyl)-4,5,6,7-tetrahydro-1H-pyrazolo[4,3-c]pyridin-3-yl)methanone |
| 167 | (4-(3-fluoro-2-chlorophenyl)piperidin-1-yl)(5-(3,3,3-trifluoropropyl)-4,5,6,7-tetrahydro-1H-pyrazolo[4,3-c]pyridin-3-yl)methanone |
| 168 | (4-(3-fluoro-2-chlorophenyl)piperidin-1-yl)(5-(2-methoxyethyl)-4,5,6,7-tetrahydro-1H-pyrazolo[4,3-c]pyridin-3-yl)methanone |
| 169 | (4-(3,4-difluoro-2-(trifluoromethyl)phenyl)piperidin-1-yl)(5-(piperazine-1-carbonyl)-1,4,5,6-tetrahydropyrrolo[3,4-c]pyrazol-3-yl)methanone |

TABLE 2

| Compound | SPA binding assay for RBP4: IC$_{50}$ (μM) | HTRF assay for antagonists of RBP4-TTR interaction: IC$_{50}$ (μM) |
|---|---|---|
| 30 | 0.01332568 | 0.04412238 |
| 32 | 0.062512598 | 0.244123897 |
| 34 | 0.020741511 | 0.053147107 |
| 36 | 0.010869769 | 0.291188749 |
| 38 | 0.026852208 | 0.200234283 |
| 40 | 0.014037221 | 0.084919195 |
| 42 | 0.424157125 | 0.791241375 |
| 63 | 0.004456853 | 0.015959612 |
| 64 | 0.00535572 | 0.020583279 |
| 65 | 0.004128382 | 0.012791498 |
| 65 | 0.00920849 | 0.012699602 |
| 65 | 0.005731617 | 0.016052657 |
| 65 | 0.005362759 | 0.012698298 |
| 66 | 0.0075 | 0.0823 |
| 67 | 0.0083091 | 0.040819847 |

TABLE 2-continued

| Compound | SPA binding assay for RBP4: IC$_{50}$ (μM) | HTRF assay for antagonists of RBP4-TTR interaction: IC$_{50}$ (μM) |
|---|---|---|
| 68 | <0.001371742 | 0.036226752 |
| 69 | 0.010003069 | 0.026712607 |
| 70 | 0.016423974 | 0.037469294 |
| 71 | 0.017068116 | 0.052577032 |
| 72 | 0.010783633 | 0.052816869 |
| 73 | 0.008501059 | 0.030581957 |
| 74 | 0.011554458 | 0.028341348 |
| 75 | 0.006948729 | 0.033963112 |
| 76 | 0.007397337 | 0.019662328 |
| 77 | 0.007956596 | 0.010567139 |
| 77 | 0.002879752 | 0.001618692 |
| 78 | 0.009495365 | 0.015829707 |
| 79 | 0.004345412 | 0.006097083 |
| 80 | 0.009116322 | 0.04059294 |
| 81 | 0.006035222 | 0.013874989 |
| 81 | 0.005257865 | 0.009751259 |
| 81 | 0.002824087 | — |
| 81 | 0.004328733 | 0.014982801 |
| 82 | 0.011621066 | 0.030784872 |
| 83 | 0.011621066 | 0.030784872 |
| 83 | <0.001371742 | 0.004846177 |
| 84 | 0.016278579 | 0.014718925 |
| 85 | 0.017878562 | 0.022412347 |
| 86 | 0.019348437 | 0.027773785 |
| 87 | 0.009458663 | 0.022161242 |
| 87 | 0.007802201 | 0.016361021 |
| 88 | 0.014654027 | 0.017992866 |
| 88 | 0.01343769 | 0.039000351 |
| 89 | 0.008837608 | 0.033041159 |
| 90 | 0.014355632 | 0.042917759 |
| 91 | 0.007058195 | 0.057659098 |
| 92 | 0.010216826 | 0.076562958 |
| 93 | 0.008001007 | 0.033595702 |
| 94 | 0.006956733 | 0.049907081 |
| 95 | 0.007780441 | 0.027841767 |
| 96 | 0.012671283 | 0.026498126 |
| 97 | 0.014325185 | 0.023974449 |
| 98 | 0.011849477 | 0.07412655 |
| 99 | 0.022481673 | 0.147330955 |
| 100 | 0.019623326 | 0.030307008 |
| 101 | 0.007438315 | 0.014065248 |
| 102 | 0.021664204 | 0.027581659 |
| 103 | 0.01602771 | 0.03032762 |
| 104 | 0.018923149 | 0.021764444 |
| 105 | 0.0111956 | 0.036352539 |
| 106 | 0.020392347 | 0.029763871 |
| 107 | 0.023393835 | 0.07700471 |
| 108 | 0.025170865 | 0.049536156 |
| 109 | 0.014933765 | 0.04188677 |
| 110 | 0.015640938 | 0.015420503 |
| 111 | 0.00688552 | 0.022103363 |
| 112 | 0.011482219 | 0.027454866 |
| 113 | 0.008568525 | 0.029698246 |
| 114 | 0.010291162 | 0.040803422 |
| 115 | 0.018874475 | 0.109320347 |
| 116 | 0.011433337 | 0.023664257 |
| 117 | 0.005480892 | 0.037691094 |
| 118 | 0.009387053 | 0.014204672 |
| 119 | 0.010706312 | 0.039428773 |
| 120 | 0.003446949 | 0.021028771 |
| 121 | 0.008840985 | 0.031786798 |
| 122 | 0.017048919 | 0.027657766 |
| 123 | 0.015052917 | 0.052167868 |
| 124 | 0.014625984 | 0.024895781 |
| 125 | 0.014989926 | 0.062101253 |
| 126 | 0.016994001 | 0.16972172 |
| 127 | 0.015876357 | 0.017030219 |
| 128 | 0.018381483 | 0.032415479 |
| 129 | 0.013783057 | 0.019545743 |
| 130 | 0.012836331 | 0.01491032 |
| 131 | 0.006360993 | 0.010914335 |
| 132 | 0.006750411 | 0.010485373 |
| 133 | — | — |
| 134 | 0.0172 | 0.0955 |
| 135 | 0.016415973 | 0.021040669 |
| 136 | 0.016716286 | 0.012001451 |
| 137 | 0.018357352 | 0.02416484 |
| 138 | 0.010124856 | 0.02443067 |
| 139 | 0.017844788 | 0.022818173 |
| 140 | 0.009283295 | 0.021890308 |
| 141 | 0.005244084 | 0.020757101 |
| 142 | 0.004882652 | 0.023217801 |
| 143 | 0.008830797 | 0.052292371 |
| 144 | 0.006170928 | 0.070312083 |
| 145 | 0.007565936 | 0.066971574 |
| 146 | 0.015873944 | 0.036497073 |
| 147 | 0.017087987 | 0.025510325 |
| 148 | 0.005121182 | 0.007411947 |
| 148 | <0.001371742 | <0.000169 |
| 149 | 0.005905695 | 0.023421638 |
| 150 | 0.004841961 | 0.023730312 |
| 151 | 0.010266809 | 0.067747522 |
| 152 | 0.003104118 | 0.027843193 |
| 153 | 0.149436555 | 0.833441155 |
| 154 | 0.150196791 | 0.384932114 |
| 155 | 0.02162571 | 0.186360166 |
| 156 | 0.01944249 | 0.247762562 |
| 157 | 0.005840561 | 0.09202995 |
| 158 | 0.008632683 | 0.036829287 |
| 159 | 0.008056546 | 0.052280303 |
| 160 | 0.009062711 | 0.019772679 |
| 161 | 0.005742747 | 0.025784179 |
| 162 | 0.00482477 | 0.01068914 |
| 163 | 0.015294165 | 0.055271368 |
| 164 | 0.013574829 | 0.074955125 |
| 165 | 0.01557141 | 0.064787312 |
| 166 | 0.012173811 | 0.037917945 |
| 167 | 0.011715962 | 0.048822888 |
| 168 | 0.015544906 | 0.081261949 |
| 169 | 0.033042848 | 0.055813322 |

EXAMPLE 109

RPB4 Binding of Additional Substituted Piperidine Compounds

An additional aspect of the invention provides analogs of the compounds of Table 1 that are active as RBP4 antagonists. These analogs contain a di- or tri-substituted phenyl ring located at the 4-position of the piperidine core. The analogs of Compounds 63-162 described herein analogously bind to RBP4 and antagonize retinol-dependent RBP4-TTR interaction.

Additional piperidine compounds, which are analogs of those described in Table 1, are tested in two in vitro assays, RBP4 binding (SPA) and retinol-dependent RBP4-TTR interaction (HTRF). These piperidine compounds bind to RBP4 and antagonize retinol-dependent RBP4-TTR interaction. This activity indicates that the compounds reduce the level of serum RBP4 and retinol.

EXAMPLE 110

Efficacy in a Mammalian Model

The effectiveness of the compounds listed in Table 1 are tested in wild-type and Abca4−/− mice. The Abca4−/− mouse model manifests accelerated accumulation of lipofuscin in the RPE and is considered a pre-clinical efficacy model for a drug reducing lipofuscin accumulation. Compounds are orally dosed for 3 weeks at 30 mg/kg. There is a reduction in the serum RBP4 level in treated animals. The levels of A2E/isoA2E and other bisretinoids are reduced in treated mice. The levels of A2-DHP-PE and atRAL di-PE are also reduced.

The effectiveness of additional piperidine compounds, which are analogs of those described in Table 1, are tested in wild-type and Abca4−/− mice. The Abca4−/− mouse model manifests accelerated accumulation of lipofuscin in the RPE and is considered a pre-clinical efficacy model for a drug reducing lipofuscin accumulation. Compounds are orally dosed for 3 weeks at 30 mg/kg. There is a reduction in the serum RBP4 level in treated animals. The levels of A2E/isoA2E and other bisretinoids are reduced in treated mice. The levels of A2-DHP-PE and atRAL di-PE are also reduced.

EXAMPLE 111

Efficacy of Compound 81 in a Mammalian Model

Figure 8:
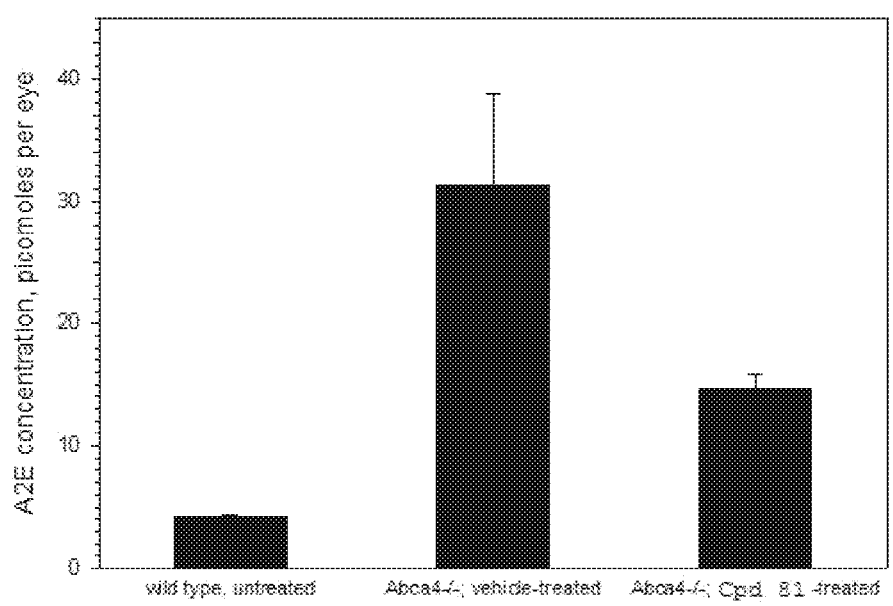
FIG. 8. Effect of Compound 81 Treatment on Bisretinoid Accumulation in Eyes of Abca4−/− mice (P=0.006; unpaired t-test).
Figure 9:
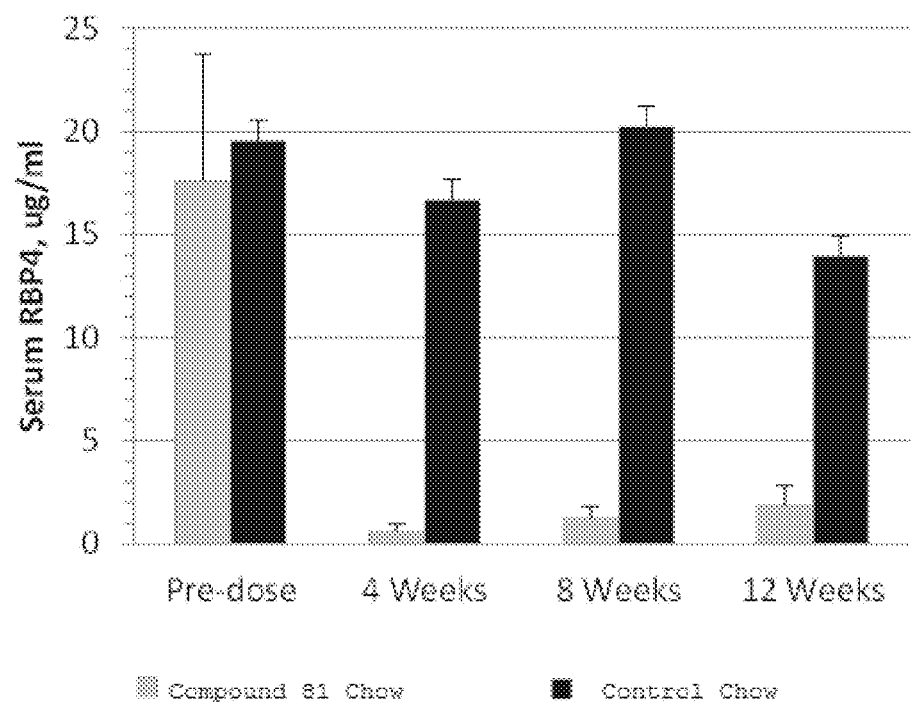
FIG. 9. Serum RBP4 Levels in Compound 81- and vehicle-treated Abca4−/− mice.

Compound 81 inhibited bisretinoid accumulation in Abca4−/− mouse model. Abca4−/− mice have A2E levels in the ~15-19 pmoles/eye range at 17 weeks old. Mice, starting at 17 weeks old, were treated with 25 mg/kg of Compound 81 for 12 weeks. There was a 53% reduction in bisretinoid content in the Compound 81-treated mice versus the vehicle-treated controls (FIG. 8). This data was consistent with complete arrest of bisretinoid synthesis from the start of the dosing regiment. Reduced bisretinoid accumulation resulted in significant serum RBP4 reduction in the Compound 81-treated mice (FIG. 9).

EXAMPLE 112

Efficacy of Additional Compounds in a Mammalian Model

Compounds 34, 36, and 38 inhibit bisretinoid accumulation in Abca4−/− mouse model. Mice, starting at 17 weeks old, are treated with 25 mg/kg of Compounds 34, 36, or 38 for 12 weeks. There is a reduction in bisretinoid content in the treated mice versus the vehicle-treated controls. This data is consistent with complete arrest of bisretinoid synthesis from the start of the dosing regiment. Reduced bisretinoid accumulation results in significant serum RBP4 reduction in the treated mice.

Compounds 30, 40, and 42 inhibit bisretinoid accumulation in Abca4−/− mouse model. Mice, starting at 17 weeks old, are treated with 25 mg/kg of Compounds 30, 40, or 42 for 12 weeks. There is a reduction in bisretinoid content in the treated mice versus the vehicle-treated controls. This data is consistent with complete arrest of bisretinoid synthesis from the start of the dosing regiment. Reduced bisretinoid accumulation results in significant serum RBP4 reduction in the treated mice.

Each of Compounds 63-80 or 82-169 inhibit bisretinoid accumulation in Abca4−/− mouse model. Mice, starting at 17 weeks old, are treated with 25 mg/kg any one of Compounds 63-80 or 82-169 for 12 weeks. There is a reduction in bisretinoid content in the treated mice versus the vehicle-treated controls. This data is consistent with complete arrest of bisretinoid synthesis from the start of the dosing regiment.

Reduced bisretinoid accumulation results in significant serum RBP4 reduction in the treated mice.

EXAMPLE 113

Administration to a Subject

An amount of a compound 81 is administered to the eye of a subject afflicted with AMD. The amount of the compound is effective to treat the subject.

An amount of a compound 81 is administered to the eye of a subject afflicted with Stargardt disease. The amount of the compound is effective to treat the subject.

An amount of any one of compounds 63-80 or 82-169 is administered to the eye of a subject afflicted with AMD. The amount of the compound is effective to treat the subject.

An amount of any one of compounds 63-80 or 82-169 is administered to the eye of a subject afflicted with Stargardt disease. The amount of the compound is effective to treat the subject.

Discussion

Age-related macular degeneration (AMD) is the leading cause of blindness in developed countries. Its prevalence is higher than that of Alzheimer's disease. There is no treatment for the most common dry form of AMD. Dry AMD is triggered by abnormalities in the retinal pigment epithelium (RPE) that lies beneath the photoreceptor cells and provides critical metabolic support to these light-sensing cells. RPE dysfunction induces secondary degeneration of photoreceptors in the central part of the retina called the macula. Experimental data indicate that high levels of lipofuscin induce degeneration of RPE and the adjacent photoreceptors in atrophic AMD retinas. In addition to AMD, dramatic accumulation of lipofuscin is the hallmark of Stargardt's disease (STGD), an inherited form of juvenile onset macular degeneration. The major cytotoxic component of RPE lipofuscin is a pyridinium bisretinoid A2E. A2E formation occurs in the retina in a non-enzymatic manner and can be considered a by-product of a properly functioning visual cycle. Given the established cytotoxic affects of A2E on RPE and photoreceptors, inhibition of A2E formation could lead to delay in visual loss in patients with dry AMD and STGD. It was suggested that small molecule visual cycle inhibitors may reduce the formation of A2E in the retina and prolong RPE and photoreceptor survival in patients with dry AMD and STGD. Rates of the visual cycle and A2E production in the retina depend on the influx of all-trans retinol from serum to the RPE. RPE retinol uptake depends on serum retinol concentrations. Pharmacological down-regulation of serum retinol is a valid treatment strategy for dry AMD and STGD. Serum retinol is maintained in circulation as a tertiary complex with retinol-binding protein (RBP4) and transthyretin (TTR). Without interacting with TTR, the RBP4-retinol complex is rapidly cleared due to glomerular filtration. Retinol binding to RBP4 is required for formation of the RBP4-TTR complex; apo-RBP4 does not interact with TTR. Importantly, the retinol-binding site on RBP4 is sterically proximal to the interface mediating the RBP4-TTR interaction. Without wishing to be bound by any scientific theory, the data herein show that small molecule RBP4 antagonists displacing retinol from RBP4 and disrupting the RBP4-TTR interaction will reduce serum retinol concentration, inhibit retinol uptake into the retina and act as indirect visual cycle inhibitors reducing formation of cytotoxic A2E.

Serum RBP4 as a Drug Target for Pharmacological Inhibition of the Visual Cycle

Figure 4:
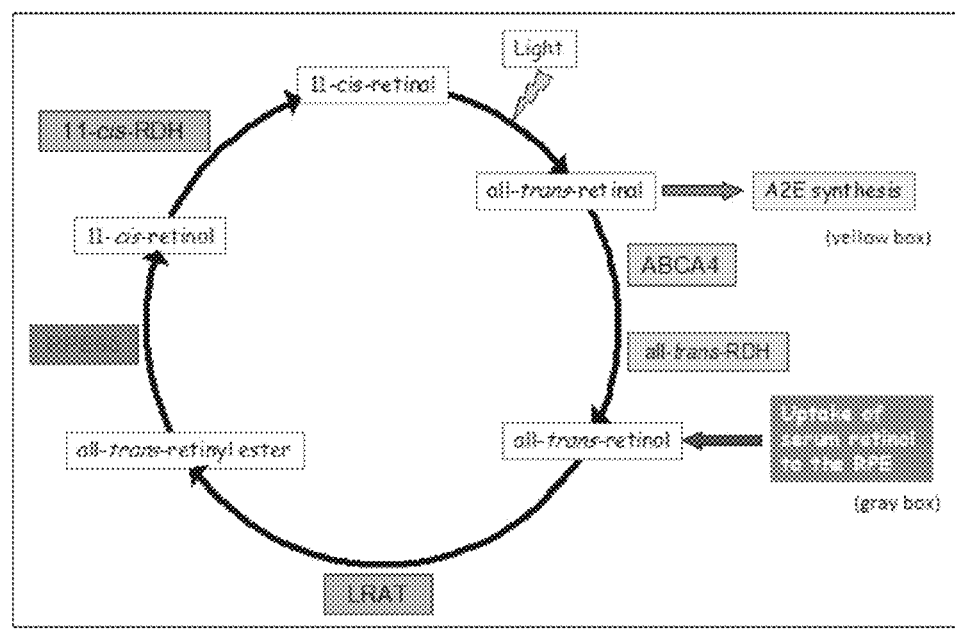
FIG. 4. Visual cycle and biosynthesis of A2E. A2E biosynthesis begins when a portion of all-trans-retinal escapes the visual cycle (yellow box) and non-enzymatically reacts with phosphatidyl-ethanolamine forming the A2E precursor, A2-PE. Uptake of serum retinol to the RPE (gray box) fuels the cycle.
Figure 5:
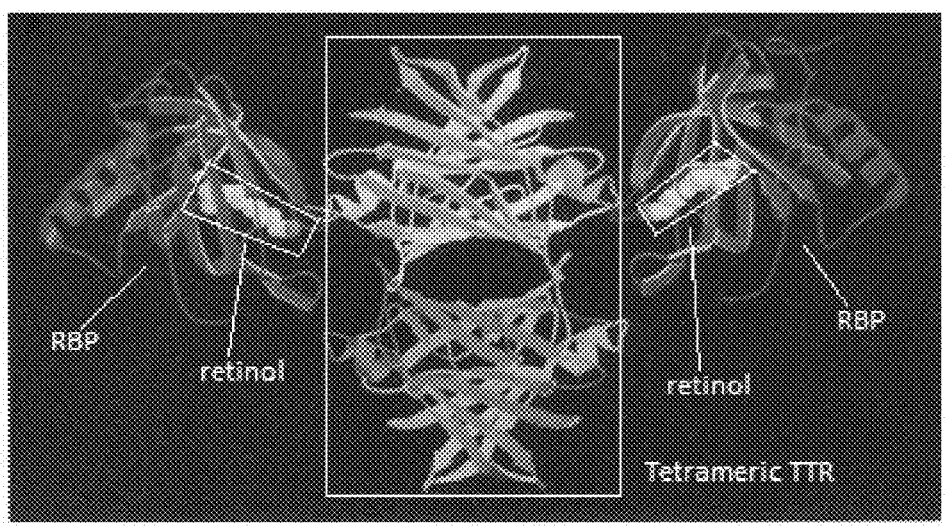
FIG. 5. Three-dimensional structure of the RBP4-TTR-retinol complex. Tetrameric TTR is shown in blue, light blue, green and yellow (large boxed region). RBP is shown in red (unboxed region) and retinol is shown in gray (small boxed region) (28).

As rates of the visual cycle and A2E production in the retina depend on the influx of all-trans retinol from serum to the RPE (FIG. 4), it has been suggested that partial pharmacological down-regulation of serum retinol may represent a target area in dry AMD treatment (11). Serum retinol is bound to retinol-binding protein (RBP4) and maintained in circulation as a tertiary complex with RBP4 and transthyretin (TTR) (FIG. 5). Without interacting with TTR, the RBP4-retinol complex is rapidly cleared from circulation due to glomerular filtration. Additionally, formation of the RBP4-TTR-retinol complex is required for receptor-mediated all-trans retinol uptake from serum to the retina.

Without wishing to be bound by any scientific theory, visual cycle inhibitors may reduce the formation of toxic bisretinoids and prolong RPE and photoreceptor survival in dry AMD. Rates of the visual cycle and A2E production depend on the influx of all-trans retinol from serum to the RPE. Formation of the tertiary retinol-binding protein 4 (RBP4)-transthyretin (TTR)-retinol complex in serum is required for retinol uptake from circulation to the RPE. Retinol-binding site on RBP4 is sterically proximal to the interface mediating the RBP4-TTR interaction. RBP4 antagonists that compete with serum retinol for binding to RBP4 while blocking the RBP4-TTR interaction would reduce serum retinol, slow down the visual cycle, and inhibit formation of cytotoxic bisretinoids.

RBP4 represents an attractive drug target for indirect pharmacological inhibition of the visual cycle and A2E formation. The retinol-binding site on RBP4 is sterically proximal to the interface mediating the RBP4-TTR interaction. Retinol antagonists competing with serum retinol for binding to RBP4 while blocking the RBP4-TTR interaction would reduce serum RBP4 and retinol levels which would lead to reduced uptake of retinol to the retina. The outcome would be visual cycle inhibition with subsequent reduction in the A2E synthesis.

Figure 6:
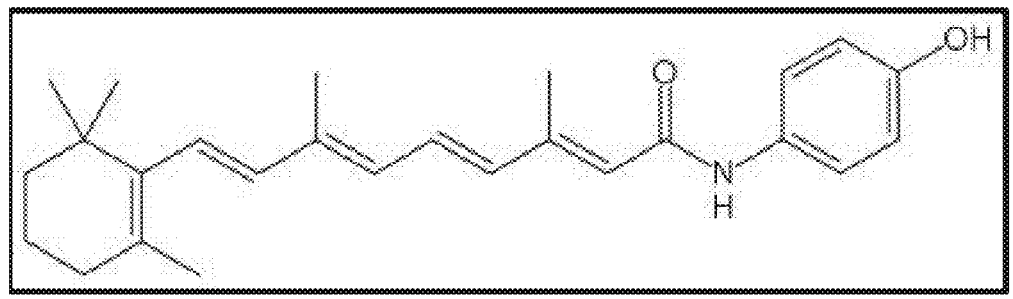
FIG. 6. Structure of fenretinide, [N-(4-hydroxy-phenyl) retinamide, 4HRP], a retinoid RBP4 antagonist.

A synthetic retinoid called fenretinide [N-(4-hydroxyphenyl)retinamide, 4HRP] (FIG. 6) previously considered as a cancer treatment (29) was found to bind to RBP4, displace all-trans retinol from RBP4 (13), and disrupt the RBP4-TTR interaction (13,14).

Fenretinide was shown to reduce serum RBP4 and retinol (15), inhibit ocular all-trans retinol uptake and slow down the visual cycle (11). Importantly, fenretinide administration reduced A2E production in an animal model of excessive bisretinoid accumulation, Abca4−/− mice (11). Pre-clinical experiments with fenretinide validated RBP4 as a drug target for dry AMD. However, fenretinide is non-selective and toxic. Independent of its activity as an antagonist of retinol binding to RBP4, fenretinide is an extremely active inducer of apoptosis in many cell types (16-19), including the retinal pigment epithelium cells (20). It has been suggested that fenretinide's adverse effects are mediated by its action as a ligand of a nuclear receptor RAR (21-24). Additionally, similar to other retinoids, fenretinide is reported to stimulate formation of hemangiosarcomas in mice. Moreover, fenretinide is teratogenic, which makes its use problematic in Stargardt disease patients of childbearing age.

As fenretinide's safety profile may be incompatible with long-term dosing in individuals with blinding but non-life threatening conditions, identification of new classes of RBP4 antagonists is of significant importance. The compounds of the present invention displace retinol from RBP4, disrupt retinol-induced RBP4-TTR interaction, and reduce serum REBP4 levels. The compounds of the present invention inhibit bisretinoid accumulation in the Abca4−/− mouse model of excessive lipofuscinogenesis which indicates usefulness a treatment for dry AMD and Stargardt disease.

The present invention relates to small molecules for treatment of macular degeneration and Stargardt Disease. Disclosed herein is the ophthalmic use of the small molecules as non-retinoid RBP4 antagonists. The compound listed in Table 2 have been shown to bind RBP4 in vitro and/or to antagonize RBP4-TTR interaction in vitro at biologically significant concentrations. Additional compounds described herein, which are analogs of compound listed in Table 2 analogously bind RBP4 in vitro and antagonize RBP4-TTR interaction in vitro at biologically significant concentrations.

Currently, there is no FDA-approved treatment for dry AMD or Stargardt disease, which affects millions of patients. An over the counter, non FDA-approved cocktail of antioxidant vitamins and zinc (AREDS formula) is claimed to be beneficial in a subset of dry AMD patients. There are no treatments for Stargardt disease. The present invention identified non-retinoid RBP4 antagonists that are useful for the treatment of dry AMD and other conditions characterized by excessive accumulation of lipofuscin. Without wishing to be bound by any scientific theory, as accumulation of lipofuscin seems to be a direct cause of RPE and photoreceptor demise in AMD and STGD retina, the compounds described herein are disease-modifying agents since they directly address the root cause of these diseases. The present invention provides novel methods of treatment that will preserve vision in AMD and Stargardt disease patients, and patients' suffering from conditions characterized by excessive accumulation of lipofuscin.

REFERENCES

1. Petrukhin K. New therapeutic targets in atrophic age-related macular degeneration. Expert Opin. Ther. Targets. 2007, 11(5): 625-639
2. C. Delori, D. G. Goger and C. K. Dorey, Age-related accumulation and spatial distribution of lipofuscin in RPE of normal subjects. Investigative Ophthalmology and Visual Science 42 (2001), pp. 1855-1866
3. F. C. Delori, RPE lipofuscin in ageing and age-related macular degeneration. In: G. Coscas and F. C. Piccolino, Editors, Retinal Pigment Epithelium and Macular Disease (Documenta Ophthalmologica) vol. 62, Kluwer Academic Publishers, Dordrecht, The Netherlands (1995), pp. 37-45.
4. C. K. Dorey, G. Wu, D. Ebenstein, A. Garsd and J. J. Weiter, Cell loss in the aging retina. Relationship to lipofuscin accumulation and macular degeneration. Investigative Ophthalmology and Visual Science 30 (1989), pp. 1691-1699.
5. L. Feeney-Burns, E. S. Hilderbrand and S. Eldridge, Aging human RPE: morphometric analysis of macular, equatorial, and peripheral cells. Investigative Ophthalmology and Visual Science 25 (1984), pp. 195-200.
6. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
7. F. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.

7. A. von Rückmann, F. W. Fitzke and A. C. Bird, Fundus autofluorescence in age-related macular disease imaged with a laser scanning opthalmoscope. Investigative Ophthalmology and Visual Science 38 (1997), pp. 478-486.
9. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
10. Sparrow J R, Fishkin N, Zhou J, Cai B, Jang Y P, Krane S, Itagaki Y, Nakanishi K. A2E, a byproduct of the visual cycle. Vision Res. 2003 December; 43(28):2983-90
11. Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401
12. Motani A, Wang Z, Conn M, Siegler K, Zhang Y, Liu Q, Johnstone S, Xu H, Thibault S, Wang Y, Fan P, Connors R, Le H, Xu G, Walker N, Shan B, Coward P. Identification and characterization of a non-retinoid ligand for retinol-binding protein 4 which lowers serum retinol-binding protein 4 levels in vivo. J Biol Chem. 2009 Mar. 20; 284(12):7673-80.
13. Berni R, Formelli F. In vitro interaction of fenretinide with plasma retinol-binding protein and its functional consequences. FEBS Lett. 1992 Aug. 10; 308(1):43-5.
14. Schaffer E M, Ritter S J, Smith J E. N-(4-hydroxyphenyl)retinamide (fenretinide) induces retinol-binding protein secretion from liver and accumulation in the kidneys in rats. J Nutr. 1993 September; 123(9):1497-503
15. Adams W R, Smith J E, Green M H. Effects of N-(4-hydroxyphenyl)retinamide on vitamin A metabolism in rats. Proc Soc Exp Biol Med. 1995 February; 208(2):178-85.
16. Puduvalli V K, Saito Y, Xu R, Kouraklis G P, Levin V A, Kyritsis A P. Fenretinide activates caspases and induces apoptosis in gliomas. Clin Cancer Res. 1999 August; 5(8):2230-5
17. Holmes W F, Soprano D R, Soprano K J. Synthetic retinoids as inducers of apoptosis in ovarian carcinoma cell lines. J Cell Physiol. 2004 June; 199(3):317-29
18. Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17
19. Fontana J A, Rishi A K. Classical and novel retinoids: their targets in cancer therapy. Leukemia. 2002 April; 16(4):463-72
20. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
21. Fontana J A, Rishi A K. Classical and novel retinoids: their targets in cancer therapy. Leukemia. 2002 April; 16(4):463-72
22. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
23. Sabichi A L, Xu H, Fischer S, Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13
24. Clifford J L, Menter D G, Wang M, Lotan R, Lippman S M. Retinoid receptor-dependent and -independent effects of N-(4-hydroxyphenyl)retinamide in F9 embryonal carcinoma cells. Cancer Res. 1999 Jan. 1; 59(1):14-8.
25. Gollapalli D R, Rando R R. The specific binding of retinoic acid to RPE65 and approaches to the treatment of macular degeneration. Proc Natl Acad Sci USA. 2004 Jul. 6; 101(27):10030-5
26. Maiti P, Kong J, Kim S R, Sparrow J R, Allikmets R, Rando R R. Small molecule RPE65 antagonists limit the visual cycle and prevent lipofuscin formation. Biochemistry. 2006 Jan. 24; 45(3):852-60
27. Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci USA. 2003 Apr. 15; 100(8):4742-7
28. Monaco H L, Rizzi M, Coda A. Structure of a complex of two plasma proteins: transthyretin and retinol-binding protein. Science. 1995 May 19; 268(5213):1039-41.
29. Bonanni B, Lazzeroni M, Veronesi U. Synthetic retinoid fenretinide in breast cancer chemoprevention. Expert Rev Anticancer Ther. 2007 April; 7(4):423-32.
30. Sunness J S, et al. The long-term natural history of geographic atrophy from age-related macular degeneration: enlargement of atrophy and implications for interventional clinical trials. Ophthalmology. 2007 February; 114(2):271-7.
31. Glickman J F et al. A comparison of ALPHAScreen, TR-FRET, and TRF as assay methods for FXR nuclear receptors. J. Biomol. Screening 2002; 7:3-10
32. Fujimura T et al. Unique properties of coactivator recruitment caused by differential binding of FK614, an anti-diabetic agent, to PPARgamma. Biol. Pharm. Bull. 2006; 29:423-429
33. Zhou G et al. Nuclear receptors have distinct affinities of coactivators: characterization by FRET. Mol. Endocrinol. 1998; 12:1594-1605
34. Cogan U, Kopelman M, Mokady S, Shinitzky M. Binding affinities of retinol and related compounds to retinol binding proteins. Eur J Biochem. 1976 May 17; 65(1):71-8.
35. Decensi A, Torrisi R, Polizzi A, Gesi R, Brezzo V, Rolando M, Rondanina G, Orengo M A, Formelli F, Costa A. Effect of the synthetic retinoid fenretinide on dark adaptation and the ocular surface. J Natl Cancer Inst. 1994 Jan. 19; 86(2):105-10.
36. Conley B, et al. Pilot trial of the safety, tolerability, and retinoid levels of N-(4-hydroxyphenyl) retinamide in combination with tamoxifen in patients at high risk for developing invasive breast cancer. J Clin Oncol. 2000 January; 18(2):275-83.
37. Fain G L, Lisman J E. Photoreceptor degeneration in vitamin A deprivation and retinitis pigmentosa: the equivalent light hypothesis. Exp Eye Res. 1993 September; 57(3):335-40.
38. Makimura H, Wei J, Dolan-Looby S E, Ricchiuti V, Grinspoon S. Retinol-Binding Protein Levels are Increased in Association with Gonadotropin Levels in Healthy Women. Metabolism. 2009 April; 58(4): 479-487.
39. Yang Q, et al. Serum retinol binding protein 4 contributes to insulin resistance in obesity and type 2 diabetes. Nature. 2005 Jul. 21; 436(7049):356-62.
40. Kim S R, et al. The all-trans-retinal dimer series of lipofuscin pigments in retinal pigment epithelial cells in a recessive Stargardt disease model. PNAS. Dec. 4, 2007, Vol. 104, No. 49, 19273-8.
41. Wu Y, et al. Novel Lipofuscin Bisretinoids Prominent in Human Retina and in a Model of Recessive Stargardt Disease. Journal of Biological Chemistry. Jul. 24, 2009, Vol. 284, No. 30, 20155-20166.
42. F. G. Holz, et al. Patterns of increased in vivo fundus autofluorescence in the junctional zone of geographic atrophy of the retinal pigment epithelium associated with age-related macular degeneration. Graefe's Archive for Clinical and

What is claimed is:

1. A compound having the structure:

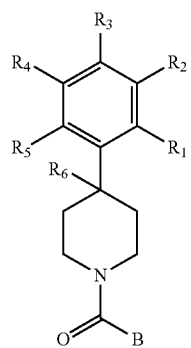

wherein
$R_1$ is $CF_3$, $R_2$ is F, $R_3$ is F, $R_4$ is H, and $R_5$ is H,
$R_1$ is $CF_3$, $R_2$ is F, $R_3$ is H, $R_4$ is F, and $R_5$ is H, or
$R_1$ is $CF_3$, $R_2$ is F, $R_3$ is H, $R_4$ is H, and $R_5$ is H;
$R_6$ is H; and
B is a substituted or unsubstituted heterobicycle having the structure:

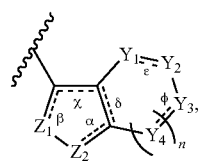

wherein
n is an integer from 0-2;
α, β, χ, δ, ε, and φ are each independently absent or present, and when present each is a bond;
$Z_1$ is N;
$Z_2$ is N or N—$R_7$,
wherein $R_7$ is H, $C_1$-$C_{10}$ alkyl, or oxetane;
X is C or N; and
$Y_1$, $Y_2$, $Y_3$, and each occurrence of $Y_4$ are each independently $CR_8$, $CH_2$, or N—$R_9$, wherein
$R_8$ is H, halogen, $OCH_3$, CN, or $CF_3$; and
$R_9$ is H, CN, oxetane, $C_1$-$C_6$ alkyl, $C_3$-$C_6$ cycloalkyl, ($C_1$-$C_4$ alkyl) ($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), C(O)$_2$—($C_1$-$C_6$ alkyl), C(O)—$NH_2$C(O)NH—($C_1$-$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2H$, ($C_1$-$C_6$ alkyl)-$CO_2$ ($C_1$-$C_6$ alkyl) or $SO_2$—($C_1$-$C_6$ alkyl),
wherein when $R_1$ is $CF_3$, $R_2$ is F, $R_3$ is H, $R_4$ is H, and $R_5$ is H, then B is other than

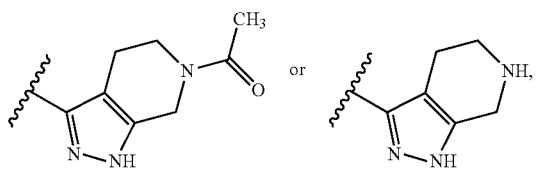 [SMILES: *c1n[nH]c2c1CCN(C(C)=O)C2 ; "or" ; *c1n[nH]c2c1CCNC2]

or a pharmaceutically acceptable salt thereof.

2. The compound of claim 1, wherein B has the structure:

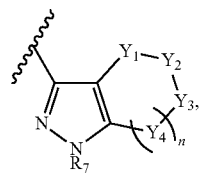

wherein
n is 0;
$R_7$ is H, $C_1$-$C_4$ alkyl, or oxetane;
$Y_1$ and $Y_3$ are each $CH_2$; and
$Y_2$ is N—$R_9$,
wherein
$R_9$ is H, CN, oxetane, $C_1$-$C_6$ alkyl, $C_3$-$C_6$ cycloalkyl, ($C_1$-$C_4$ alkyl)($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), C(O)$_2$—($C_1$-$C_6$ alkyl), C(O)—$NH_2$ C(O)NH—($C_1$-$C_6$ alkyl), C(O)—($C_6$ aryl), C(O)—($C_6$ heteroaryl), C(O)-pyrrolidine, C(O)-piperidine, C(O)-piperazine, ($C_1$-$C_6$ alkyl)-$CO_2H$, ($C_1$-$C_6$ alkyl)-$CO_2$($C_1$-$C_6$ alkyl) or $SO_2$—($C_1$-$C_6$ alkyl),
or a pharmaceutically acceptable salt thereof.

3. The compound of claim 1, wherein B has the structure:

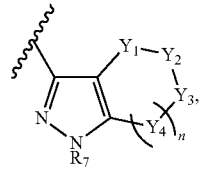

wherein
n is 1;
$R_7$ is H, $C_1$-$C_4$ alkyl, or oxetane;
$Y_1$, $Y_2$ and $Y_4$ are each $CH_2$; and
$Y_3$ is N—$R_9$,
wherein
$R_9$ is H, CN, oxetane, $C_1$-$C_6$ alkyl, $C_3$-$C_6$ cycloalkyl, ($C_1$-$C_4$ alkyl)($C_3$-$C_6$ cycloalkyl), ($C_1$-$C_6$ alkyl)-$OCH_3$, ($C_1$-$C_6$ alkyl)-$CF_3$, C(O)—($C_1$-$C_6$ alkyl), C(O)₂—(C₁-C₆ alkyl), C(O)—NH₂C(O)NH—(C₁-C₆ alkyl), C(O)—(C₆ aryl), C(O)—(C₆ heteroaryl), C(O)-pyrrolidine, C(O)-piperidine, C(O)-piperazine, (C₁-C₆ alkyl)-CO₂H, (C₁-C₆ alkyl)-CO₂(C₁-C₆ alkyl) or SO₂—(C₁-C₆ alkyl), or a pharmaceutically acceptable salt thereof.

4. The compound of claim 1, wherein B has the structure:

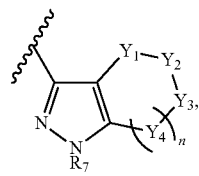

wherein n is 1;

R₇ is H, C₁-C₄ alkyl, or oxetane;

Y₁, Y₃ and Y₄ are each CH₂; and

Y₂ is N—R₉, wherein

R₉ is H, CN, oxetane, C₁-C₆ alkyl, C₃-C₆ cycloalkyl, (C₁-C₄ alkyl)(C₃-C₆ cycloalkyl), (C₁-C₆ alkyl)-OCH₃, (C₁-C₆ alkyl)-CF₃, C(O)—(C₁-C₆ alkyl), C(O)₂—(C₁-C₆ alkyl), C(O)—NH₂C(O)NH—(C₁-C₆ alkyl), C(O)—(C₆ aryl), C(O)—(C₆ heteroaryl), C(O)-pyrrolidine, C(O)-piperidine, C(O)-piperazine, (C₁-C₆ alkyl)-CO₂H, (C₁-C₆ alkyl)-CO₂(C₁-C₆ alkyl) or SO₂—(C₁-C₆ alkyl), or a pharmaceutically acceptable salt thereof.

5. The compound of claim 1, wherein B has the structure:

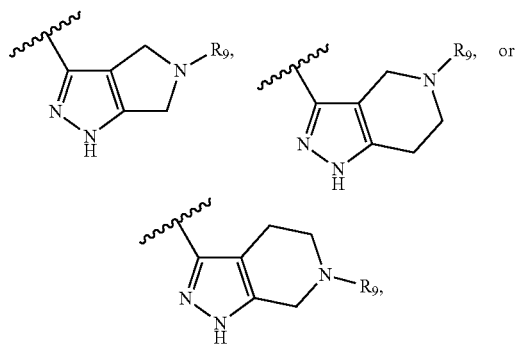

wherein

R₉ is H, CN, oxetane, C₁-C₆ alkyl, C₃-C₆ cycloalkyl, (C₁-C₄ alkyl)(C₃-C₆ cycloalkyl), (C₁-C₆ alkyl)-OCH₃, (C₁-C₆ alkyl)-CF₃, C(O)—(C₁-C₆ alkyl), C(O)₂—(C₁-C₆ alkyl), C(O)—NH₂C(O)NH—(C₁-C₆ alkyl), C(O)—(C₆ aryl), C(O)—(C₆ heteroaryl), C(O)-pyrrolidine, C(O)-piperidine, C(O)-piperazine, (C₁-C₆ alkyl)-CO₂H, (C₁-C₆ alkyl)-CO₂(C₁-C₆ alkyl) or SO₂—(C₁-C₆ alkyl).

6. The compound of claim 5, wherein wherein R₉ is SO₂—CH₃, C(O)—CH₃, C(O)—CH₂CH₃, C(O)—CH₂CH₂CH₃, C(O)—CH(CH₃)₂, C(O)—CH₂CH(CH₃)₂, C(O)-t-Bu, C(O)—OCH₃, C(O)—NHCH₃,

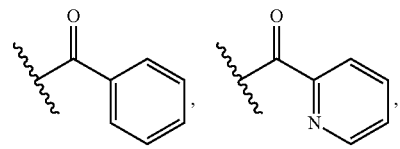

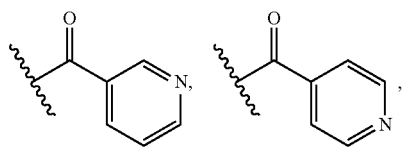

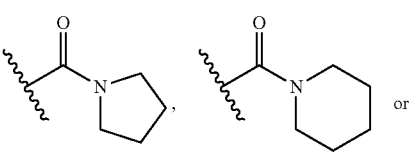

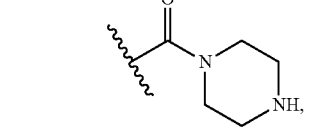 or

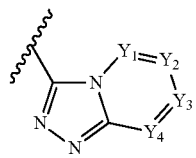

or a pharmaceutically acceptable salt thereof.

7. The compound of claim 1, wherein B has the structure:

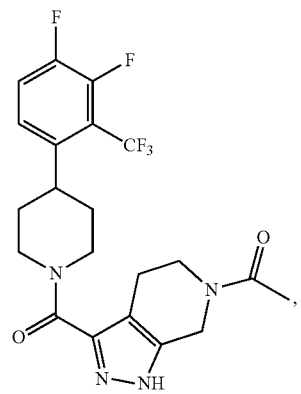

wherein

Y₁, Y₂, Y₃ and Y₄ are each independently CR₈ or N, wherein each R₈ is independently H, halogen, OCH₃, CN, or CF₃, or a pharmaceutically acceptable salt thereof.

8. The compound of claim 1 having the structure:

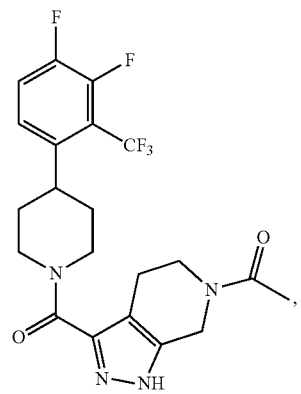 [SMILES: CC(=O)N1CCc2c(C(=O)N3CCC(c4ccc(F)c(F)c4C(F)(F)F)CC3)n[nH]c2C1]

or a pharmaceutically acceptable salt of the compound.

9. The compound of claim 1 having the structure:

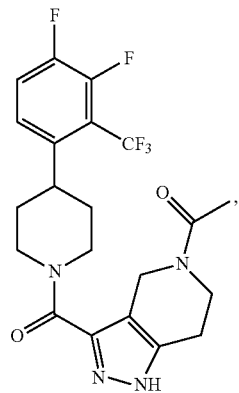 [SMILES: CC(=O)N1CCc2[nH]nc(C(=O)N3CCC(c4ccc(F)c(F)c4C(F)(F)F)CC3)c2C1]

or a pharmaceutically acceptable salt of the compound.

10. The compound of claim 1 having the structure:

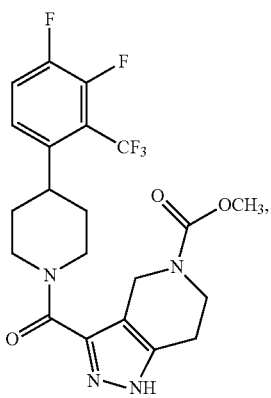 [SMILES: COC(=O)N1CCc2[nH]nc(C(=O)N3CCC(c4ccc(F)c(F)c4C(F)(F)F)CC3)c2C1]

or a pharmaceutically acceptable salt of the compound.

11. The compound of claim 1 having the structure:

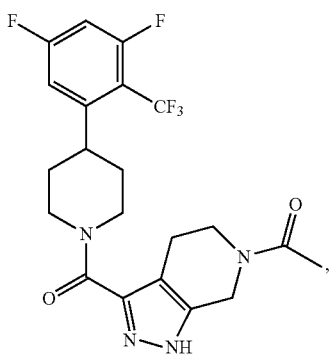 [SMILES: CC(=O)N1CCc2c(C(=O)N3CCC(c4cc(F)cc(F)c4C(F)(F)F)CC3)n[nH]c2C1]

or a pharmaceutically acceptable salt of the compound.

12. The compound of claim 1 having the structure:

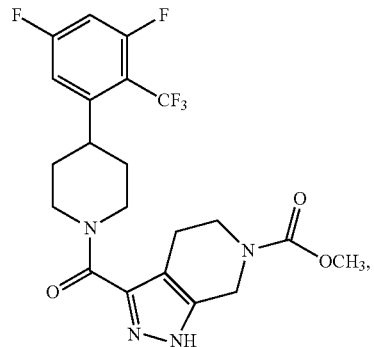 [SMILES: COC(=O)N1CCc2c(C(=O)N3CCC(c4cc(F)cc(F)c4C(F)(F)F)CC3)n[nH]c2C1]

or a pharmaceutically acceptable salt of the compound.

13. The compound of claim 1 having the structure:

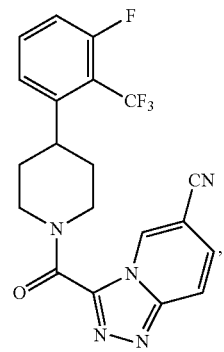 [SMILES: N#Cc1ccc2nnc(C(=O)N3CCC(c4cccc(F)c4C(F)(F)F)CC3)n2c1]

or a pharmaceutically acceptable salt of the compound.

14. The compound of claim 1 having the structure:

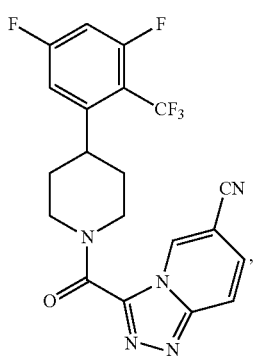 [SMILES: N#Cc1ccc2nnc(C(=O)N3CCC(c4cc(F)cc(F)c4C(F)(F)F)CC3)n2c1]

or a pharmaceutically acceptable salt of the compound.

15. The compound of claim 1, wherein $R_1$ is $CF_3$, $R_2$ is F, $R_3$ is F, $R_4$ is H, and $R_5$ is H, or a pharmaceutically acceptable salt of the compound.

16. The compound of claim 1, wherein $R_1$ is $CF_3$, $R_2$ is F, $R_3$ is H, $R_4$ is F, and $R_5$ is H, or a pharmaceutically acceptable salt of the compound.

17. The compound of claim 1, wherein $R_1$ is $CF_3$, $R_2$ is F, $R_3$ is H, $R_4$ is H, and $R_5$ is H, or a pharmaceutically acceptable salt of the compound.

18. A pharmaceutical composition comprising the compound of claim 1 and a pharmaceutically acceptable carrier.

19. A method for treating a disease characterized by excessive lipofuscin accumulation in the retina in a mammal afflicted therewith comprising administering to the mammal an effective amount of the compound of claim 1, wherein the disease characterized by excessive lipofuscin accumulation in the retina is Age-Related Macular Degeneration, dry (atrophic) Age-Related Macular Degeneration, Stargardt Disease, Best disease, adult vitelliform maculopathy or Stargardt-like macular dystrophy.

* * * * *

UNITED STATES PATENT AND TRADEMARK OFFICE
CERTIFICATE OF CORRECTION

Page 1 of 2

PATENT NO. : 10,072,016 B2
APPLICATION NO. : 15/722760
DATED : September 11, 2018
INVENTOR(S) : Konstantin Petrukhin et al.

It is certified that error appears in the above-identified patent and that said Letters Patent is hereby corrected as shown below:

In the Specification

In Column 106, Line 60, the portion of the chemical name reading "[4,3-c]" should read as --[3,4-c]--.

In Column 107, Line 1, the portion of the chemical name reading "[4,3-c]" should read as --[3,4-c]--.

In Column 109, Line 10, the portion of the chemical name reading "[3,4-c]" should read as --[4,3-c]--.

In Column 109, Line 11, the portion of the chemical name reading "(30)" should read as --(32)--.

In Column 111, Lines 16-18, the chemical name reading "(6-ethyl-4,5,6,7-tetrhydro-1H-pyrazolo[3,4-c]pyridin-3-yl)(4-(3-fluoro-2-(trifluormethyl)phenyl) piperidin-1-yl)methanone" should read as --(6-(cyclopropylmethyl)-4,5,6,7-tetrahydro-1H-pyrazolo[3,4-c]pyridin-3-yl)(4-(3-fluoro-2-(trifluoromethyl) phenyl)piperidin-1-yl)methanone--.

In Column 152, the second listed compound "77" should be renumbered as --78--.

In Column 152, compound "78" should be renumbered as --79--.

In Column 152, compound "79" should be renumbered as --80--.

In Column 153, compound "80" should be renumbered as --81--.

In Column 151, the structure of Compound 73 reading " 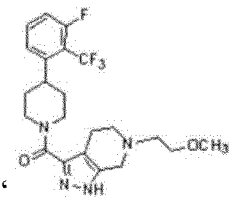 " should read as Signed and Sealed this
Fourth Day of February, 2020

Andrei Iancu
*Director of the United States Patent and Trademark Office*

CERTIFICATE OF CORRECTION (continued)
U.S. Pat. No. 10,072,016 B2

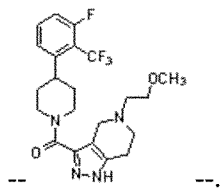

-- --.

In Column 153, the second listed compound number "81" and the accompanying structure " 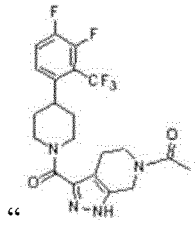 " should be deleted.

UNITED STATES PATENT AND TRADEMARK OFFICE
CERTIFICATE OF CORRECTION

PATENT NO.         : 10,072,016 B2
APPLICATION NO.    : 15/722760
DATED              : September 11, 2018
INVENTOR(S)        : Konstantin Petrukhin et al.

Page 1 of 1

It is certified that error appears in the above-identified patent and that said Letters Patent is hereby corrected as shown below:

In the Claims

Claim 1, Column 185, Lines 49-55, replace

"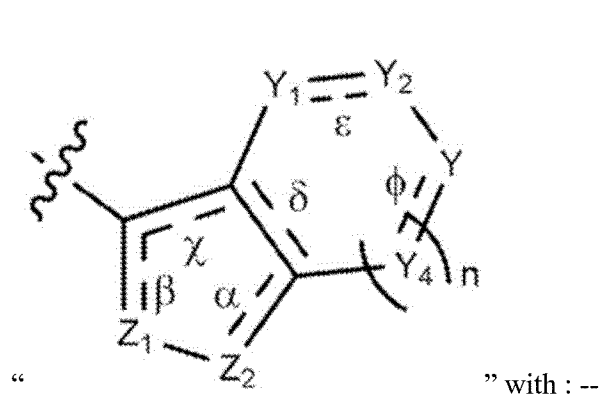" with : --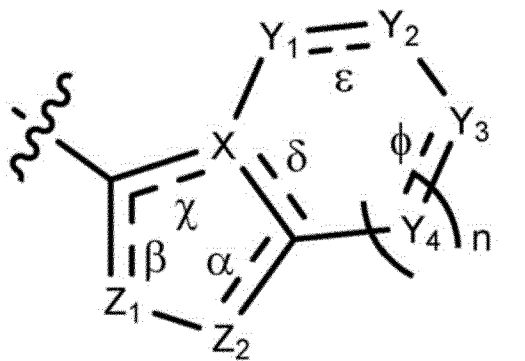--

Signed and Sealed this
Third Day of December, 2024

Katherine Kelly Vidal
*Director of the United States Patent and Trademark Office*